United States Patent
Paturu

(10) Patent No.: US 9,555,052 B2
(45) Date of Patent: Jan. 31, 2017

(54) INTRAUTERINE FETAL GROWTH RESTRICTION—THE BIOCHEMICAL RATIONALE OF TREATMENT MODALITIES INCLUDING EXTRAPERITONEAL TRANSAMNIOTIC FETAL SUPPLEMENTS

(71) Applicant: Sumathi Paturu, Birmingham, AL (US)

(72) Inventor: Sumathi Paturu, Birmingham, AL (US)

( * ) Notice: Subject to any disclaimer, the term of this patent is extended or adjusted under 35 U.S.C. 154(b) by 78 days.

(21) Appl. No.: 13/815,468

(22) Filed: Mar. 5, 2013

(65) Prior Publication Data

US 2014/0330246 A1 Nov. 6, 2014

Related U.S. Application Data

(63) Continuation-in-part of application No. 10/460,170, filed on Jun. 13, 2003, now Pat. No. 8,389,483.

(51) Int. Cl.

| | | |
|---|---|---|
| *A61K 31/7004* | (2006.01) | |
| *A61M 25/00* | (2006.01) | |
| *A61M 39/06* | (2006.01) | |
| *A61K 31/51* | (2006.01) | |
| *A61K 9/00* | (2006.01) | |
| *A61M 39/02* | (2006.01) | |
| *A61M 5/172* | (2006.01) | |
| *A61M 39/04* | (2006.01) | |

(52) U.S. Cl.
CPC ......... *A61K 31/7004* (2013.01); *A61K 9/0019* (2013.01); *A61K 31/51* (2013.01); *A61M 5/1723* (2013.01); *A61M 25/00* (2013.01); *A61M 25/0017* (2013.01); *A61M 39/0208* (2013.01); *A61M 39/04* (2013.01); *A61M 39/06* (2013.01); *A61M 2039/0205* (2013.01); *A61M 2039/0223* (2013.01); *A61M 2039/0235* (2013.01)

(58) Field of Classification Search
None
See application file for complete search history.

(56) References Cited

PUBLICATIONS

Nicolini et al., "Effects of Fetal Intravenous Glucose Challenge in Normal and Growth Retarded Fetuses" Horm Meta Res (1990) vol. 22 pp. 426-430.*
Beischer et al., "Intrauterine Growth Retardation" Australian and New Zealand Journal of Obstetrics and Gynaecology (1983) vol. 23 No. 4 pp. 191-196.*

* cited by examiner

*Primary Examiner* — Eric Olson

(57) ABSTRACT

Intrauterine fetal growth restriction (IUGR) is an affliction of a disparaging spectrum, placental insufficiency being the major inciting pathology. The resultant fetal hypoglycemia is alleviated by intravenous hypertonic D-glucose 25-50% maternal supplements, by improving the $V_{max}$ of placental substrate transfer, as per Michaelis-Menten model. Fetal normoglycemia so restored in turn surprisingly improves fetal hypoxia, hypercapnia if any, lactic acidemia, acidosis, oliguria with/without oligohydromnios, hypertriglyceridemia, and the fetal nutrient, mineral and vitamin acquisition. The list being phenomenal can only convince an inquiring reader by a biochemical sojourn into the aquatic world of the fetus, herein described. Maternal carbohydrate predominant, essential amino acids/fatty acids rich IUGR-diet incorporating maximal amounts of vitamin and minerals are highly beneficial for attainable placental $V_{max}$. Transamniotic isotonic D-glucose supplement via minimally invasive 'Suprapubic extraperitonial pelvic approach' for amniotomy (Sumathi Paturu's technique) with a Subcutaneously Implanted Pregnancy Port (SIPP) catheter is the additional therapy advocated.

8 Claims, 28 Drawing Sheets

Generation of malate from oxaloacetate in the cell cytosol

FIGURE - 5B
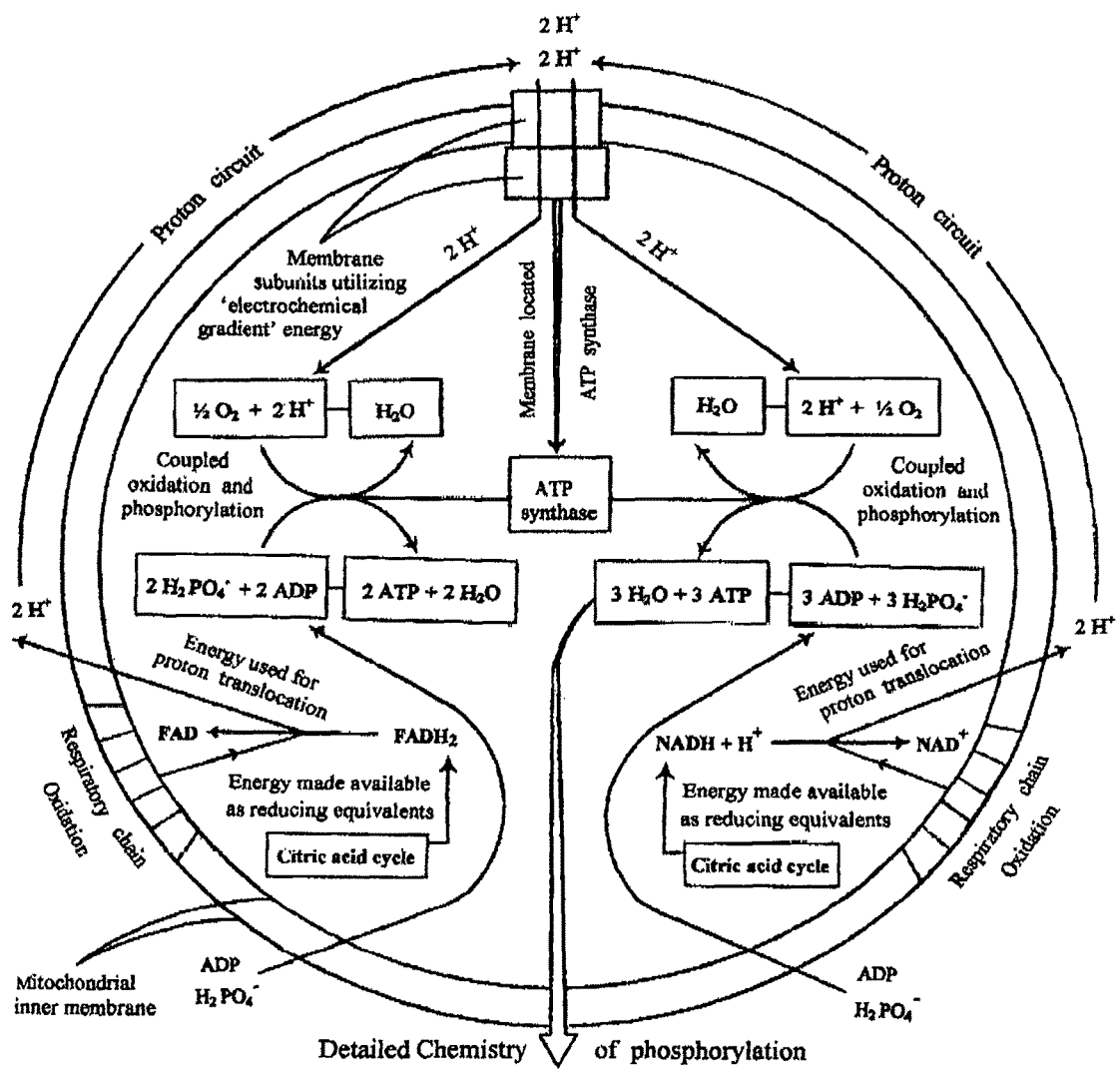
Detailed Chemistry of phosphorylation
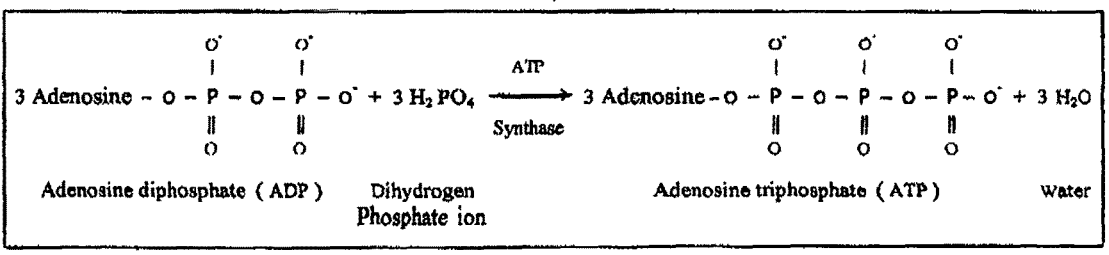

FIGURE - 13

| TABLE -1, The generation of ATP via D-Glucose catabolism | | | |
|---|---|---|---|
| Metabolic pathway involved | Enzyme catalyst | Mode of ATP production or use involved | Number of ATP formed |
| Glycolysis | Glyceraldehyde 3-phosphate dehydrogenase | Oxidation of 2 NADH via resp. chain | 6 |
| | Phosphoglycerate kinase | Substrate level phosphorylation | 2 |
| | Pyruvate kinase | Substrate level phosphorylation | 2 |
| | | Total ATP gain | 10 |
| | | ATP used through 'hexokinase' and 'phosphofructokinase' | - 2 |
| | | Net ATP gain | 8 |
| Formation of acetyl-CoA | Pyruvate dehydrogenase | Oxidation of 2 NADH via resp. chain | 6 |
| Citric acid cycle | Isocitrate dehydrogenase | Oxidation of 2 NADH via resp. chain | 6 |
| | α-ketoglutarate dehydrogenase | Oxidation of 2 NADH via resp. chain | 6 |
| | Succinate thiokinase | Substrate level phosphorylation | 2 |
| | Succinate dehydrogenase | Oxidation of 2 FAD2 via resp. chain | 4 |
| | Malate dehydrogenase | Oxidation of 2 NADH via resp.chain | 6 |
| | | Net ATP gain | 30 |
| | | Total ATP per molecule of glucose under aerobic conditions | 38 |
| | | Total ATP per molecule of glucose under anaerobic conditions | 2 |

FIGURE - 14

TABLE-2, The summary of $CO_2$ production within the fetal body

| Source of $CO_2$ production | Needed elements/processes | The source of the elements |
|---|---|---|
| 6 $CO_2$ - Through aerobic oxidation of 1 molecule of D-glucose - to acetyl- CoA, and the Krebs citric acid cycle intermediates | 1 Molecule of glucose, and 6 of molecular $O_2$ | D-glucose, and $O_2$ - both mainly derived through placental diffusion, from maternal sinusoids. |
| Anaerobic glycolysis | No $CO_2$ produced | |
| 3 $CO_2$ via pentose phosphate pathway (the HMP shunt) | 3 Molecules of D-glucose, and 3 $NADP^+$ | $NADP^+$- primarily derived via fetal lipogenesis in the milieu of fetal normoglycemia: fetal synthesis of 1 molecule of palmitic acid generating 14 $NADP^+$; D-glucose derived from maternal sinusoids. |
| 1 $CO_2$ via each amino acid | Glycine, valine, tyrosine, phenylalanine, tryptophane and histidine. (some involving synthesis of specialized products) | $CO_2$ source - by amino acid catabolic break-down outside the citric acid cycle. |
| Beta oxidation | No $CO_2$ produced | |
| 7 $CO_2$ - via synthesis of 1 molecule of palmitic acid; However, 7 $CO_2$ are reused in the synthesis of 1 molecule of Palmitic acid | Fatty acid synthesis in the cytosol, from acetyl-CoA | Glucose is the source of acetyl-CoA; 4 glucose molecules and 15 ATP are needed for the synthesis of one molecule of palmitic acid |
| $CO_2$ from lipids/amino acids: during disposal as Krebs cycle intermediates, or the precursors (2-3 $CO_2$ by each intermediate) | Oxygen, and operative citric acid cycle | Oxygen - through placental diffusion; Amino acids and lipids - via the placental transfer, or through fetal synthesis from D-glucose. |

FIGURE - 15

TABLE-3, The effects of the therapeutic interventions of D-Glucose supplements, and the IUGR diet on the placental transfer of the maternal substrates

| Element or compound involved in placental and fetal transport | Mechanism of transport | Effect of the D-glucose supplements, or the IUGR diet on the placental transfer mechanism |
|---|---|---|
| 1. Simple carbohydrates (by IV D-glucose and by IUGR diet) | Facilitated diffusion* controlled by insulin | - Multi-fold increase in placental carrier transport by increasing V max, secondary to exceeding increase in placental D-glucose substrate (S). |
| Complex carbohydrates (by IUGR-diet) | Sustained release of hexose sugars from the maternal blood, also by facilitated diffusion | - same as above, to a lesser extent. |
| 2. Amino acids | Facilitated diffusion through cell membrane carriers, controlled by insulin | - Through maternal hyperglycemia, and through restoration of normal insulin levels in the fetal compartment, as an effect of restored fetal normoglycemia.<br>- Through ↑ amino acid substrates (S), as an effect of maternal IUGR diet, thus increasing the Vmax, for heightened transplacental amino acid transport via facilitated diffusion. |
| | Active transport † | - Through generation of ATP, as an effect of restored normoglycemia in the placenta, and in the fetus. |
| 3. Fatty acids / lipids | Simple diffusion | - Maternal hyperglycemia sparing some maternal fat utilization, and increasing the placental gradient of FFA.<br>- The IUGR diet proportionally increasing the essential fatty acids in the maternal circulation. |
| 4. Minerals, vitamins, and trace elements. | Active transport, some involving 'antiport' | - Through generation of ATP in optimal amount as an effect of restored normoglycemia in the placenta, and in the fetus. |

\* Facilitated diffusion - specific carrier mediated transport, when maternal fetal substrate ratio is > 1;
† Active transport - specific carrier mediated transport needing ATP, when maternal fetal substrate ratio is < 1

FIGURE - 16

TABLE -4, Glucose / O₂ spent vs. ATP generated via Glycolysis-Abbreviated Citric acid Cycle during the synthesis of 1 molecule of Cerebronic acid - involving either 1 or 2 Citrate diversion into FFA synthesis; further comparison of ATP yield with the full-fledged glycolysis-citric acid cycle

| Citrate diversion into lipogenesis | Glucose spent | Acetyl-CoA spent | O₂ spent | Net ATP generated in glycolysis - citric acid cycle | ATP / O₂ ratio |
|---|---|---|---|---|---|
| 2-citrate diversion - | 6 | 12 | 12 | 84 | 7 |
| 1-citrate diversion - | 12 | 12/12 | 48 | 312 | 6.5 |

Glucose / O₂ spent via full-fledged glycolysis-citric acid cycle

| | 1 | 2 | 6 | 38 | 6.3 |

FIGURE - 17

TABLE -5, The hemodynamics of feto-placental circulation compared to the hemodynamics of the non-pregnant controls

| The artery / vein | PO2 ( mm / Hg ) | PCO2 ( mm / Hg ) | Author |
|---|---|---|---|
| Uterine artery | 95 | 32 | Longo ( 1972 ) |
| Uterine vein | 40 | 40 | Longo ( 1972 ) |
| Intervillous space ( IVS ) | 30-35 | 38 | PO2 ( Pritchard et al ) |
| Umbilical artery | 15 | 48 | Longo ( 1972 ) |
| Umbilical vein | 27 | 43 | Longo ( 1972 ) |

( note : the $PCO_2$ of 43 of umbilical vein is much higher than 38, of the IVS, despite equilibration with the maternal blood )

Non pregnant controls -

| | | | |
|---|---|---|---|
| Systemic ( venous blood ) | 40 | 45 | |
| Interstitial fluid | 40 | 45 | |
| Lung alveoli | 104 | 40 | |
| Pulmonary ( oxygenated blood ) | 104 | 40 | |

( after equilibrating with alveolar air, and before the entry of bronchial venous blood )

FIGURE - 18

TABLE-6, The Biophysical Profile ( BPP ) Scoring Assessed over a stretch of 30 minutes

| Criterion | Score of 2 | Score of 0 |
|---|---|---|
| 1. Nonstress test ( NST ) | Reactive. | Non-reactive |
| 2. Amniotic fluid | At least one 2 cm pocket ( measured in two planes perpendicular to each other ), that is, a 2 × 2 cm pocket. | No 2 × 2 cm pocket |
| 3. Fetal breathing | ≥ 1 Fetal breathing. | Abnormal or absent |
| 4. Fetal movements | ≥ 3 Gross body or limb movements during 30 minutes. | Less than 3, or absent |
| 5. Fetal tone | ≥ 1 Flexion or extension of the extremity, or opening and closing of hand. | Abnormal or absent |

FIGURE -19

ALGORITHM FLOW SHEET FOR GROUP-B, 26-31 weeks ( BPP score ≤ 6 ): for D-glucose 25% ( DG 25 ) maternal intravenous ( IV ) therapy, starting twice daily ( 1 am & 10 am ), with progressive increments

---

DAY - 1: DG25 ( 12.5 g, as 50 ml IV bolus over 3-5 minutes ) - starting at 10 am; check BPP at 3 pm ( see text for incorporated Fetal Heart Rate ( FHR ) monitoring at scheduled intervals throughout the treatment ) -

↙ ↘

| | |
|---|---|
| BPPS fallen from base line ( CAT- 2 ) | BPPS ≥ 6 ( CAT- 1 ): Continue treatment twice daily, with 2 day increments as in Group-A. Check BPP at 3 pm every 2 days during DG25 increments. If BPPS falls, and will not revert back with slower increments, then treat as CAT- 2. |

↓

Intermittent O₂ therapy ( IOT ) for CAT-2: as 6 L / minute starting after 3 pm BPP testing ( switch to continuous O₂ therapy for persistent adverse FHR changes ).

↓

DAY - 2:                Check 8-9 am BPP

↙ ↘

| | |
|---|---|
| BPPS ≤ 4 ( CAT- 3 ) start continuous O₂ ( COT ) if not on, with 6L / minute, on DG25 for 2 days; then EVDC of 10 am DG25 with IOT ( with FHR ½ hour before, and BPP check at 3 pm ) to decide for the 10 am & 1 am DG25 to be with COT or IOT. | BPPS ≥ 6 ( CAT- 4 ) IOT tolerated: continue for 2 days, followed by EVDC of 10 am DG25 with no O₂ and FHR and BPP checking, to decide if 1 am DG25 to be given with / without IOT. |

↙     ↘                                     ↙     ↘

| BPPS ≤ 4 COT indicated ↓ no further BPPS change → severe placental impedance for D-glucose: transamniotic D-glucose therapy indicated. Check AF-LA. | BPPS > 4 continue IOT as CAT- 4 | BPPS < 6 change back to IOT - if no improvement in BPPS, follow as per CAT- 3. ↓ Check AF-LA. | BPPS ≥ 6 on DG25 with no O₂, continue with every 2-day increments of DG25, so as to give thrice daily → then change to DG50. |

---

BPP - biophysical profile; BPPS - BPP score; CAT - category; COT - continuous O₂ therapy ; EVDC - every day challenge. see text for weaning of COT or IOT; DG - D-glucose; IOT - intermittent O₂ therapy : to be started along with DG25-50, as 6L / minute - tapered after 2 hours, with decrements every ½ hour, as 6L → 5L → 4L → 2L → stop; FHR - fetal heart rate; AF-LA - amniotic fluid lactic acid level.

FIGURE - 20

TABLE -7, THE FETAL MONITORING / TREATMENT INTERVENTION TABLE
PATIENT'S NAME :                                                    DOB:

| Diagnostics ( the base line data to be noted on day-1 ) & interventions | Date: day-1 | D: day | D: day | D: day | D: day | D: day | D: day |
|---|---|---|---|---|---|---|---|
| Hypertonic / isotonic D-glucose therapy ( specify strength / frequency ) - | | | | | | | |
| Uterine fundal height in cm ( also note clinical oligohydromnios ) - | | | | | | | |
| Fetal ultrasound: note fetal weight & oligo-hydromnios ( abnormal AF < 2 × 2 cm ) - | | | | | | | |
| UA: S / D ratio ( $\geq$ 2.6 abnormal); PI ( > 2 SD abnormal ) - | | | | | | | |
| MCA: S / D ratio; PI - as a serial study ( < 5$^{th}$ percentile abnormal ) - | | | | | | | |
| MCA - PI / UA - PI - serial recordings ( ratio < 1.08 abnormal ) - | | | | | | | |
| Ductus venosus flow velocity wave form ( the a-wave pattern ) ( not a routine ) - | | | | | | | |
| Umbilical vein flow velocity waveform ( FVW ) ( not a routine ) - | | | | | | | |
| Fetal heart : rate / variability / pattern - | | | | | | | |
| Non stress test ( NST ) - | | | | | | | |
| Biophysical Profile ( BPP ) Score - Note abnormalities and later improvement | | | | | | | |
| Initial AF lactate ( AF-LA ) level, or AF lactate / creatinine ratio ( L / C ratio ) - | | | | | | | |
| Oxygen ( O$_2$ ) therapy: intermittent ( IOT ) - continuous ( COT ) - | | | | | | | |
| AF- LA level before O$_2$ therapy - AF- LA level after O$_2$ therapy - | | | | | | | |

D- Date;  UA - Umbilical Artery;  MCA - Middle Cerebral Artery;  S / D - Systolic Diastolic flow velocity ratio;  PI - Pulsatility Index ;  AF - Amniotic Fluid.

FIGURE - 21

TABLE - 8, 30 MINUTE BIOPHYSICAL PROFILE SCORE CHARTING

PATIENT'S NAME / DOB :

| Nonstress test | Amniotic fluid | Fetal breathing | Fetal movements | Fetal tone | Date |
|---|---|---|---|---|---|
| Within 20 minutes of test Reactive : score 2 Non-reactive: score 0 (with acoustic stimulation) | Atleast 1 pocket size: 2 × 2 cm : score 2 < 2 × 2 cm : score 0 | $\geq 1$ : score 2 Absent : score 0 | $\geq 3$ : score 2 < 3 : score 0 | Flexion / Extension F / E $\geq 1$ : score 2 Absent : score 0 | Preg. weeks; Total score |
| ---- | ---- | ---- | ---- | ---- | ---- |
| ---- | ---- | ---- | ---- | ---- | ---- |
| ---- | ---- | ---- | ---- | ---- | ---- |
| ---- | ---- | ---- | ---- | ---- | ---- |
| ---- | ---- | ---- | ---- | ---- | ---- |
| ---- | ---- | ---- | ---- | ---- | ---- |
| ---- | ---- | ---- | ---- | ---- | ---- |
| ---- | ---- | ---- | ---- | ---- | ---- |

FIGURE - 22

TABLE-9, The amniotic fluid composition during normal pregnancy

| AF constituents | 16 weeks | 34-36 weeks | Author |
|---|---|---|---|
| Osmolality ( mosm / L ) | 275 | 265 with continued decrease to term | Whitfield CR |
| Sodium ( mEq / L ) | 136 | 132 with continued decrease to term | Whitfield CR |
| Total Protein ( g / L ) | 4.0 | 3.0 with continued decrease to term | Whitfield CR |
| Urea ( mmol / L ) | 2.8 | 3.8 with continued decrease to term | Whitfield CR |
| Creatinine ( mg / L ) | 49 | 149 with continued increase to term | Whitfield CR |
| Lecithin ( mg / L ) | 20 | 30-100 with terminal increase | Whitfield CR |
| Total lipids | 480 mg / L | | Gadd L |
| Fatty acids | 240 mg / L | | Gadd L |
| Glucose | At lower concentration than, but proportional to maternal serum level | | Gadd L |
| Amino acids | Found in same concentrations as in the maternal plasma | | Gadd L |
| Chloride, $K^+$, $Ca^{2+}$, $Mg^{2+}$ and phosphate | Resemble the concentrations of maternal extracellular fluid | | Gadd L |
| $CO_2$ | High | | Gadd L |
| | $PCO_2$ - 57 mm / Hg | | Rooth et al ( 1961 ) |
| Lactate / lactic acid | Less than 10.1 mmol / L | | Pardi et al ( 1987 ) |

FREE FATTY ACID SYNTHESIS, PALMITIC ACID CHOSEN AS THE PROTOTYPE

---

REACTION-3

$$CH_3-CO.CoA + CO_2 + ATP \xrightleftharpoons[]{\text{Acetyl-CoA carboxylase}} {}^-COO-CH_2-CO.CoA + ADP + Pi$$

---

REACTION-4

$$\underset{\text{Acetyl-CoA}}{\overset{\beta\quad\alpha}{CH_3-CO\ CoA}} + \underset{\text{Melonyl-CoA}}{{}^-COO-CH_2-CO.CoA} \rightarrow \underset{\underset{O}{\|}}{CH_3-C-CH_2-CO.E} + CO_2 + 2\,CO\text{-}A$$

Aceto acetyl enzyme ( 3 ketoa cyl enzyme )

---

REACTION-5

$$\underset{O}{\overset{\beta\quad\alpha}{CH_3-\underset{\|}{C}-CH_2-CO\ E}} + 2\,NADPH+H^+ \xrightarrow{\text{3-keto acyl reductase}}$$

Aceto acetyl enzyme ( 3 ketoacyl enzyme )

$$CH_3-CH_2-CH_2-CO.E + 2\,NADP^+ + H_2O$$

Butyryl enzyme
or a 4-carbon acyl enzyme

FREE FATTY ACID SYNTHESIS, PALMITIC ACID CHOSEN AS THE PROTOTYPE

REACTION - 6

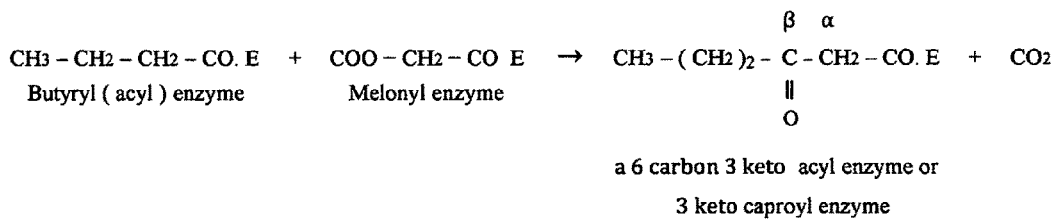

$$CH_3-CH_2-CH_2-CO.E \; + \; COO-CH_2-CO \; E \; \rightarrow \; CH_3-(CH_2)_2-\overset{\beta}{\underset{\underset{O}{\|}}{C}}-\overset{\alpha}{CH_2}-CO.E \; + \; CO_2$$

Butyryl (acyl) enzyme    Melonyl enzyme a 6 carbon 3 keto acyl enzyme or
3 keto caproyl enzyme

REACTION - 7

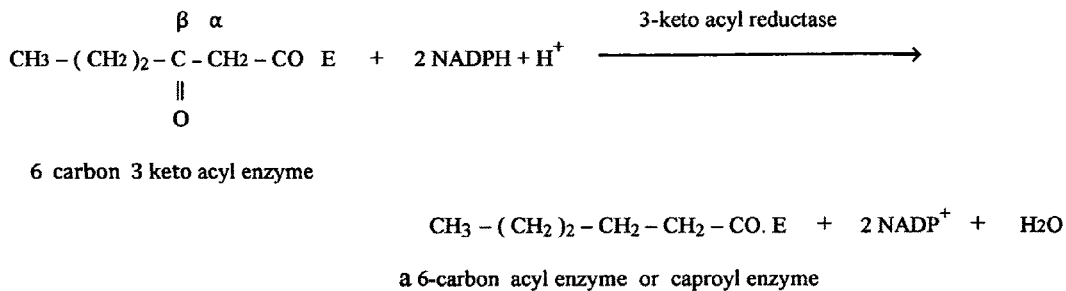

$$CH_3-(CH_2)_2-\overset{\beta}{\underset{\underset{O}{\|}}{C}}-\overset{\alpha}{CH_2}-CO \; E \; + \; 2\,NADPH + H^+ \xrightarrow{\text{3-keto acyl reductase}}$$

6 carbon 3 keto acyl enzyme $$CH_3-(CH_2)_2-CH_2-CH_2-CO.E \; + \; 2\,NADP^+ \; + \; H_2O$$

a 6-carbon acyl enzyme or caproyl enzyme

REACTION - 8

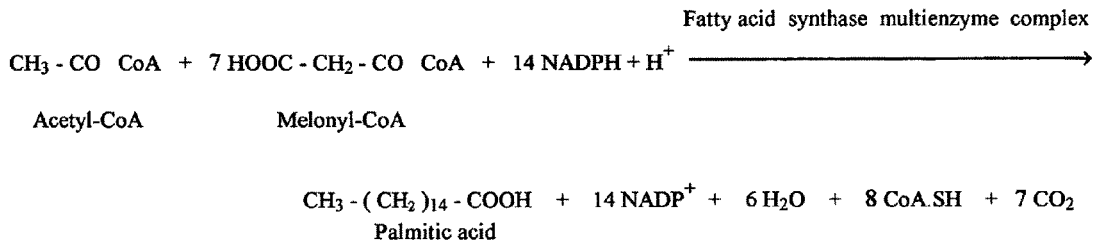

$$CH_3-CO\;CoA \; + \; 7\,HOOC-CH_2-CO\;CoA \; + \; 14\,NADPH+H^+ \xrightarrow{\text{Fatty acid synthase multienzyme complex}}$$

Acetyl-CoA      Melonyl-CoA $$CH_3-(CH_2)_{14}-COOH \; + \; 14\,NADP^+ \; + \; 6\,H_2O \; + \; 8\,CoA.SH \; + \; 7\,CO_2$$
Palmitic acid

BETA OXIDATION OF FREE FATTY ACIDS, PALMITIC ACID CHOSEN AS THE PROTOTYPE

---

REACTION - 3

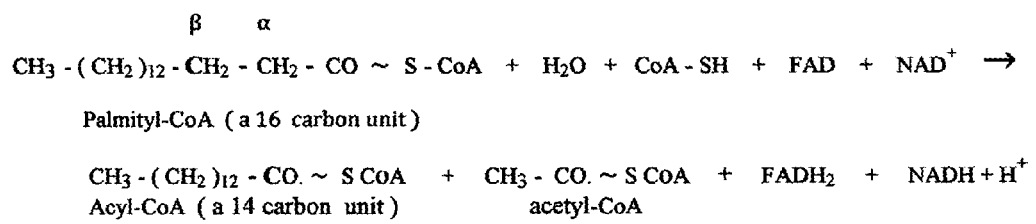

$$CH_3-(CH_2)_{12}-\overset{\beta}{CH_2}-\overset{\alpha}{CH_2}-CO\sim S\text{-}CoA + H_2O + CoA\text{-}SH + FAD + NAD^+ \rightarrow$$

Palmityl-CoA (a 16 carbon unit)

$$CH_3-(CH_2)_{12}-CO.\sim SCoA + CH_3-CO.\sim SCoA + FADH_2 + NADH+H^+$$
Acyl-CoA (a 14 carbon unit)       acetyl-CoA

---

REACTION - 4

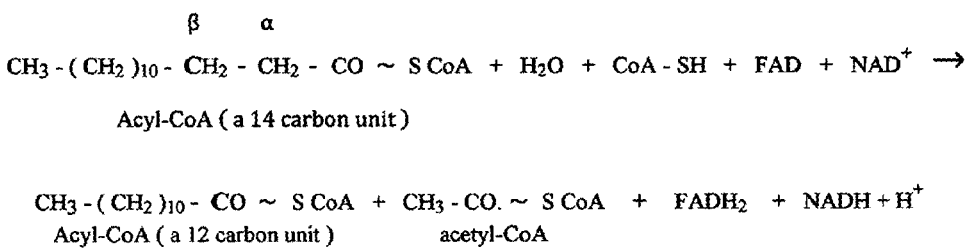

$$CH_3-(CH_2)_{10}-\overset{\beta}{CH_2}-\overset{\alpha}{CH_2}-CO\sim SCoA + H_2O + CoA\text{-}SH + FAD + NAD^+ \rightarrow$$

Acyl-CoA (a 14 carbon unit)

$$CH_3-(CH_2)_{10}-CO\sim SCoA + CH_3-CO.\sim SCoA + FADH_2 + NADH+H^+$$
Acyl-CoA (a 12 carbon unit)     acetyl-CoA

---

A simplified depiction of urea synthesis, schematically shown

INTRAUTERINE FETAL GROWTH RESTRICTION—THE BIOCHEMICAL RATIONALE OF TREATMENT MODALITIES INCLUDING EXTRAPERITONEAL TRANSAMNIOTIC FETAL SUPPLEMENTS

The embodiment of this invention is directed to an exemplary and an innovative treatment involving 'Intra Uterine Growth Restriction' (IUGR) of a human fetus, a long known and incurable but treatable maternal-fetoplacental pathology, resulting in significant mortality and morbidity of the fetus/neonate. The basic and clinical science research for alleviation of this elusive disease by investigators worldwide is so far disappointing. The author inventor endeavors to disclose in this specification a simple yet clinically proved successful treatment, and its biochemical rationale. For a disease so disparagingly prevailed for decades, the said treatment disguised as simple, nevertheless demanded ramifications of its rationale that are by no means simple, and efforts had been made to elaborate it with an infallible scientific reasoning of a compelling depth and breadth, as never done before of the subject matter. One can envision the alleviation in toto of a formidable pathology, as if the pieces of an intricate puzzle were put together. It further needed to counter the skepticism of an inquiring reader that is only viewed as truly justified. Hence the following elaboration has become arduous and rather voluminous, the Author Inventor also being no less skeptical and inquiring.

The definition for IUGR fetus/small for gestational age (SGA) infant is as follows—'Fetuses afflicted with Intrauterine Growth Restriction (IUGR) of whatever etiology, or Small for Gestational Age (SGA) neonates/infants of whatever etiology are those whose estimated/attained birth weights are below the tenth percentile, for the corresponding gestational age.'

The most common cause of intrauterine growth restriction of a human fetus is vascular in nature, resulting in placental vascular insufficiency, thus decreasing the transfer of D-glucose (the dextroisomeric form of glucose), the prime fetal nutrient, across the placenta. Accordingly, as an interventional measure to alleviate the fetal IUGR of placental insufficiency, the specification enumerates a therapeutic measure of transamniotic isotonic D-glucose supplements in this continuation-in-part (CIP) application, however such treatment is in addition to the concomitant maternal intravenous (IV) hypertonic D-glucose supplements, previously initiated and invariably required, for the reasons that will be elaborately explained. Such interventions working in conjunction can counter the fetal hypoglycemia (defined as a sub-optimal blood glucose concentration), and also as a result the other associated metabolic derangements accountable for placental insufficiency.

BRIEF DESCRIPTION OF THE INVENTION

The specification is directed to a novel invention encompassing many an unanticipated modalities in the specified treatment for Intrauterine Growth Restriction (IUGR) of a human fetus, mainly due to placental insufficiency.

As mentioned, a disclosure of providing transamniotic fetal supplements of isotonic 5% DEXTROSE (the commercially available form of D-glucose) is herein described, as an additional therapeutic measure of effectively by-passing the placental impedance, after the fetus is found to be not optimally responsive to maternal intravenous hypertonic D-glucose supplements to induce maternal hyperglycemia (defined as a rise in blood glucose concentration above specified normal range).

The Maternal Intravenous Hypertonic D-Glucose Treatments with or without Transamniotic D-Glucose Treatments Causing Induced Maternal Hyperglycemia and Restoring Feto-Placental Normoglycemia, Improve the Adverse Consequences of Placental Insufficiency as Below—

1. Improvement of feto-placental hypoxia (a demand-supply mismatch of oxygen at the tissue level having immediate or delayed adverse consequences).
2. Improvement of fetal hypercapnia (above normal blood $CO_2$ with possible adverse consequences), if any.
3. Improvement of fetal oliguria (suboptimal urine production) and oligohydromnios (suboptimal amniotic fluid volume, corresponding to the gestational age)—mostly consequent to improved fetal urea production.
4. Improvement of fetal acidosis (excess hydrogen ion concentration in the blood, leading to lowering of blood pH), including ketoacidosis.
5. Improvement of fetal lactic academia (excess of blood lactate levels) leading to lactic acidosis that needs a special and separate mention apart from acidosis specified under subsection-4.
6. Improvement of fetal hypertriglyceridemia (the triglycerides circulating in the blood in a concentration above the normal standard value, or range).
7. Improved acquisition by the fetus, of major nutrients like essential/non-essential amino acids, fatty acids, and also of minerals, vitamins, and trace elements.
8. Improvement of the following, by the effect of primarily D-glucose derived-ATP mediated active transport: (a) placental L-arginine uptake for the synthesis of nitric oxide, responsible for feto-placental vasodilatation and placental vasculogenesis, (b) placental D-lysine uptake, responsible for feto-placental neovasculogenesis—both in turn improving feto-placental hypoperfusion, hypoxia, and over all feto-maternal exchange.
9. Improved and rapid neuronal lipogenesis of fetal brain, with exponential glucose and oxygen salvage, primarily due to accomplished 2-citrate diversion towards the said neuronal lipogenesis, instead of 1-citrate diversion, prevailing during glucose scarcity.
10. Improved production of ATP, the ultimate and ubiquitous need for all life forms, and for all life-sustaining subcellular activities, being generated by citric acid cycle, the final pathway of the predominantly prevailing glucose metabolism within the normal fetus, and is also the ultimate meeting point for the metabolic pathways of proteins and lipids.

Transamniotic Isotonic Dextrose Fetal Supplements—

Transamniotic fetal supplement of isotonic 5% dextrose is advisable to treat severely growth restricted fetuses after the prior maternal IV hypertonic D-glucose supplements, and the associated therapeutics are exhausted. The phenomenon of in-utero fetal swallowing of amniotic fluid (AF) is taken advantage of, in this additional modality of treatment. The majority of the physiochemical improvements or consequences of improved fetal hypoglycemia accomplished through maternal IV D-glucose supplements herein detailed are expected to be operative in the fetus with the therapeutic modality of transamniotic D-glucose fetal supplements also, accomplished by means of by-passing the afflicted placenta and directly involving the fetus.

Through a Subcutaneously Implanted Pregnancy Port (SIPP) catheter, a device specifically modified for obstetric purposes, the amniotic cavity is approached by a minimally invasive surgical procedure, accomplished through an extraperitoneal route for which a novel procedure is devised by

BRIEF DESCRIPTION OF THE DRAWINGS

FIG. 1A: A schematic illustration of the placental D-glucose transport in normal pregnancy—said transport involving the substrate (in this case, the D-glucose) in normal physiological concentrations of the maternal blood/placental sinusoids.

FIG. 1B: A schematic illustration of the placental D-glucose transport in an untreated IUGR pregnancy of placental insufficiency—depicting reduced number of tertiary stem villi involved in the transport of the substrate (in this case, the D-glucose) in normal physiological concentrations of the maternal blood/placental sinusoids.

FIG. 1C: A schematic illustration of the placental D-glucose transport in IUGR pregnancy of placental insufficiency, treated with maternal hypertonic D-glucose IV supplements—said treatment resulting in exceeding maternal/sinusoidal concentration of substrate (in this case, the D-glucose), and a consequent heightened maximal reaction rate (the $V_{max}$) leading to improved placental D-glucose transport—as an effect and expression of MICHAELIS—MENTEN EQUATION, and the kinetics that model the effect of substrate concentration on the rate of reaction velocity.

FIG. 5B: A schematic reaction showing the mitochondrial oxidative phosphorylation—depicting the phosphate group ($PO_4^+$) added to ADP as wholly derived from $H_2PO_4^-$ (the dihydrogen phosphate ion). It also shows the simultaneous oxidation of 2 $H^+$ by ½ $O_2$, to form water (the coupling of oxidation and phosphorylation).

13. FIG. 13: showing Table-1—The generation of ATP via D-Glucose catabolism.

14. FIG. 14: showing Table-2—The Summary of $CO_2$ production within the fetal body.

15. FIG. 15: showing Table-3—The effects of the therapeutic interventions of D-Glucose supplements, and the IUGR-diet on the placental transfer of the maternal substrates.

16. FIG. 16: showing Table-4—Glucose/$O_2$ Spent vs. ATP generated via 'Glycolysis-Abbreviated Citric Acid Cycle' during the synthesis of 1 molecule of cerebronic acid, involving either 1 or 2 citrate diversion into FFA synthesis; further comparison of ATP yield with full-fledged glycolysis-citric acid cycle.

17. FIG. 17: showing Table-5—Hemodynamics of fetaplacental circulation compared to the hemodynamics of non-pregnant controls.

18. FIG. 18: showing Table-6-30 Minute Biophysical Profile (BPP) Scoring.

19. FIG. 19: showing Maternal IV hypertonic D-Glucose treatment protocol Algorithm depicting—ALGORITHM FLOW SHEET FOR GROUP-B, 26-31 weeks (BPP score≤6): for D-glucose 25% ($DG_{25}$) maternal intravenous (IV) therapy, starting twice daily (1 am & 10 am), with progressive increments.

20. FIG. 20: showing Table-7—The fetal monitoring and treatment intervention table.

21. FIG. 21: showing Table-8—30 minute Biophysical Profile (BPP) Score charting.

22. FIG. 22: showing Table-9—The amniotic fluid composition during normal pregnancy.

23. FIG. 23A: showing Chemical equations involving the reaction-3, reaction-4, and the reaction-5 of the free fatty acid synthesis, palmitic acid chosen as the prototype.

FIG. 23B: showing Chemical equations involving the reaction-6, reaction-7, and the reaction-8 of the free fatty acid synthesis, palmitic acid chosen as the prototype.

24. FIG. 24: showing Chemical equations involving the reaction-3 and the reaction-4 of the beta oxidation of free fatty acids, palmitic acid chosen as the prototype.

DETAILED DESCRIPTION OF THE INVENTION

Figures 1A, 1B, 1C:
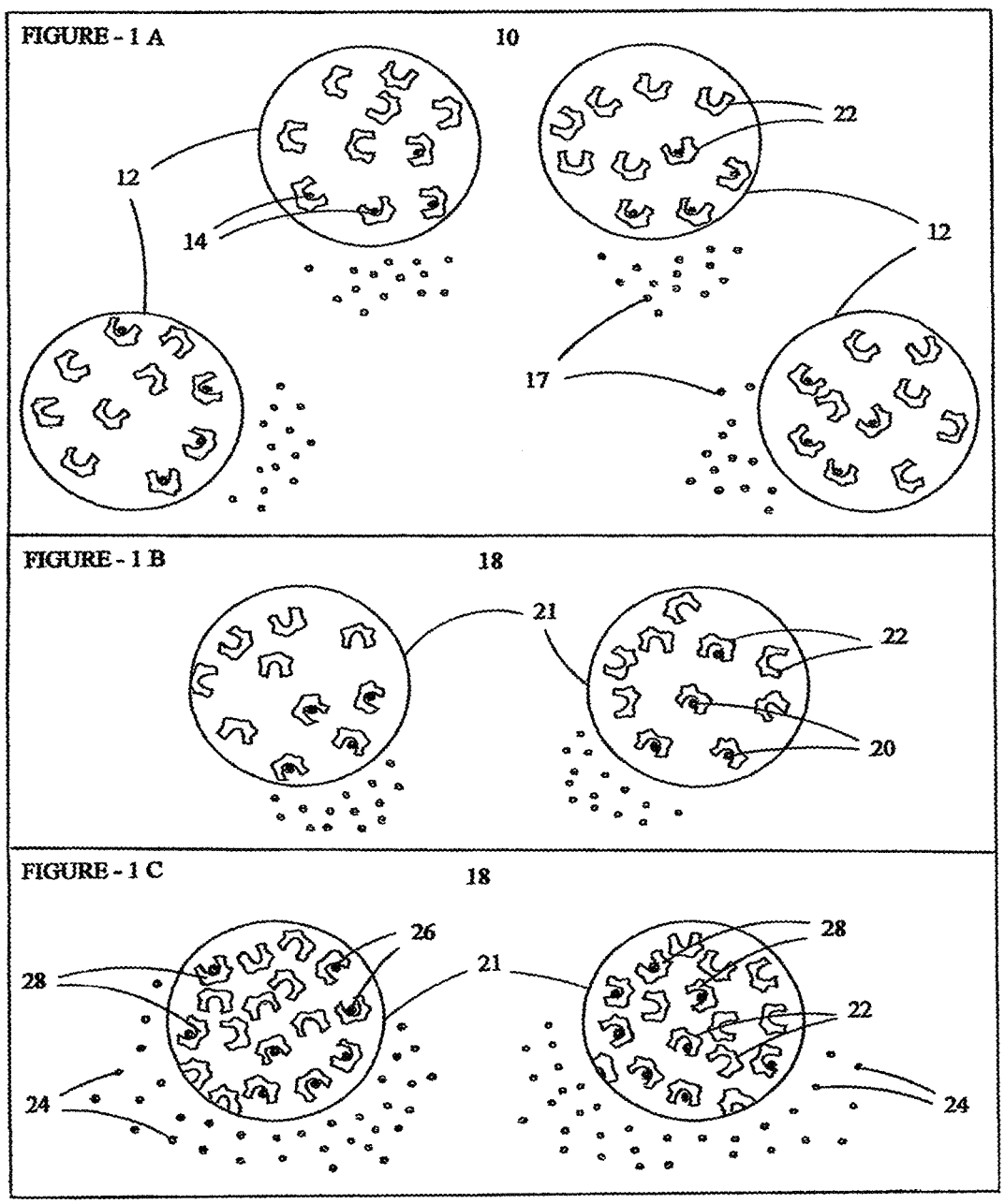
FIG. 1A, FIG. 1B, and FIG. 1C: are the schematic illustrations of the specific effects of increased substrate (D-glucose) concentration, and as a result, its heightened placental transport, as an expression of MICHAELIS-MENTEN EQUATION that models the general effects of substrate concentration on the velocity of the reaction rate, said effects being applicable to all the three clinical situations illustrated in FIG. 1A, FIG. 1B & FIG. 1C, and are described below—

This embodiment of invention is directed to an exemplary and novel treatment for the Intra Uterine Growth Restriction (IUGR) of a human fetus, a maternal-fetoplacental pathology, resulting in significant mortality and morbidity of the fetus/neonate. The specification encompassing a biochemical, clinical, and a surgical discussion of compelling depth and breadth, envisions total alleviation of a multi-faceted disease, for long elusive and misunderstood. Placenta, exalted to the central stage among the fetal membranes, can be considered as an indispensable structural and functional appendage of many organ systems of the fetal body that the neonate disposes off, after its nine months of intrauterine stay. Placenta being so crucial, its dysfunction or insufficiency often makes an indelible mark on the fetus, affecting diverse aspects of prime functions of: gaseous, nutrient, and substance exchange including selective transport of passing or restricting of certain maternal plasma components; substance synthesis including synthesizing in alliance with the fetus, optimal quantities of pregnancy hormones like estriol, essential throughout gestation—that the term fetoplacental unit is aptly phrased.

Chronic placental insufficiency of vascular nature decreases the placental transfer of D-glucose that was noted earlier as the most important of the fetal nutrients, resulting in on-going fetal hypoglycemia. The other metabolic derangements also resulting from placental insufficiency, like fetal hypoxia, to mention the most menacing of the group, can be countered by the fetus to a moderate extent, once the hypoglycemia has been corrected, whereas there are of no fetal devices to correct its hypoglycemia in the first place. A means of transamniotic fetal supplementation of 5% DEXTROSE, infused through a novel device named Subcutaneously Implanted Pregnancy Port (SIPP) catheter, also involving a novel surgical procedure of suprapubic extraperitoneal transamniotic insertion of the said SIP port-catheter are herein described, as an additional therapeutic measure for effectively by-passing the placental impedance (after the confirmed fetal unresponsiveness to the exhaustive therapeutic modalities associated with the maternal intravenous hypertonic glucose supplements), thereby accomplishing a means of improving the fetal hypoglycemia.

An accelerated 'facilitated diffusion' can be achieved at the placental interface by therapeutically creating a transient and intermittent maternal hyperglycemia by 25-50% hypertonic D-glucose bolus infusions to the mother, given over multiple times in a day, after it is confirmed that fetal IUGR is of placental vascular origin, and such maternal treatment continued until the delivery of the fetus/neonate.

In a clinical setting as complex as fetal IUGR, the isolated transamniotic treatment of fetal nutrients is not deemed effective. The placenta consumes as much as 50-60% of glucose and even in diseased states it is responsible to metabolize, transform, transport, and synthesize for and in alliance with the fetus many substances that are necessary for optimal pregnancy outcome, like glucose and lactate transport and estriol synthesis—to mention a few. It must accomplish energy/ATP (adenosine triphosphate) consuming active transport-concentration of essential nutrients and biologic substances via primarily glucose-generated ATP. Therefore, it is evident that the transamniotic glucose supplement alone is a moot pursuit, if not done in conjunction with maternal intravenous hypertonic glucose supplements also, as such concomitant therapy nourishes the feto-placental unit, which throughout pregnancy is both a structural and a functional unit. The question of the effectiveness of the transamniotc D-glucose supplements can only be answered if said invariable functional accompaniments are somehow helped to be achieved by the afflicted placenta. Otherwise, intrauterine demise of the fetus happens despite an apparently adequate transamniotic D-glucose treatments. Transamniotc D-glucose supplement is the last step in the algorithmic tree (discussed in the second half of this specification) of the treatment for intrauterine fetal growth restriction, as it is also an invasive procedure. Accordingly, the physician should know by no uncertain terms, why, how, and in what circumstances the transamniotic D-glucose treatment needs to be clinically pursued.

The great therapeutic effects firmly linked to the objective physiochemical principles of the D-glucose supplements and the rationale are described first under the section of 'THE MATERNAL INTRAVENOUS HYPERTONIC D-GLUCOSE TREATMENTS' that will soon follow, the discussion of which is rather elaborate. Most of the therapeutic feto-placental effects therein described are similarly applicable to THE TRANSAMNIOTC FETAL D-GLUCOSE SUPPLEMENTS via the SIPP catheter (encountered in the last part of this specification), and hence are not further repeated under its section A Case Study At the outset, it is relevant to describe a clinical case study of successfully treating a severe case of fetal IUGR, during the years 1983-84, by the Author Inventor as a practicing ob/gyn. in India, as it is the basis for this writing of significant depth that aided the author inventor decades later to fully comprehend what was once successfully treated, but was only incompletely understood at that time.

This single case study was with reference to a primi gravida in her early twenties who was found to have severely growth restricted fetus in the middle of second trimester. She was well nourished and was from good socioeconomic background, and there were no obvious etiological factors, that could be accounted for the identified fetal IUGR. After monitoring the growth of the fetus by assessing fundal height (a clinical norm of fetal measure in the past) for 3-4 more weeks, it was confirmed that the uterine size was not progressing, and that the patient had severely growth restricted fetus. As the pregnancy was remote from term, and the bed rest in left lateral position had not helped, 20% IV bolus of hypertonic D-glucose 50 cc twice daily was started, and in 2-3 weeks, an undoubted and immediate catch up of fetal growth was observed. The patient had more frequent pre-natal follow ups, and the treatment was diligently continued with increments, as also the patient was admirably cooperative. Nearing term, she was delivered by elective cesarean section. The baby had an Apgar score of 10, and to the great delight of everybody involved, the weight was also appropriate for the gestational age (AGA). No adverse effects due to induced maternal hyperglycemia were expected, nor were any observed in the mother through-out her gestation, and she tolerated the treatment far beyond expectations.

The observed fetal growth restriction was undoubtedly severe, but with mere hypertonic intravenous D-glucose treatment and no other (except for standard doses of prenatal vitamins and minerals), the mother delivered an AGA baby, who obviously had caught up with standard growth curve, as though glucose supplement alone, and nothing else was needed. It was evident that by mere fetal normoglycemia therapeutically restored, the fetus alleviated multitude of associated metabolic problems all by itself.

A Clinical Model as the Basis for the Treatment—

Fetal macrosomia, a known consequence of uncontrolled maternal diabetes mellitus (DM) served as a clinical model about which the therapeutic modality of this invention was/is based. Maternal hyperglycemia without super-concentration of any other element or of nutrient in the maternal blood, can accomplish accelerated fetal growth in diabetes mellitus. It exemplifies not only an accelerated placental glucose transfer secondary to maternal hyperglycemia, but also of an accelerated fetal growth response to such accelerated transfer. Extensive research by past investigators in this subject matter proved beyond reasonable doubt that fetal growth is indeed mediated by fetal hyperglycemia, and secondary fetal hyperinsulinism, via the islet-cell hypertrophy of the fetal pancreas. Accordingly, this superb clinical model proved the normal placental ability of accelerated glucose transfer, and of the resultant fetal growth response by macrosomia, both together serving as the needed translational clinical outcome to the biochemical phenomenon of maternal hyperglycemia—a naturally observed consequence that might not have been otherwise available or proven, except by targeted research. However, the difference between the diabetic pregnancy and the treatment setting of IUGR in the above discussed case study, that is, the glaring prevalence/perception of fetal hypoxia, hypercapnia (as described by past researchers), and of acidosis, due to placental insufficiency of IUGR is by no means over looked in this discussion.

Though a single case study, it was extraordinarily impressive because of the severity of growth restriction, and the lack of confounding variables (one could be 100% certain that Indian women, at least decades ago, were never habituated to alcohol, smoking, or drugs) that clinched the diagnosis of a primary placental insufficiency of vascular origin. The present writing painstakingly endeavors to explore a physiochemical support for the specified invention—how the fetus, by mere restoring of its normoglycemic state, or improving of a hypoglycemic state, could have possibly accomplished such an impossible feat, undoubtedly witnessed, though until this time, not completely understood.

The Maternal Intravenous Hypertonic D-Glucose Treatments

In the diverse maternal/fetal states that cause fetal IUGR, the disease primarily afflicting placental vasculature causes more of declined functional unit area than declined unit volume of the placenta, primarily due to failed placental elaboration (into tertiary terminal villi within the normally mature placenta, over all attaining the structural intricacy of a branching tree, that it is aptly called as the 'placental tree'). Such decline in the placental functional unit area with decrement fetoplacental exchange in its interface has resulted in fetal hypoglycemia, and consequently in fetal growth restriction.

Based on the foregoing clinical model of diabetic pregnancy, and based on the fact that the D-Glucose is the prime fetal nutrient, the invention contemplated a biochemical and clinical relief, achieved by transient therapeutic hyperglycemia effectuated in the mother (an induced diabetic state) by intravenous 25-50% hypertonic D-glucose bolus infusion, 50-100 cc twice or thrice daily. By such maternal super concentration of D-glucose achieved via an IV infusion, the deprived fetal circulation receives proportionally more D-glucose, presented through the placenta in higher concentration per unit surface area/unit volume, yet in its unchangeable and afflicted milieu. The function of placental glucose carriers operating that far in a sub-optimal level becomes maximal during the maternal hyperglycemic phase, a biochemical phenomenon explained in significant detail in the immediate subsequent sections.

Chronic vascular disease of the mother, especially preeclampsia was conventionally linked as the predominant cause of fetal growth restriction, mediated through placental vascular insufficiency. A wide spectrum of generalized placental vascular insufficiency (of whatever etiology) is the major pathology of concern to be alleviated through the therapeutic modality of the present invention. Normally, as pregnancy advances the uteroplacental blood flow gradually increases mainly due to spiral arterial remodeling. Very early on, due to trophoblastic invasion, the endothelium and the smooth muscle layers of the myometrial spiral vessels are replaced by trophoblast, with loss of spiral artery vascular resistance. The lacunae further created in the syncytiotrophoblast by cytotrophoblastic invasion, and their filling with blood, results in dilated pools of maternal blood sinusoids that are responsible for the shunt effect of the placenta. In an IUGR pregnancy, the trophoblastic invasion is limited, with failure of myometrial spiral arteries becoming low resistance vessels. Such placental failure in surface area elaboration, and failure in sinusoidal volume/pressure effect dynamics can find relief by exceeding substrate supplements, as will be soon explained by the biochemically derived principles of transcellular substrate transport.

Across the placenta the transfer of D-glucose, the prime fetal substrate central to this discussion, is accomplished by carrier mediated, stereospecific, non-concentrating, and no-energy expending process that can be saturated, said process termed as 'facilitated diffusion'.

The Biochemical Basis for Hypertonic D-Glucose Treatment—

The Michaelis-Menten model is an expression of the relation of substrate (substance) concentration and the resultant rate of an enzyme/hormone/carrier mediated chemical reaction, either by 'active transport' or by 'facilitated diffusion', said 'carrier' either cell membrane or cytosol located.

In what follows, the D-glucose needs to be considered as the 'substrate', and the GLUT-1 & GLUT-3 as its substrate-carriers, located in the placental cell membrane. The hormone involvement is also emphasized, the hormone relevant in this context being insulin.

In a typical chemical reaction involving an enzyme/hormone, or in a membrane transport mediated by a substrate-carrier (involving either active transport or facilitated diffusion), if the concentration of the substance/substrate (S) is increased while all other factors are kept constant, the measured initial velocity $v_1$ (that is the velocity attained when very little substance/substrate has reacted with its enzyme/hormone/carrier) increases until it reaches a maximum attainable velocity ($V_{max}$) and can increase no further, even with further increase of the substance/substrate (S), when the enzyme/hormone or carrier is said to be saturated.

If (S) is the substrate concentration, the 'Michaelis constant' ($K_m$) is the substrate concentration at which the initial velocity $v_1$ is half of the maximal attainable velocity ($V_{max}/2$) at a particular concentration of the enzyme or carrier involved/available in a reaction. When (S) is approximately equal to $K_m$ value, $v_1$ is very responsive to changes in (S), and the enzyme/carrier is working at half maximal efficiency. When the substrate concentration (S) far exceeds the $K_m$ value, the initial velocity $v_1$ is maximal ($V_{max}$). Furthermore, in this situation the reaction's maximal velocity $V_{max}$ is almost instantaneous, as all the available enzyme/carriers are able to bind to the exceeding amounts of substrate (S) all at once, and no further binding possible.

Under physiological D-glucose concentrations of the maternal blood, the placental carrier transporters for glucose were found to be far in excess, with a reserve able to accommodate further addition of an exceeding amount of D-glucose presented at the placental interface (as in the diabetic model). This implies that the carriers are always functioning in suboptimal manner under physiological D-glucose concentrations. Insulin heightens the recruitment of such carrier molecules from the intracellular pool. At times of placental compromise, the unit surface area of placental terminal villi are still transporting glucose in a manner similar to unaffected placental villi. However, the underlying problem in IUGR is the markedly reduced total surface area of the terminal villi that diminish the over-all glucose transport per unit time. Therapeutic maternal hyperglycemia with increased substrate (S) concentration not only increases $v_1$ to $V_{max}$ of each transport carrier, but also increases the number of such maximally functioning carriers recruited (also as a result of proportionally increased insulin levels). That is, the heightened D-glucose facilitated diffusion in this instance is the multiplied product of attained $V_{max}$×the maximally recruited carriers, all working at $V_{max}$, the $V_{max}$ being instantaneous in time. The said instantaneous $V_{max}$ therapeutically attained, is highly significant in IUGR with markedly diminished/reversed diastolic filling of umbilical vessels, and only the normally shorter systolic time (of each cardiac cycle) providing for any placental exchange.

Failure in the development of terminal villi whose contribution for maternal-fetal exchange increases exponentially during 31-36 weeks of gestation, could account for fetal IUGR. This was found to be associated with reduced umbilical artery end diastolic flow, which is otherwise increased in normal pregnancy. Histometric support of this hypothesis is provided by the observations of reduced terminal villi volumes as well as reduced surface areas of the placentae of the IUGR fetuses (Tesdale F, 1984). Failure in the 'fall of maternal peripheral vascular resistance' by 16%, observed throughout a normal pregnancy, can also be expected in this context.

The FIG. 1A, the FIG. 1B, and the FIG. 1C schematically illustrate the effect of exceeding substrate (D-glucose) concentration on the placental cell mediated transport, namely facilitated diffusion involving cell membrane/cytosolic substrate carriers that are present in surplus to be recruited as the substrate concentration (the D-glucose in this instance) demands. The FIG. 1A schematically shows normal placenta (10) depicted by four circled units (a hypothetical number chosen for schematic illustration, and so are all the other quantitative numerals specified in this paragraph) representing four terminal villi (shown by numeral 12) that can transport carrier-bound substrate or glucose molecules, a total of sixteen (as four molecules in four units) under physiological glucose concentration in the blood. Some such substrate molecules are shown numbered as 14 in the drawing having complimentary binding contacts with the carriers (22). The unbound glucose molecules are shown with numeral 17 in the drawing. The villi units in the IUGR placenta (18) (FIG. 1B) can carry only eight carrier bound glucose molecules (numbered as 20 in the drawing) due to only half the number (represented as two units) of terminal villi units (21), or half the surface area/volume available for contact with maternal sinusoids, per unit time of fetal cardiac cycle. It has to be noted that the operative glucose carriers (22) can be either located in the cell wall membrane or can be intracellular, but are schematically represented as one circular pool. During maternal hypertonic glucose supplements (as in FIG. 1C), due to exceeding number of glucose molecules (numbered as 24 in the drawing) presented in the sinusoids, and as a result an instantaneously attained $V_{max}$ (yet with the unchangeable surface area/volume of the terminal villi units of an IUGR placenta), sixteen molecules of glucose (some numbered as 26 in the drawing) are bound to the additionally recruited glucose carriers (28) that are always there in surplus in the cell unit (despite reduced number and reduced surface area of the terminal villi in IUGR), to be recruited by the manipulated factor of surplus glucose (24) in the maternal sinusoids.

Effects of Placental Insufficiency Other than Hypoglycemia—

Fetal hypoxia, hypercapnia, lactic acidosis, and impaired feto-maternal exchange across the placenta are the biochemical consequences for long conventionally linked to the primarily declined placental function. Yet this specification convincingly proves by available objective data that the therapeutic intervention of IV hypertonic glucose supplement in and by itself effectively relieves the said biochemical consequences. Such observation/deduction conforming to the needed 'as a whole inquiry' carries enormous significance in dispelling the possible skepticism that—glucose supplement might relieve fetal hypoglycemia, but the other invariable associations of placental insufficiency such as hypoxia and the like are still detrimental to the fetal well-being, and hence the proposed treatment is of no consequence.'

The D-Glucose, the Fittest Fetal Fuel—

There are operational mechanisms in pregnancy to minimize glucose utilization by the mother, thereby making it available to the fetus, glucose being its prime nutrient, intended by nature. Human Placental Lactogen (HPL), a pregnancy hormone secreted by the placenta, and normally present in the mother but not in the fetus, is believed to be blocking the peripheral uptake and utilization of D-glucose by maternal tissues, while also promoting the mobilization and utilization of free fatty acids (FFA) by the mother for energy requirements. Fats and proteins are also transported across the placenta, but they play a major role only in anabolic function of rapid tissue accretion needed for optimal fetal growth, or for targeted bodily functions, but not for the catabolic energy-yielding purposes within the fetus. The scientific rationale why D-glucose is the chosen fetal fuel for the therapy, and not any other major nutrients acclaimed as equal (the proteins), or superior (the lipids) in 'food caloric value' focuses on the nature's rationale itself (and hence this invention's) for its selection as the fittest. Such biochemical derivation is very relevant to this discussion, as other supplements if promoted as prime fetal nutrients (at the expense of glucose) are clearly detrimental, and may not be considered as potential fetal energy/ATP sources.

The major compromise that has direct bearing in fetal demise/deterioration in the setting of fetal IUGR is undoubtedly linked to fetal hypoglycemia and fetal hypoxia. GLUCOSE because of its dominant function in the ultimate catabolic oxidation via the 'citric acid cycle' is pivotal in generating ATP, the source of life and energy. Though OXYGEN ($O_2$) is breathed-in by all living organisms, and taken up by the fetus from the maternal source, ultimately it is the cellular respiration and 'oxidative phosphorylation' via molecular oxygen within the mitochondria, the 'power house' organelles of the cell, that are ultimately responsible for generating ATP, via the maneuvers of the D-glucose mediated 'citric acid cycle'.

Accordingly, what happens at large at the organ level is ultimately reflected at the cellular and biochemical level and vice versa, and understanding such micro-functions of cell organelles as the ultimate ATP generators to sustain life is the only clue to explore or search for any convincing relief to be sought for the significant fetal deficits such as hypoglycemia and hypoxia, while the placental pathology itself may not be alleviated. It necessitates the in-depth biochemical discussion of the major (the carbohydrate, lipid, and protein), and some minor fetal metabolic pathways invariable for discovering what is yet undiscovered, or for dispelling legitimate concerns that may not be by other means explained, nor over ruled. The compelling motivation for such diligent exploration is the author inventor's successful case study itself that proved that there is something intriguing that is yet to be explored and found. What is found is truly intriguing as was thought (though some are universally known biochemical/biophysical facts under different context), and is herein elaborated in the following sections.

The Carbohydrate Metabolism

The carbohydrates, characterized by a basic compact structural formula $C_{(n)}H_{(n)}O_{(n)}$ (the carbon, hydrogen, and oxygen being present in varying number n) are the aldehyde or ketone derivatives of polyhydric alcohols, existing either as isomeric straight chains or as stable 5 carbon (furanose) or 6 carbon (pyranose) ring structures. The most interesting and foremost member of the class, the glucose, a hexose sugar (one having 6 carbon atoms) is represented in a compact chemical formula as $C_6H_{12}O_6$, and the $H^+$ and $O_2$ present in the same ratio as that of water molecule may be noted, as the carbohydrates are water-rich substrates, a property responsible for their bulk (compared to the fats/lipids that are water-desiccated during their synthesis from the parent carbohydrates, as can be observed later in this discussion, and hence are acclaimed to carry higher energy in the same unit weight), and such structure representing the hydrogen-oxygen ratio of water molecule can also be noted in the triose, tetrose, and pentose sugars.

The Carbohydrates are Classified as—

1. Monosaccharides—they are carbohydrates that can not be further reduced to simpler forms. They comprise of trioses (ex.—dihydroxyacetone, the important intermediate of glycolysis), tetroses, pentoses (ex—the ribose sugars of DNA and RNA), and of hexoses (ex—glucose, fructose, and galactose), each containing 3, 4, 5 or of 6 carbon units respectively. All dietary complex carbohydrates are broken down, and are absorbed into the body in simpler monosaccharide form, such as glucose.
2. Disaccharides—they are made of 2 monosaccharide units (ex—sucrose and lactose).
3. Polysaccharides—they are made of more than 10 monosaccharide units (ex—starches, dextrins).

The major pathways of carbohydrate metabolism having substantive clinical and biochemical significance, and relevant to this discussion, are—
 1. The Glycolysis (the Embden-Meyerhof pathway),
 2. The Krebs Citric Acid Cycle (or the tri-carboxylic acid cycle), and
 3. The Hexose Monophosphate (HMP) Shunt, or the Pentose Phosphate Pathway (PPP).

The Pathway of Glycolysis (the Embden-Meyerhof Pathway)

Glycolysis, the initiating pathway for the D-glucose metabolism, occurs in the cytosol (the cytoplasm) of the cell, and is unique in that it can occur either aerobically or anaerobically. It is also the main initiating metabolic pathway of fructose, galactose, and also of the other carbohydrates, derived from the diet. It is schematically shown in the FIG. 2.

Figure 3A:
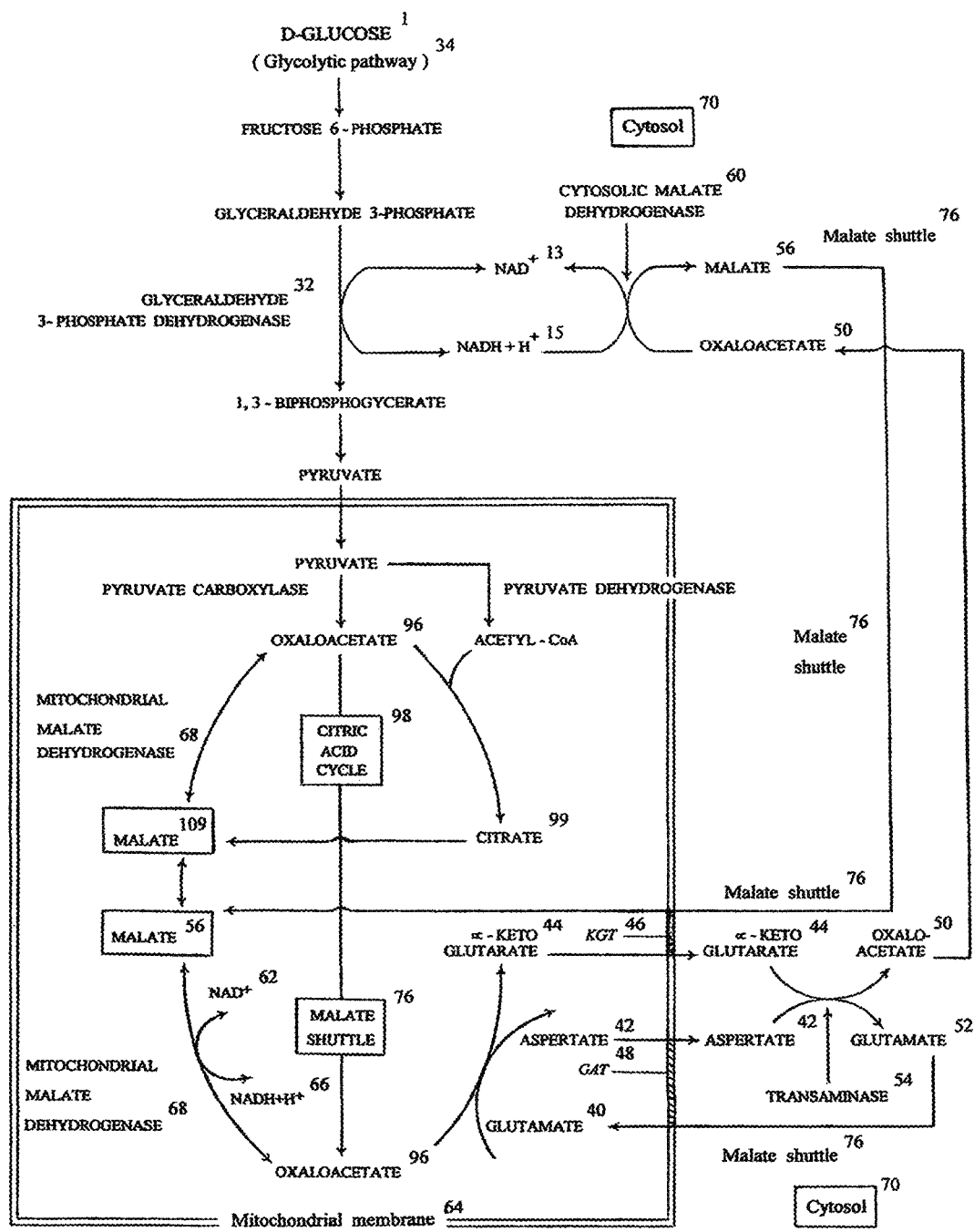
FIG. 3A: A schematic illustration of the biochemical steps of the Malate Shuttle—depicted as an ongoing operation between glycolysis and the citric-acid cycle, as a means of transferring the cytosolic reducing equivalents (the 2 $H^+$) into the mitochondria.

The Steps of Glycolysis are as Follows—
 1. D-Glucose (1), to start with, is phosphorylated to glucose 6-phosphate (2), an irreversible reaction, catalyzed by hexokinase (glucokinase), using ATP in the presence of $Mg^{2+}$.
 2. Glucose 6-phosphate (2) is reversibly converted to fructose 6-phosphate (3), the reaction catalyzed by phosphohexose isomerarse.
 3. Fructose 6-phosphate (3) is further irreversibly phosphorylated to fructose 1, 6-biphosphate (4) through an enzyme catalysis involving phosphofructokinase, in the presence of $Mg^{2+}$, also utilizing one molecule of ATP.
 4. Fructose 1, 6-biphosphate (4) (a 6-carbon moiety) is cleaved by aldolase into two triose phosphates (3-carbon moieties)—the glyceraldehyde 3-phosphate (5), and the dihydroxy acetone phosphate (6). This is also a reversible reaction.
 5. Glyceraldehyde 3-phosphate (5) and dihydroxyacetone phosphate (6) are inter-convertible by the enzyme action of phosphotriose isomerase. The inter-conversion is also reversible. However, only glyceraldehyde 3-phosphate (5) can continue further into the next step of glycolysis. The other isomeric form, the dihydroxyacetone phosphate (6) is the important intermediate of glycolysis that forms the link to the pathway of lipogenesis (7) via formation of glycerol 3-phosphate (8), one molecules of which incorporates 3 molecules of free fatty acids (FFA) (9) in the formation of one molecule of triglyceride (TGD) (11).
 6. Glyceraldehyde 3-phosphate (5) is reversibly oxidized to 1,3-biphosphoglycerate (16) by the enzyme glyceraldehyde 3-phosphate dehydrogenase, a reaction that is dependent on $NAD^+$ (13) (the nicotinic acid adenine dinucleotide). In this reaction, the $NAD^+$ (13) is reduced to $NADH+H^+$ (15) (the nicotinic acid adenine dinucleotide with hydrogen ion). This reaction is significant, as the $NADH+H^+$ (15) formed in the reaction in turn transfers the reducing equivalents (the 2 $H^+$) to the mitochondria (via the malate shuttle, shown in FIG. 3, described later) for the oxidative phosphorylation

(33) in the respiratory chain. Two of NADH+H⁺ (15) are produced during this reaction, as all the reactions are duplicated due to two trioses formed during step-4 above, and both separately continued through the further steps of glycolysis, in the form of glyceraldehyde 3-phosphate (5). Whereas the right side of the reaction shows the pathway to oxidative phosphorylation (33) and/or lipogenesis (7), the left side of the reaction shows the alternate pathway of anaerobic glycolysis (111) (involving lactate dehydrogenase, 103) (FIG. 2) prevailing in hypoxic/anoxic conditions, when citric acid cycle is not materialized, as will be explained later.

7. The 1,3-biphosphoglycerate (16) transfers a high energy phosphate group (~$\textcircled{P}$)) onto ADP (the adenosine diphosphate) to form ATP, while itself is converted to 3-phosphoglycerate (19). This substrate level phosphorylation, which is reversible, is catalyzed by phosphoglycerate kinase in the presence of $Mg^{2+}$. As two molecules of triose phosphates are formed in step-4, two molecules of ATP are also generated at this step per single molecule of glucose.

8. The 3-Phosphoglycerate (19) is isomerized to 2-phosphoglycerate (23) by the enzyme phosphoglycerate mutase.

9. The 2-phosphoglycerate (23) is involved in a dehydration reaction catalyzed by enolase to form phosphoenolpyruvate (25), in the presence of $Mg^{2+}$.

10. Phosphoenolpyruvate (25) then transfers a high energy phosphate group onto ADP to generate ATP, while itself is transformed to (enol) pyruvate (27). This is also a substrate level phosphorylation catalyzed by the enzyme pyruvate kinase in the presence of $Mg^{2+}$. It has to be noted that 2 ATP are also produced during this substrate level phosphorylation from one molecule of glucose. This reaction is irreversible.

11. (Enol) pyruvate (27) by a spontaneous nonenzymatic isomerization is irreversibly converted to (keto) pyruvate (29), or simply called pyruvate (29), the end product of glycolysis under all aerobic conditions.

Evidently, 2 molecules of pyruvate (29) are produced from 1 molecule of glucose (1) at the end of glycolysis in the cytosol, both to enter citric acid cycle (98) under aerobic conditions.

The formulae of the intermediates in the pathway of glycolysis (or of any pathway herein discussed) can be found in any standard text book of biochemistry, as this writing aims at simplification of presentation to the targeted readers. Harper's Illustrated Biochemistry is best recommended for such purpose, to interested readers.

The Formation of Acetyl-CoA from Pyruvate—

The pyruvate formed in the cytosol is transported into the mitochondrion. In the inner mitochondrial membrane, the pyruvate is oxidatively decorboxylated to acetyl-CoA (acetyl Co-enzyme A) (97) by a multi-enzyme complex, the 'pyruvate dehydrogenase complex'. One molecule of $CO_2$ is also generated in this step. This reaction is irreversible, and requires the presence of thiamine (the vitamin $B_1$), FAD (the flavin adenine dinucleotide, or the flavoprotein), NAD⁺, and lipoamide. It is clinically relevant to note that in states of thiamine deficiency pyruvate accumulates causing pyruvic acidosis, with the symptoms of beri-beri. The requirement of thiamine is proportional to the carbohydrate intake. In this reaction, NAD⁺ is reduced to NADH+H⁺, which in turn transfers reducing equivalents (2 H⁺ or protons) to the 'respiratory chain' under aerobic conditions, producing 6 ATP from 2 pyruvate molecules derived from 1 molecule of glucose. The formation of acetyl-CoA (97) and $CO_2$, from the oxidation of pyruvate (29) within the mitochondria, and the acetyl-CoA (97) so generated entering the citric acid cycle (98) are also illustrated in the FIG. 2.

The Krebs Citric Acid Cycle

Figure 4:
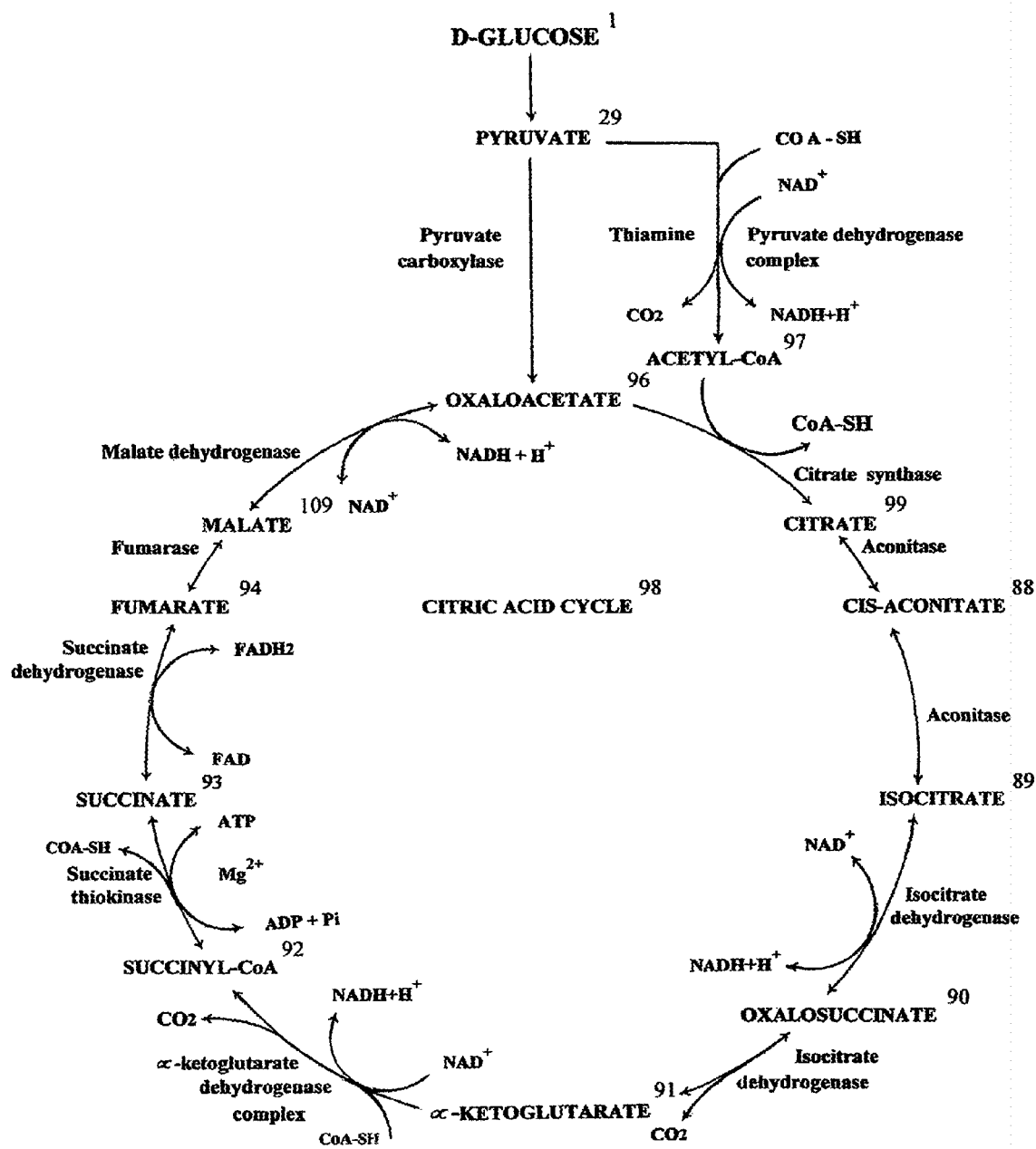
FIG. 4: A schematic biochemical illustration of the citric acid cycle—that is the ultimate aerobic pathway of the D-glucose catabolism showing the generation of the reducing equivalents (4 $NADH+H^+$ and 1 $FADH_2$), the generation of one substrate level ATP, and the generation of 3 carbon dioxide ($CO_2$) molecules, via combustion of a single molecule of pyruvate. The figure also illustrates the formation of acetyl-CoA and oxaloacetate (both originating from pyruvate) that enter the citric acid cycle as the parent molecules, however the oxaloacetate regenerating at each turn of the cycle, whereas acetyl-CoA is added at each turn.
Figure 5A:
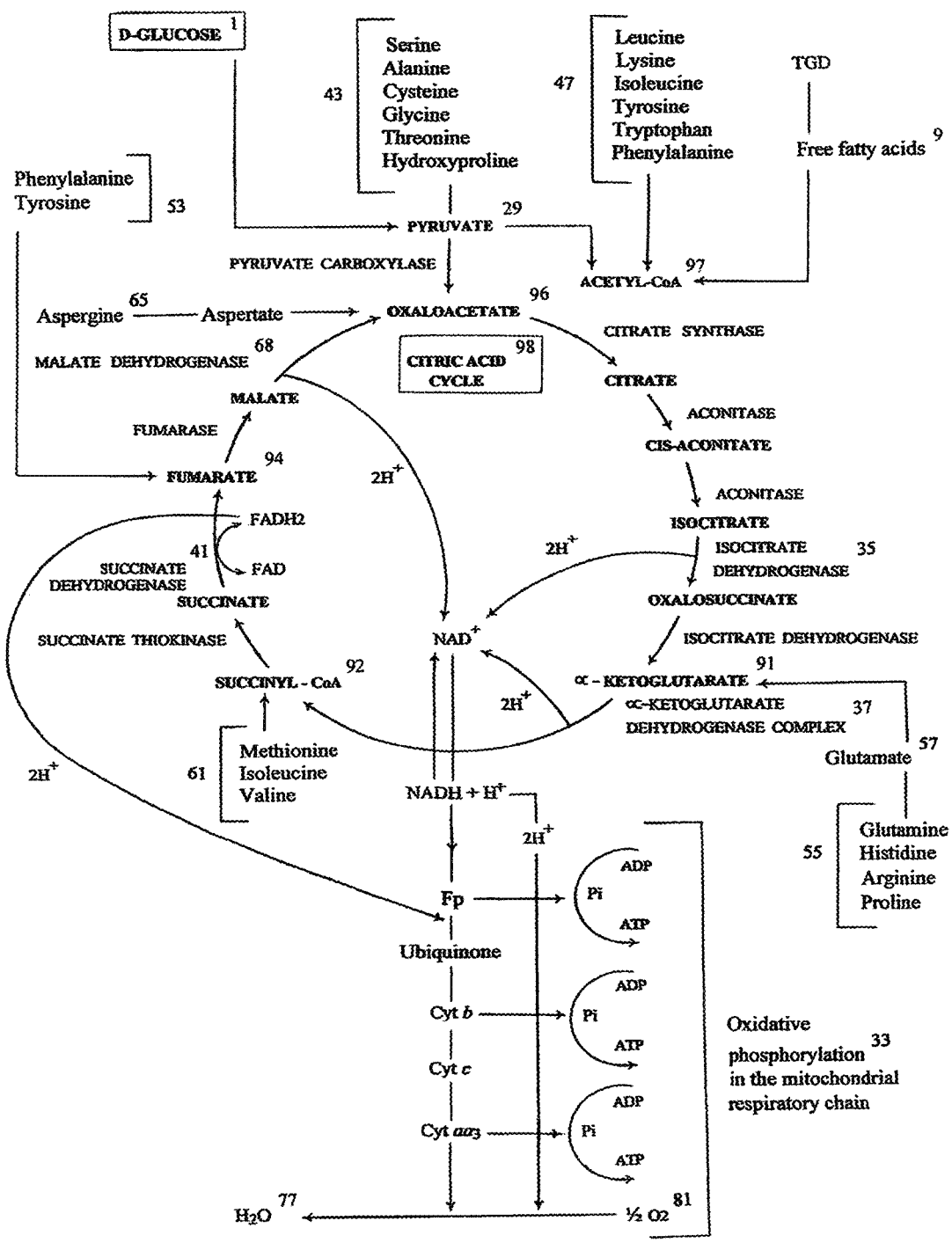
FIG. 5A: A schematic illustration of the biochemical pathway of the mitochondrial oxidative phosphorylation—depicting the ultimate merging of the carbohydrate, protein, and of the lipid metabolic pathways into the citric acid cycle, and the transfer of the citric acid cycle generated reducing equivalents, the 2 $H^+$ (the protons) to the mitochondrial respiratory chain, so synthesizing ATP, via the coupling of oxidation and phosphorylation.

The Krebs citric acid cycle (98) or the tricarboxylic acid cycle (FIG. 4) is the final common path way for the catabolic aerobic oxidation of all major food stuffs, the carbohydrates, the proteins, and the lipids that are metabolized to either acetyl-CoA (97), or to the other intermediates of the citric acid cycle (98), to be channeled into this life sustaining, ATP generating final cyclic maneuver, the substrate for oxidative phosphorylation, via the 'respiratory chain' (FIG. 5A). The enzymes of the citric acid cycle (98) are located in the inner mitochondrial membrane where the enzymes of the respiratory chain are also found. The intermediates of citric acid cycle (98) also play a vital anabolic role in lipogenesis (described in the following pages), gluconeogenesis, amino acid synthesis/inter-conversion via α-ketoglutarate (91), and also in the synthesis of other specialized products like heme from succinyl-CoA (92) of the citric acid cycle (98).

The Krebs Citric Acid Cycle is Described as Below—

1. Acetyl-CoA (97) formed from pyruvate (29) interacts with oxaloacetate (96) also derived from pyruvate (29) (by the enzymatic action of pyruvate carboxylase), to form a tricarboxylate, the citrate (99). This reaction is irreversible and is materialized by the enzyme citrate synthase. Only a small quantity of oxaloacetate (96) is needed for the oxidation of large quantity of acetyl-CoA (97). It is for the reason that in this cyclic pathway, oxaloacetate (96) is regenerated during each turn of the cycle, whereas the acetyl-CoA (97) needs to be continuously supplied from pyruvate (29), generated as the end product of glycolysis.

Figure 2:
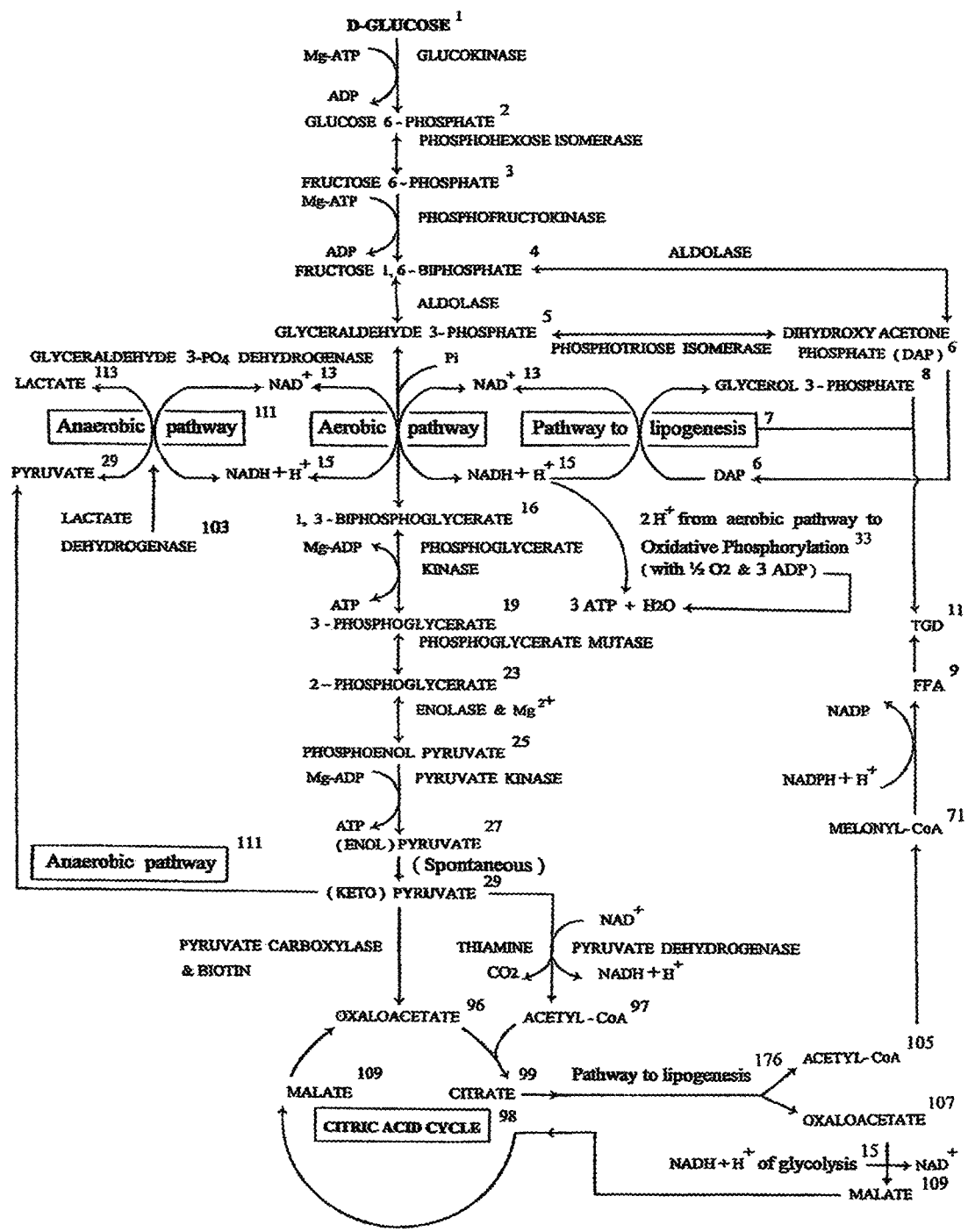
FIG. 2: A schematic illustration of glycolysis, and its links to related biochemical pathways of lipogenesis. It depicts
   The aerobic glycolytic pathway of the D-glucose metabolism (shown as the main pathway leading into the citric acid cycle).
   The anaerobic glycolytic pathway of the D-glucose metabolism (shown as a pathway depicted in the left half of the illustration).
   The conjunctional role of glycolysis-citric acid cycle in fetal lipogenesis (shown as the pathways depicted in the right half of the illustration).
Figure 6:
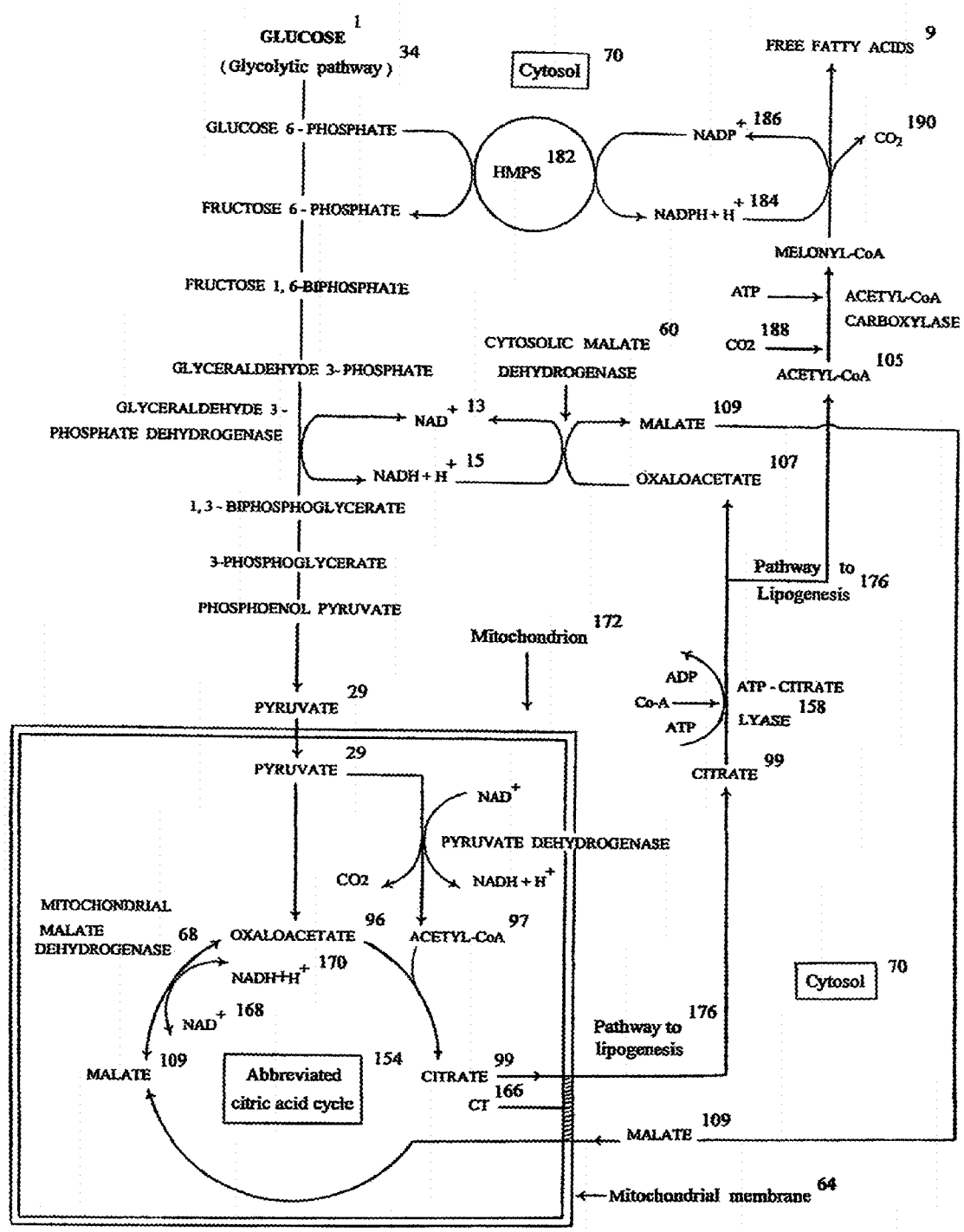
FIG. 6: A schematic illustration of the biochemical pathways of 'Lipogenesis via Glycolysis and Abbreviated Citric acid Cycle' in the fetal tissues.

2. Citrate (99) is isomerized first to cis-aconitate (88) and then to isocitrate (89) by the enzyme aconitase. Citrate (99) is one of the two intermediates of citric acid cycle (98) that can freely get out of the mitochondria, so as to form the anabolic link to extra mitochondrial fatty acid (FFA) (9) synthesis (FIG. 2 and FIG. 6). In the cytosol (70) of the tissues specializing lipogenesis (176), citrate (99) reforms oxaloacetate (107) and acetyl-CoA (105), the latter being the integral building block in the free fatty acid (FFA) (9) synthesis.

3. Isocitrate (89) is dehydrogenated by isocitrate dehydrogenase to form oxalosuccinate (90), and during this process the NAD⁺ is reduced to NADH+H⁺. The oxalosuccinate (90) remains enzyme bound, but subsequently is decarboxylated to α-ketoglutarate (91) in the presence of $Mg^{2+}$ or $Mn^{2+}$ ions, and during this process one molecule of $CO_2$ is also produced. 1 NADH+H⁺ produced during the reaction generates 3 ATP via the respiratory chain.

4. α-ketoglutarate (91) is decarboxylated by a multienzyme complex, the α-ketoglutarate dehydrogenase complex resulting in the formation of succinyl-CoA (92). This enzyme complex is similar to pyruvate dehydrogenase complex that oxidizes (keto) pyruvate (29) to acetyl-CoA (97). Hence in this reaction similar co-factors like thiamine, lipoate, FAD, NAD⁺ and CoA are required. One molecule of $CO_2$ is similarly liberated in this reaction. 1 NADH+H⁺ produced generates 3 ATP.

5. Succinyl-CoA (92) is converted into succinate (93), in the presence of $Mg^{2+}$ through the enzymatic action of succinate thiokinase (succinate synthase). ADP is converted into ATP during this reaction, a single example of substrate level phosphorylation in the citric acid cycle.

6. Succinate (93) by a dehydrogenation process forms fumarate (94) by the enzyme succinate dehydrogenase. FAD is bound to the enzyme and is reduced to $FADH_2$ (the reduced form of flavin adenine dinucleotide) which directly transfers reducing equivalents to ubiquinone of the respiratory chain to reform FAD. It can be noted at this point that only 2 ATP are produced during this step by the flavoprotein.

7. Fumarate (94) by condensation with water forms malate (109), catalyzed by the enzyme fumarase or fumarate hydratase.

8. Malate (109) is converted in this last step of the citric acid cycle (98) to one of the parent compounds, the oxaloacetate (96), by malate dehydrogenase in a $NAD^+$ dependent reaction that also generates $NADH+H^+$. 3 ATP are produced during this step. This reaction is significant through its involvement in malate shuttle (FIG. 3A), wherein as mentioned before, the reducing equivalents ($H^+$) from the continuous extra-mitochondrial formation of $NADH+H^+$ (via glycolysis) are transported into the mitochondria as malate (109). It is for the reason that the mitochondria, the sole substrate for the oxidative phosphorylation (33) (FIG. 5A) are impermeable to cytosolic $NADH+H^+$.

It can be noted that during combustion of 1 molecule of D-glucose (1), a total of 6 $CO_2$ molecules are liberated: (a) 2 $CO_2$, during the formation of 2 acetyl-CoA (97) molecules from 2 pyruvate (29) molecules, and (b) 4 $CO_2$, from the steps of citric acid cycle (98) (also involving 2 cycles).

The Generation of High Energy Phosphate by Oxidative Phosphorylation Via the Respiratory Chain—

The outlines of the scheme of oxidative phosphorylation are illustrated in the FIG. 5A. To understand this process of biologic oxidation that yields high energy ATP in all living cells, it is essential to understand/define the biochemical processes of 'oxidation' and 'reduction'.

Oxidation is the addition of oxygen to, or removal of hydrogen from an element or compound. Essentially, it is removal of electrons. Reduction is the addition of hydrogen to or removal of oxygen from an element or compound. Essentially, it is gain of electrons. Accordingly, many reactions of biologic oxidation can take place via dehydrogenation (through dehydrogenase enzyme complexes that cannot use oxygen as a hydrogen acceptor) even without the participation of molecular oxygen.

In the aerobic organisms, during the oxidative phosphorylation (33) that takes place inside the respiratory chain of the mitochondria, the oxidation is tightly coupled to phosphorylation (Mayes P A) to generate the high energy intermediate, the ATP. Most of such energy to be liberated during the oxidation (the catabolism) of carbohydrates, proteins, and of fats is made available within the 'respiratory chain' of the mitochondrial matrix as reducing equivalents (2 $H^+$ of $NADH+H^+$ or $FADH_2$) that are collected and are transported for their final interaction with molecular oxygen (½ $O_2$) (81) to form water ($H_2O$) (77). The respiratory chain contains a number of redox carriers, arranged in sequence as—the $NAD^+$ linked dehydrogenase, the flavoprotein, the ubiquinone, and the 'cytochromes' that are cytochrome b (cyt b), cyrochrome $c_1$ (cyt $c_1$), cytochrome c (cyt c), and cytochrome $aa_3$ (cyt $aa_3$), arranged in that order. Each of the respiratory chain complexes acts as a 'proton pump'. According to Mitchell's chemiosmotic theory, through the process of oxidation in the respiratory chain, energy is derived that is used for the translocation of protons ($H^+$) to the exterior of mitochondrial inner membrane. The mitochondrial membrane being generally impermeable to ions, especially protons, their accumulation outside the mitochondrial inner membrane creates an electrochemical potential difference across the membrane that is used to drive the ATP synthase to form ATP during the availability of ADP and Pi (the inorganic phosphate or the $PO_4^-$). ATP synthase is located in the adjacent inner mitochondrial membrane.

The inner mitochondrial transporter system also has phosphate transporter (that allows the transport of inorganic phosphate that passes readily as $H_2PO_4^-$ ion) that exists in combination with adenine nucleotide (the ADP and ATP) transporter. In the so called process of 'oxidative phosphorylation' (33) the molecular oxygen (81) derived from the respiration of the organism in fact makes no structural contribution to ATP, and actually forms $H_2O$ (77) (in the final chemical reaction of 'oxidation' within the respiratory chain, combining with 2 $H^+$ of $NADH+H^+$ or $FADH_2$. The phosphate group added to ADP is wholly derived from $H_2PO_4^-$ (the dihydrogen phosphate ion, entering the inner mitochondrial membrane through its transporter). It is shown in a schematic form in FIG. 5B (A schematic chemical reaction showing the mitochondrial oxidative phosphorylation).

The merging into the Krebs citric acid cycle (98), of proteins (amino acids) (of groups 43, 47, 53, 55, 61, and 65) and lipids (the free fatty acids) (9) into the Krebs citric acid cycle (98) as acetyl-CoA (97), or as the citric acid cycle (98) intermediates for their final catabolic disposal to generate substantial amounts of ATP, is also shown in the FIG. 5A. The amino acids of—group 43 produce pyruvate (29); group 47 produce acetyl-CoA (97); group 53 produce fumarate (94); group 55 produce glutamate (57) and then α-ketoglutarate (91); group 61 produce succinyl-Co-A (92). Aspergine (65) produces oxaloacetate (96). In the respiratory chain, as mentioned in the foregoing, the oxidative phosphorylation (33) of $NADH+H^+$ generated in the reactions catalyzed by isocitrate dehydrogenase (35), α-ketoglutarate dehydrogenase complex (37), and malate dehydrogenase (39) produces 3 ATP, whereas the flavoprotein (the $FADH_2$) generated in the reaction catalyzed by succinate dehydrogenase (41) produces only 2 ATP. When either 1$NADH+H^+$ or 1 $FADH_2$ participates in the oxidative phosphorylation (33), ½ $O_2$ (81) is utilized to interact with the reducing equivalents (the 2$H^+$) to form water ($H_2O$) (77), and also 3 or 2 ATP respectively.

A total of 6 $O_2$ is required to completely oxidize 1 molecule of D-glucose to produce 38 ATP, as can be observed in the Table-1, The Generation of ATP via D-glucose Catabolism, shown in FIG. 13. This factual knowledge is important in understanding the 'best economics' of glucose as the fetal fuel to generate ATP, and the frugality of this hexose sugar is never found during the catabolic use of proteins or of lipids, in terms of oxygen expended during similar gain of ATP for the fetus deemed to thrive in relatively hypoxic states in utero. The rather complicated process of oxidative phosphorylation is only briefly outlined here, the in-depth enumeration of which is beyond the scope of this discussion, but can be found in any standard text book of biochemistry.

Anaerobiosis and Lactic Acidosis—

Under anaerobic conditions (111), the end product of glycolysis is lactate (113) that is derived from pyruvate (29). The scheme of anaerobiosis or anaerobic glycolysis (111) is also shown in FIG. 2 on the left side of the reaction catalyzed by glyceraldehyde 3-phosphate dehydrogenase. The reaction involving anaerobic glycolysis (111) is catalyzed by lactate dehydrogenase, when the NADH+H$^+$ (15) is oxidized to NAD$^+$ (13) during the process, while pyruvate (29) itself is reduced to lactate (113). As pyruvate (29) is not the end product, the citric acid cycle (98) is not effectuated in the anaerobic conditions (111).

However, glycolysis can be continued even during hypoxic/anoxic states, but with the continued availability of glucose (1), when NADH+H$^+$ (15) generated in step-6 of glycolysis (described in an earlier section), is used to reduce pyruvate (29) to lactate (113) (FIG. 2), and the NAD$^+$ (13) so generated in the step involving lactate dehydrogenase can be further used for the step-6 of glycolysis to proceed, so that only 2 ATP are generated from 1 molecule of D- from being used in the mitochondrial oxidative phosphorylation (33) of the respiratory chain (shown on the right side of the step catalyzed by glyceraldehyde 3-phosphate glucose (1) at the substrate level, the 2 NADH+H$^+$ (15) of step-6 of glycolysis, precluded dehydrogenase) to otherwise produce an additional 6 ATP (3 ATP from 1 NADH+H$^+$). With the availability of glucose (1), though the anaerobic glycolysis can be continued indefinitely in hypoxic conditions, it has the adverse effects of causing fetal lactic academia, only rescued by oxygen.

The Malate Shuttle—

The Malate shuttle (76) (illustrated in FIG. 3A, part of it shown as the bottom half of the ovoid maneuver) is very important to understand the many facets of carbohydrate metabolism, as essentially, the benefits of aerobic glycolysis cannot be reaped without this ongoing maneuver. The NADH+H$^+$ (15) is continuously formed from NAD$^+$ (13) in the cytosol (70).

through the reaction involving glyceraldehyde 3-phosphate dehydrogenase (32) of glycolysis (the glycolytic pathway) (34). However, the mitochondrial membrane (64) is impermeable to NADH+H$^+$ (15), and for the needed oxidative phosphorylation of the reducing equivalents, their transfer through the mitochondrial membrane (64) requires substrate pairs on each side of the membrane barrier, and is achieved via the glycerophosphate shuttle, or the malate shuttle (76). The latter being more prevalent, and being more pertinent to the present discussion for the needed comprehension also of a very important subject matter of lipogenesis (involved in rapid fetal brain neurogenesis) to be discussed in the subsequent sections, it needs elaboration for its precise understanding.

Figure 3B:
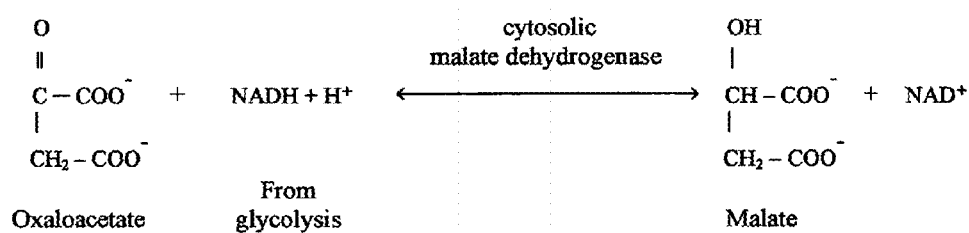
FIG. 3B: The biochemical reaction depicting generation of malate from oxaloacetate in the cell cytosol.

1. Essentially in this shuttle (76), oxaloacetate (96) of citric acid cycle (98) (shown in the FIG. 3A, as the upper half of the ovoid maneuver) gets out of the mitochondria and comes in as malate (56), and hence the originator of the shuttle is oxaloacetate (96) that needs to be transported out from the mitochondria. The complexity of the shuttle (76) is due to the fact that oxaloacetate (96) can not penetrate the mitochondrial membrane (64). It must react with glutamate (40) that is transaminated by the mitochondrial transaminase to aspartate (42), while itself is changed to α-ketoglutarate (44) in the process, that can easily penetrate the mitochondrial barrier. It can be noted that α-ketoglutarate (44) and citrate (99) are the only two intermediates of citric acid cycle (98) that can get out into the cytosol (70) through the mitochondrial barrier, whereas malate (56) can come in, in exchange with either, however involving separate and specific transporter for each.
2. The α-ketoglutarate (44) is transported out through mitochondrial membrane (64) via the ketoglutarate transporter (KGT) (46) (the KGT can be noted in FIG. 3A as a rectangular solid area within the mitochondrial membrane, 64), whereas the aspartate (42) is transported out through the glutamate/aspartate transporter (GAT) (48) (the GAT can be noted in FIG. 3A as a hatched rectangular area within the mitochondrial membrane, 64).
3. Within the cytosol (70) further interaction between the two i.e the α-ketoglutarate (44) and aspartate (42) reconstitutes oxaloacetate (50) and glutamate (52), in a reaction involving the cytosolic transaminase (54).
4. The regenerated oxaloacetate (50) in the cytosol (70) interacts with NADH+H$^+$ (15) that is continuously generated via glycolysis (34) to produce malate (56) and NAD$^+$ (13), the reaction being catalyzed by the cytosolic isoenzyme, the malate dehydrogenase (60). The reaction is shown in FIG. 3B.
5. The malate (56) can pass into the mitochondrion, via the ketoglutarate transporter (KGT) (46) in exchange with more of α-ketoglutarate (44) coming out of the mitochondrion, for the shuttle to be on-going.
6. The glutamate (52) reenters the mitochondrion through glutamate/aspartate transporter (GAT) (48) so as to continue the shuttle.
7. Within the mitochondrion the malate (56) interacts with NAD$^+$ (62) to regenerate oxaloacetate (96) and NADH+H$^+$ (66) (that forms 3 ATP), catalyzed by mitochondrial malate dehydrogenase (68) in the usual manner as in the last step of the citric acid cycle, however, the 'reducing equivalents' (of NADH+H$^+$) (66) evidently are transferred from the cytosol (70) in the form of malate (56) through the shuttle (76), and hence the credit of 3 ATP acquired is normally accounted to glycolysis (34), and it is obviously in addition to the 3 ATP gained through malate (109) formed also through full revolution of the citric acid cycle (98). As normally the malate (56) of malate shuttle (76) merges into the citric acid cycle (98), and can be imperceptible from malate (109) formed as the end product of the full revolution of the citric acid cycle (98) itself, both the products (56, 109) are shown connected through a bidirectional arrow (FIG. 3A) through which the malate of either pathway is implied to terminate into a common mitochondrial malate pool.

The central arrow of the ovoid maneuver originating from oxaloacetate (96) passing through citric acid cycle (98) to enter malate shuttle (76), though seemingly happening outside citric acid cycle (98), this part of malate shuttle (76) can be noted only as part of citric acid cycle (98).

It can be noted that the steps of forming α-ketoglutarate (44') from oxaloacetate (96) via malate shuttle (96) are very different from the steps involved for the formation of the same via the citric acid cycle (98) (see FIG. 4).

The Hexose Monophosphate Shunt (HMP Shunt) or the Pentose Phosphate Pathway—

The pentose phosphate path way or the HMP shunt is a specialized route of glucose metabolism, as it mainly has anabolic significance, and accordingly does not generate ATP. It has the following two major synthetic functions—
1. Formation of NADPH+H$^+$ (the phosphorylated form of nicotinic acid adenine dinucleotide and the hydrogen ions) from NADP$^+$ (the phosphorylated form of nicotinic acid adenine dinucleotide), the NADPH+H$^+$ deemed to be participating as a hydrogen donor during the synthesis of free fatty acids (FFA), and the steroids.
2. Formation of D-riboses, the pentose sugars vital for the synthesis of nucleotides, and the nucleic acids, the DNA and the RNA (deoxyribonucleic acid and the ribonucleic acid).

The pentose phosphate pathway or the HMP shunt (HMPS) is a more complex path way than glycolysis. 3 molecules of glucose give rise to 3 molecules of ribose sugars, and it can be noted also that 3 molecules of $CO_2$ are produced in this process. The $NADP^+$ (the phosphorylated form of nicotinic acid adenine dinucleotide) is used in the path way as the hydrogen acceptor. The process is extra-mitochondrial and is more active in tissues predominantly engaged in the synthesis of free fatty acids, and of steroids. No oxygen is used in the pentose phosphate path way, as obviously the reducing equivalents (the $2H^+$) acquired by the coenzyme $NADP^+$ via the path way are meant to be used for the anabolic syntheses of free fatty acids, steroids etc.

The Physiological Significance of Lipids and Proteins—

The significance of glucose as the predominant fetal fuel for the reasons of its high ATP yield, and accordingly as the chosen fetal nutritional supplement in the treatment modalities of this invention can be best appreciated only in the light of the discussion of the lipid and of the protein metabolic path ways within the fetal body, the latter path way most surprisingly expending oxygen/ATP in a rather extravagant manner even before its end products gaining some similar number of ATP as the other merging metabolic end products, via the ultimate steps of the landmark meeting point, the citric acid cycle. This knowledge, acquired in the light of the biochemical and mathematical equations/evaluations is needed for an understanding that is reliable and objective.

The Lipid Metabolism

LIPIDS in their simple form are heterogeneous group of compounds that are essentially ESTERS of fatty acids with various alcohols, the fatty acid straight chain in natural form existing either as a saturated or unsaturated aliphatic carboxylic acid.

The lipids comprise the major constituents of human diet, and are significant for their high energy value per unit volume/weight, and accordingly, are efficient energy storehouses of the body. The lipids comprise the following major classes (the knowledge of which is deemed essential in understanding a later landmark discussion of a surprisingly enormous oxygen gain during rapid neuronal lipogenesis of normal fetal brain vs. the fetal brain in IUGR with faltered lipogenesis, being deprived of the building blocks, the D-glucose)—

Simple lipids,
Complex lipids,
Precursor or derived lipids, and
Neutral lipids.

1: Simple lipids—these are esters of saturated or unsaturated fatty acids with various alcohols (ex—glycerol, sphigosine). The acetic acid, palmitic acid, stearic acid etc. are the examples of saturated fatty acids, whereas linoleic, linolenic, arachidonic, and ω3 hexaenoic acids are examples of unsaturated fatty acids. Palmitic acid, and ω3 hexaenoic acids (that ultimately form complex phospholipids in the brain starting from chain elongation of palmitic acid) are synthesized in humans, whereas the linoleic, linolenic, and the arachidonic acids are essential fatty acids that are to be primarily acquired from food, either as plant or animal derived sources.

2. Complex lipids—these are esters of fatty acids and alcohol, also containing additional groups like a phosphoric acid residue, a carbohydrate, or a protein, as in the following groups—
   a. Phospholipids—are lipids containing an ESTER of fatty acid and alcohol, and additionally, a phosphoric acid residue.
   b. Glycolipids—are lipids also containing an ESTER of fatty acid and alcohol, and instead of a phosphoric acid residue, they contain a carbohydrate (galactose, or less often glucose).
   c. Other complex lipids—examples are aminolipids, lipoproteins, and sulfur containing sulfolipids.

3. Precursors or derived lipids—the precursor lipids include fatty acids, glycerol, and other alcohols (the precursors of lipids, as the name imply). The derived lipids include steroids, hormones, lipid soluble vitamins, fatty aldehydes, and ketone bodies.

4. Neutral lipids—these are so named as they are uncharged, and exemplify acylglycerols (the mono-, di-, or tri-glycerides), cholesterol, and the cholesterol esters.

The Biosynthesis of Free Fatty Acids (FFA)

This discussion is important as the lipogenesis is an integral part of the developing brain (and the thermoregulatory subcutaneous adipose tissue), and it is critical to know how best this vital organ can be spared from growth restriction by obviating the need for otherwise excessive amount of molecular oxygen. As the 16 carbon atom fatty acid, the palmitic acid is the predominantly synthesized fatty acid in the fetus (that can be further elongated to a fatty acid with 24 carbon atoms chain in certain tissues, as in the brain), it is chosen as the prototype example for the present discussion of fetal fatty acid biosynthesis.

It was noted in the foregoing discussion of the carbohydrate metabolism (under subsection-2 of the citric acid cycle) that acetyl-CoA is an intermediate that is formed from pyruvate after its entry into the mitochondria, and that it is the building block of the fatty acids. The lipid anabolic process starts at the outset as the glucose catabolic process (the glycolysis) that expends $O_2$, and also generates ATP in that process.

It has to be noted that though acetyl-CoA, the building block of the free fatty acids is generated within the mitochondria from pyruvate, the synthesis of palmitic acid (and all fatty acids) is extra-mitochondrial (cytosolic).

The Biosynthesis of the Free Fatty Acids (FFA), with Palmitic Acid Chosen as the Prototype for Discussion, is as Below—

1. Acetyl-CoA (97), the building block of free fatty acids (FFA) (9) (FIGS. 2 and 6) formed in the mitochondria can not penetrate the mitochondrial barrier to enter the cytosol (70) (the site of FFA synthesis), and hence has to form citrate (99) via the citric acid cycle (98), and the citrate (99) so generated can get out into the cytosol (in exchange with malate, 109), through the mitochondrially located citrate transporter (CT) (166).

2. Citrate (99), in its pathway to lipogenesis (176) within the cytosol (70), is cleaved to acetyl-CoA (105) and oxaloacetate (107), (FIG. 2 and FIG. 6), a step that uses ATP, and is catalyzed by ATP citrate lyase (FIG. 6).

3. Acetyl-CoA (105) in the cytosol (70) is carboxylated to melonyl-CoA (71) in the presence of ATP by acetyl-CoA carboxylase. This reaction requires $HCO_3^-$ as the source of $CO_2$ (188) (188) (FIG. 6), biotin, a B-complex factor, and manganese. The involved reaction-3 is shown in FIG. 23A.

4. Melonyl-CoA (71) condenses with one more acetyl unit, when $CO_2$ (190) (added in the previous step) is liberated (in FIG. 6, after the formation of melonyl-CoA, the overall process is shown in a single step, unelaborated). As this reaction takes place while the reacting molecules are still attached to the surface of an enzyme complex, the fatty acid synthase multienzyme complex (E), it is depicted as such in the exemplified reaction. The involved reaction-4 is shown in FIG. 23A.

5. Reduction of β-keto group of aceto acetyl enzyme (3-keto acyl enzyme) by 2 NADPH+H⁺ catalyzed by 3-keto acyl reductase, gives rise to an enzyme bound 4-carbon acyl enzyme or 4 carbon butyryl enzyme which is a saturated enzyme bound fatty acid (butyric acid is the third member of the fatty acid series, containing 4 carbon atoms). The involved reaction-5 is shown in FIG. 23A.

NADPH+H⁺ is readily available as the by-product of IMP shunt that is cytosolic also. HMP shunt (HMPS) is highly active in most of the fetal tissues, including the placenta, due to the function through the shunt, of production of ribose sugars (needed for the DNA and RNA, essential for fetal/placental cell replication). The carbohydrate oxidative reactions of HMPS reduces NADP⁺ to NADPH+H⁺ that is the main source of hydrogen required for the reductive synthesis of fatty acids, as in case of palmitic acid, a total of 28 H⁺ ions are added through its biosynthesis, via the NADPH+H⁺.

6. In a reaction similar to reaction 4 above, another melonyl unit is added to the carboxyl end of the 4 carbon butyryl enzyme to generate a 6 carbon 3-ketoacyl enzyme that is still enzyme bound. One molecule of $CO_2$ is also liberated in the process in a similar manner. The involved reaction-6 is shown in FIG. 23B.

The product of the reaction can be named as 3-keto caproyl enzyme (caproic acid is the fifth member of fatty acid series containing 6 carbon units).

7. The new 6 carbon 3-keto acyl enzyme or 3-keto capryol enzyme is then reduced to the corresponding 6 carbon saturated fatty acid, the 6 carbon acyl enzyme or caproyl enzyme, by 2 NADPH+H⁺ through the enzyme 3-ketoacyl reductase in a reaction similar to reaction 5 above (also involving similarly named enzyme), and the involved reaction-7 is shown in FIG. 23B.

8. In the next step there will be again addition of melonyl unit to elongate the 6 carbon acyl enzyme to 8 carbon 3-keto acyl enzyme. Such repetitive and alternating additions of melonyl enzyme and then the 2 H⁺ of NADPH+H⁺ to first produce a 3-keto acyl enzyme, and then a corresponding saturated fatty acid enzyme respectively, result in the production of 16 carbon Palmitic acid through chain elongation by 2-carbon addition, followed by 2 H⁺ addition each time. The fatty acid (the palmitic acid) so formed is still enzyme bound, but splits off at the end, as free 16 carbon palmitic acid: $CH_3-(CH_2)_{14}-COOH$. The sequence can be stated as: the addition of 2 carbon units by melonyl-CoA to the carboxyl end of the fatty acid chain with formation also of a 3 keto group, followed by reduction of the 3 keto group with 2 H⁺ of 2 NADPH+H⁺.

The summated equation of the biosynthesis of palmitic acid from acetyl-CoA and the melonyl-CoA as reaction-8 is shown in FIG. 23B.

It can be understood that a total of 8 acetyl-CoA units, or 4 glucose molecules are required in the biosynthesis of 1 molecule of palmitic acid, consuming a total of 15 ATP in the process (during cleavage of 8 citrate molecules, and formation of 7 melonyl-CoA units).

Coming back to reactions 1 and 2 of palmitic acid (FFA, 9) synthesis, it was stated that in its process of lipogenesis (176) through melonyl-CoA (71) pathway, the citrate (99) gets out of mitochondria into the cytosol (70) (FIG. 6), and within the cytosol (70), it is cleaved to acetyl-CoA (105) and oxaloacetate (107) (FIG. 2 and FIG. 6). The oxaloacetate (107) generated in the cytosol reacts with NADH+H⁺ (15) (that is continually produced through glycolysis) to form malate (109) which gets into the mitochondria in exchange with more of citrate (99) coming out, for the further continuation of free fatty acid (9) synthesis/lipogenesis. NADH+H⁺ (15) oxidized to NAD⁺ (13) is further used in the glycolytic process (FIG. 6).

FIG. 2 also shows the pathway of lipogenesis (7) involved in triglyceride (TGD) (11) formation from glycerol 3-phosphate (8), derived from the dihydroxyacetone phosphate (6) of glycolysis, by the incorporation of (3 molecules of) free fatty acids (FFA) (9).

The β-Oxidation of Lipids—

Fatty acid catabolism by oxidation, otherwise called as β-oxidation, like the citric acid cycle, is mitochondrial, and utilizes NAD⁺ and FAD as coenzymes, and aerobically generates ATP via the mitochondrial respiratory chain. Compared to D-glucose oxidation via glycolysis, fatty acid oxidation is a more oxygen consuming process, in terms of similar ATP gain. The end products of β-oxidation of fatty acids are multiple units of acetyl-CoA, destined to enter citric acid cycle to be subsequently catabolized in a similar manner as the acetyl-CoA molecule derived from glucose itself (or from any other source that merges into the cycle). Just as the β carbon unit (3 carbon unit from the carboxyl end) of the growing fatty acid chain was reduced during fatty acid synthesis as described in the foregoing section, the β carbon unit of the fatty acid chain is oxidized in successive steps during this process, to cleave an acetyl-CoA unit each time. The fatty acids by their high yield of acetyl CoA, are enormous sources of energy compared to similar unit volume or weight of protein or carbohydrate, as virtually fatty acid synthesis is a 'desiccative process' (of the parent glucose molecule) that eliminates water as shown in reactions 5 and 7 of its synthesis from the water-rich carbohydrate precursors. Make note of the addition of 1 molecule of water (that was earlier lost in the synthesis) in reaction-3 below, as each molecule of acetyl CoA is cleaved. The β-oxidation of palmitic acid, the chosen prototype of the group, is described in the following discussion.

1. The fatty acid in the cytosol is first activated to an active fatty acid or acyl-CoA (or the palmityl-CoA) by acyl-CoA synthetase located in the outer mitochondrial membrane—a reaction that requires ATP, which is reduced to AMP and PPi.

2. Within the mitochondrial matrix two carbon units at a time are cleaved from the acyl-CoA molecule, starting at the carboxyl end. In the following reactions the compact formula of the 16 carbon unit palmitic acid, $CH_3-(CH_2)_{14}-COOH$ is shown as:

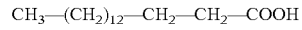

$$CH_3-(CH_2)_{12}-CH_2-CH_2-COOH$$

with two of its $CH_2$ groups shown as discrete α and β carbon groups, to high-light the reactions involving these groups.

3. The first step within the mitochondria is the oxidative removal of two hydrogen atoms from the 2 (α) and 3 (β) carbon units of the acyl-CoA through the enzymatic action of acyl-CoA dehydrogenase in the presence of the coenzymes FAD (that is reduced to $FADH_2$), and NAD⁺ (that is reduced to NADH+H⁺), with also an addition of 1 molecule of water. The oxidative phosphorylation of $FADH_2$ via the respiratory chain yields 2 ATP, whereas that of NADH+H⁺ yields 3 ATP (with a total gain of 5 ATP), each reduced co-enzyme using ½ $O_2$ (and a total of 1$O_2$) in the process. The reaction cleaves 1 molecule of acetyl-CoA from the fatty acid chain.

It has to be noted that in the concerned reactions 3 and 4 shown in FIG. 24, it is the highlighted (in bold print) third or the β-carbon unit of the 16 carbon acyl-CoA that is oxidized by the oxygen of the water molecule (the β-oxidation) in a series of steps. To start with, the α and β groups that are the 2 and 3 carbon units ($CH_2$—$CH_2$) respectively, are oxidized to CH=CH by FAD. Then in a reaction involving $H_2O$, $NAD^+$ and CoA-SH, they are transformed to CO—$CH_3$ following which the 1 and 2 carbon units of the fatty acid chain (the 1 carbon unit remaining as carboxyl carbon CO, but the second α-carbon unit $CH_2$ has been changed earlier to $CH_3$) are cleaved to form acetyl-CoA, while the β-carbon will be forming the carboxyl carbon CO of the new fatty acid chain. The $FADH_2$ and $NADH+H^+$ are formed at the end of these reactions. The summated overall reaction-3 is shown in FIG. 24.

4. The cleavage of the subsequent molecules of acetyl-CoA from the remaining 14 carbon unit fatty acid chain (the acyl-CoA) can be shown as in the equation of the reaction-4. In this equation, the compact formula of the 14 carbon atom acyl-CoA of reaction-3 is again shown with 2 of its $CH_2$ groups as discrete α and β groups, to clarify the chemical action involved in these groups. The oxidative process involving the α- and the β-carbon units (the 2 and 3 carbon units) are similar, as is summated for the overall reaction-3. The involved overall process as reaction-4 is shown in FIG. 24.

In the reaction-4, one more molecule of water is consumed, and the β carbon unit of the fatty acid becomes the carboxyl carbon unit of the new acid, containing 12 carbon units, while the second molecule of acetyl-CoA is cleaved. Repetition of the sequence results in the cleavage of the whole fatty acid chain into units of acetyl-CoA. In the case of palmitic acid, the sequence is repeated 7 times, to yield 8 molecules of acetyl-CoA, and 35 ATP (7×5), with the consumption of 7 $O_2$ and 2 high energy phosphates, the latter used for the initial activation of fatty acid. There is a net result of 33 ATP during the complete catabolic β-oxidation of palmitic acid to 8 units of acetyl-CoA.

Why Less Oxygen is Needed when Carbohydrates are Metabolized—

It had been discussed that during glycolysis-citric acid cycle, when 1 molecule of D-glucose is metabolized, 6 $O_2$ are used, and also 6 $CO_2$ are produced. It makes the RQ (the respiratory quotient) of D-glucose/carbohydrates as 1. RQ is the ratio of the number of $CO_2$ molecules produced, and the number of $O_2$ molecules consumed ($CO_2/O_2$) during a metabolic process in an unit time. When fats are metabolized the RQ falls to 0.7. It is because of the fact that in the carbohydrate molecule there is enough oxygen present to oxidize the hydrogen present within the molecule to produce water ($H_2O$), and hence oxygen from extrinsic sources is needed only to oxidize the carbon (to produce $CO_2$) present within the molecule. It was earlier noted how all the carbohydrates—the trioses, tetroses, pentoses, and the hexoses contain $H^+$ and $O_2$ in the same ratio as that of the water molecule (it is high-lighted in the compact formula of glucose below).

When fat is combusted the oxygen present within is not sufficient so that extrinsic oxygen is needed to oxidize both its hydrogen and carbon atoms (Chatterjee C C).

The RQ is exemplified below as in the metabolic break down of glucose, the prototype carbohydrate, and tristearin (a triglyceride composed of 1 molecule of glycerol, and 3 of stearic acid) taken as the prototype lipid.

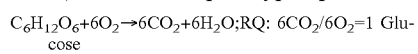
$C_6H_{12}O_6 + 6O_2 \rightarrow 6CO_2 + 6H_2O$; RQ: $6CO_2/6O_2 = 1$ Glucose

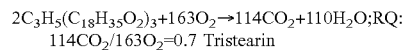
$2C_3H_5(C_{18}H_{35}O_2)_3 + 163O_2 \rightarrow 114CO_2 + 110H_2O$; RQ: $114CO_2/163O_2 = 0.7$ Tristearin As can be seen in the above equations, 6 molecules of $O_2$ are used in the combustion of glucose to produce 6 $CO_2$, and the 6 $H_2O$ molecules liberated were already present within the glucose molecule as high-lighted, whereas for the combustion of 2 molecules of tristearin, 163 molecule of $O_2$ are required to oxidize 220 $H^+$ to produce 110 $H_2O$, and also to oxidize 114 carbon atoms to produce 114 $CO_2$, as the $O_2$ present within the 2 tristearin molecules are only 6.

The Keto Acidosis—

The above discussion of fatty acid beta oxidation clarifies that when fats are utilized as the source of energy, the acetyl-CoA are generated in enormous numbers. They are destined to merge into citric acid cycle for their further catabolic disposal. In times of diminished glucose availability as in IUGR, due to lack of sufficient amounts of oxaloacetate, that has to be derived from glucose, acetyl-CoA can not merge into citric acid cycle. Its further fate is to form ketone bodies—the acetoacetic acid, beta hydroxybutyric acid, and acetone. These are strong acids that are responsible for ketoacidosis. Their disposal is an oxygen consuming path way that further saturates fetal oxidative machinery.

Additionally, the fetal hypoglycemic states with proportional hypo-insulinemia, the fat depots are mobilized by the unopposed hormonal lypolytic effects (insulin being anti-lipolytic), with resultant formation of acetyl-CoA in enormous amounts, fated for ketoacidosis. By fat utilization via beta oxidation, not only 33% of excess oxygen is used, but also more is required, to dispose of ketone bodies, and alleviate the acidosis. There is sufficient evidence in the literature to indicate that in the healthy fetus of normoglycemic status, all the lipid components crossing the placenta are used for anabolic purposes and invariable bodily functions, and rarely for catabolic purposes.

The Protein Metabolism

PROTEINS are complex and generally high molecular weight organic compounds made of AMINO ACIDS that are distinguished by the presence of an amine group (—$NH_2$), a carboxylic acid group (—COOH), and an aliphatic or aromatic side chain of variable structure specific to each of the amino acid, the amino acids being aggregated into long chains by peptide linkages that in turn are bound by hydrogen bonds, electrostatic forces, and salt bridges, as well as by many others.

The so called nutritionally essential amino acids (10 in number) must be only derived from the diet, and the rest, the non-essential amino acids (also 10 in number), by virtue of their short biosynthetic pathways, can be synthesized within the body. Despite the nomenclature, all twenty two of the 'proteinogenic' amino acids are essential for optimal health, in all stages through life. Though glucose is considered as universal fetal fuel, there is uncompromised need for all amino acids throughout the intrauterine life—not only as the structural elements of the muscle bulk of the developing fetus, but also as the integral micro-components that range from enzymes, hormones, and neurotransmitters to nucleic acids that make up the essential architecture of DNA and RNA.

Proteins/amino acids, unlike D-glucose, are extravagant members in terms of expending oxygen or ATP throughout their metabolic processes, including processes involved in disposal of some of their end products. Indeed their oxygen or ATP requirements are even more than their above discussed lipid counterparts, and their use as energy source as in IUGR is undoubtedly coupled with enormous ATP/oxygen wastage. Proteins are the unique members that generate major excretory products—the ammonia, uric acid, $CO_2$, and the creatinine that all need immediate and ongoing disposal, whereas $CO_2$ is the only excretory product culminating from the breakdown of the carbohydrates and of the fats. For the disposal of the toxic by-product of protein break down i.e. the ammonia ($NH_3^+$, derived from the amino group), significant energy needs to be expended for the synthesis in the liver, of relatively non-toxic urea, from the ammonium radical and the $CO_2$.

The metabolic energy yielding end products of protein break-down comprise of pyruvate, oxaloacetate, or acetyl-CoA, or else the intermediates of the path way of citric acid cycle (the succinyl-CoA, α-ketoglutarate etc.), wherein they merge for their ultimate catabolic disposal, to produce ATP via the respiratory chain. The discussion of urea synthesis is essential to understand the needs of ATP in this cyclic maneuver of ammonia excretion, invariable due to amino acid utilization of whatever nature, within the fetal body.

Figure 25:
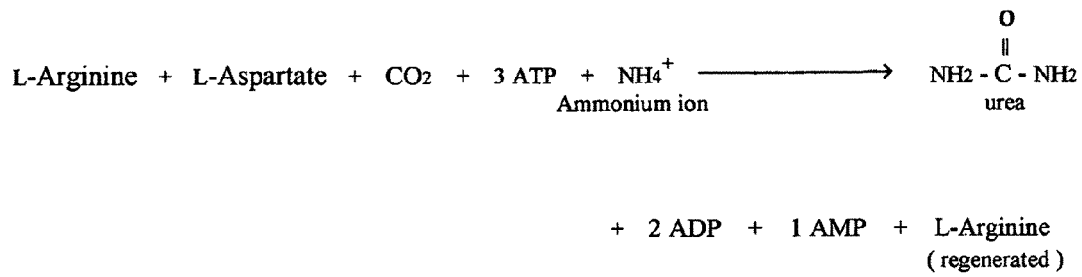
FIG. 25: showing A simplified depiction of urea synthesis, schematically shown.

Urea Synthesis— the urea cycle starts with L-Arginine that combines with water, to cleave 2 of its amino groups as urea ($NH_2$—CO—$NH_2$), while also forming ornithine that combines with carbomyl phosphate (that is formed by 1 molecule of $CO_2$ and 1 ammonium ion, in the presence of 2 ATP, the latter forming 2 ADP, using 2~$\textcircled{P}$), to form citrulline. One more molecule of ATP is again consumed to be liberated as AMP and $PP_1$ (also using 2~$\textcircled{P}$) in a reaction wherein citrulline proceeds, with also an integral participation of the amino group of L-aspertate to form fumarate, also regenerating L-arginine in the process. Fumarate regenerates L-aspertate to continue the urea cycle in conjunction with the regenerated L-arginine. In this process, an equivalent of 4 high energy phosphates (4~$\textcircled{P}$) are used for the disposal of 2 amino groups of each molecule of urea, and hence it can be deduced that 2 high energy phosphates 2~$\textcircled{P}$) are used for the disposal of 1 amino group (metabolized to 1 molecule of ammonia) of any amino acid. A simplified reaction of urea synthesis is schematically shown in FIG. 25.

The Metabolic End Products of Amino Acids Enter the Citric Acid Cycle with ATP Debt; However, the Metabolic Processes are Vital Fetal Requirements, as Discussed Below—

The above mentioned ATP debt is similar to oxygen debt the muscle incurs after intense activity. It is intended to express that in an IUGR fetus, the supposedly energy/ATP yielding major food group, the 'protein', in its catabolic break down and via its by-products (through ammonia, during its non-toxic disposal) expends significant amount of oxygen and/or ATP with a net loss of ATP, before any of it can be produced later on, in the citric acid cycle. Net loss is the term herein used to denote ATP spent for other than energy-yielding or anabolic purposes or pathways, or oxygen spent in unusual amounts. Such net loss incurred, as exemplified through the maneuvers of some of the amino acids, is summarized below—

1. Histidine—it is metabolized to α-ketoglutarate (that ultimately merges citric acid cycle). No ATP is produced via production of $NADH+H^+$ during its catabolic break down, yet 2 molecules of ammonia are produced in the process that expend 4 ATP, to be incorporated into urea. Hence, there is a net loss of 4 ATP. Nevertheless, this essential amino acid, as its metabolite N-Formiminoglutamate (Figlu) is vital for its role in folate metabolism, and the need of folic acid is invariable for normal fetal development.

2. Tryptophan—this is the only amino acid that utilizes three of molecular oxygen (3 $O_2$) during its metabolism, and generates acetyl-CoA, with no production of ATP in the process. Due to the presence of 2 amino groups, 4 ATP are lost in urea production. As each $O_2$ is equivalent to/produces 6 ATP via respiratory chain, for a hypoxic fetus there is a theoretical net loss of 22 ATP during its metabolism. However, tryptophan is an essential amino acid, and its metabolite, the 3-hydroxy-anthranilic acid is required for the synthesis of nicotinic acid (the niacin) and of the nicotinamide, the latter being the source in the body for $NAD^+$, the universal coenzyme (cofactor) required in all metabolic path ways. Ironically, the most needed of amino acid is also the most expensive to the fetus. However, nature has devised that the ubiquitous coenzyme $NAD^+$ to be completely recyclable during its most vital function of oxidative phosphorylation. It can be surmised that this amino acid is used by the normal fetus for vital metabolic/synthetic purposes, and never for exclusive energy yielding purposes.

3. Arginine—it is an amino acid containing more than two amino groups. Two are disposed of as urea, exceptionally without use of energy, yet the other two will need 4 ATP to be expended for their ultimate disposal as urea. However, the role of arginine is significant—as insulin secretogogue; in urea synthesis; in the production of nitric oxide (responsible for fetoplacental vasorelaxation, trophoblastic invasion, and for placental vasculogenesis) whose half-life is only 3-4 seconds, and needs to be continuously produced in the body for its specified vital functions during pregnancy or otherwise.

4. With threonine, there is net loss of 3 ATP. With methionine there is a net loss of 4 ATP, however, it is vital that it generates choline, needed for the synthesis of acetylcholine, lecithin and sphingomyelin. Lysine, aspergine, Glutamine—with 2 amino groups, there is 4 ATP loss with each.

Rest of the amino acids have to invariably expend at least 2 high energy phosphates in a similar manner consequent to their catabolic break down, outside the citric acid cycle (unless the $NH_4^+$ is used for synthesis of non-essential amino acids in an IUGR fetus) and no amino acid escapes such fate (except arginine, disposing off two amino groups initially, without expending ATP, as above specified), though some form different intermediate amino acids that have to yet ultimately undergo deamination to form ammonia, and then urea, by using 2 high energy phosphates. If all the ATP losses (including 22 of them for tryptophan) are combined for all twenty of the 'proteinogenic' amino acids, they amount to a total loss of 73 ATP for the group as a whole, with an average loss of 3.65 ATP for each of the amino acid in situations that the fetus uses its muscle mass for energy yielding purposes, with a net gain of few ATP only via citric acid cycle.

In an optimally growing fetus the ammonium ion ($NH_4^+$) and the glutamine (derived from ammonia in tissues) are used for the synthesis of non-essential amino acids, thus maintaining positive nitrogen balance (unlike an adult whose nitrogen intake matches nitrogen excretion) essential for growth. In IUGR, the fetal body protein is used for dire energy needs with net gain of only few ATP. The normal AF urea content is 2.8 mmol/L at 16 weeks and 3.8 mmol/L at 34-36 weeks, with increase to term, which is 3 times lower in concentration than its content in the fetal urine itself. The non-essential amino acids are in turn synthesized from other amino acids and the carbohydrate intermediates, and hence can be a suboptimal process in the IUGR fetus that is obviously forced to the verge of negative nitrogen balance. The energy expending urea synthesis may be impaired in IUGR with consequent oliguria, urea being a powerful osmotic diuretic. It is also questionable if an IUGR fetus can maintain an optimal blood ammonia level. A need of ATP requiring waste disposal is not encountered in glucose/fatty acid catabolic combustion.

The Standard Food Energy Comparisons—

Conventional standardization of food energy for the sake of comparing nutritive values of foods takes into account only the kcal of energy they produce per unit mass. The carbohydrates and proteins are considered to produce the same amount of energy, and the fats double that energy. It has to be noted that these comparisons are made in terms of unit mass. Carbohydrates available in nature are packed with substantial water content per unit mass, their $H^+$ and $O_2$ content configured in the same ratio as that of water molecule (as 2:1). On the contrary, the fats are desiccated during their biosynthesis from the parent carbohydrates (review biosynthesis of palmitic acid wherein during steps 5 and 7, a water molecule is lost). Accordingly, one may not be misguided by such comparisons (meant for adults/ex-utero food energy standards) while appraising the fetal energy economics, as discussed in the following—

1. The economics of oxygen is highly critical—The value of different classes of fetal fuels has to be determined with great discretion, due to the fact that it has to be measured in terms of calories of energy or ATP generated per unit amount of oxygen expended, as the economics of oxygen is strictly accountable due to the relative hypoxia that the fetus has to survive in-utero. Ex-utero, the expenditure of oxygen is not critical, with the unrestricted supply of oxygen inherent to such milieu, except in disease states where there is supply-demand mismatch of oxygen.

2. The standard food energy comparison also does not take into account the ATP expended (vs. ATP generated) by any food group—In other words, the net ATP available for energy expenditure after the metabolic consequences of any food source, is disregarded.

Accordingly, the adult standards of food energy comparisons are irrelevant to apply to fetal nutrition and growth. The proteins that are otherwise considered as equivalent to carbohydrates, and fats considered as superior yielding double in terms of the energy/nutritive value, indeed drastically fall short of such exalted expectations while the fetal energy requirements in the uterine habitat are critically appraised, as is befitting to such eco-system.

The Oxygen Consumption Vs. ATP Yield/Loss During Glycolysis, β-Oxidation, and During Catabolic Protein Break-Down—

The consumption of $O_2$ and the corresponding yield/loss of ATP during β oxidation of palmitic acid can be compared to glycolysis (when 4 glucose molecules are spent), equalized for similar yield of 8 acetyl-CoA. It can also be compared to protein catabolic break-down—in this instance, 8 amino acids can be equalized (to represent the class of proteins), as they can produce 8-acetyl-CoA units or equivalents, before entering citric acid cycle. The yield or loss of ATP with each of the food group can be shown as below—

Oxidation of 4 molecules of D-glucose—8 acetyl-CoA-8 $O_2$-+56 ATP

Beta oxidation of palmitic acid—8 acetyl-CoA-7 $O_2$-+33 ATP

Catabolic processes of 8 amino acids—8 acetyl-CoA- none--29.2 ATP

As per the above, via glycolysis, 1 $O_2$ produces 7 ATP, whereas via beta oxidation only 4.7 ATP are produced. That is, via glycolysis, the 7 ATP generated consuming 1 $O_2$, are generating 2.3 more ATP compared to beta oxidation, when similar amount of oxygen is expended. It is significant that per 100 ATP so produced, the glycolytic pathway of D-glucose is generating 32.85 more ATP, or the ATP yield via glycolysis is 32.85% more, compared to beta oxidation. Evidently, 32.85% ($\frac{1}{3}^{rd}$ of requirements) is also the equivalent amount of $O_2$ salvage, or reduced oxygen requirement via the glycolytic path way of D-glucose. It will be noted that no oxygen is expended, but proteins as a class lose an average of 3.65 ATP per amino acid as a metabolic consequence, and hence a total loss of 29.2 ATP, with 8 of the protein (amino acid) by-products entering citric acid cycle with similar ATP debt, even before they can gain ATP (12-15 per amino acid) in the cycle.

A healthy fetus maintains a positive nitrogen balance. However, urea being a major constituent of the amniotic fluid, significant urea formation in the fetus is deemed invariable, and so also the ATP loss, though much lower in a healthy fetus than the absolute theoretical calculation as above. Starting as the size of a single cell ovum or a fertilized egg, and attaining in-utero of the size of a full term fetus of 3.5 kg or more in 280 days, nothing in nature and in health, can surpass the growth potential of the developing fetus. For such unsurpassed growth, Oxygen is as valuable a fetal currency as the food sources it consumes in a relatively hypoxic uterine habitat. With 32.85% excess of energy (ATP) provisions (or 32.85% of reduced $O_2$ expenditure, compared to the 'most superior lipids' of the food group) in terms of food energy yield vs. oxygen spent, glucose is but the most fitting fuel of the fetus during its in-utero stay through ten lunar months.

The IUGR-Diet with Vitamins and Other Essential Nutrients—

It can be stated that the passage of all the essential nutrients through the placenta are impaired in placental insufficiency. Thiamine and the other B-complex factors would not be an exception, and they are better supplied through oral supplements rather than transamniotic. Such deficits can be primarily due to placental impedance, and secondarily due to hypoglycemia and impaired D-glucose derived-ATP mediated active transport, necessary for their passage into the fetal compartment, as will be extensively discussed in later sections. Thiamine is essential in its catabolic role of conversion of pyruvate to acetyl-CoA. If the fetus is deficient in it, substantially increasing glucose loads can be over-whelming to the fetus, and can cause pyruvic acidosis, and all the path ways where glucose and pyruvate are needed come to a halt. Additionally, pyruvic acidosis in the mother due to pre-existing thiamine deficiency exaggerated after glucose load, with beri-beri like symptoms can cause acute/chronic maternal heart failure. Accordingly, planned supplementation of thiamine (initially as 100 mg IM/IV before any glucose supplements, and oral tablets later) is essential to all patients, as mal-nutritional state for whatever reason (vomiting, alcoholism, food pica, or a suboptimal nutrition and suboptimal use of prenatal care in developing countries) can be common, and is under-diagnosed in this subset of patients. 100 mg of thiamine supplements would increase the levels of thiamine presented at the inter-villous space, thus ensuring adequate amounts reaching fetal circulation (by achieved $V_{max}$ of substrate transfer mediated by the cell membrane transporters/carriers, as discussed earlier, and this can be applicable to all the supplements). Only small amounts of thiamine are stored in the body (25-30 mg), and its daily need increases as the carbohydrate intake increases.

In the adults, unlike other vitamins, daily/short term thiamine requirements are calculated based on concomitant carbohydrate intake. The hypothesis of relative thiamine deficiency of the mother or of the fetus in the face of impeding glucose load may not be practically found in all growth restricted fetuses, but as there is no easy way of knowing, additional supplements at least would not harm.

Niacin or nicotinic acid, from which NAD and NADP are synthesized, and riboflavin from which FAD is produced in the body, are also essential for optimal carbohydrate metabolism. So also, the folic acid and the phosphate supplements (see the role of phosphate in the section of 'oxidative phosphorylation') are essential. It was discussed under the section of protein metabolism, how the fetus has to expend significant ATP (being 22), during the catabolic break down of one molecule of tryptophan, if 1 NAD/NADP were to be synthesized from this amino acid in the fetal body, and many such have to be synthesized, as the requirement of this coenzyme is a mandate to every cell, metabolizing or replicating.

For patients with fetal IUGR on IV D-glucose supplements, with or without also of transamniotic supplements, it is therapeutic to advise a diet mostly of carbohydrates, both simple and complex, for the immediate and for the sustained release of hexose sugars, and the proteins and fats as per pregnancy requirements, but rich in essential amino acids, essential fatty acids, vitamins, and minerals—called the IUGR diet. The idea is based on the advantage of mostly carbohydrate utilization by the fetus, and likely fat anabolism in the fetal body (a process very essential for developing brain), and no fat or protein catabolism for energy requirements through excesses of extrinsic supplies (FFA and amino acids coming across the placenta are best laid down to make up the body bulk of the fetus). The above, by no means imply that the so called non-essential amino acids or non-essential fatty acids are not essential to the fetal growth and maturity. Maternal supply of these are equally important, as per the normal pregnancy requirements, as even the normal fetus may not adequately biosynthesize them. Snacks similar to IUGR diet are advisable between meals and during mid-night. Due to pregnancy pica, and the specific dietary requirements, it is imperative that these patients have a consult with a dietician, and also with a diabetic endocrinologist until they are stabilized.

Along with the diet that usually contains complex carbohydrates, to also ensure intake of simple, rapidly absorbable hexose sugars (as specified in the above IUGR diet), 25 grams of D-glucose powder in water, taken by mouth few minutes before each meal and breakfast, and along with each snack, should be a mandate, incorporated into the maternal dietary protocol for the treatment of fetal IUGR both at home, and in the hospital. At least 1 egg with each meal including breakfast is strongly advised, as this simple and the least expensive diet is a reference protein against which all proteins are measured for their quality and for the completeness of essential and of highly useful amino acids. Based on moderate prevalence of vegetarians by ethnicity/religion or habit, it can be easily accepted by any patient type. The essential amino acid arginine is an insulin secretagogue, whose action can be preserved even when glucose stimulated insulin secretion is impaired (Powers A C). Arginine is also essential for nitric oxide synthesis needed for—fetal vascular, umbilical luminal, and placental sinusoidal relaxation. Marine Fish can also be included in the diet. Fish oils were proved to increase birth weight in a study of natural birth weight in Faroe islands (compared to that in Denmark where fish is the staple diet (Olsen et al, 1986). The principal marine fish oil is ω3 eicosa pentanoic acid that competes with the arachidonic acid as a substrate for the cyclooxygenase enzyme, to produce prostacycline rather than thromboxane $A_2$ ($DxA_2$) (Leaf A et al, 1988). Prostacyclin is the nature's potent vasodilator, with probable action at the placental level.

The Accompanying Problems of Placental Insufficiency—their Causes, Normal Fetal and Pregnancy Adaptation, and Possible Relief by Induced Fetal and Placental Normoglycemia by Transvenous or Transamniotic D-Glucose Supplements Along with the IUGR Diet It is a legitimate concern that the isolated treatment of impaired placental glucose transfer by therapeutically induced transient episodic hyperglycemic state in the mother can not correct the other problems of feto-maternal exchange, inherent to the placental insufficiency, and all these problems not modifiable and operating together would be still detrimental to the fetal well-being. It is also a critical concern that adequate glucose availability in hypoxic conditions can lead to anaerobiosis and lactic acidosis. The seemingly legitimate concerns as the foregoing, in the face of therapeutically induced normoglycemic status of the fetus, need in depth biochemical exploration. It is the ultimate aim of this writing to detail the intricacies and prove, also by valid scientific data, that the maternal hypertonic D-glucose supplements can indeed correct the other problems of placental insufficiency also to a moderate extent, so that a healthy fetus with acceptable in-utero weight gain can be anticipated. There are few not well known yet superb benefits of restoring the optimal glycemic status at the feto-placental level that are also enumerated under this section, along with the discussion of the much feared and notorious metabolic problems of placental insufficiency that were well documented in the medical literature, but so far not clinically or theoretically (a critically and a rationally woven thought can be the forerunner of an equally rational clinical solution) alleviated, to the satisfaction of a critical or an inquiring reader. They are listed below, and later discussed in that order, in the following sections.

1. Improved fetal hypoxia (a demand/supply mismatch of oxygen at tissue level, having immediate or delayed adverse consequences).

2. Improved fetal hypercapnea (above normal blood $CO_2$ that can have adverse effects), if any.

3. Improved fetal oliguria (suboptimal urine production) and oligohydromnios (suboptimal amniotic fluid volume, corresponding to the gestational age)—with improved fetal urea production.

4. Improved fetal acidosis (excess hydrogen ion concentration in the blood lowering blood pH), including ketoacidosis.

5. Improved fetal lactic academia (excess of blood lactate, with impeding lactic acidosis) and lactic acidosis (both mainly due to anaerobic glycolysis), that need a special and separate mention apart from acidosis specified under sub-section-4 above, as unlike fetal acidosis in general, fetal lactic acidosis is only responsive to alleviation of fetal hypoxia.

6. Improved fetal hypertriglyceridemia.

7. Improved fetal acquisition of major nutrients like amino acids and fats, and also of minerals, vitamins, and trace elements.

8. Improved feto-maternal exchange—(a) by glucose, insulin, and ATP mediated placental L-arginine active transport and synthesis of nitric oxide, the latter effectuating feto-placental and umbilical vasorelaxation; (b) by glucose derived ATP mediated placental D-lysine active transport, with consequent feto-placental neo-vasculogenesis.

9. Improved rapid neuronal lipogenesis of fetal brain, with exponential glucose and oxygen salvage, primarily due to accomplished 2-citrate diversion towards the said neuronal lipogenesis, instead of 1-citrate diversion, prevailing during glucose scarcity.

10. Improved ATP production (via operating citric acid cycle, secondary to restored fetal normoglycemic status), the ultimate key as the ubiquitous need for all life forms, and for all life sustaining subcellular activities.

In the enlisted and discussed problems of placental insufficiency there are some that are naturally improved by normal fetal/pregnancy adaptations in an otherwise normal pregnancy, whereas the failed adaptations are positively altered by the therapeutically induced maternal hyperglycemia or by the transamniotic isotonic D-glucose supplements, with consequent fetal normoglycemia.

1. The Improvement of Fetal Hypoxia—

Impaired oxygen diffusion across placenta is a deleterious consequence of placental insufficiency. In the fetus there are many adaptive devices inherently developed, or else manifested in an exaggerated manner due to placental insufficiency, as is described below. If that fail, the therapeutically induced feto-placental normoglycemia can surprisingly alleviate the problem.

1. The fetus has high cardiac out-put, proportional to the normally high fetal heart rate (an average of 140/minute) showing beat to beat variation in relation to oxygen demand. The minute volume, as a multiplied product of stroke volume and the heart rate is widely variable, responding to transient or relatively prolonged hypoxic insults in-utero.
  2. The fetus has high RBC (red blood corpuscles) count, and the RBC also has high MCHC (the mean corpuscular hemoglobin concentration), both substantially increasing the fetal blood oxygen carrying capacity per unit volume, and unit time.
  3. The Bohr effect, and the Haldane effect—

In the fetus the Bohr effect, and the Haldane effect are normally facilitated in the following manner—
  (a) Secondary to maternal hyperventilation induced by progesterone, there is lowered $PCO_2$ in the maternal placental sinusoids. The low $PCO_2$ of the sinusoids to start with causes net higher diffusion of $CO_2$ (with a diffusion coefficient 20 times more than that of $O_2$) from fetal blood, thus reducing the $PCO_2$ of the fetal blood proportionally.
  (b) the fetal blood becomes more alkaline as a result of (a). The effects of (a) and (b) in the fetal blood shift the hemoglobin oxygen dissociation/association curve to the left of higher oxygen association, due to the Bohr effect that says—'the oxygen affinity towards hemoglobin is inversely proportional to the $H^+$ ion concentration, and it is also inversely proportional to the $PCO_2$.' The foregoing two changes consequent to Bohr effect in the fetus are further augmented by (c) below.
  (c) the fetal Hgb (hemoglobin) having low affinity to 2,3-DPG (2, 3-diphosphoglycerate) (the 2, 3-DPG causes stability of deoxyhemoglobin)—a property responsible for the greater affinity of oxygen to fetal hemoglobin (see also subsection-6 under this discussion containing further elaboration).

Conversely, in the maternal blood, uptake of $CO_2$ and fixed acids (like lactic acid) decreases the oxygen affinity for hemoglobin with further release of oxygen (the double Bohr effect). Additionally, in the fetal blood, binding of $O_2$ with hemoglobin releases more of $CO_2$ from the blood by the Haldane effect, thus increasing oxygen carrying capacity of fetal hemoglobin. The Haldane effect says that 'the binding of $O_2$ with hemoglobin releases more of $CO_2$ from the blood' which is indeed the reverse of Bohr effect. The Haldane effect works in the opposite way in the maternal blood, causing more of $CO_2$ pick up, and in turn also more of oxygen release.

4. Normoglycemia can compensate for relative fetal hypoxia, that is, glucose can compensate for oxygen lack—Utilization of fats for energy requirements as in β-oxidation not only in starvation but also in conditions of normal feeding accounts for about $\frac{1}{3}^{rd}$ excess of oxygen consumed (33% more) in the process, as was shown in the previous sections. With adequate D-glucose supplements, exclusive D-glucose utilization compensates for oxygen lack in the IUGR fetus, as it—(1) precludes beta oxidation of fetal fat depots, saving 33% or $\frac{1}{3}^{rd}$ of the requirements; (2) prevents fetal body muscle protein break down for energy purposes, the protein usage being far worse in ATP wastage than oxidation of free fatty acids, as was confirmed in the earlier section; (3) it may be acknowledged at this time that 400% of absolute oxygen salvage is also achieved via 2-citrate diversion into rapid fetal lipogenesis in a well-fed state, instead of 1-citrate diversion of glucose scarcity, the further details of which will be noted in section-9 of this subject.
  5. The D-glucose improving placental sinusoidal flow/oxygen delivery—The placenta structurally resembling an arteriovenous shunt decreases the maternal peripheral vascular resistance, which in turn increases maternal stroke volume, thus increasing the filling of the placental sinusoids. During pregnancy, the uterine vascular tributaries i.e. the spiral arteries, after entering placenta progressively dilate, until they form placental sinusoids with pooling of maternal blood, in which the fetal capillaries are bathed. Visually, the systemic vasculature resembles the bare 'winter trees' devoid of leaves, whereas during pregnancy, the spiral vessels ending in pools of sinusoids resemble the 'trees of spring', with bunches of leaves and flowers. Maternal peak cardiac output, which is found to be 48% higher than non-pregnant levels is maintained through the gestational period of 28-30 weeks, but subsequently falls through the rest of pregnancy to term.

It is tempting to think that the growing uterus rising from the pelvis may play a significant role in increasing the maternal peripheral vascular resistance, and the falling of cardiac out-put around 28-30 weeks. The aorta bifurcates at the level of fourth lumbar vertebra, and the inferior vena cava commences at the level of fifth lumbar vertebra, and the growing uterus reaches this height at about 28-30 weeks. Before that period, there are no pressure effects on the common iliac vessels that travel in close association with the lateral pelvic wall, untouched by the gravid uterus, thus causing the placental shunt fully manifest. The forward curvature of the lumbosacral junction (the sacral promontory) can be exaggerated by maternal lordosis generally assumed during this stage of pregnancy, further causing pressure effects. Some remedial measures, to subdue the pressure effects on the great vessels, beneficial at least to a few, are advocated in the later part of this writing.

The placental pooling due to increased maternal stroke volume, and due to the decreased peripheral vascular resistance of the placental shunt is also important for the reason that fetal heart rate is twice that of the maternal heart rate, and the placental sinusoidal oxygen and substrate reserves presented through one maternal cardiac cycle must adequately serve for sufficient oxygen/substrate exchange through two of fetal cardiac cycles, as befitting of the fetal hemoglobin avidly binding the sinusoidal oxygen reserves. The glucose, insulin, and ATP mediated L-arginine active transport through placental sinusoids and then through the vascular endothelial cells cause nitric oxide synthesis restoring fetal and umbilical vessel and placental sinusoidal relaxation—with pooling of oxygen rich maternal blood around the terminal villi, and restored flow volume and velocity in the fetal and umbilical vessels.

6. The fetal hemoglobin (Hgb) has higher affinity for oxygen—In the peripheral tissues, a relative hypoxic state in an adult causes increased accumulation of 2,3-diphosphoglycerate (the 2, 3-DPG), an unique metabolite of glycolysis in the erythrocyte. The DPG greatly stabilizes the T form or the deoxygenated form of the hemoglobin (Hgb), rather than the R form or the oxygenated form of Hgb. The 2, 3-DPG binds more wealdy to the fetal Hgb than to the adult Hgb, because the $H_{21}$ residue of the gamma chain of fetal Hgb is the amino acid serine rather than histidine (of adult Hgb), and serine can not contribute to the stability of 2, 3-DPG to be positioned in the central cavity of Hgb molecule (Rodwell V W). Hence the 2, 3-DPG has no significant effect on the stabilization of the T or the deoxygenated form of fetal Hgb, and is responsible for the fetal Hgb having higher affinity for oxygen. Thus, even during hypoxic states, the fetal Hgb binds avidly with whatever oxygen that is remaining in the placental sinusoids. In the adult, the 2, 3-diphosphoglycerate increases in the red cells during hypoxic state of the peripheral tissues that aids the oxyhemoglobin to unload more of $O_2$.

The above discussion of increased affinity of oxygen to fetal hemoglobin that augments oxygen pick up at the placental level, can also give a room for concern of how oxygen can possibly override such affinity to fetal hemoglobin, to be delivered at the fetal tissue-capillary level.

The mechanism can be as follows, and such mechanism is restored in the IUGR fetus by therapeutic D-glucose supplements. A healthy adult is on a mixed diet of major food stuffs, the carbohydrates, proteins, and the lipids, their catabolic processes generating 6 $CO_2$, 4 $CO_2$, and 4 $CO_2$ respectively, when equalized to 1 molecule of glucose (or 2 acetyl-coA), thus bringing down the average adult RQ (the ratio of $CO_2$ generated and the $O_2$ expended) to 0.85, the RQ of the carbohydrates, proteins, and the lipids being 1, 0.8, and 0.7 respectively (the RQ is only a rough parameter as it involves $O_2$ expended also, but serves the purpose overall in this context). However, in the normal fetus, as the D-glucose combustion for energy virtually replaces others, it results in an average RQ of 1, also supported by the fact that the RQ of the normal fetal tissues in vitro is 1. There is also predominant fetal lipogenesis that uses and then liberates 7 $CO_2$ (the $CO_2$ 'cycling') for each molecule of palmitic acid synthesized, coupled with ongoing pentose phosphate pathway in all fetal tissues, generating 1 $CO_2$ per 1 glucose molecule (see Table-2 of FIG. 14 showing the sources of $CO_2$ within the fetal body). There is also accumulation of lactic acid, glutamic acid, o-oxoglutaric acid, and pyruvic acid in the fetal tissues (lowering the pH). The diffusion of such fixed acids into maternal circulation was proved by experiments of Rooth & Nilsson (1964), and Stembera & Hodr (1966). The $CO_2$ and fixed acids generated in a healthy adult on a mixed diet can be taken as the optimal amount needed to normally effectuate the Bohr effect of oxygen delivery at the capillary level. Thus, the healthy fetus gains over its adult counterpart, by generating significantly more of $CO_2$, and by having a relatively lower pH at the tissue-capillary level, thereby overcoming the greater affinity of oxygen to its hemoglobin at the capillary level (the fetal venous capillary and tissue pH may not be truly reflected by the pH of the umbilical artery carrying the deoxygenated blood, wherein the arterial-venous blood is invariably admixed). The fetal skin and subcutaneous tissues having high $CO_2$ levels, due to diffusion of $CO_2$ from the amniotic fluid (wide infra), and due to ongoing adipose tissue lipogenesis, is actually to its great advantage, as it facilitates optimal oxygen delivery from the utmost skin terminals of the arterial tree. In the fetal brain, the rapid neuronal lipogenesis with $CO_2$ 'cycling' similarly facilitates the heightened Bohr effect of oxygen delivery. Combustion of fat stores and muscle mass for energy purposes in an IUGR fetus causes low absolute $CO_2$ production that impairs oxygen unloading at the capillary level (though lowered pH in an IUGR fetus can be compensating to some extent) making the unique property of the fetal hemoglobin, and any adaptive fetal polycythemia futile in this context, creating a vicious cycle of fetal tissue hypoxia, only relieved by D-glucose supplements and restoring a normoglycemic status.

It was proposed that fetal $O_2$ dissociation is accomplished because the fetus operates at the steepest part of hemoglobin-$O_2$ dissociation curve (Nicolaides et al), but it only tells what it is, but not how or why it is. As per the higher fetal hemoglobin-$O_2$ affinity as an effect of 2, 3-DPG, fetal hemoglobin-$O_2$ association and dissociation curves can not be one and the same (as in an adult), but they are. The reason is, as was discussed, the higher fetal $CO_2$ production and its higher $H^+$ ion concentration can perfectly equate to oppose and override the dictates of the 2, 3-DPG at the fetal tissue capillary level. How the fetus survives at $PO_2$ of 27 mm/Hg, whereas the adult needs ventilator support at about the $PO_2$ of 60 mm/Hg is not the issue of discussion herein.

7. Absolute oxygen salvage of 400% by the Fetal brain—the therapeutic D-glucose supplements sufficiently aid in the rapidly accomplished neuronal lipogenesis within the fetal brain by diversion of 2-citrate molecules (instead of one) derived from 1 molecule of D-glucose, into lipiogenesis, wherein 400% of absolute $O_2$ salvage and 200% of absolute glucose salvage are accomplished. This is true of any rapid lipogenesis (as also the adipose tissue) that dominates in the last trimester as in a well-fed state of the fetus that is responsible for such $O_2$ salvage. The details are discussed in section-9 of this subject.

8. Amniotic fluid (AF) oxygen supply normalized or heightened, due to improved energy and volition of fetal swallowing—the section 'Other important Source of Petal Oxygen Supply' discusses how AF is a source of substantial fetal oxygen supply.

2. The Improvement of Fetal Hypercapnia—

Impaired excretion of $CO_2$, that is, the exchange of $CO_2$ at the placental site is a reasonable concern in placental insufficiency. The fetus normally has the following adaptations for $CO_2$ disposal, that can be improved due to therapeutic maternal D-glucose supplements, in the setting of IUGR:

(1) The diffusion coefficient of $CO_2$ is 20 times higher than that of $O_2$, and its diffusion across the cell membranes including the lipid bilayer is instantaneous. The progesterone induced maternal hyperventilation with fall in maternal $CO_2$ further compliments the $CO_2$ diffusion across the placental interface. Accordingly, the $CO_2$ diffusion across the placenta can be still satisfactory, even when the oxygen diffusion is moderately impaired.

(2) The $CO_2$ sequestration during fetal lipogenesis—lipogenesis is significantly improved by restored normoglycemia within the fetus. $CO_2$ is required in the initial steps of fatty acid synthesis involving carboxylation of acetyl-CoA to melonyl CoA. In the synthesis of palmitate, 7 molecules of $CO_2$ are used, each derived from blood bicarbonate pool, all being subsequently liberated as $CO_2$, during the fatty acid synthesis. However, this cyclic engagement of $CO_2$ in fetal lipogenesis sequestrates significant amount of $CO_2$ to the area of fatty acid synthesis, relieving the placenta a substantial burden of its disposal.

(3) The carbon dioxide disposal by urea synthesis—urea synthesis by fetus increases as pregnancy advances, and significant amount of $CO_2$ is used in the process. One molecule of $CO_2$ and one molecule of ammonia are continuously added to the cyclic-maneuver of urea synthesis, consuming 4~(P), and such an energy consuming pathway can be impaired during supply-demand mismatch of ATP, and can be relieved by induced fetal normoglycemia or improved fetal hypoglycemia with proportionally improved fetal ATP synthesis, as is discussed in a later section.

(4) Low Carbon dioxide production in fetal IUGR—$CO_2$ is more of a by-product of carbohydrate metabolism. It is imperative that 1 molecule of glucose and 6 $O_2$ are expended to generate 6 molecules of $CO_2$ via glycolysis-citric acid cycle. 3 molecules are also produced through a3 molecules of D-glucose inter-conversion into pentose sugars via HMPS (hexose monophosphate shunt that needs the enzymatic action of $NADP^+$, only supplied by ongoing lipogenesis (that regenerates the $NADP^+$), for which optimal D-glucose is also essential. However, tissue replication in general (needing DNA/RNA via the shunt), and lipogenesis in particular being restricted in IUGR, $CO_2$ production by this pathway is substantially lower. Additionally, the HMPS needs D-glucose at the outset for such pentose inter-conversion. Only few amino acids produce $CO_2$ in their catabolic break-down. Fatty acid synthesis generates significant amount of $CO_2$, however, similar number is cyclically used in the synthesis. The sources of $CO_2$ production within the fetal body is summarized in Table-2 of FIG. 14 (The outlines of $CO_2$ production within the fetal body).

It is obvious that in IUGR, the $CO_2$ production is directly proportional to the food substrates (mainly D-glucose, and the lipid-protein by-products merging in citric acid cycle, said by-products also generating $CO_2$ just as the end products of glycolysis) being available, and being utilized by the fetus (also with concomitant use of molecular oxygen, as citric acid cycle, the major generator of $CO_2$ is aerobic), and the placental insufficiency imposes $CO_2$ burden that is only proportional to that of associated hypoglycemia and of hypoxia, and no more (except during oligohydromnios), this stated without giving due regard for 20 times more efficient diffusion of $CO_2$ via placental route, compared to oxygen diffusion through the same route.

(5) Carbon dioxide needed for the body's base reserve—$CO_2$ is also essential for the bicarbonate ($HCO_3^-$) reserve in the fetal body. Obviously, $CO_2$ should not be viewed as merely a product of excretion. This is not to overlook the fact that the acid base balance is ultimately based on the ratio of carbonic acid and bicarbonate, to be maintained as 1:20. Both being produced by $CO_2$, any further comments in this context can be only viewed as too simplistic, without needed elaboration.

(6) Naturally heightened Haldane effect in the fetus, further augmented by glucose supplements—fetal hemoglobin with more affinity for $O_2$, avidly binds with it in the placental sinusoids, even at low $PO_2$. As per Haldane effect, binding of $O_2$ with hemoglobin causes more of $CO_2$ release from the (fetal) blood. It works in the opposite way in the maternal blood, effectuating more of $CO_2$ pick up. The natural Haldane effect in the fetus is proportional to the naturally high fetal hemoglobin-$O_2$ affinity, being further facilitated by the following means—(a) Glucose, insulin and ATP mediated active transport, placental arginine uptake, nitric oxide synthesis (needing enzymatic action of NADPH, generated via placental HMP shunt, also involving D-Glucose precursors), and consequent placental sinusoidal dilatation—resulting in improved $O_2$ transfer to the fetal hemoglobin, (b) the glucose-ATP driven Iron active transport with improved MCHC, preserving/restoring the natural affinity of $O_2$-fetal hemoglobin.

The renewed glucose metabolism in the fetus can generate proportional amount of $CO_2$. In the glycolysis-citric acid cycle, for the aerobic combustion of 1 molecule of glucose, 6 $O_2$ molecules are used, and also 6 $CO_2$ molecules are liberated. That means, combined glucose-$O_2$ utilization always generates $CO_2$ in direct proportion. Furthermore, maternal hyperoxygenation, effectuated in this treatment protocol (discussed in the later sections), also facilitates Haldane effect at the placental level, that is, more of $O_2$ picked up by fetal hemoglobin also facilitates more of $CO_2$ to be released from it, to enter the maternal compartment. Therefore, in the face of artificially and therapeutically improved fetal oxygenation (but yet with prevailing placental insufficiency), a resultant fetal hypercapnia may not be feared, especially in view of the naturally heightened fetal Haldane effect. Haldane effect can be considered as the body's evolutionary achievement as a cause and effect phenomenon in the case of life-sustaining diffusion of vital gases, the $O_2$ vs. $CO_2$. That is, when oxygenation improves, $CO_2$ that also increases in direct proportion needs to be let out, also in the same proportion as the $O_2$ is increased.

Additional Source of Fetal Carbon Dioxide Content—

The fetus also has additional $CO_2$ source—the amniotic fluid. Amniotic fluid has significantly high $CO_2$ content. Because of its high diffusion coefficient through any tissue types, $CO_2$ diffuses easily into the amniotic fluid from the highly vascular and metabolically active myometrium (with exponentially increased cellular mitochondria, and very active citric acid cycle that generates significant amounts of $CO_2$) around the whole of amnion all through pregnancy. The fetus swallowing amniotic fluid also swallows significant amounts of $CO_2$. It is obvious that through the portal circulation the $CO_2$ enters the fetal liver, where it is utilized for urea synthesis to dispose of ammonia from the fetal blood. Fetal blood so depleted of excess $CO_2$ and also of toxic ammonia, enters the inferior vena cava and then the right atrium, from where the blood is preferentially diverted to the left atrium to enter the proximal aorta, the supplier of more oxygenated and detoxified blood to the fetal vital organs (the heart and the brain).

The above discussion makes it clear that $CO_2$ plays vital role in the fetal body, and the prevalence of hypercapnia is not to be unduly feared for the reason that the $CO_2$ production in the fetal body is actually proportional to both oxygen and carbohydrate utilization, and more importantly the $CO_2$ diffusion across the placenta is deemed to be efficient. It needs to be further stressed that glucose/oxygen deprived IUGR fetus will have proportionally decreased $CO_2$ production.

However, there are clinical situations in which the so far discussed biochemical norm can be off-set. The very high diffusion coefficient of $CO_2$ that serves the fetus well at the placental site, can also be its undoing, that in the case of oligohydromnios the amniotic cavity can be highly saturated with $CO_2$, which the fetus swallows, falling into a vicious cycle of hypercarbia (hypercapnia) and acidosis. The $CO_2$ can also diffuse into the fetal blood through the umbilical cord. The sequential elaboration of such fetal acidosis is done in the following section-3.

3. The Improvement of Fetal Oliguria, Oligohydromnios, and of the Fetal Academia—

There are instances in literature where placental insufficiency was mentioned to be associated with exponential hypercapnia and acidemia (Nicolaides et al 1989). This seems untenable as $CO_2$ production is deemed to be low in IUGR (for the reasons explained above), as the fetus is also deprived of oxygen/D-glucose, the sources of $CO_2$ via the citric acid cycle. There must be an independent mechanism responsible, because the source of $CO_2$ production/hypercapnia is evidently not the D-GLUCOSE in an IUGR fetus, and in this setting, the possible causes of such findings can be complex, and can be explained as below—

The AF normally is high in $CO_2$, which an IUGR fetus continues to swallow, but there can be impaired disposal of $CO_2$ in the fetal liver. Ammonia normally combines with $CO_2$ in the fetal liver to form urea, both being so removed from portal circulation. Synthesis of 1 molecule of urea expends 4 high energy phosphates which means significant energy is expended in making this product of excretion (see also the discussion of urea synthesis in the earlier section of 'Protein metabolism'). Deficiency of ATP from citric acid cycle due to hypoglycemia or hypoxia, can be responsible for less or no urea formation, leading to fetal oliguria, as urea is a powerful osmotic diuretic. A simplified reaction of urea synthesis is schematically shown in FIG. 25, wherein the 3 ATP resulting in 2 ADP and 1 AMP, instead of 3 ADP, will amount to expending 4~$\text{P}$.

1) Low or no urea production in the fetal liver and the fetal oliguria can lead to oligohydromnios. However, due to high diffusion coefficient of $CO_2$ (a property that makes it naturally attracted to water molecule), the diffusion of $CO_2$ from the myometrium (that is metabolically very active through pregnancy, generating $CO_2$ via citric acid cycle) into the amniotic cavity will continue, and its proportion starts to mount steeply due to lowered amniotic fluid volume. Impaired distal circulation and hence lowered renal perfusion (as also the impaired umbilical artery perfusion) in IUGR can also primarily and independently contribute to oligohydromnios, and the amniotic cavity can be virtually a small sac of carbonated water for the fetus to swallow.

2) With exceeding $CO_2$ content in the AF, even for small amount of it swallowed, the fetus will be swallowing fluid highly saturated with $CO_2$ that will be entering into the fetal blood via portal circulation, but not disposed of as urea due to impaired urea cycle, and will be invariably reflected in the umbilical artery via its transit to the placenta, where it may be disposed of. $CO_2$ can also diffuse into the umbilical cord from the AF. In the absence of urea production and progressing oligohydromnios, a vicious cycle of $CO_2$ accumulation sets up within the fetal blood.

3) Though the AF is known to contain the amino acids (for needed L-aspergine and L-arginine for urea synthesis) in a proportion similar to maternal plasma so as to enter the portal circulation after fetal swallowing, to aid ongoing hepatic urea synthesis, still sufficient amounts of D-glucose, and ongoing citric acid cycle are required for the significant amount of ATP needed for urea production. It was earlier noted that both the specified amino acids are also regenerated to further continue in the cyclic maneuver of urea synthesis, implying ATP availability to be critical and paramount.

It can be summarized that fetal oliguria can be primarily due to renal hypoperfusion or primarily due to suboptimal urea production, or a combination of both in severe cases. It is obvious that improved fetal D-glucose levels and adequate ATP synthesis deemed to operate in optimal urea production leading to osmotic diuresis, can break the vicious cycle of fetal oliguria and oligohydromnios.

4. The Improvement of Fetal Acidosis—

Acidosis is an anticipated concern in acutely or chronically distressed fetuses. It can be more so in the setting of fetal IUGR due to the combined effects of—

(1) lactic acidosis secondary to hypoxia,
(2) keto-acidosis secondary to hypoglycemia, and
(3) depleted reserves of the bicarbonate base ($HCO_3^-$) that is generally replenished through the citric acid cycle. The depletion of $HCO_3^-$ base in a similar setting can be clinically seen in diabetic ketoacidosis, wherein despite the prevailing low levels of blood $HCO_3^-$, by mere insulin supplements and by the restoration of blood glucose utilization via the citric acid cycle, blood $HCO_3^-$ is mostly replenished, and the acidosis corrected. In this clinical setting of diabetic ketoacidosis, supplemental $HCO_3^-$ is rarely needed, except in extreme life threatening conditions of acidosis.

Relief of Acidosis Secondary to Fetal Lipogenesis (and Curtailed Lipolysis) by Restored Fetal Normoglycemia—

In IUGR, restored normoglycemia and fetal fatty acid synthesis as a result, not only regenerate oxidized coenzymes $NADP^+$ but also use hydrogen ions. 28 hydrogen ions, generated through HMPS, are used in the synthesis of one molecule of palmitic acid. During the later months of pregnancy, the lipogenesis that takes place in a normoglycemic fetus can dispose of enormous amount of hydrogen ions from the fetal body During hypoglycemia there will not be any lipogenesis. On the other hand, lipolysis and beta oxidation are initiated for energy requirements, further made prominent by decreased insulin levels secondary to hypoglycemia (insulin is anti-lipolytic that normally antagonizes the many lipolytic hormones in the body—like the growth hormone, the adrenocorticotropic hormone, and the glucagon), but the acetyl-CoA so produced in unduly large number finds no entry into citric acid cycle (for also due to faltered citric acid cycle due to hypoglycemia and hypoxia), and is fated to produce ketone bodies that are moderately strong acids that are oxidized in preference to glucose, thus saturating the oxidative machinery.

Acidosis can also be produced when IUGR is also associated with fetal oliguria/oligohydromnios, a grave clinical concern that can virtually lead to a moribund fetus. This scenario was described elaborately in the immediate preceding section-3.

5. The Improvement of Fetal Lactic Acidosis/Pyruvic Acidosis—

This is discussed separately from fetal acidosis in general, as fetal lactic acidosis is unique that it is only alleviated by resolution of fetal hypoxia, its causative pathology. The D-glucose supplements can correct the inciting pathology by improving fetal hypoxia by various means (as discussed in the section of 'Improvement of fetal hypoxia') further helped by D-glucose generated ATP driven active transport of vitamin/mineral supplements to a fetus also deficient in these, the supplemented thiamine aiding pyruvate entering citric acid cycle, thereby heightening the reversible lactate dehydrogenase reaction oxidizing lactate to pyruvate. If not, supplemental oxygen therapy can alleviate acidosis as will be seen in the elaborate discussion in a subsequent section. The last section of this writing further delineates the importance of vitamin/mineral supplements (especially thiamine and other B-complex factors) to a deficient SGA neonate with unrelenting lactic acidosis/pyruvic acidosis, despite restored or aided oxygenation.

During hypoxia the fetus can resort to anaerobic glycolysis by reducing pyruvate to lactate. Due to lack of pyruvate, the citric acid cycle is not made possible. Only the restoration of normoxia (optimal blood/tissue oxygenation that meets the demands) can relieve lactic acidosis, when pyruvate is oxidized to lactate via reversal of the step catalyzed by lactate dehydrogenase. In a deficient fetus, thiamine supplements may be needed, to aid pyruvate to be further oxidized to acetyl-CoA, to enter the citric acid cycle, thereby heightening oxidizing lactate to pyruvate (see also the last section of this specification 'Neonatal care of an IUGR baby').

Lactate is an important fetal substrate being constantly supplied to the fetus by the placenta. As glycogen formation is not without higher ATP consumption, the placenta stores glucose less as glycogen, and more as lactate, the predominant placental carbohydrate reserve that it supplies to the fetus throughout gestation, the best example of nature's efficiency, of what looks like nature's folly. The glycogen synthesis expends 2 ATP for each glucose molecule to be incorporated, whereas lactate production generates anaerobically 2 ATP with a total potential gain of 4 ATP in its making, compared to the alternate means of placenta storing glucose as glycogen. This is of great advantage during transient hypoxic episodes with yet available glucose. The fetal brain, heart, and skeletal muscle can convert lactate into pyruvate, via the lactate dehydrogenase reaction, when the $NAD^+$ is converted to $NADH+H^+$ to generate 3 ATP aerobically, as the hypoxic episode had passed, while the overall ATP yield to the fetoplacental unit is similar to that of aerobic glycolysis of 1 molecule of glucose. However, the overall process of glycogenesis followed by glycogenolysis by the placenta itself loses 1 ATP for 1 glucose. The lactic acidemia becomes a metabolic concern only after prolonged anaerobic glycolysis of glucose by the fetus during unrelenting hypoxic conditions as in placental insufficiency, whereas normally lactate is the fetal fuel just like D-glucose, only efficiently saved. Nonetheless, it can not be concluded without saying that 'no two metabolic products cause more apprehension to the explorers of fetal medicine than the lactate/lactic acid and the $CO_2$, as it is hard to fathom when they may turn against, as similar to man's tools, the swords and the guns, they also both save and kill!

Persistent fetal lactic acidosis can be reflected in the AF (amniotic fluid), as kidney is an effective organ both in metabolizing and excreting the lactic acid, and fetal urine passed into AF can reflect the fetal lactic acid levels. Fetal kidney also excretes progressively increasing amounts of creatinine as the organ matures in its function. Thus AF creatinine content is a reflection of fetal maturity.

The placenta metabolizes significant amounts of glucose anaerobically, and the lactate can diffuse into the AF, the maternal circulation, or into fetal circulation, but mostly it will be supplied to the fetus. The maternal venous blood lactic acid/pyruvic acid ratio is 10, whereas it is 12 in the fetus. When the maternal food consumption itself is low, as during the stretch of time between dinner and breakfast, the placenta supplies it's reserves of lactate to meet the fetal needs. The placenta metabolizes 80% of glucose extracted from maternal blood anaerobically, to convert it into/store it as lactate (L. Myatt). In fact, the placental uptake of glucose is more (50-60%) than the fetus during early months of pregnancy, and it declines only towards term when the placental pentose phosphate pathway (the HMP shunt, predominantly required for placental elaboration) and other previously dominant anabolic pathways gradually diminish (L. Myatt). Lactate utilization accounts for 25% of oxygen consumption in a normal fetus, and contrary to expectations, high fetal lactate levels will not account for/result in fetal acidosis (J. A. Low). High rate of placental permeability to lactate was observed in hemochorial placentae, as the human placenta.

During IUGR with associated hypoxia, the fetus becomes the sole producer of lactate/lactic acid, and the placenta becomes an important site to clear the excess fetal lactic acid, and ceases to be the lactate producer/supplier, as there appears an impaired $H^+$/lactate co-transport in the basal membrane of the syncytiotrophoblast in term or pre-term IUGR pregnancies, compared to the appropriately grown controls (P. Settle et al). It seems reasonable to contemplate that the intrinsic glucose needs of the placenta having not been met in the setting of IUGR, the placenta loses its reserves of stored lactate, so that it may not supply the usual provisions of lactate to the fetus.

Most of the fetus neonates with perinatal hypoxia/asphyxia are found to have markedly elevated lactic acid levels in the AF and also in the neonatal urine samples (as will be discussed in the last section of this specification). It is a legitimate concern that these prove that glucose availability is not the concern in majority, and why the glucose supplements are needed. But that may not be the absolute fact, though it is a reasonable concern. The lactic acid levels can be elevated both with optimal or suboptimal glucose availability, as hypoxia can accompany both. Accordingly, elevated lactic acid levels can not positively rule out fetal hypoglycemia as it can positively rule in hypoxia.

6. The Fetal Hypertriglyceridemia—

Economides and associates (1990) who measured fetal triglyceride (TGD) levels demonstrated fetal hypertriglyceridemia that correlated with the degree of fetal hypoxemia. Barker and colleagues (1993) at the United Kingdom's medical research unit had over 20 years researched the causes of adult mortality and morbidity in relation to possible adverse intrauterine life, and found increased risks of hypertension and atherosclerosis in the context of IUGR.

In this writing, the author attributes the adult hypertension and atherosclerosis of above studies to the mode of hypertriglyceridemia produced in the IUGR fetuses (as discussed below) that could be persistent for significant part of intrauterine life. Experimental results in animal and in human atherosclerosis studies suggest that the fatty streak represents intimal lesions resulting from focal accumulation of lipoprotein in the vascular intima. Recruitment of leucocytes to the nascent fatty streak and their adhesion to vascular intima are further made easier due to sluggish laminar flow because of polycythemia and of hyperviscosity of blood in the IUGR fetus. In this set up at least some amount of thrombotic reaction in the focal atheromatous area is possible. As per the 'Virchow's Triad', the thrombosis of a vessel wall depends on three factors—the velocity of the blood flow, the viscosity of the blood, and the nature (injury, if any) of the vessel wall, all being present in the IUGR fetuses in an adverse manner. Accordingly, a ground work is already laid out in-utero, as a thromboatheromatous plaque in the vessel wall, as an operation of Virchow's triad in the set up of persistent hypertriglyceridemia of intra uterine life that can likely progress and manifest as atherosclerosis and hypertension in adult life.

The initiation and the perpetuation of fetal hypertriglyceridemia in fetal IUGR can be as follows—insulin is a potent positive stimulus for lipogenesis, and a negative stimulus for lipolysis. It inhibits the activity of the hormone sensitive lipoprotein lipase responsible for adipose tissue lipolysis, thereby preventing the release of FFA and glycerol. In IUGR, there is prolonged and persistent hypoglycemia causing hypoinsulinemia (or hypoinsulinism) resulting in the unopposed action of other hormones like the growth hormone, glucagon, and the adrenocorticotropic hormone that stimulate the lipolytic action of hormone sensitive lipoprotein lipase. However, because of the lack of oxygen for the beta oxidation of the liberated FFA, they are not used. In this setting, the esterification of FFA with glycerol in other tissues results, causing fetal hypertriglyceridemia (hypertriacylglycerolemia).

There can be additional factors operating in the young adult life of the SGA infants who suffered IUGR. Despite hypoglycemia and secondary hypoinsulinemia (hypoinsulinism) the IUGR babies who survived adverse intrauterine life have been shown to mount adequate insulin response postnatally. This is evidenced by the fact that diabetes, if at all manifests, is only transient in the SGA infants during their neonatal life. However, diabetes can be a problem for them as young adults, as the growth restricted islet cell mass of pancreas (due to persistent hypoglycemia of intrauterine life) that is hypoplastic (in proportion to the fetal glycemic status) but not vestigial, may be adequate to cope up with the blood glycemic demands of early childhood, but not of the young adulthood, when insulin requirements increase. Moderate hypoinsulinemia again becomes manifest, with the consequent lipolysis (insulin being anti-lipolytic), and hypertriglyceridemia (as described above). For significant number of years it can go unsuspected and undiagnosed, due to its uncommon age prevalence, and no associated family history. This will further add to and result in ongoing atherosclerosis and hypertension. The set up is similar to the untreated adult diabetes mellitus, with its associated risks of hypertension, atherosclerosis, and of the early onset coronary artery disease. For such clinical manifests, the adult diabetes is categorized as a coronary artery disease (CAD) risk factor, and the imposed risk considered significant enough to be categorized as equivalent to diagnosed/established CAD.

Obviously, correction of fetal hypoglycemia with the consequent correction of hypoinsulinemia is the only remedial measure to correct the fetal hypertriglyceridemia.

7. Improvement in Placental and Fetal Acquisition of Major Nutrients (Amino Acids and Lipids), Minerals, Vitamins, and Trace Elements in IUGR, a Relief Expected by Intravenous Vitamin and Mineral Supplements Along with Ongoing Oral and Intravenous D-Glucose, and IUGR-Diet—

(1) The Placental Acquisition of D-Glucose

It was adequately described how glucose is transported through cell membrane by facilitated diffusion in the section 'The biochemical basis for hypertonic D-glucose treatment'. In that context it was also discussed how the Michaelis-Menten expression denotes the relation of substrate concentration and the resultant rate of an enzyme/hormone, or a carrier mediated chemical reaction, either by active transport or by facilitated diffusion. It was discussed with figurative illustration (FIG. 1A, FIG. 1B, and FIG. 1C) how the maternal hypertonic D-glucose supplements with exceeding substrate (S) concentration can cause exponential improvement in placental D-glucose transport, by maximal recruitment of substrate carriers imposed by substrate demand, each carrier in turn operating with a velocity approaching $V_{max}$, wherein the $V_{max}$ can be instantaneous in time.

Michaelis-Menten equation can also be applicable to the transport of all the placental substrates (discussed under this section) whose concentration can be greatly improved at the placental interface (by the IV supplements initially, and then by means of the ongoing IUGR diet implemented to all the afflicted mothers) such transport further enhanced indirectly by induced normoglycemic status improving ATP production that heightens the placental concentrating process of maternal substrates by 'active-transport', operative for a great many substances direly needed by the fetus, but present in lower concentrations in the maternal compartment.

(2) The Placental Acquisition of Amino Acids

The amino acids are needed for anabolic needs like bulk lay-over of fetal body muscle mass, and biosynthesis of specialized products such as (a) hormones, (b) enzymes and coenzymes, and (c) neurotransmitters, to mention a few.

It is a saving provision that the AF contains amino acids in the same proportion as the maternal extracellular fluid, and the fetal swallowing of AF can be a significant means of their acquisition, but not optimal, and hence the contribution of placental transfer is invariable.

Amino acid transport across the trophoblast can be achieved by different means, as follows—

1. Active transport—it plays a role in the transport of certain amino acids, prevailing in lower concentrations on the maternal side, that is, the maternal fetal ratio is less than 1, when facilitated diffusion is no longer applicable. The process being ATP dependent, increased glucose availability and ATP production as a result makes the active transport of amino acids possible.
2. Facilitated diffusion—most amino acids are transported to inside of essentially all cells by facilitate diffusion, a mechanism involved also in glucose transport, and was already described. Additionally, insulin, as in glucose transport, enhances the amino acid transport achieved via facilitated diffusion. Insulin's effect is neither on glucose nor on the amino acids, but it is on the regulation and recruitment of the involved cell-carriers/transporters. The laws of facilitated diffusion allows placental diffusion of amino acids only down the concentration gradient, which means that maternal fetal amino acid ratio has to be more than 1, or else, their placental passage has to be achieved via energy dependent active transport, the IUGR diet (eggs) with exceptional substrate concentration, especially of essential amino acids obviating such need.
3. Sodium co-transport (symport)—In this mechanism, it is the concentration gradient of sodium across the cell membrane that provides energy for the amino acid transport. The involved carrier has carrier sites both for sodium and for the amino acids. As the aliphatic or the aromatic side chain of the amino acids are very diverse in structure, different carrier systems are operative and specific to different types of amino acids.
4. Hormonal regulation—estrogen helps amino acid transport in the uterus that is mainly responsible for its enormous growth during pregnancy. Similarly, growth hormone influences amino acid transport through all cells.
5. Pyridoxine—Transport of few amino acids are also pyridoxine ($B_6$) dependent.

The IUGR Fetus and the Effect of IUGR Diet—

The amino acids may not be adequately acquired by the fetus in the setting of placental insufficiency. There is documented evidence in the literature that the cordocentesis of SGA fetuses afflicted with growth restriction in-utero showed lower amino acid levels, compared to their appropriately grown (AGA) counterparts, and this especially involved essential amino acids that the placenta must transfer. As the levels of placental transporters were found to be unaffected in the placentae of growth restricted fetuses, it can be deduced that it is the effect of the failed placental elaboration, and reduced surface area that influence the amount of amino acids to be transported. The beneficial clinical manipulation through IUGR diet is based on the fact that the rate at which the amino acids transport through a membrane by facilitated diffusion, based also on Michaelis-Menten model, depends on—
(a) The placental concentration gradient—it is affected by an exceeding amino acid content in the advocated IUGR diet. Such heightened gradient can also change energy requiring active transport to facilitated diffusion.
(b) The amount of available carriers—it has no significant bearing in this setting, as the placental carriers are far from saturated by the substrate normally. Restored insulin levels make both the glucose and amino acid carriers available across the cell membrane.
(c) The rapidity with which a physical or chemical reaction takes place between the carrier and its substrate—such chemical interaction is better accomplished during the short span of fetal systole in IUGR, when the filling of the terminal villi is more effective than during diastole when there can be little end diastolic filling, or absence of increased end diastolic flow velocity (as discussed in a later section). As the reaction velocity is being affected also by substrate concentration (S) even when other factors are kept constant, $V_{max}$ can be instantaneous, when substrate (S) availability is in exceeding amount, as provided by the IUGR diet.

The fetal heart rate being 140 per minute, and as the cardiac cycle's systolic time is unchanged at any rate, to make such high heart rate and the systolic villus filling alone effective, the placental carriers must function in a 'speed mode' so as to carry enough of needed fetal substrates. Hence, if $v_1=V_{max}$, by a manipulated high substrate (S) concentration, the substrate transfer can be instantaneous. The maternal heart rate being only half that of fetal heart rate, the pools of placental sinusoidal structure normally compensate with enough of such substrate reserve lasting through two of the fetal cardiac cycles.

Restored Transcellular Amino Acid Transport within the Fetal Body Secondary to Normoglycemia and Normalized Insulin Effects, and Further Transport from the AF—

It is of great significance that glucose supplements and the consequent fetal normoglycemia bestow the double benefit of heightened transcellular transport of both glucose and of the amino acids within the fetal body, via the hormonal effects of insulin on both.

AF has amino acid concentration similar to that of maternal plasma. Sodium and amino acid co-transport may play a role in absorption of these amino acids across the cell barriers of fetal interior (the intestines) permeated by AF. At least four different carrier systems are involved, and AF sodium content is almost as high as maternal extracellular fluid.

(3) The Placental Acquisition of Lipids and Free Fatty Acids (FFA)

Only few substances are soluble in water and also in the lipid bilayer of the cell membrane, such few of physiological importance being the oxygen, the carbon dioxide, and the FFA. The primary factor that determines how rapidly a substance can diffuse through the lipid matrix of a cell membrane is the rate of the solubility of the substance itself. The fatty acids themselves being lipids, solubility barrier in the lipid bilayer of the cell membrane should be of no concern, and they are easily diffusible by means of 'simple diffusion' across the lipid layer of cell membrane requiring no carriers, such diffusion proportional to the concentration gradient.

The major factor in determining the transfer of free fatty acids across the placenta is the maternal levels of circulating free fatty acids. The function of Human Placental Lactogen (HPL) is blocking of the peripheral uptake and utilization of glucose by maternal tissues, while also promoting the mobilization of free fatty acids (FFA) from the fat depots, for utilization by the mother. The elevation of serum total lipids, phospholipids, and of FFA during pregnancy is enormous, with a progressive increase towards term. The total lipids increase by 46%, and the FFA by 60% during 37-40 weeks of pregnancy. Such high values assure high maternal gradient across the placenta for simple diffusion of lipids and the FFA (both the essential and non-essential free fatty acids) into the fetal circulation. The fatty acids so derived contribute to the structural components of the cell membranes, and to the cellular architecture of the brain that is predominantly lipid. The rising albumin levels of the fetus can further help to carry, and mount the levels of fatty acids. The therapeutic maternal hyperglycemia can also spare FFA utilization to some extent by the mother.

The increased content of maternal essential fatty acid levels via IUGR diet will also proportionally increase placental transfer of these fatty acids by the similar principle of simple diffusion. If the FFA levels were found by the investigators to be much lower in the fetus than the mother, it probably is because they are immediately incorporated into the fetal anabolic processes that further provides needed concentration gradient, or else the simple diffusion of the FFA would cease. Moreover, the enormous rise of FFA in the mother is purposeful. The molecular weight of the concerned FFA has a bearing on the kinetics of diffusion, the low molecular weight FFA like the palmitic acid diffusing more rapidly than the high molecular weight FFA like the oleic acid, though the latter is a predominant FFA of the maternal adipose tissue. The palmitic acid is indeed the integral building block of the rapidly developing fetal brain, as will be seen in the later discussion, and hence also is the one most needed from the maternal compartment.

(4) The Placental Acquisition of Minerals, Vitamins, and Trace Elements

Many of circulating fetal elements that are absolutely essential for its optimal growth, like calcium, iron, magnesium, and iodine are found to be at higher levels in the fetal side than that of the maternal side, and they are not synthesized by the fetus.

To cite a clinical example, in the case of iron transport, despite severe anemia clinically manifesting in a mother, her fetus is rarely anemic. That is why it was appropriately said that the fetus thrives at the expense of its mother. Such optimal fetal growth in adversity, is achieved by the transcellular, ATP dependent, and of a carrier mediated active transport, by the placental concentrating process, directed to vitamins, minerals, and trace elements, that can be normally scarce in amounts in the maternal blood, yet are absolutely needed more by the fetus.

Active Transport—

The active transport obeys the same laws of chemical combination of the substrate with the carrier molecule, and a specific carrier molecule (for example—calcium binding protein, or the phosphorous binding protein) is required to transport each type of, or each class of substance(s) having natural affinity for its carrier that makes the two of them combine readily on the outer surface of the cell, yet on the inside of the cell, energy in the form of ATP is needed for their dissociation, this may also needing an enzyme catalysis.

Iron Transport— iron is transported through the placental tissue by active transport. Over all, about 375 mg of iron is needed by the fetus, to be deposited as hemoglobin in its red blood cells. During the first few months of pregnancy, the placenta grows rapidly and enormously, yet when the fetal growth can be only described as diminutive in comparison. It is for the reason that placenta avidly accumulates proteins, calcium, and iron, to be stored in and used during the later months of pregnancy, when the absorption of some of these elements by the maternal gastrointestinal system is less than optimal. Iron accumulation by the placenta is more rapid than that of calcium and of the phosphates, and in fact it is concentrated in the progestational endometrium during the luteal phase, even prior to implantation. This iron, ingested by the trophoblastic syncytial giant cells of the embryo is required for the formation of red blood cells even at this stage. One third of iron at term is stored in the fetal liver, intended for the use of the neonate during the early months of life. Placenta functions similar to the fetal liver from early on in terms of the storage of both carbohydrates and iron, to be liberated and furnished when the fetal demands are more. The D-Glucose supplements with restored acquisition of glucose by the placenta and the fetus can enhance the process of active transport of iron by readily available supply of ATP. It can improve the fetal MCHC. It in turn can regress the fetal polycythemia, and reduce the excessive production of the fetal erythropoietin. Though they are mainly the secondary effects of fetal hypoxia, yet improved fetal iron and improved MCHC can have positive effects in this setting.

(b) Calcium, Magnesium, and Phosphorous Transport—

About 23 grams of calcium and 14 grams of phosphorous are accumulated by an average fetus. Half of this gain is during the last 4 weeks of pregnancy, when also there is rapid bony ossification, and maximal fetal growth. As a saving measure, urinary excretion of calcium falls during pregnancy, coupled with that of increased intestinal absorption, probably due to estrogen influence. Only extreme maternal deficiency of calcium will reflect in the fetus as congenital rickets, which indicates that the maternal stores were very deficient, or that the pregnancy defenses failed by some other means. In the case of calcium, there are additional factors that are also at play in the mother, like the Vitamin-D/parathyroid hormone level, just as in the non-pregnant state, and the placental cells are no exception to that influence (see also the calcium-magnesium antiport below, with regarding placental calcium acquisition). Just as calcium, phosphorous is also physiologically linked to the above influences. The foregoing discussions of the metabolic path ways of major food stuffs made very clear of the need of phosphorous in all anabolic and catabolic processes through its vital role as ATP, generated by the participation of inorganic phosphate ($H_2PO_4^-$, the dihydrogen phosphate ion) in the life sustaining process of the mitochondrial oxidative phosphorylation.

Magnesium is very essential to the fetus because of its need in all reactions where ATP/ADP are the substrates. It is transported through the cell membrane probably by active transport involving the calcium-magnesium antiport (an antiport system moves two molecules in opposite directions) in the same manner as the sodium and potassium ions are transported involving the sodium-potassium ATPase (in the sodium potassium antiport, the active transport involves potassium, an intracellular cation coming into the cell, whereas sodium, an extracellular cation getting out, and the system normally transports 3 of sodium ions to the outside of the cell, and 2 of potassium ions to the inside).

Magnesium is mainly an intracellular cation, and calcium an extracellular cation. In the magnesium-calcium antiport, involving calcium ATPase, magnesium ions are probably transported into the cell, and calcium ions to the outside. This explains the bidirectional transport of calcium in the mammalian placentae. Despite its outward flux during calcium-magnesium antiport, calcium transfer is independently controlled and achieved by the facilitation of vitamin-D and parathyroid hormone, and also by passive diffusion down an electrochemical gradient via calcium channels, as maternal calcium levels are maintained far higher than the non-pregnant levels. Furthermore, fetal net acquisition of calcium is aided by calcium binding protein that protects the intracellular calcium from becoming too high, any intracellular excess being not amicable to the normally intended cellular functions.

(c) Iodine Transport— the placenta can actively transport iodide ion by means of active transport, as iodide is essential for the synthesis of the thyroid hormone by the fetal thyroid gland, and the maternal thyroid hormone crosses the placental barrier only to a limited extent, as obviously, it will impair the development and maturation of fetal thyroid gland by negative feed-back, the hormone secreted by the fetus deemed to be imposing such feedback.

Fetal Acquisition of Minerals and Trace Elements Through Amniotic Fluid (AF)— while all the inorganic substances like the minerals and trace elements can pass through the placenta only by active transport, they can yet diffuse into the amniotic cavity (in dissolved and suspended state in maternal extracellular water), via the intercellular and intracellular canalicular system all through the amnion by means of passive diffusion that needs no energy expenditure. The minerals and trace elements are present in the AF in the amounts proportional to their concentrations in the maternal extracellular fluids. The fetus can swallow these elements of the AF, but obviously not in amounts that can correct the deficiency imposed by normally needed major placental concentration.

(d) Vitamin Transport— the vitamins are transported across placenta by 'active transport' expending ATP, and are found to be in much greater concentrations on the fetal side. The ascorbic acid (the vitamin-C) levels on the fetal side are found to be thrice that of the mother.

The Mechanism of Active Transport, and its Relevance to Therapeutic Glucose Supplements—

In states of ATP depletion as in IUGR, the transfer of the essential Minerals, vitamins, and trace elements is invariably diminished, adding to the other major problems of this disease state. Glucose via citric acid cycle being the major generator of ATP, the therapeutic D-glucose supplements relatively improve the diminutive transport of these very essential fetal growth factors, operating irrespective of maternal gradient, and in conjunction with the normally surplus provision of available cell membrane 'carriers'. Maternal IV vitamin and mineral supplements prior to IV glucose, along with IUGR-diet also containing these in high amounts, further facilitate the $V_{max}$ of their placental transport. All the fore going can effectively override placental impedance to a moderate extent The Effect of Insulin on Placental Glucose Transport in Normal and in Diabetic Pregnancy, as Relevant to the Treatment Involved—

With the discussion of the major transports and the knowledge of the vital control of insulin on the transcellular glucose transport, as elaborately detailed so far, it is a legitimate question how the babies of mothers with uncontrolled diabetes are growing to be macrosomic. When insulin positively controls the carrier function of the glucose transporters, how the molecular glucose is overcoming the placental barrier imposed by insulin deficiency or resistance, in poorly controlled diabetic pregnancy.

Before the advent of insulin, diabetic women conceiving and carrying the baby to term were rare. Accordingly, it is obvious that the diabetic pregnancies became common clinical concern after the insulin therapy became the indispensable tool of the obstetricians.

Maternal diabetes with fetal macrosomia is probably mostly evident in Type II obesity associated diabetes in whom central obesity is the culprit, the obese adipocytes in this setting being capable of producing peptides including cytokines that are capable of modulating the insulin response by causing first insulin resistance, and then hyperinsulinemia. The hyperinsulinemia can in turn lead to down-regulation of cell receptor sites for insulin, on the insulin-sensitive tissues. Thus the target tissues over time become markedly insulin-resistant in these patients, who in turn need some treatment intervention. Marshall R N et al and Posner B I et al in 1974 demonstrated that the placental binding protein of insulin is similar in molecular weight and function to the insulin receptor protein found on the fat and on the liver cells, that are also unaffected by a subject's insulin resistance. When diabetic women conceive, the placenta just as the fat depots is unaffected by maternal diabetes, and the maternal hyperinsulinemia proportionately increases glucose transfer across the placental interface, first leading to fetal islet cell hypertrophy, and then fetal macrosomia.

Table-3 of FIG. 15, depicts 'The effects of the therapeutic intervention of the D-glucose supplements, in conjunction with the IUGR diet, on the placental transfer of the maternal substrates'.

8. The Effect of Maternal Hypertonic D-Glucose Supplements on Placental L-Arginine and D-Lysine Uptake: The Relief of Hypoxia by Improved Feto-Placental Nitric Oxide (NO) Synthesis, and Placental Vasculogenesis—

Effects of Glucose on L-Arginine Uptake—

Nitric oxide (NO) is a potent vasodilator throughout the body, and it is synthesized from the essential amino acid L-arginine by the action of Nitric oxide synthase. It uses NADPH as a cofactor. Nitric oxide has a very short half-life of 3-4 seconds, which means it needs to be continually synthesized. As L-arginine has to be supplied by the mother, increased supplements of essential amino acids via IUGR diet (as egg protein, a rich source of all essential amino acids, with every meal), by improved substrate (S) concentration and also $V_{max}$, will improve its placental intake/transfer so that it can be effective locally—in the spiral vessels, in the vinous capillaries, and also in the umbilical circulation for generating the needed nitric oxide so as to facilitate their vasorelaxation.

The transplacental transport of certain essential and the non-essential amino acids occurs by active transport as specified earlier, for which ATP is essential. Maternal hypertonic glucose supplements improve the ATP synthesis apart from also providing the needed NADPH generated from the carbohydrate metabolism, involving pentose phosphate pathway (the placenta itself has active pentose phosphate pathway). Active transport is also the mechanism by which L-arginine is transported into the endothelial cells of any vessel wall, including those of the umbilical vessels. Such improved impedance both in the placenta and in the fetal vessels shall have great bearing in incrementing both the flow velocity and of the flow volume in these vessels to over-ride the 'critical closing pressure' (wide infra) consequently relieving hypoxia and hypoglycemia, and also of the accompanying multitude of adverse effects involving the placental exchange. The nitric oxide has unrefuted benefits on penile sinusoidal circulation causing pooling of blood, and similarly placental sinusoidal flow is undoubtedly benefited, which is also proved as below.

The following researchers from Chile, South America, recently made interesting observations of the role of Nitric Oxide in the growth of the fetoplacental unit and its circulation, and also of the effect of D-glucose in L-arginine transport through cell membrane—

Krause et al (2011) in their placental study proved that nitric oxide is essential in placental trophoblastic invasion, cellular respiration, and also in maintaining the vascular tone. They further proved that it also represents the main vasodilator function of the placental vessels, and that it participates in placental vasculogenesis through the angiopoietin signaling molecules. Hence its role is important even in alleviating prevailing placental pathology.

Sobrevia et al (2009) observed that D-glucose and insulin increased L-Arginine transport and CGMP accumulation in the Human Umbilical Vessel Endothelial cells (HUVEC). It is plausible as noted by the observations of these researchers that glucose enhanced (and insulin mediated) 'active transport' is involved in the specified L-arginine transport.

Casanello et al (2009) in the research involving HUVEC of normal and IUGR pregnancies, observed that the HUVEC of IUGR exposed to both normoxia (optimal amount of tissue oxygen that meets metabolic demands) and hypoxia, and HUVEC of normal pregnancy exposed to hypoxia, exhibited reduced L-arginine transport, and reduced nitric oxide synthesis. They concluded that the IUGR cells were either not responsive, or maximally affected by hypoxia.

The above observations by Casanello et al can be the result of lack of glucose (needed for synthesis of ATP for arginine active transport) in the HUVEC of IUGR pregnancy that could have caused reduced L-arginine transport, and reduced nitric oxide synthesis, despite normoxia. Oxygen also being a requirement for ATP synthesis, hypoxia is expected to cause reduced L-arginine transport, and reduced nitric oxide synthesis in both normal and in IUGR affected HUVEC, both being similarly subjected to hypoxia either by natural or by artificial means.

Other Positive Effects of Fetoplacental Nitric Oxide Production—

Wilcox et al in 1989 reported reduced platelet (PLT) count in the cord blood collected at delivery from both normotensive and hypertensive patients, whose fetal Doppler umbilical cord studies exhibited high placental vascular resistance. They hypothesized that there is increased PLT aggregation and consumption, as a result of the said placental pathology of increased vascular resistance. Or, the primary pathology could be a local imbalance in favor of excess thromboxane $A_2$ (responsible for potent vasoconstriction and PLT aggregation) and consequent damage to placental micro-structure, resulting in placental insufficiency (Nicolaides K. H and Campbell S, 1991). Nitric oxide apart from causing vasorelaxation, also acts on platelets, to effectuate PLT anti-aggregation (Kniss D A. 2001). Essentially, in the above study of Wilcox et al there could be impaired Nitric oxide production, resulting both vasoconstriction and also PLT aggregation and consumption.

It can be concluded that hypertonic glucose supplements not only directly relieve hypoglycemia, but also by effectuating ATP-arginine induced nitric oxide synthesis, indirectly induce both vasculogenesis and vasorelaxation, and alleviate the placental vascular damage and thereby the impaired exchange of uteroplacental insufficiency, thus breaking a vicious cycle.

Effects of D-Glucose on D-Lysine Uptake, and the Placental Vasculogenesis—

Debatosh Datta (2007) observed that monomeric lysine was found to expand biomass (cell population) at the least possible time compared to other physicochemical means. It was also observed that D-lysine can induce neovascular growth in all tissues types.

In the placental bed, D-lysine still has to be transported into the cell through active transport expending ATP, to exert such vasculogenesis. In case of established trophoblastic failure, D-glucose supplement is crucial to break the vicious cycle of placental insufficiency (as was described above I n case of L-arginine deficiency), and to stimulate trophoblastic villous elaboration, by supplying ATP needed for placental D-lysine uptake.

9. The Positive Effects of Hypertonic Glucose Supplements on the Growth and Maturation of Vital Organ Like Fetal Brain—

No Organ in the Developing Fetus Needs More Glucose than the Fetal Brain.

Whereas all the tissues need glucose for energy, and as the currency of ATP (that is, for catabolic purposes), the fetal brain needs it as its very building blocks (for anabolic purposes). So it can be said that in the fetal organogenesis, in the brain's rapidly progressive architecture, glucose is the brick, whereas everything else, including oxygen (ignoring its gaseous form) serves only as its cement. Moreover, glucose also has to additionally supply needed energy in the brain, as elsewhere. In this context, the requirement of glucose in the developing fetal brain as being enormous, is but anticipated. Unless one explores the biochemical architecture of the brain, it is hard to fathom that all its lipid components indeed took their origin from glucose, and its quantity incorporated also can be unimaginable to a casual reader. It is for the reason that the brain's integral lipids are very long chain fatty acids, the most important being the cerebronic acid, made up of 24 carbon atoms, that require $1/3^{rd}$ more of acetyl-CoA molecules than the 16 carbon palmitic acid, the most synthesized fatty acid of the fetal body. Hence the most fundamental, and some so far unexplored issues of fetal brain's biochemical architecture, and the best of glucose/oxygen economics warrant discussion here, especially in the context of even normally prevailing relative hypoxia in-utero. The inquiry that by what biochemical path ways the excess (in absolute numbers) of glucose/oxygen expenditure by the fetus is normally curtailed in this setting is crucial, as it was never explored before with the needed emphasis on the critical glucose/oxygen economy.

Symmetrical Vs. Asymmetrical Fetal Growth Restriction—

As defined in the introductory paragraphs, fetuses or neonates whose estimated/attained birth weights are less than the tenth percentile are considered growth restricted, as per the prevailing US guidelines, this being more stringent than the fifth percentile that is the standard cut off in other countries.

The IUGR fetuses or SGA babies are classified either as being symmetrically small, or asymmetrically small. This discretion is clinically significant that symmetrically grown IUGR fetuses or SGA infants shall not be mistaken as premature.

1. Asymmetrically small—in these IUGR fetuses/SGA infants, the length and the head circumference (HC) are normal or near normal, whereas the abdominal circumference (AC) and the weight are low. This is the so called 'brain sparing effect' in a growth restricted fetus, achieved by auto-regulation that directs blood flow preferentially to vital organs, the brain, the heart, and the adrenals (mostly by anatomically predestined means), at the expense of other organs including the kidneys. This can be significant in causing fetal oliguria leading to oligohydromnios.
2. Symmetrically small—in these fetuses/SGA infants, both the abdominal circumference (AC) and the weight are low as in the prior group, but so are the head circumference (HC) and the length.

At the onset of the third trimester the fetal head is normally larger in comparison to its length and the abdominal girth, though the fetus's earlier striking tadpole configuration is less obvious at this time. Such disposition begins to change even more, starting $29^{th}$ week of gestation when as a result of the initiation of fetal lipogenesis and of the glycogen storage in the liver, the abdominal girth/growth accelerates. The head and the abdominal circumferences equalize by 34 weeks, which however is not the case in the asymmetrically grown IUGR fetuses.

The above discussion highlights that even in IUGR, the nature's defenses strive hard to preserve the integrity of fetal vital organs, especially the brain. However, a failed potential for intellectual fulfillment is not rare in this subset of pediatric population, as measured by low IQ, or as suboptimal educational attainment. In human, the myelination of brain is most rapid from the $7^{th}$ month of fetal life, the time when the fetal brain is most susceptible to the effects of under nutrition, for whatever reason. This is also the time the fetal IUGR usually makes itself manifest clinically. This makes the objective of diagnosing the fetal IUGR an imperative from early on, and the treatment of every pregnancy so afflicted a much sought after clinical endeavor so that no child will be losing the innate potential it is genetically endowed with.

Fetal Lipogenesis and its Role in Fetal Brain Development—

The human brain is predominantly made of fats, comprising mainly of phospholipids and of glycolipids as the major structural components. The outlines of these biochemical entities were already specified in the section of 'Lipid Metabolism', and they are herein elaborated.

The PHOSPHOLIPIDS of the brain made of sphingomylins, are composed of—
1. Ceramide: it is made up of—
   (a) Sphingosine—it is an alcohol analogous to glycerol (glycerol is contained in the more familiar triglycerides of adipose tissue), but it is a complex amino alcohol that contains amino acid serine, and the palmitic acid.
   (b) Fatty acid—it is made of cerebronic acid, a very long chain fatty acid with the characteristic 24 carbon atoms, and primarily derived from palmitic acid.
2. Choline, and
3. Phosphoric acid.

That is, the brain's phospholipids made of sphingomylin, essentially consist of: palmitic acid, serine, cerebronic acid, and phosphoryl-choline (choline & phosphoric acid).

The GLYCOLIPIDS of the brain are cerebrosides. They also contain sphingosine fatty acid combination (the ceramide) as in sphingomyelins, but a galactose moiety is attached to the ceramide instead of the phosphoryl-choline residue found in the sphingomyelins. Its structural elements are as shown below—
1. Ceramide: it is made up of—
   Sphingosine (containing palmitic acid, and serine), and
   Fatty acid (the cerebronic acid).
2. Galactose—a hexose carbohydrate, which is unique to the glycolipids of the brain.

That is, the brain's glycolipids made of cerebrosides essentially consist of: palmitic acid, serine, cerebronic acid, and galactose.

By what was earlier discussed in the section of lipid metabolism, it was made clear that 8 acetyl-CoA units or 4 glucose molecules are required in the biosynthesis of 1 molecule of 16-carbon palmitic acid. Similarly, the biosynthesis of the 24-carbon cerebronic acid needs 12 acetyl-CoA, or 6 glucose molecules as structural elements, which however is achieved by chain elongation.

Microsomes are the site of chain elongation for fatty acids with even number of carbon atoms, starting from $C_{10}$ upward, using melonyl-CoA as the 2-carbon donor, and NADPH+H$^+$ as the reductant, in a manner similar to fatty acid synthesis, as described earlier with reference to the biosynthesis of palmitic acid.

The Economics of Glucose-Oxygen in the Fetal Brain's Neuronal Lipogenesis, and the Possible Path Way Involved for the Best of Glucose/Oxygen Salvage—

The Scheme of the Initiation of the Neuronal Lipogenesis Via Glycolysis-Abbreviated Citric Acid Cycle (LGACC) in the Fetal Brain—

The synthesis of very long chain fatty acids in the fetal brain needs significant expenditure of both glucose and oxygen. However, in this anabolic process of fetal brain, starting from glucose molecules as the originators, the brain's fatty acid synthesis also generates moderate amount of ATP. It is for the reason that at the outset it involves the ATP generating catabolic steps of glucose in the pathway of glycolysis, yielding acetyl-CoA that are needed as the building blocks of the palmityl-CoA. It also needs to be noted at this point that the brain's glycolipids and phospholipids contain both cerebronic acid (of 24 carbon units) and palmitic acid (of 16 carbon units), which together amount to a need of a total of 20 acetyl-CoA (i.e. 10 glucose molecules) altogether, for the formation of 1 molecule of either a glycolipid or a phospholipid. But in the following discussion the focus is confined to the synthetic requirements of cerebronic acid, the longest chain fatty acid, because for the needed calculations the exemplified cerebronic acid alone can serve the purpose.

The Initiating Steps of the Lipogenesis Via Glycolysis-Abbreviated Citric Acid Cycle (the LGACC) in the Fetal Brain—

The fetal Lipogenesis via Glycolysis-Abbreviated Citric acid Cycle (LGACC) (154) is shown in the FIG. 6. The Acetyl-CoA (97) formed from pyruvate (29) in the mitochondrion (172) can not penetrate the mitochondrial membrane (64) to enter the cytosol (70), the site of fatty acid (9) synthesis. Accordingly, it has to enter citric acid cycle to form citrate (99) which can get out into the cytosol (70), as virtually only two carbohydrate intermediates, the α-ketoglutarate and the citrate (99) can freely leave the mitochondria without permeability barriers. In the cytosol (70), the citrate (99) is cleaved by ATP-citrate lyase (158) to acetyl-CoA (105) and oxaloacetate (107), with also consumption of 1 ATP that is transformed to ADP. The acetyl-CoA (105) so reformed can engage in cytosolic free fatty acid (9) synthesis, as in the melonyl-CoA pathway, involving 1 ATP (that is reduced to 1 ADP), 1 molecule of $CO_2$ (188), and the NADPH+H$^+$ (184), as described earlier. The reformed oxaloacetate (107), just as in the later part (the cytosolic part) of malate shuttle can react with the NADH+H$^+$ (15) that is being continuously formed in the cytosol (70) via the glycolytic pathway (34) to form malate (109) catalyzed by cytosolic malate dehydrogenase (60) that can enter the mitochondrion (172) in exchange with some more of citrate (99) getting out of the mitochondrion (172) through the citrate transporter (CT) (166), so facilitating the pathway to lipogenesis (176) on-going. NAD$^+$ (13) regenerated is further used to continue the glycolytic process. Malate (109) can only exchange with citrate (99) in this transport. Malate (109) then enters the (abbreviated) citric acid cycle (154) to form oxaloacetate (96) catalyzed by mitochondrial malate dehydrogenase (68), while also reducing NAD$^+$ (68) to NADH+H$^+$ (170) (that can generate 3 ATP) as in the usual manner of the final step of the full-fledged citric acid cycle. This is the 'abbreviated citric-acid cycle' (154) that accomplishes the initiation of fatty acid (9) synthesis in the tissues specializing lipogenesis, as the brain. It is made possible by the incorporation of glycolysis, the citrate forming first step, and also the last step of citric acid cycle, further incorporating the integral functional aspects of 'proton transfer' into the mitochondrion (172) from the cytosol (70), otherwise normally achieved in the cell by the malate shuttle (76). Each citrate molecule (99) (needed for fatty acid synthesis) getting out of the mitochondrion (172) needs malate (109) in exchange coming in (as needed substrate pair). Only in 1 citrate diversion (elaborated below) into FFA (9) synthesis, malate shuttle (76) is needed for the transfer of one among the two of the cytosolic NADH+H$^+$ (15) generated from 1 molecule of glucose. The term 1 citrate diversion denotes that at least half of the acetyl-CoA (97) molecules derived from D-glucose (1) are engaged in full-fledged citric acid cycle, and hence not engaged in lipogenesis.

FIG. 6 also shows HMPS (182), the pathway of carbohydrate inter-conversion (involving D-glucose, 1), that continuously supplies NADPH+H$^+$ (184) to the free fatty acid (9) synthesis, wherein it is oxidized to NADP$^+$ (186) to reenter the shunt (182). FIG. 6 further shows $CO_2$ (188) being used, and $CO_2$ (190) that is subsequently liberated during the free fatty acid (9) synthesis.

The abbreviated citric acid cycle in tissues active in lipogenesis, is only speaking of the ultimate fate of each and such majority of glucose molecules being combusted in the above manner (though otherwise destined for a full-fledged citric acid cycle), and not of the whole scene of metabolic cycles/activity going on in the cell or its mitochondria, because as a whole, there can be imperceptible merge of both path ways, as some full-fledged citric acid cycles are invariable in any cell.

The question that arises at this point is whether both citrate molecules generated from a single molecule of glucose are diverted to fatty acid synthesis, or one will continue into full citric acid cycle to generate needed ATP. Due to the sheer number of acetyl-CoA molecules needed for each molecule of cerebronic acid generated, it seems plausible that both citrate molecules are diverted into fatty acid synthesis that also accounts for significant glucose and oxygen salvage. The economics of both glucose and oxygen (in absolute numbers) shows dramatic difference if both citrate molecules are diverted to fatty acid (cerebronic acid) synthesis, as opposed to only one is diverted, the other being continued through the full-fledged citric acid cycle, generating ATP in the usual manner.

The ATP Yield Vs. $O_2$ and Glucose Expended in Either 1 Citrate Diversion, or in 2 Citrate Diversion is Explained as Follows—

2-Citrate Diversion— in this process, 8 ATP are generated via glycolysis with 1 molecule of glucose (with $1O_2$ expended). So also, 6 ATP are generated when 2 acetyl-CoA molecules are formed (with $1O_2$ expended). The two citrate molecules will be cleaved to 2 molecules of oxaloacetate, and 2 molecules of acetyl-CoA in the cytosol by ATP-citrate lyase. The 2 acetyl-CoA molecules will participate in fatty acid synthesis, whereas the 2 molecules of oxaloacetate in the cytosol will be reduced to malate by 2 $NADH+H^+$ generated via glycolysis). as in the last steps of cytosolic malate shuttle. The 2 molecules of malate will return to mitochondria to form 2 molecules oxaloacetate through mitochondrial malate dehydrogenase. However, no ATP can be credited for this reaction of the last step of citric acid cycle, as the transformation of oxaloacetate to malate is accomplished by using the reducing equivalents generated in glycolysis, and as in a malate shuttle, the 6 ATP generated via the mitochondrial malate dehydrogenase are accounted to glycolysis, and not to the citric acid cycle. There is no complete revolution of the typical citric acid cycle that generates another molecule of malate. Accordingly, the total ATP generated in this process via glycolysis-citric acid cycle of 1 molecule of glucose is 14 (8 ATP from glycolysis, and 6 ATP during the formation of 2 acetyl-CoA), expending a total of 2 $O_2$. For 1 molecule of cerebronic acid to be synthesized, the fetus spends 6 molecules of glucose (and 12 of acetyl-CoA), and 12 molecular $O_2$, generating 84 ATP in the process (see Table-4).

FIG. 16 shows the Table-4 that outlines—Glucose and $O_2$ spent vs. ATP generated via 'Glycolysis-Abbreviated Citric acid Cycle' during the synthesis of 1 molecule of cerebronic acid—involving either 1 or 2 citrate diversion into FFA synthesis; further comparison of ATP yield with the conventional full-fledged glycolysis-citric acid cycle.

1-Citrate Diversion— in this process, one-citrate molecule continues into the full-fledged cycle to produce 12 additional ATP, with a total of 26 ATP generated with 1 molecule of glucose, 4 oxygen being expended in the process. However, with a total of 12 glucose molecules needed for 1 molecule of cerebronic acid to be synthesized, the fetus is bound to spend 48 molecules of $O_2$, however with 312 ATP generated (see Table-4 of FIG. 16).

With reference to 1-citrate diversion in Table-4 of FIG. 16, 12/12 acetyl-CoA signifies that 12 of them are diverted to fatty acid synthesis, whereas 12 are continued into full-fledged citric acid cycle.

With 1-Citrate Diversion, the Theoretically Probable Absolute Excess of Glucose and $O_2$ Spent, and the Excess ATP Generated, Compared to 2 Citrate Diversion, are—

| | |
|---|---|
| Glucose spent | 2 times more (200% more) |
| $O_2$ spent | 4 times more (400% more) |
| ATP yield | 3.7 times more |
| ATP yield (per 1 $O_2$) | 6.5 during 1-citrate diversion vs. 7 during 2-citrate diversion (6.5/7) that is, 7.1% more of ATP production during 2-citrate diversion. |

Comparison with the Full-Fledged Glycolysis-Citric Acid Cycle—

Comparing the above to the ATP gain and oxygen expenditure via the regular full-fledged glycolysis-citric acid cycle of a single glucose molecule (when 38 ATP are produced per 6 $O_2$), it can be noted that the yield per $1O_2$ is 6.3 ATP ($6.3/1O_2$), whereas during 2-citrate diversion the yield per $1O_2$ is 7 ATP ($7/1O_2$). This seems optimistic, because though glucose spent during fetal neuronal lipogenesis via 2-citrate diversion is 2.7 times more to generate similar ATP as the regular citric acid cycle (that is, 6 glucose generating 84 ATP vs. 1 glucose generating 38 ATP), the oxygen expenditure is lowered by 10% for similar ATP yield.

It can also be deduced that the D-glucose supplements enormously aid fetal brain development while the oxygen requirements are reduced by 10% for similar generation of ATP, whereas the absolute $O_2$ requirement itself is reduced by 400% by the rapid anabolic process accomplished in a set unit time (time vs. acquired glucose supply/lipogenesis) by 2-citrate diversion (as in a well-fed state), wherein the absolute glucose requirements are also reduced by 200%. This deduction is of extreme significance when one can be concerned or skeptical about possible adverse effects of prevailing hypoxia in the setting of therapeutic D-glucose supplements. The 400%+10% $O_2$ salvage is apart from 33%+ of oxygen salvage achieved by curtailing beta oxidation of fats, and by preventing the fetal body muscle protein utilization for energy requirements (the $ATP/O_2$ salvage being more from the latter). It may be noted that the activity of ATP-citrate lyase is increased during carbohydrate availability, induced by insulin.

It can be understood that when glucose availability is limited, the fetus has to divert at least 1 citrate molecule towards full-fledged citric acid cycle, to generate needed ATP per unit time, as also the lipogenesis is slowed, the activity of ATP-citrate lyase being proportional. However, the cerebral circulation being anatomically privileged, its contribution derived in full force from the highly oxygenated blood of the arch of the aorta before the origin of the ductus arteriosus, in most instances of IUGR, there is brain-sparing effect, the brain (as also the heart) spared from the lack experienced in the distal circulation, as by the kidneys. The cycling $CO_2$ during brain's lipogenesis can locally heighten the Bohr effect of $O_2$ release, overcoming fetal hemoglobin-$O_2$ affinity. In symmetrically small SGA infants with smaller head circumference, the fetus must be in chronic heart failure with also proportionally severe glucose and oxygen deprivation. The adrenal is also anatomically privileged despite its proximity to the kidney, each adrenal, disproportionate to its size, deriving rich and diverse arterial supply from four different sources (one from the aorta itself). In the so called fetal 'auto-regulation' of blood flow, the favored fetal anatomy involving arterial disposition of the vital organs is an obvious saving provision, as can be seen in the adrenal vs. the adjacently located kidney, whereas the physiological fetal auto-regulation involving the heart and brain responsive to impaired flow, can be comparable to its adult counterpart.

The above calculated numbers need additional comment. As was clarified above, following the combustion of a single molecule of glucose, the acetyl-CoA diverted to fatty acid synthesis in an unit time is doubled in 2-citrate diversion, so that lipogenesis can be achieved rapidly and effectively with drastically less glucose/oxygen expenditure (in absolute numbers) even in the situations of relatively low glucose/oxygen availability. However, this is achieved at the expense of high number of ATP that could have been otherwise generated by 1-citrate diversion. Nevertheless, it may not be overlooked that the first and the foremost concern during fetal organogenesis is the lipogenesis needed as an exponential process in the rapidly developing fetal brain, and everything else must be concerted in that direction. However, for the sheer number of acetyl-CoA needed for glycolipid/phospholipid synthesis, ATP is being generated in significant numbers from glycolysis alone which path way is invariable for the needed acetyl-CoA, and in this unique context, the citric acid cycle, though esteemed for its economics, is rather a wastage, and can be mostly by-passed. It also may be noted that the fetal brain compensates for the absolute number of ATP lost via lipogenesis by the exceeding amount of glycolysis, but spending less of oxygen, and more of D=glucose (being the building block), which is supplied in this therapeutic endeavor. It also follows that the fetus can engage in some full-fledged citric acid cycles when the ATP requirements within the brain are more, that is, the fetal brain's metabolic maneuvers at any time rely upon the brain's energy vs. growth requirements. The full-fledged citric acid cycles are also needed for the merging intermediates of the brain's amino acid metabolism, that is significant in view of its neuroendocrine and neurotransmitter functions.

The Energy Versus Growth Requirements within the Fetal Brain—

Fetal Growth and Maturation—

The fetal brain's growth requirements are enormous, whereas energy requirements are substantially less compared to its adult counterpart. It merely means to say that the fetal brain is quiescent, but not inert. Only its heart can surpass the brain in the amount of ongoing functional activity in quantity and quality, needed for continued survival in its unpredictable aquatic environment. The brain's sympathetic and parasympathetic circuits are very active even at this stage, as the heart rate should respond by beat to beat variation to the hypoxic insults, or to the hypotensive episodes, the input carried by para-sympathetic afferent. Hence, the brain's neuro-transmitters must be synthesized extremely rapidly. The fetal heart rate being double that of an adult, the brain's basal sympathetic out flow is also very active and very rapid. The fetus in addition has very potent brain-endocrine system, the hypothalamo-pituary axis being functional from very early on, that controls the adrenals, the thyroid, and the gonads, in terms of both growth and function. While such functions unsurpassed, the brain's cortical functional activity, and the activity of the neuronal circuits essential for volitional motor activity are minimal, making its ATP requirements far less in comparison to the growth requirements. It can be aptly said that the fetus with its uncomparable growth potential, is not only a feeding larva, but also a resting pupa, and there needs to be a very fine balance achieved between its growth and its required gain of ATP.

Because a sheer number of acetyl-CoA units are needed/produced for fetal brain development, and the process being also accompanied by moderate ATP yield that is proportional to the normally low fetal activity/energy requirements, it is prudent to say that the abbreviated citric acid cycle with predominant 2-citrate diversion is the main path way, and the full-fledged citric acid cycle (with more glucose-oxygen expenditure with high ATP yield) as needed, being the additional path way in the fetal brain. As per the popular belief some full-fledged citric acid cycles are invariable, one reason among the few being—for the end products of protein break down to merge in the cycle, as there is active amino acid metabolism also in the brain (where there is seemingly only of glucose trafficking, and of lipid manufacturing) for the synthesis, and for the rapid turn-over of multitude of neurotransmitters like—GABA, epinephrine, norepinephrine, acetylcholine, dopamine etc.

The earlier discussion was about the merits of 2 citrate vs. 1 citrate diversion into lipogenesis, but the significant amount of ATP consumed later for lipogenesis itself is unchanged, starting from citrate cleavage. All the anabolic processes are energy consuming. During the nine months of fetal intrauterine stay of which pregnancy is about, most of the energy is deservingly devoted for such anabolic needs. What Makes the Glycolysis-Abbreviated Citric Acid Cycle in the Fetal Tissues Engaged in Lipogenesis a Possibility, and Yet Generates any ATP at all—

It can be said that the citric acid cycle is an ultimate testament of the body's achievement in efficiency and economy. However, a substantial number of glucose molecules after glycolysis can by-pass the full-fledged cycle, as long as the concerned reducing equivalent (the 2 $H^+$ or protons) generated via the glycolytic process are connected to the mitochondrial respiratory chain at least through one ATP generating step of the citric acid cycle. The step involving glyceraldehyde 3-phosphate dehydrogenase of glycolysis is connected to mitochondrial respiratory chain through the last step of citric acid cycle (involving mitochondrial malate dehydrogenase) by means of some maneuvers similar to malate shuttle, and the subsequent step involving the pyruvate dehydrogenase complex being mitochondrial, is directly connected to the mitochondrial respiratory chain. Obviously, it is easy to short-circuit many steps of citric acid cycle, and yet generate ATP, and hence it can be clearly stated that the abbreviated citric acid cycle that many glucose molecules must pursue is fully compatible with cell function in the sites of active lipogenesis in-utero. It is also compatible with sufficient ATP production even while only 14 ATP are being produced with each D-glucose molecule via the glycolysis-abbreviated citric acid cycle, as the sheer number of such cycles accounts to a substantial total ATP.

Are the Predominant Abbreviated Citric Acid Cycles (ACC) Compatible with Optimal Cell Function?

This question can be answered by critically examining the intermediates of the citric acid cycle. The most important of these are citrate, malate, α-ketoglutarate, and the succinyl-CoA that are intimately and essentially connected to other vital metabolic path ways. In the ACC, the citrate and the malate are the target intermediates, and hence the focus can be diverted to the other two. The α-ketoglutarate is essential for protein metabolism, for its pivotal role involving the deamination of many of the α-amino acids. The brain cells also need it for such process, for the many activities that go on in the brain involving the amino acid metabolism. The Dopamine, the epinephrine, and the norepinephrine are synthesized in the brain from tyrosine, but are metabolized with no involvement of α-ketoglutarate. GABA is synthesized from L-glutamate, and its metabolism in the brain involves the need of α-ketoglutarate. The succinyl-CoA is essential for heme synthesis, but obviously its need is more in the erythropoitic tissues, and not necessarily in the sites active in lipogenesis.

The Allosteric/Regulatory Inhibition Controlling the Cell's Own ATP Synthesis—

In the tissues specializing in lipogenesis, such function predominates, and the cell is capable of controlling its own ATP production only as needed, and no more.

1. The steps involving combustion of food stuffs, and of the flow of reducing equivalents in the respiratory chain of mitochondria for oxidative phosphorylation are step-wise, allosterically controlled and efficient, rather than explosive or wasteful (Mayes P A).

2. In the mitochondria, the oxidation and phosphorylation are tightly coupled (Mayes P A). That means, without the availability of ADP for phosphorylation, the oxidation expending molecular oxygen cannot proceed. The availability of ADP is in turn controlled by the body's utilization of ATP, thus reducing it to ADP. Essentially, when there is adequate availability of ATP within the cell for needed biochemical activities, and no more ATP is needed (as can be evident by the relative unavailability of ADP within the cell), no more of it is produced in the mitochondria.

3. The function of ADP/ATP transporter which permits entry of cytosolic ADP into, and the ATP out of mitochondria is rate limiting. The overall rate of a simple or complex series of biologic reactions is determined by the slowest step in such series which is rate limiting to the entire series (Guyton A C). Under a resting condition as the fetus is, the concentration of ADP in the cells is very low, and the chemical reactions that depend on ADP, the most important being oxidative phosphorylation with ADP as its substrate, can be slow also, thus ADP being the rate limiting factor for all energy/ATP producing metabolic pathways of the body.

4. Insulin, increased during glucose availability and satisfied ATP needs (a scenario helped by D-glucose supplements) stimulates lipogenesis in the fetus, the most important effect being increasing the activity of acetyl-CoA carboxylase needed for synthesis of melonyl-CoA, the building block of fatty acids. Such diversion curtails the citrate continuity into the citric acid cycle, that in turn preventing the excesses of oxidative phosphorylation.

5. The fatty acid synthase complex and the acetyl-CoA carboxylase are the enzymes unique for their ability to adapt to the body's immediate requirements. Insulin increased during glucose availability and hence satisfied ATP needs (a scenario helped by D-glucose supplements) also plays a role in inducing the gene expression of these enzymes, and thus causing their biosynthesis. This enhances the fetal brain's anabolic process, and prevents the ATP generating catabolic path ways.

6. The activity of ATP-citrate lyase is increased during carbohydrate availability, and decreased during its lack. It is also induced by insulin. This state of affairs enhances lipid anabolism, and diminishes the glucose/citrate catabolism (a scenario also helped by D-glucose supplements).

Serine Needed for the Phospholipid/Glycolipid Synthesis is Synthesized by the Intermediate of Glycolysis—

Serine, the only amino acid needed for brain phospholipids/glycolipids is synthesized by 3-phosphoglycerate, the intermediate of glycolysis. Thus the predominant glycolysis-abbreviated citric acid cycle in the fetal brain is self-sufficient in generating also other elements needed for fetal brain development. One glucose molecule is utilized for generating 2 molecules of serine. This adds one more molecule of glucose expended for 2 molecules of brain's ceramide synthesized.

The Maternal Fatty Acid Transfer—

At this point, after analyzing the tremendous amount of fatty acid 'lay over' that is to be rapidly accomplished in the fetal brain during the last months of its life in utero, it is also a legitimate issue to discuss if the fetus must solely engage in its fatty acid synthesis, or if there is significant placental transfer of maternal fatty acids to be incorporated to form the longer chain fatty acids of the brain, or the adipose tissue triglycerides, and if so, by what proportion? The answer is evidence based. As was mentioned, the free fatty acid (FFA) transfer across the placenta is by simple diffusion as per the concentration gradient, and it is compounded by the fact that there are no cellular components on the maternal part of the placenta, the whole maternal compartment being pools of blood, whereas the fetal side is made of only the syncytio-cyto-trophoblast and the fetal vessel wall that the fatty acids have to maneuver through. This anatomical ease accomplishes significant fatty acid transfer needed for the human fetus, whose lipid lay-over in the brain is significant for its voluminous size to be ultimately achieved. The immediate fatty acid anabolic 'lay over' in needed sites probably also accounts for the fetus maintaining lower FFA concentration contributing to higher gradient for continued simple diffusion through the placental interface. Such rapid fetal lipogenesis is in contrast to the heightened maternal lipolysis at such time, to maintain ongoing high maternal-fetal FFA concentration gradient/transfer.

There is support for such theoretical ease of placental fatty acid transfer. It was demonstrated directly in the sheep (Van Duyne et al, 1960). When radioactive fatty acids were injected intravenously into the mother, they appeared in fetal circulation in few minutes. It can also be confirmed by the observation that the essential fatty acids were found in the adipose tissues of the new born infants (Bagdade and Hirsh, 1966).

It was hypothesized by past researchers, that the fatty acid composition of fetal adipose tissue shows that the synthesis de novo assumes greater significance in the later part in-utero. This was evidenced by the fact that towards the end of fetal life, the proportion of linoleic acid (an essential amino acid to be supplied by the mother) in the fetal adipose tissue decreases, and the proportion of palmitic acid (that can be synthesized by the fetus from acetyl-CoA via melo-nyl-CoA path way) increases, and at birth, the adipose tissue of the neonate contains only one tenth of linoleic acid, and twice the amount of palmitic acid compared to the adipose tissue of the adult. Accordingly it was hypothesized that synthesis de novo assumes greater significance, which was thought to be further supported by the fact that such fatty acid composition of the neonate closely resembles that of animals fed with high carbohydrate, and poor fat diet (N. B. Myant).

The above observations and conclusions by past researchers may infer that there can be predominant de novo fatty acid synthesis by the fetus at term, but it may not necessarily represent the specified proportion, in the manner implied. It is due to the following reasons, as put forth by the author inventor, validated by laws governing the kinetics of diffusion. Palmitic acid is synthesized by the fetus, and linoleic acid is not, but it does not rule out or clearly quantify how much palmitic acid is also supplied by the mother. The non-essential fatty acids are transferred also across the placenta, just like the essential fatty acids, without any differentiation (Leslie Myatt). It also does not rule out more of palmitic acid transfer. Maternal lipogenesis increases in linear fashion to a maximum at 25 weeks, when it continues as a plateau to term. Maternal lipolysis predominates in the later part of pregnancy, when there is ongoing de-esterification, and fat mobilization from the past-laid maternal fat depots, by the action of HPL. It can raise the circulating maternal free palmitic acid level that can cross the placenta by diffusion, through concentration gradient. The FFA levels reach a maximum of 4-5 times of non-pregnant levels in the later part of pregnancy. At 37-40 weeks of gestation, the maternal FFA levels increase exponentially by 60%. In an adult on balanced diet (like a pregnant woman), the adipose tissue subcutaneous fat contains oleic acid 47% (18 carbon mono-unsaturated fatty acid), palmitic acid 20% (16 carbon saturated fatty acid), and linoleic acid 11% (18 carbon unsaturated fatty acid). The adipose tissue of new born infant contains palmitic acid as 40%, oleic acid 25%, and linoleic acid 1% (Hirsch, 1965). The fatty acids pass through the lipid bilayer of cell membrane by simple diffusion, and as per the kinetics of diffusion, with the diffusion rate being inversely proportional to the molecular weight of a molecule, it is possible that though the 18-carbon unit oleic acid is present in higher concentration in the maternal fat depots and in the maternal blood, its diffusion across the placenta must be slower, compared to that of the 16-carbon unit palmitic acid with lesser molecular weight and smaller chain length, which after entering the fetus can be directly laid down to form the triglyceride molecules of the fetal subcutaneous adipose tissues. The proportion of linoleic acid in maternal plasma is lower, and in addition, its molecular weight is higher, and the chain length longer than that of the more predominant palmitic acid.

Moreover, the linoleic acid, in whatever amount it is derived from the mother, is more essential to be incorporated as a component of the structural lipids of the cell and the mitochondrial membranes, especially of the central nervous system, apart from synthesizing $C_{20}$ eicosanoids, prostanoids, leukotrienes, lipoxins, and arachidonates in the growing fetus. It can be viewed as a precious commodity not to be expendable otherwise, such as to be deposited in the adipose tissue.

It can be reasonably concluded that in a normal fetus the significant amounts of the maternal fatty acids are mostly laid down in the manner transferred from the placenta, and the fetus need not synthesize all that is required. Manipulation of maternal diet can also proportionally increase such transfer. Above all, as discussed, nature's device of exceeding maternal lipolysis through HPL of pregnancy is important and purposeful, as such scheme is also coupled with maternal utilization of FFA instead of glucose for energy, as the latter also needs to be diverted to the fetus. It also is worth noting that maternal high carbohydrate diet/circulating glucose can generate more triglycerides of her adipose tissues than the high fat diet (though the latter can directly contribute to the rise of circulating FFA in the maternal blood to be used as her fuel), most of the maternal tissues being resistant to insulin effects, whereas her fat depots and the placenta are not.

Maternal D-Glucose Supplements can Substitute for/Correct the Fetal Oxygen Lack, Via Maternal Lipogenesis, Resulting in 'Ready-Made FFA' Transfer—

It is clear from the foregoing paragraph that the maternal glucose is the raw material for the maternal fat depots from early on in pregnancy that is mobilized later on when the fetal demands are more in its phase of lipogenesis. It signifies the needed maternal circulating carbohydrate (by IV or dietary supplements) as the indirect element (for synthesizing maternal FFA) to be incorporated during fetal lipogenesis, and as the direct element of optimally transferred circulating glucose in the fetus that also engages in de novo lipogenesis. That means, the mother synthesizes FFA to transfer them 'ready-made' when the fetus is in its 'speed mode' of lipogenesis later on, obviating a tremendous need of glucose/oxygen by the fetus. At the conclusion, it is worth stressing that D-glucose substitutes for $O_2$ lack, with an oxygen salvage in the fetal brain as—(a) 400% of absolute oxygen salvage by 2-citrate diversion (instead of one) during sufficient glucose availability, for the rapidly accomplished fetal neuronal lipogenesis (or lipogenesis in general), and an additional 10% ATP/oxygen salvage through LGACC; (b) 33% by obviating the brain's utilization of FFA as fuel; (c)>33% by preventing ATP expending amino acid utilization which in turn needs more of full-fledged glucose/$O_2$ expending citric acid cycles also; (d) fetal gain of predominantly D-glucose-derived maternal FFA, thus obviating an otherwise exceeding fetal need of ATP/$O_2$. Such deduction helps to alleviate the possible concern that hypertonic D-glucose supplements seem disproportionately high compared to the amount of oxygen the fetus can avail. The glucose needed in this context is indeed disproportionately high in the rapid fetal lipogenesis compared to the oxygen needed, the glucose expenditure being 2.7 times more, but the oxygen needed for the same amount of ATP synthesis is 10% less than what is spent by the tissues elsewhere.

Fetal Adipose Tissue Lipogenesis—

Acquisition of fat in the subcutaneous adipose tissues of the fetus in the later months of pregnancy has multiplicity of purposes: physiological awakening of thermoregulation soon after birth to meet the unpredictable temperature fluctuations ex-utero, and the heat required being provided by the adipose tissue; the relative fetal hypoglycemia due to abrupt cut off of maternal provisions, and explosion of physical activity in all parts of the newborn including vigorous crying, such an absolutely vital activity in high tempo at birth and after, needing tremendous energy, and the neonate left to be solely relying on burning its fat stores. With the subcutaneous fat depots being sub-optimal, a significantly deprived IUGR baby devoid of baby-fat appears like a 'little adult' with a typical 'wizened look' which is not hard to discern.

The amount of glucose needed for the adipose tissue lipogenesis can be comprehended by acknowledging the fact that one molecule of triglyceride (TGD) is formed by the esterification of one molecule of glycerol with three molecules of free fatty acids. A new born infant has predominantly 16-carbon atoms palmitic acid (40%), or 18-carbon atoms oleic acid (25%) in its subcutaneous tissues. Accordingly, the three molecules of free fatty acids in the fat depot TGD need 24-27 acetyl-CoA or 12-13.5 glucose molecules, and inclusive of the ½ molecule of glucose needed for glycerol synthesis, just one TGD molecule needs 12.5-14 of glucose molecules in its formation. Based on such high toll on the available glucose, it seems that even in normal fetus, acquisition of FFA from the maternal compartment is invariable addition to fetal de novo synthesis. It was already noted that glucose expenditure in absolute amount is curtailed by 200%, and the absolute oxygen needed is 400%+10% less during rapid fetal neuronal lipogenesis, and such saving provision is applicable to the lipogenesis in the subcutaneous adipose tissues also, that is strongly in favor of therapeutic D-glucose supplements.

10. Improvement of ATP Synthesis, the Ultimate Key as the Ubiquitous Need for all Life Forms, and for all Life-Sustaining Subcellular Activities—

It was sufficiently stressed on multiple occasions how the citric acid cycle of the D-glucose metabolism is life sustaining through its pivotal role in ATP production. During fetal hypoglycemia and hypoxia, citric acid cycle will cease to be operative, and the D-glucose supplements improve not only fetal hypoglycemia but also fetal hypoxia to a significant extent as clearly evidenced by the foregoing objective data. It is also sufficiently clear that no biological function can ever happen without ATP in the fetus, and that the lack of ATP by the cessation of citric acid cycle can culminate in death, and lack of glucose can culminate in the cessation of the citric acid cycle. As a translation of what is herein deduced, it can be stated—for the fetus in-utero 'glucose is life', and life is being given to the fetus by its supplements.

The Other Important Source of Fetal Oxygen Supply: The Amniotic Fluid—

It seems rather phenomenal that the fetal umbilical vein alone can supply all the needed oxygen for the enormous growth accomplished by the fetus through a mere span of ten lunar months. It makes one contemplate that there must be other source(s) so far not suspected. The fetal aquatic environment can be such source. It seems against nature's intensions that the amniotic fluid (AF) being the sole fetal world, can be a dormant environment rather than an active contributor to the fetal growth and maturation in every possible manner. After all, the endless oceans can accommodate enough oxygen to support its vast aquatic life, and it is a testament to the fact that water is a satisfactory carrier of oxygen, as the focus of interest at this point is towards the myometrial and decidual interstitial fluid as a suitable milieu for oxygen transit, though through a short span of distance. The extracellular water of the vertebrates and the primate humans is known to contain similar electrolyte composition of the waters of the oceans (Goldberger E, 1980), such biological property reflective of the vast nature preserved through billions of years. Additionally, it was already confirmed by past researchers that AF does contribute to, and is essential for optimal fetal growth. It was also observed that the $PCO_2$ of the AF is very high (R. Lisle Gadd, 1970, and Nicolaides et al 1989), probably in the range of 48 mm/Hg (Rooth et al), mostly due to the virtue of its high solubility/diffusion coefficient. To substantiate the fact that AF can also be a significant source of fetal oxygen supply, it is important to understand the dynamics of oxygen and $CO_2$ carriage in the pregnant and non-pregnant systemic circulation, their release at the level of placental intervillous space and the tissue capillaries elsewhere, along with the dynamics of the partial pressures of oxygen and $CO_2$ at these sites. The complex biological principles of the terrestrial life forms are geared towards more efficiency of oxygen carriage/supply, by virtue of its natural gaseous existence in the lungs than it is as per its existence in lowered proportion in the aqueous ecosystem of the oceans. However, the fetal activity in its fluid world in solitude is after all far less than that of the innumerable aquatic forms of the oceans, restlessly in motion, yet gaining their fair share of oxygen.

The placental pools of maternal blood can be considered as the source of fetal exchange with the maternal blood, whereas the amniotic fluid can be considered as the source of fetal exchange with the maternal extracellular/interstitial fluid compartment that the AF closely parallels.

The Hemodynamics of the Feto-Placental Circulation—
The Pulmonary Gaseous Exchange in a Healthy Adult— the partial pressure of oxygen ($PO_2$) in the alveoli is 104 mm/Hg. The pulmonary blood equilibrates well with the alveolar gases, and hence the purified blood leaving the lungs also has the same $PO_2$ of 104 mm/Hg. However, after it is joined by the bronchial venous blood, it is reduced to 95 mm/Hg. Hence, essentially the systemic arteries terminating into the arterioles and capillaries have the same $PO_2$ of 95 mm/Hg.

The Gaseous Exchange at the Interstitial Spaces in a Healthy Adult— at the tissue interstitial spaces the $PO_2$ is 40 mm/Hg with effective filtration gradient of 55 mm/Hg at the arterial capillary level. The capillary and venous blood $PO_2$ equilibrate effectively with that of tissue interstitial space, and accordingly, the venous blood leaving the tissues has $PO_2$ of 40 mm/Hg. In fact, in the interstitial spaces the $PO_2$ could be more, when the rate of blood flow is increased. The blood flow, if increased by 400%, as of the muscle during muscular exercise, the $PO_2$ in the interstitial fluid can increase from 40 to 66 mm/Hg, and a maximum of even 95 mm/Hg can be achieved by markedly increased blood flow (Guyton A C). The uterine tissues during pregnancy with significantly increased vasculature, and exceeding metabolic activity can attain higher interstitial fluid $PO_2$, which however, was not explored as a targeted issue by past researchers.

Diffusion at the Tertiary Villi where the Fetal Umbilical Vessels Terminate—

The uterine artery has a $PO_2$ of 95 mm/Hg. However, due to the sinusoidal architecture of the maternal placental compartment conforming to an arteriovenous shunt, the $PO_2$ of the uterine spiral arteries falls to a level of 30-35 mm/Hg in the sinusoidal spaces (Pritchard J A. et al). However, in the uterine vein, the $PO_2$ again rises back to 40 mm/Hg (as in the rest of the maternal systemic venous circulation), being joined by the venous blood of the rest of the myometrium with its $PO_2$ probably higher before equilibration, a testament that the myometrial interstitial $PO_2$ is greater than 40 (40 being the $PO_2$ of the tissue interstitial spaces elsewhere) due to the greatly increased uterine vascularity. The foregoing set of numbers, and other similar data that follows, are shown in Table-5 of FIG. 17 (The hemodynamics of feto-placental circulation compared to the hemodynamics of non-pregnant controls).

The fetal umbilical artery (carrying fetal deoxygenated blood) has a $PO_2$ of 15 mm/Hg which after exchange with the maternal blood rises to only 27 mm/Hg in the umbilical vein (carrying fetal oxygenated blood). The Bohr effect can be summated as—'the hemoglobin-oxygen binding affinity is inversely proportional to the it ion concentration, and is also inversely proportional to that of the $CO_2$ concentration'. Accordingly, in the placental sinusoids there is shift to the left of fetal oxygen-hemoglobin dissociation/association curve (such shift being a reflection of higher $O_2$-hemoglobin affinity or association) due to the following (a) and (b) that can be described as—

(a) low $PCO_2$ of the sinusoids to start with (due to maternal hyperventilation) causes diffusion of $CO_2$ (whose diffusion coefficient is 20 times that of $O_2$) from fetal blood, thus reducing the $CO_2$ of the fetal blood proportionally, such lowered $CO_2$ of the fetal blood in turn causing heightened oxygen affinity to fetal hemoglobin, as per the Bohr effect,
(b) fetal blood becoming more alkaline as a result of (a) also causes heightened oxygen affinity to fetal hemoglobin, as per the Bohr effect.

The (a) and (b) resulting from Bohr effect are further aided by (c) in the following—
(c) low affinity of fetal hemoglobin to 2, 3-DPG (2, 3-diphosphoglycerate) (the 2, 3-DPG causes stability of deoxyhemoglobin). Due to the left-ward shift of fetal hemoglobin's oxygen dissociation/association curve in the placental sinusoids due to (a), (b), and (c), the fetal hemoglobin can carry more oxygen even at a low $PO_2$ of maternal sinusoids.

However, based on the plotting of oxygen-hemoglobin dissociation/association curve that is sigmoid, due to the prevailing low $PO_2$ in the sinusoids, despite the shift to the left of the oxygen dissociation/association curve, the fetal hemoglobin oxygen saturation will be only 68% (Longo 1972), and not 97% (the saturation of hemoglobin achieved in the lungs), as the $PO_2$ of 30-35 mm/Hg in the sinusoidal spaces does not correlate with the plateau of the oxygen-hemoglobin dissociation/association curve in the manner the plateau of the oxygen-hemoglobin dissociation/association curve correlates at the alveolar spaces with the $PO_2$ of the alveoli as high as 104 mm/Hg, facilitating maximum hemoglobin saturation. However, the low $PO_2$ of 27 mm/Hg of the fetal arterial blood is still effective for the reason that only 5 mm/Hg of $PO_2$ is sufficient to support the oxidative metabolic function of the cell, as a function of cytochrome oxidase (Rodwell V W et al).

The $PCO_2$ of the umbilical vessels show interesting values. The umbilical artery carrying fetal impure blood has $PCO_2$ of 48 mm/Hg, and the umbilical vein carrying the fetal oxygenated blood has a $PCO_2$ of 43 mm/Hg. The uterine artery $PCO_2$ is 32 mm/Hg during pregnancy due to maternal hyperventilation, and after an exchange with the fetal blood, it increases in the intervillous space to an average value of 38 mm/Hg.

As shown in the Table-5 of FIG. 17, the above equilibrated $PCO_2$ values of placental exchange show a marked difference from the equilibrated values of the systemic circulation of the non-pregnant controls, where the $PCO_2$ of the venous blood indeed equilibrates to 45 mm/Hg of the interstitial fluid, and the pulmonary deoxygenated blood is also equilibrated with that of the alveolar air, the latter happening normally with in a fraction of a millimeter, and within the $\frac{1}{3}^{rd}$ transit time of the pulmonary capillary blood (Guyton A C). It is due to the high diffusion coefficient of $CO_2$, and because of the fact that the $PO_2$ in the alveoli being very high, falling in the plateau range of the $O_2$ association (thus maximizing the Haldane effect of $CO_2$ release). At the placental level, the explanation is not as easy or as straight forward, for the equilibration that is seemingly not attained. The umbilical vein $PCO_2$ seems to have not equilibrated with the maternal sinusoidal $PCO_2$ despite the high diffusion coefficient of $CO_2$, and a lower prevailing maternal sinusoidal $PCO_2$, a more suitable milieu (due also to the natural fetal Haldane effect), for the expected equilibration than that of the capillary end of the systemic circulation.

In fact, there is no valid biochemical/physiological explanation to put forth, for failure of the umbilical vein $PCO_2$ to be lowered, as expected. But the situation may not be what it seems as. Due to very high diffusion coefficient of $CO_2$, the amniotic fluid (AF) $PCO_2$ probably attains very high values of 48 mm/Hg, as observed by the past researchers, and due to its instantaneous diffusion even through tissue planes, it can equilibrate easily with the $PCO_2$ of the traversing umbilical vein making it higher than the previously equilibrated lower levels after an exchange with the maternal blood at the intervillous space. Because of its volatility and high diffusion coefficient, the $CO_2$ diffusion from the AF into the cord blood can be instantaneous. The AF water diffusion is 50 ml/hour into the cord blood, during the mid/late pregnancy (Plentil 1961). It is significant to note that the diffusion capacity of $CO_2$ across the alveolar membrane, for long had not been measured, as the diffusion is instantaneous, and the difference across being immeasurable (Guyton A C).

Studies of acid base status of amniotic fluid (AF) was published by Rooth, Sjostedt, and Caligara (1961). They concluded that the pH and the $CO_2$ tension in the AF reflect corresponding values of the umbilical artery (in the range of 45-60 mm/Hg), and those of the fetal subcutaneous tissues, and that towards the end of pregnancy there is significant increase in the carbon dioxide tension of AF from 51 to 58 mm/Hg. Lower numbers were indicated in their later studies, though the exact numbers were not specified. It is questionable whether these observations of AF are the cause or effect of what are reflected in the umbilical artery, and in the fetal subcutaneous tissues. It is most plausible they are the cause. Except for fetal urine, there is no fetal contribution to the AF later in pregnancy, and its chemistry and volume are mainly a result of exchange with the maternal extracellular fluid, the AF being replaced every 3 hours. Accordingly, if the umbilical artery and the fetal subcutaneous tissues show similar pH and $PCO_2$ values as those of AF, it is due to the rapid diffusion of $CO_2$ from the AF into the fetal tissues and the umbilical cord, proportionally raising the values both in the umbilical artery and the vein. Even if the normal fetus generates more of $CO_2$, there is no physiological means of how it is reflected in the AF, except through fetal urine that $CO_2$ is not a constituent of. Hence it is most plausible that the $CO_2$ from the AF has diffused incessantly into the umbilical cord, and also into the fetal subcutaneous tissues, its original source being the uterine myometrium itself that surrounds the whole of the non-placental amnion.

It was previously discussed that the AF content of $CO_2$ can be very high, especially in oligiohydromnios. It is highly critical to explore how the $CO_2$ of the AF has attained such high value despite the low maternal $PCO_2$ of 40 mm/Hg in the uterine vein (45 in non-pregnant controls), and 32 mm/Hg in the uterine artery (lower than non-pregnant value of 40) and 38 mm/Hg in the placental intervillous space. The explanation can be as follows—The $CO_2$ is mainly the product of carbohydrate metabolism, especially of the citric acid cycle. The citric acid cycle is deemed to be very active in rapidly enlarging uterus all through pregnancy. Though the essential amino acids needed for protein synthesis are required to be supplied from the maternal diet, most of the non-essential amino acids can be synthesized by the mother from carbohydrate sources. Alanine and hydroxyproline are synthesized from pyruvate; glutamate and glutamine that make up the largest amino acid pool of the body are intimately associated with, and are synthesized from $\alpha$-ketoglutarate by transamination of $\alpha$-ketoglutarate. Aspertate and aspergine are formed from oxaloacetate; serine is derived from 3-phosphoglycerate; and glycine formed from glyoxalate. The uterus enlarges 16 times in weight at term from its non-pregnant state. This is mostly through hypertrophy (enlargement of the diameter/length of individual muscle fiber), and very less through hyperplasia (increase in the number of muscle fibers). There is great expansion of sarcoplasm of the enlarged muscle cells that store ATP, glycogen (synthesis of which needs significant number of ATP), and creatine phosphate that also stores ATP in an alternate form in the muscle. When proteins are synthesized, large portions of ATP are also used to form the peptide linkages that store energy in the linkages. These indicate that there must be very actively ongoing citric acid cycle in the uterine musculature for the generation of needed amino acids, and the needed ATP. There is evidence that there is enormous proliferation of mitochondria in each cell, for needed ATP production, and for ongoing glucose combustion. In a virtual uterine protein anabolic process, just as in the lipid anabolic process of lipogenesis, the carbohydrate catabolic process is intertwined. It increases the $CO_2$ generated by exponential amounts in the proliferating uterine musculature/decidua that can immediately diffuse into the adjacent AF. As the diffusion of the gas is directly proportional to the diameter of the space it diffuses into, it will be more into the amniotic cavity (with very high transverse and longitudinal diameter) rather than the uterine venous capillaries. This localized rise of $CO_2$ in the enlarging uterine interstitium can happen, despite the low $CO_2$ tension elsewhere in the maternal body. The amniotic cavity being a low resistant high volume chamber, and the solubility coefficient of $CO_2$ being very high (that is, $CO_2$ is physically and chemically attracted to the water molecule), the $CO_2$ diffusion that is instantaneous through any of the tissue planes (including the amnion), can be significant towards the AF, than into the uterine venous circulation.

As an alternative, dissociation of urea ($NH_2$—CO—$NH_2$) of the AF to $CO_2$ can be thought of, though it will raise toxic ammonia levels of AF which the fetus has to swallow. The fetal liver is capable of handling ammonia again entering through the gut, by reformation of urea. However, the biochemical support for urea dissociation into ammonia, after it is formed, is not found, except when exposed to urea splitting bacteria in the bladder, as in cystitis. Despite long standing uremia in an end stage renal disease, only blood urates, hippurates, indoles, benzoates, phenols, and polyamines are normally found to be elevated, but not the ammonia.

It may be noted that the uterine vein $PCO_2$ is 40 mm/Hg, whereas it is only 38 mm/Hg in the placental intervillous space (the former most probably the equilibrated value, such equilibration being instantaneous for $CO_2$). It indicates that there is definite higher non-placental myometrial contribution of $CO_2$ to the uterine vein which implies that myometrial interstitial $PCO_2$ must be greater than 40 mm/Hg to start with, that later equilibrated to 40 mm/Hg, joining with the intervillous blood as it drains into the uterine vein. In essence, the myometrial contribution of $CO_2$ to the AF is far greater whereas the fetal contribution is questionable The ultramicroscopic structure of the amnion demonstrates that there are significant intracellular and complex intercellular canalicular system all through the layers that transmit fluid from the maternal interstitial compartment to the amniotic cavity. However, there is selectivity, as AF does not truly represent all the constituents of maternal interstitial fluid. Yet, the respiratory gases of interest follow the laws of gaseous diffusion in the same manner: (1) in a gaseous mixture, (2) as dissolved gases in a solution, or (3) when changing from gaseous phase into a dissolved state in liquids. Paradoxically, the cell membrane is even less restrictive than the liquid barrier for the passage of the respiratory gases (Guyton A C).

And due to the avascular nature of the amnion, the $PCO_2$ of the interstitial fluid, and not the arterial capillary end, is relied on. It can be stated that through the traversing transcellular and intercellular canalicular system of the amnion, there is a continuum of the uterine interstitial fluid, of which the respiratory gases are part of. And if there is an occasional cell membrane intervening, it poses no barrier to either $O_2$ or $CO_2$. The following laws of Net gaseous diffusion into a chamber (Guyton AC) are herein applicable. The amniotic cavity in this instance can be considered as a closed fluid chamber amenable to similar laws of gaseous diffusion—

1. Greater the pressure difference ($P_1$-$P_2$) across, greater will be the diffusion (Henry's law of solubility coefficient of gases), that is, the diffusion is from higher to lower pressure, $P_1$ and $P_2$ being the involved higher and lower pressures respectively.
2. Greater the solubility of a gas (S), greater will be the diffusion (Henry's law of solubility coefficient of gas).
3. Greater the cross-sectional area (A) of the chamber of diffusion, greater is the diffusion.
4. Greater the molecular weight of the gas (MW), lesser will be the diffusion, that is, the rate of diffusion is inversely proportional to the square root of its molecular weight (Graham's law of gaseous diffusion).

Based on the above laws of gaseous diffusion, the net diffusion of $CO_2$ is 20 times that of $O_2$, because of its very high solubility coefficient (S) that makes it to be chemically and physically more attracted to its solvent, in this case, the water molecule. Accordingly, it is not a surprise, nor it is unexplainable, if the AF content of $CO_2$ has been found to be very high.

The uterine myometrium being the source of the high AF $CO_2$ content is further supported by the fact that in IUGR, the AF was found to contain exceedingly high amounts of $CO_2$ (as was documented by Nicolaides et al, 1989), but as per the foregoing biochemical discussion in the previous sections, it is very obvious that in IUGR, the fetus is deprived of both glucose and $O_2$, the invariable elements needed for $CO_2$ production, and anaerobic glycolysis generates no $CO_2$. Hence the source of AF $CO_2$ can be only the myometrium, and never an IUGR fetus, though fetal oliguria and oligohydromnios can concentrate it within the AF (see the section 'Fetal oliguria and oligohydromnios').

The Possible Oxygen Diffusion into the AF

The above deduction undoubtedly proves the possible high $CO_2$ diffusion from maternal extracellular spaces of myometrium into AF. As its rise in the AF is not subtle due to high solubility/diffusion coefficient, and was well documented, though the source was not explored being implied as fetal (Gadd R L, 1970; Nicolaides et al, 1989), it nevertheless gives room to contemplate such possibility with oxygen diffusion also, though not with the same ease or proportion. It was already mentioned that the interstitial fluid $PO_2$ can approach a maximum of 95 mm/Hg, if there is significant increase in the rate of blood flow, and of the metabolic activity of the organ (Guyton A C), and both are inevitable during pregnancy. The blood flow is augmented in exceeding proportions because of the shunt effect of the placenta that decreases the peripheral resistance markedly in the uterine artery and its tributaries supplying the whole of the uterus. It follows that the $PO_2$ of the interstitial compartment of pregnant uterus can be higher than 40 mm/Hg (the value of interstitial $PO_2$ elsewhere), and it is evidently much higher than the $PO_2$ of the placental sinusoids. Though historically the amnion overlying the placenta is considered as the significant contributor to the volume and to the contents of the AF, as far as oxygen diffusion is concerned, the non-placental uterine area conforms to a source of higher oxygen diffusion secondary to higher $PO_2$, and as a result higher net diffusion gradient into the non-placental interstitial uterine compartment, and then into the AF (further aided by the benefit of the in-vicinity placental shunt effect that actually pulls the blood from uterine artery, and from the systemic circulation).

Based on the Above Formula of the Rate of Net Diffusion of a Gas, the Following Observations for the Diffusion of $O_2$ into AF can be Made—

1. The $PO_2$ of the uterine interstitial fluid can be higher during pregnancy, in areas surrounding the non-placental amnion. This is in contrast to the low oxygen pressure in the AF itself. This will increase the net diffusion, due to increased pressure gradient of oxygen $(P_1-P_2)$ across the amnion channels. The selectivity of the amnion may not be applicable to the gases of biological interest, and to the laws of gaseous diffusion universally governing the kinetics of gaseous diffusion, either through solids or fluids, and either into gaseous or fluid compartments/chambers.

2. The cross-sectional area (A) of the amniotic cavity (either longitudinal or transverse), configured as a chamber, is very high, thus increasing the rate of diffusion of $O_2$.

3. The molecular weight (MV) of $O_2$ is low (32). This is inversely proportional to the rate of diffusion. With regard to free molecules not attached to others (unlike $CO_2$, $O_2$ is a free molecule), linear movement at high velocity is possible (Guyton A C).

4. With regard to the distance of the gas to be traveled, in this context, the area of importance is the AF very adjacent to the uterine wall itself where the fetal face and the oral area are located, and the fetal swallowing is effectuated. It is the narrower and the highly vascular lower uterine segment in the cephalic presentation. Hence, the distance needed to travel by the molecular oxygen is very less. Obviously, as the oxygen travels towards the center of the amniotic cavity, its effective AF concentration probably diminishes due to a factor of dilution. Even after engagement, until the descent during labor when it touches the pelvic floor, deflexed attitude of the fetal head is prevalent which makes its facial approximation with the uterine wall more feasible. This causes the fetal swallowing of AF with higher $O_2$ content, before the gas is diffused.

Even after the descent and flexion of the fetal head, in the commonly prevailing left occipito-anterior position, due to the high concavity of the sacrum and the similar curvature the uterus tends to maintain below the pelvic inlet during labor, the fetal oral area will be still facing the concavity of the posterior pelvic cavity below the overhanging promontory of the sacrum, making the fetus swallow the AF very close to the uterine wall. It can be further said that the neonatal rooting reflex (so strongly prevalent in the neonates, and is most basic for their instinctive acts of cooperatively seeking the maternal breast, suckling, swallowing, and survival) must have been sufficiently rehearsed by the fetus in-utero, making it reflexively turn its head towards that side, whenever the uterine wall/AF motion touches its either cheek (by maternal position or movement). This helps the mechanism of fetal swallowing taking advantage of the uterine disposition that is closest to its cephalic orientation, even in complete head-flexed attitude. It obviously facilitates the fetus swallow more of oxygen and the solutes of AF that are the products of diffusion through the amnion, and in the same token, less of its urine excreted at the opposite uterine pole will be swallowed, as also more of it will be exchanged with maternal circulation before equilibrated with the AF of the cephalic pole. The IV hypertonic or the transamniotic isotonic glucose supplements, apart from improving fetal strength for swallowing, will also enhance the sweetness of the AF, making the fetal swallowing more voluntary. The normal new born behavior as observed by past researchers is a testament to all the above statements. The awake and a hungry newborn exhibits rapid searching movements responding to tactile stimuli, as far away as the sides of the jaw and the head (Brazelton 1986). The new born also has fine appreciation of taste, exhibiting preferential suckling response (with overall less pauses) when fed with different concentrations of sugar solutions, and great resistance to saline feeds (Johnson & Salisbury, 1975), more of such experiences increasing the complexity of the responses.

What makes the oxygen diffusion across the cells of the amnion, and the interstitial fluid that permeates its canalicular system, a possibility—

From the intervillous space, to reach the fetal hemoglobin, oxygen has to traverse the following barriers before being bound to the fetal hemoglobin—

1. Maternal plasma, 2. Syncytiotrophoblast, 3. Cytotrophoblast, 4. A compact villous stroma made of fibroblasts, delicate collagen fibers, and of Hofbauer cells, 5. Fetal capillary wall made of fully mature endothelial cells, and 6. Fetal plasma.

It means to say that before oxygen enters fetal hemoglobin, it traverses through maternal and fetal plasma interstitial fluid, and in addition, few cellular compartments. Similarly, oxygen can effectively traverse the membranous barrier of the amnion.

High AF Amino Acids—

It is worthy of note that AF amino acid concentration is same as that of maternal plasma (R. Lisle Gadd), whereas glucose is present in lower concentration. The proteins are also lower. It is obvious that the amino acids have diffused into the AF from the uterine myometrium. Due to enormous growth and enlargement of the uterus to 10-20 times its non-pregnant size, there has to be high amino acid turn over in the organ. Such high amino acid turn over, and the increased concentration as a result, are deemed to be reflected in the uterine interstitial fluid, and in turn in the AF (most probably by transit through intracellular and complex intercellular canalicular system of the amnion, as a cell pore size is much smaller than the molecular size of any amino acid). It is similar to the high trafficking of a raw material, needed for a local manufacture. The increased demand/metabolic rate/turn-over of a substance in conjunction with increased vascularity of an organ, can accelerate its diffusion into the organ. Similar effect can be observed with respect to oxygen diffusion into the myometrium, also subject to similar setting, as oxygen is also a needed raw material for the profoundly increased mitochondrial citric acid cycle in each of the myometrial cells, saving ATP and glycogen. It was adequately stressed that cell/fluid barriers are deemed to be insignificant for oxygen diffusion, and hence its simple diffusion should far surpass the amino acid transit via the amnion. The diffusion of $O_2$ should be more efficient also for the reason that the oxygen having lower molecular weight than the amino acids, yet has to encompass smaller span of distance to exert its desired effect over the fetus, and AF collection for measuring amino acid levels must have been randomly drawn, not necessarily from the AF adjacent to the uterine wall, and their levels are still equal to the maternal interstitial fluid.

The above matter of oxygen diffusion sufficiently into the AF is scientifically grounded, based on:

1. The standard laws of gaseous diffusion (as elaborately outlined earlier in this discussion favoring oxygen diffusion) across cell membranes and body cavities.
2. The presently available knowledge of the gaseous exchange at the lung and tissue capillary level based on the partial pressures of concerned gases, and their operative net diffusion gradient (the partial pressure and diffusion gradient of $O_2$ during pregnancy deemed higher in non-placental myometrium/decidua).
3. The proved high $CO_2$ content of AF by many past researchers (that was based on laws of gaseous diffusion and exchange of biological gases, as stated in 1 and 2 above).
4. The AF amino acid content approximating that of maternal extracellular fluid, so reflected due its high turn-over in the adjacent uterine interstitium during pregnancy. Similar higher turnover in the myometrium is expected of oxygen also, with the laws of diffusion in fact favoring better oxygen diffusion than that of the amino acids.
5. The high $PO_2$ of non-placental uterine interstitium further enhanced by the 'in-vicinity' placental shunt effect.

It can be concluded that the maternal D-glucose supplements will increase the AF glucose content (also relieving the existing oligohydromnios, in a similar manner polyhydromnios is observed in maternal DM), and the improved volume as well as the palatability will heighten fetal swallowing of AF that contains more of glucose with sufficient amounts of oxygen also for its aerobic oxidation (the intravenous hypertonic D-glucose therapy that is initially implemented can also supply needed ATP and the energy needed for swallowing, even in a previously moribund fetus). The isotonic D-glucose transamniotic supplements have similar direct effects.

The Portal Circulation and the Fetal Liver Functioning Like 'Fetal Lung'—

The fetal interior exposed to the amniotic fluid is substantial. The high $CO_2$, also swallowed by the fetus through AF will not adversely affect the hemoglobin-$O_2$ binding, as otherwise dictated by Bohr effect. Once $CO_2$ enters the portal circulation, it forms carbonic acid and then bicarbonate, thus lowering both $CO_2$ and hydrogen ion concentration, so effectuating fetal hemoglobin-$O_2$ binding. It is the bicarbonate so formed becoming the source of $CO_2$ for liver urea synthesis. The merging of the portal blood with that of the inferior vena cava further lowers the blood's hydrogen ion concentration, facilitating more of $O_2$-hemoglobin binding, thus highly enriching the $O_2$ content of the vena caval blood before it reaches the right atrium. The fetal portal system and the liver sinusoids indeed are functioning as 'fetal lung', disposing of $CO_2$, and maximally effectuating $O_2$-hemoglobin binding. The indisputable support is—despite the large volume of highly deoxygenated blood within the vena cava, derived from the lower fetal body, after the entry of portal blood, the vana caval blood is as well oxygenated as the blood of the umbilical vein, which can only happen with a significant contribution of bound and unbound $O_2$ from the merging portal blood also. However, the pulmonary deoxygenated blood is not oxygenated to any extent in the lung similarly permeated by AF, Bohr effect being not facilitated, due to persistent high $CO_2$ and hydrogen ion concentration in the traversing blood. However, it is favorable, as any rise in $PO_2$ of the pulmonary blood will drop the flow into the ductus arteriosus. $O_2$ is a potent pulmonary vasodilator, and hence a rise in $PO_2$ of the pulmonary vascular bed can make it a lower pressure circuit, thereby dampening the flow of ductus into the aorta (and possibly the leftward flow through foramen ovale also). However, once the pulmonary blood enters the left atrium, by merging of the highly oxygenated blood from the right atrium, the $CO_2$ and the hydrogen ion concentration of the blood will fall, and the unbound oxygen coming in from the pulmonary circuit may bind with hemoglobin, the Bohr effect now being operative. The initial hemoglobin-$O_2$ binding can cause more of binding, such normally 'facilitative' or 'cooperative' oxygen-hemoglobin binding making the emerging left ventricular blood highly oxygenated.

The Biochemical Aspects of the Maternal Carbohydrate Metabolism

It has been generally assumed that carbohydrate tolerance is impaired in pregnancy, and thus pregnancy constitutes a diabetogenic stress to the mother. The fact that diabetes is first manifested during pregnancy, and that the diabetic women frequently require increasing amounts of insulin as pregnancy advances, and the occurrence of glycosuria during pregnancy—are all cited as evidence to support this view. It is possible that it could be present earlier but uncovered during pregnancy, as it is a milestone event in time, and it is common rather than an exception that the mother as a whole is deservingly put under microscope, making the incidence of gestational diabetes seem more than its actual numbers.

However, interestingly, the normal fasting or post prandial/post glucose challenge blood sugar shows very close parallelism (in its values and fluctuations) with the non-pregnant controls during pregnancy, in marked contrast to levels or patterns prevalent in diabetes itself.

Insulin Resistance

Pregnancy is characterized by major physiological adjustments affecting every system of the body. The changes are frequently in a scale otherwise unseen in healthy non-pregnant controls, and can be legitimately subject to diagnostic concern and confusion. A major change and a matter of great intrigue is the normally disproportionately elevated maternal serum insulin levels in the face of perfectly maintained blood glucose levels (in fact at a slightly lower level than the non-pregnant controls). Many other maternal serum values of clinical significance also show deviations that have to be interpreted with discretion.

There is reason for believing that many of the maternal changes are purposeful and mostly harmless, being directed to the welfare of the fetus. The fetal status in pregnancy is no doubt physiologically exalted, as obviously it is the only way that the theme of pregnancy can be accomplished. 'The fetus thrives at the expense of the mother' can be clinically evidenced by the fact that even when the mother is profoundly anemic due to iron deficiency, her fetus has grown well, and is rarely anemic. The author inventor had seen many such cases where the mothers' tongues were papery pale, with their hearts pounding in hyper-dynamic circulation that gave room for concern how they ever survived pregnancy. But the delivered fetuses were pink to their extremities, as evidently the placenta concentrated iron very efficiently. It can seem as though the placenta worked solely and faithfully for the fetus, and conspired against the mother.

The Insulin Peak and the Insulin Antagonists—

Blood insulin levels rise through pregnancy both in fasting state, and after glucose load. The insulin peak is especially dramatic late in pregnancy (from 125 μU of early pregnancy, it can rise in mid pregnancy to 175 μU, and it can be 340 μU in late pregnancy) (Spellacy W N et al, 1963 and 1965). This paradox of increased amount of circulating insulin while normal glucose levels are prevailing in the pregnant organism, is due to the presence of anti-insulin factors like glucocorticoids, estrogen, and the progesterone, but the most important insulin antagonist, as specified earlier, is the HPL, a polypeptide produced by the syncytiotrophoblast of the placenta. HPL produced by the placenta is only present in the maternal blood, but not in the fetus. Other possible culprits contemplated by past researchers are—(1) increased levels of xanthurenic acid—it is an accumulated tryptophan metabolite that can bind to insulin decreasing its biologic activity, when the normal metabolic pathways of tryptophan are altered due to pyridoxine deficiency, usually prevalent in pregnancy (Zartman E R et al, and Spellacy W N. et al, 1972); (2) decreased chromium levels in pregnancy—chromium couples with insulin and may potentiate its metabolic activity in the peripheral tissues (Davidson I W F, Burt R L, 1973); (3) Freinkel et al (1958) and Posner B I et al (1974) proposed that placenta destroys insulin with at least two soluble insulinase enzymes, and thereby there is need for more of its production.

But the possible role of the exponentially elevated maternal FFA levels, and the events encompassing it and others, in causing maternal hyperinsulinemia, as contemplated in this writing by the author inventor, are discussed in the subsequent paragraphs.

HPL—

HPL produced in enormous quantities by the placenta has great physiological significance during pregnancy. It causes increase of FFA content in the maternal circulation by mobilizing the lipid stores, and in this respect seems to be more dominant than insulin, because insulin is anti-lipolytic. Once there is increased FFA, the maternal tissues utilize more of it (in the adult human the FFA is the first fuel to be catabolically used—Mayes P A) sparing glucose to be diverted to feto-placental circulation which is a slower process, because the amount of glucose spared from all tissues of maternal body is much more and generalized, compared to the substantially lower amounts of glucose getting into the fetus only through the narrow channel of the umbilical cord (thus the maternal body intended to be acting as a glucose reservoir, for the sustained glucose supply to the fetus). As long as there is persistent normoglycemic levels of circulating glucose, it is expected to release insulin from maternal pancreas. However, the HPL, apart from mobilizing FFA from fat stores, also prevents insulin's effects on the cell membrane 'carrier transporters' of glucose in the maternal tissues, while the released free fatty acids further compete with glucose for their own utilization by the maternal tissues.

The Maternal Pancreatic Response—

The maternal pancreas is only conditioned to produce insulin as a glycemic response, but does not perceive that insulin and also glucose are not being effectively used by the maternal tissues, except the placenta, and the fat depots. However, this fundamental homeostatic control though somewhat distorted during pregnancy is still not ineffective, because the rise of insulin proportional to glucose level (indeed a disproportionately high insulin rise) is needed to enable facilitated diffusion at the utero-placental interface, and to build maternal fat depots from early on, and is very relevant to enact the theme of pregnancy.

The Lack of Placental Resistance to Insulin Even in Diabetic Pregnancy—

As explained before, the placental tissues are deemed to be sensitive to insulin action even in diabetic pregnancy, as evidenced by fetal macrosomia, despite the maternal insulin resistance. Marshall R N et al and Posner B I et al in 1974 demonstrated that the placental binding protein of insulin is similar in molecular weight and in function to the insulin receptor protein found on the cell membranes of the maternal fat and the liver cells, that are also unaffected by the subject's insulin resistance, as obesity in diabetes is common rather than an exception.

The Stimulus for Maternal Lipogenesis—

(1) Insulin—Insulin normally is lipogenic. Hence, insulin rise is also important for the needed maternal fat deposition. It was previously mentioned that Vallence-Owen in 1965 had suggested that during insulin resistance as in diabetes, there is impaired uptake of glucose by the muscle, but not by the adipose tissues. It seems to be true also in pregnancy, as the essential fat deposition is not impaired, as would be expected of maternal insulin resistance. Such mechanism of fat deposition is obvious even in pre-diabetes, as in these patients, more the insulin resistance, more can be the manifest obesity.

(2) The biochemical factors—Biochemically, it is obvious that though hormone sensitive lipoprotein lipase (that is responsible for lipolysis) inhibition by insulin is impaired, the insulin's action on lipogenic enzymes like acetyl-CoA carboxylase, ATP-citrate lyase, and fatty acid synthase has not seemed to be similarly undermined. This makes possible in the maternal tissues for both lipogenesis and lipolysis to be simultaneously ongoing, but at a different degree during different times. The maternal lipogenesis is dominant when the fetal FFA demands are less, almost showing a linear progression up to $25^{th}$ week, when the curve gets plateaued until term. The mother seems to de-esterify these fat depot stores later on during pregnancy when the circulating FFA levels are found to be maximum during 37-40 weeks. It correlates with peak fetal lipogenesis, when the fetus can incorporate at this time, the maternally derived FFA. In response to the same amount of hyperinsulinemia, the maternal lipid metabolic response during each trimester of pregnancy had proved to be different. In the second trimester as during the post-partum, the insulin's inhibitory effect on lipolysis seems to be 51% of non-pregnant controls, whereas in the third trimester it seems to be only 30% (Sivan et al, 1999) making maternal lipolysis maximally manifest during this period, for rapid fetal fat accretion, incorporating the maternally derived FFA.

(3) Hormonal effects—Estrogen rise during pregnancy also seems to play a very important role in fat deposition, as it is very obvious that this sex hormone is what sets apart the sexual characters of the female body (apart from the absence of androgens), and the same fat distribution can be evident in men castrated before puberty. It is obviously an evolutionary accomplishment of the races so as the females, needed for multiplication of the species, are not to be expendable biologically, as a result of intermittent food shortage (NB. Myant). The presence of progesterone during pregnancy shall have added effect to lipogenesis acting at the hypothalamic level (F. E. Hytten).

The Author's Theory to Account for the Manifest Maternal Hyperinsulinemia During Normal Pregnancy—

1. The Role of the Circulating FFA of the Maternal Blood in Causing Maternal Insulin Resistance and Hyperinsulinemia—

(a) The very high maternal insulin levels when corresponding maternal blood sugar per deciliter is normal, the latter steadily consistent with non-pregnant controls through gestation, give the impression that the insulin peak is a deliberate overshoot, being manifestly exaggerated, despite the allowance given to all anti-insulin factors deemed to operate during pregnancy. It must be purposeful, as insulin levels and effects during pregnancy are not only related to glucose homeostasis, but also seem to be related to lipid homeostasis. Unusually high lipogenesis needed for building maternal fat depots is primarily induced by enzyme-stimulating action of insulin. Such insulin elevation is effectuated because glucose is not the only insulin stimulant. Increased level of FFA in the blood is also an insulin stimulant, such FFA increase as already stated, being primarily induced by the action of HPL. However, in this situation, the presence of both glucose and elevated FFA levels of blood are needed for the pancreatic insulin release (G. Grodsky). Such combination is accomplished, and it prevails all through pregnancy, as glucose levels are maintained as well, by the HPL antagonizing maternal glucose utilization in the muscle. The FFA level is remarkably high in pregnancy that reaches a maximum in the later part that also correlates with the towering peak of insulin surge at this time. At 37-40 weeks of gestation, the FFA levels are 1226 µEq/L (768 µEq/L in the non-pregnant controls), a 60% increase (Burt, 1960). Insulin peak during late pregnancy is 340 µU/dl, whereas it is only 125 µU/dl during early pregnancy (Spellacy W N et al, 1965), as earlier mentioned. Such dramatic increase of FFA can create an obese adipocyte, in the setting of rapid onset hormone regulated maternal lipogenesis.

(b) In the adult human the FFA is the first fuel to be catabolically used, thus sparing glucose oxidation, and in that manner, the elevated FFA can block the effects of insulin in the insulin-sensitive peripheral tissues, especially the muscle (Mayes P A, Regulation of carbohydrate & Lipid Metabolism, page 263: Text book of Harper's Review of Biochemistry', $19^{th}$ edition). Consequently, it triggers a cascade of events, such as hyperinsulinemia and the insulin receptor down-regulation. When pronounced, it can set up a stage for gestational diabetes, which following postpartum—(i) may resolve, in case the insulin receptor down regulation (IRDR) is reversed, when the HPL induced FFA peak regresses, (ii) may not resolve, if the IRDR is not reversed. The consequence can be an interplay between hereditary factors vs. others.

The maternal insulin peak seems to be the summative effect of anti-insulin factors (that are classically attributed to causing hyperinsulinemia), and also due to elevated FFA levels, as the insulin peak mirrors more of the heightened FFA levels late in pregnancy, than the steady state of blood glucose levels throughout. It is not to overlook the fact that the insulin peak also correlates with the blood glucose peak that is not as dramatic as the FFA peak, and that without insulin resistance on glucose homeostasis, such insulin peak would have resulted maternal hypoglycemia.

In the second trimester as during the post-partum, the insulin's inhibitory effect on lipolysis seems to be 51% of non-pregnant controls, whereas in the third trimester it seems to be only 30% (Sivan et al, 1999) making maternal lipolysis maximally manifest during this period, for rapid fetal fat accretion. The lipolysis of third trimester is due to (many of) anti-insulin hormonal effects, that rise the FFA levels to the peak, which in turn can rise insulin levels, as insulin's inhibition on lipolysis is blunted, but not the stimulatory effect of FFA levels on insulin secretion (in a manner similar to glucose-insulin homeostasis, that insulin gets secreted as glycemic effect, while glucose itself is insensitive to its effect).

2. The Maternal Fat Deposition in Causing Maternal Insulin Resistance and Hyperinsulinemia—

The maternal lipogenesis shows a linear progression from very early on, up to $25^{th}$ week, when the curve gets plateaued until term. The fat deposition during pregnancy is mostly central, a state that resembles non-pregnant central (trunkal) obesity. It can be speculated that the fat deposition (central obesity) acquired in pregnancy in such short term (due to many factors as seen in the preceding subsection of 'stimulus for maternal fat deposition') and at such rapid pace can also be accompanied by its associated pervasive features of insulin-resistance and hyperinsulinemia, just as seen in non-pregnant obesity, mainly triggered by the obese-adipocyte, that is typically seen in central obesity. In non-pregnant central obesity, the molecular link between obesity and insulin resistance/effect seen in tissues such as liver, muscle, and in the fat tissue (Jeffrey S. Flier et al) can be explained as due to: FFA that are increased, and capable of impairing insulin action on glucose receptor sites; resultant hyperinsulinemia itself that can induce cell membrane insulin-receptor down-regulation; intracellular lipid accumulation in the adipoctyes, creating an 'obese-adipocyte', obesity generally being caused more by increasing in cell size rather than in the number of the adipocytes; various peptides including cytokines produced typically by obese-adipocytes are capable of modifying insulin action, an obese adipocyte being not only a lipid storage unit, but also an active endocrine cell that releases numerous agents in a regulated fashion. A factor called 'resistin' secreted by adipocytes can increase insulin resistance in this setting.

In essence, the exceedingly high circulating FFA, the rapid-onset maternal fat deposition, and the obese adipocyte, all associated with pregnancy, can in unison exert powerful inhibitory effect on normal insulin action, and can explain the inordinately high insulin peak. Such mechanism of fat deposition and obesity being also obvious in pre-diabetes, and the fact that weight reduction even of modest nature can increase insulin sensitivity—are the testaments to what are likely induced by obesity and obese-adipocytes, as stated above. The recently evolved concept of metabolic syndrome, has central (abdominal) obesity, hyperlipidemia, and insulin resistance as three of the five features in its constellation of associated metabolic disturbances.

It can also be understood now that the maternal adjustments, as can be deduced from the scope of the discussion, are the result of an already over stretched adaptation even during normal pregnancy, being so many operational devices put together, to divert the circulating glucose to the fetus, which can not be enabled any more during fetal IUGR of placental insufficiency. Maternal IV glucose supplement is similar to, but accomplished by easier means than what the maternal adaptive devices in pregnancy are trying hard to achieve. Glucose tolerance curves after IV glucose load show slightly lower values in all stages of healthy gestation, compared to the non-pregnant controls. Inferentially, there is evidence basis to believe that IV glucose supplements are well tolerated during pregnancy than in non-pregnant state that provides a sound basis for effectuating such clinical contemplation, however careful to stress in patient education that insulin resistance is inherent to pregnancy, and is inevitable.

How the Induced Therapeutic Maternal Hyperglycemia is Different from Diabetic State—

1) In the setting of fetal IUGR, following the therapeutically induced maternal hyperglycemia with IV D-glucose, the induced hyperglycemic peak is transient, and is of a very short duration, a maximum of an hour, mostly simulating an IV glucose challenge test, or the postprondial peak after a heavy meal, whereas in uncontrolled diabetes the hyperglycemic peak is persistent.

2) In diabetes, fetal hyperglycemia has resulted, whereas following the therapeutic maternal hyperglycemia in an IUGR pregnancy, the fetal hypoglycemia is corrected.

3) There is accompanying maternal ketosis in uncontrolled diabetes that is responsible for fetal anamolies, if such ketosis is significant during the first trimester, but ketosis is not part of the clinical picture in therapeutic maternal hyperglycemia.

Accurate Management of Fetal IUGR by Reliable Menstrual History—

Conventionally, the obstetric follow up and delivery of normal and at-risk pregnancy are done by the back-up of a reliable menstrual history as well as diagnostic imaging. Some can be insistent about delivering on a particular gestational week of pregnancy (as also advocated in the delivery protocol of this writing), which can be best determined by reliable menstrual history. Outside the clinical context of fetal IUGR, such stringent calculation is needed for managing a post-dates fetus also.

History— when the menstrual cycle is not of typical 28 days, the 'pregnancy wheel' may not give the exact gestational age, as the wheel is geared to the typical 28 days cycle. A few days correction needs to be done—an addition or a subtraction, based on whether the cycle is longer or shorter, which makes it easy to falter or go wrong as it is the case when two different corrections need to be applied, instead of one common correction directed to either situation.

Said correction or adjustment of days should be done based on ovulation timing, which is usually 14 days before the first day of the next expected menstrual period (or 14 days before the date of the missed period in the event of pregnancy). It is because the life of the corpus luteum is 14 days, unless the event of conception dictates otherwise, to prolong its continued function of progestational support, until the placenta completely takes over such function.

As long as the menstrual cycles are regularly timed, one should always endeavor to correct the deviant duration of the cycles. For a shorter cycle, for example a 23 days cycle, with a difference of 5 days from the standard 28 days cycle, 5 days are counted back or subtracted from the day-1 LMP. For a longer duration cycle, such as a 32 days cycle, 4 days are added to the day-1 LMP. It can be simply explained to a medical student or a junior, as—compared to the standard 28 days cycle, a shorter cycle is rushed to go forward in time (that is, with reference to the variable pre-ovulatory phase), and hence the days have to be counted back or subtracted from the day-1 LMP, and the vice versa, for a longer cycle. Correcting LMP may imply that the LMP is at fault. On the contrary, that is, it is properly timed; but amenable for correction. It is the ovulation that is rushed or delayed, yet it is written on stone and obviously not amenable to change, and being positioned like the sun within the solar system, the events and rules of the conception revolve around it. Indeed, LMP is a proxy chosen for pregnancy dating, and it is also a proxy amenable for correction, directed to an otherwise improper dating. Similar correction can be done to the EDD also, but it is a better proposition to aim the correction to what is at fault, that is, the menstrual cycle itself. Whenever a deviant duration of regularly timed cycles is encountered, a 'Corrected LMP' (CLMP) should be conventionally mentioned next to it, and the patient notified to always inform that date as the LMP, as it is possible that her labor (or the presumed labor) may be encountered by an unfamiliar obstetrician (including those staffing an ER) who may not have the chance to go through the details in her chart. It is also a part of better management goals, to instruct the patient—to inform about the treatment she is on, and the earliest gestational week that her delivery was proposed to be best contemplated, allowing reasonable 'catch up' of fetal growth, unless there is a compelling indication to act differently, like an impeding fetal demise. Only corrected LMP and not corrected EDD can make such planning feasible, as corrected EDD is clearly irrelevant in this situation, as it may be irrelevant in many other clinical situations also. It is in the patient's best interest that her regular obstetrician is consulted.

When the Menstrual Cycles are Regularly Timed, but are Deviant in Duration, the Following is Applicable—

'To get the corrected LMP (CLMP), note the difference in days between the patient's menstrual cycle and the standard 28 days cycle, and count back those days from the day 1 LMP of a rushed shorter cycle, and add those days to the day 1 LMP of a lagging prolonged cycle', or else 'count back 28 days from the date of the missed period, whether the cycles are shorter or longer.'—Sumathi Paturu's rule of Corrected LMP.

With the corrected LMP (CLMP) date configured in the manner as specified above, one can use the 'pregnancy-wheel' or the Nägele's rule' to calculate the EDD from the corrected LMP. The Nägele's rule states—to get the EDD, add 7 days to the first day of LMP, and count back 3 months. The Nägele's rule is very helpful when the 'pregnancy-wheel' is not handy.

Clinical Bed-Side Evaluation—

To avoid observer bias, a single blind study can be used for the research of any obstetric theme, in which unmarked paper strips can be used to mark the fundal height that can later be measured over a marked calipers. Or, the paper measure strip can also be used, one side unmarked for blinding. In obstetrics, a placebo effect on the fetal subject or the mother is not an expected clinical obstacle.

Ultrasound Evaluation of Gestational Age

When dates are uncertain, and as ultrasound estimation of fetal age by weight is discrepant in IUGR, standard ultrasound measurements may provide additional information about the correct gestational age of the fetus for properly planning an early delivery true to the gestational maturity.

Due to the brain sparing effect of IUGR, the ratio of the head and the abdominal circumference (HC/AC) is in the $90^{th}$ percentile in 60% of cases of fetal IUGR. The Trans Cerebellar diameter (TCD) may be valuable (as the nomogram of Goldstein et al, 1987) in an IUGR pregnancy, and it remains consistent throughout, independent of fetal IUGR. The gestational age (in weeks) corresponds with the TCD in millimeters until 22 weeks, but the TCD accelerates after. Ossification of Distal Femoral Epiphysis Occurs Predictably Around 32 Weeks, and the Proximal Tibial Epiphysis Ossifies Around 35 Weeks.

These two ossification centers can be noted as prominent echoes distinct from the rest of the bone image. Presence of distal femoral epiphysis of greater than 3 mm along with the presence of any proximal tibial epiphysis can indicate a mature lung in almost all IUGR fetuses (Galan H L, 2003). Advanced Diagnostic and Prognostic Parameters in the Clinical Management of Fetal IUGR—

Vascular Doppler Ultrasound Evaluation—the Doppler 'Flow Velocimetry Waveforms' (FVW):

The vascular Doppler study depends on the observations that: (1) the emitted ultrasound wave can be reflected, and the wave frequency can be changed, when a moving object within the circulatory system like the RBC is encountered by the sound wave; (2) the degree of change in the reflected and returning sound signal can be used to calculate the velocity/speed and the direction of the reflector (the RBC); (3) the over-all vascular Doppler FVW form shows a clear systolic and also a clear diastolic component. All these principles are used to evaluate the resistance to blood flow in the utero-placental circuit, and in turn the degree of placental insufficiency in an IUGR pregnancy. The effects of placental resistance are also mirrored in the fetal vasculature, though manifest with different intensity in different vessels, also showing a different chronology as can be expected, based on the anatomical site of the vessel depicting the changes.

Doppler Monitoring of the Uteroplacental Circulation—

As pregnancy advances the uteroplacental blood flow gradually increases, mainly due to spiral arterial remodeling. Very early on, due to the trophoblastic invasion, the endothelium and the smooth muscle layers of the spiral vessels are replaced by trophoblast, with loss of spiral arterial resistance. The lacunae further created in the syncytiotrophoblast by the cytotrophoblastic invasion and their filling with blood from maternal spiral arteries result in dilated blood pools of maternal sinusoids that are responsible for the shunt effect of the placenta. In pregnancies complicated by IUGR, the trophoblastic invasion is limited, with a failure of the myometrial spiral arteries becoming low resistance vessels.

In normal pregnancy, the remodeling of spiral arteries dramatically decreases the peripheral resistance, an unique change that in turn can also be reflected in the Doppler Flow Velocimetry Waveforms (FVW) of the uterine arteries. It can be meaningfully discerned and interpreted, if the pre-pregnancy wave pattern of the uterine artery or any artery in general is understood.

The normal non-pregnant (uterine) arterial pulse tracing: a normal arterial pulse tracing typically shows an upstroke followed by a down stroke. The UPSTROKE is abrupt without any secondary waves on it, and represents the initial part of ventricular systole. The DOWN STROKE in the middle has a sharp depression called as 'dicrotic notch' or the 'post-systolic notch', as this marks the early part of ventricular diastole. The dicrotic notch is due to sharp fall of pressure in the arterial tree caused by the rolling back of aortic blood towards the left ventricle at the beginning of ventricular diastole, when the ventricular pressure sharply falls. The rest of the down stroke of the pulse tracing represents ventricular diastole when normally there is no further filling of the systemic circulation until the next systole, when there is an abrupt systolic upstroke again.

The typical uterine arterial tracing changes in pregnancy are mostly due to the dilated placental sinusoidal shunt effect that continuously draws in the blood with no rolling back towards the left ventricle in this part of circulation, during the very early part of the ventricular diastole. There is also some continued filling of the placental sinusoidal spaces by the placental shunt-suction effect even through the late diastole, as if there is 'spiral artery stealing' of blood from the rest of the systemic circulation. These changes are shown in the uterine artery flow velocity wave forms (FVW) of a normal pregnancy, depicted as:

(1) loss of post-systolic notch (the dicrotic notch) in the middle of the down stroke of the tracing, by about 26 weeks of gestation, and (2) continued end diastolic flow filling shown as lifting of the down slope of the last part of diastolic tracing far up from the base line that continues until the next systolic upstroke.

However, these normal pregnancy changes are absent in the uterine artery wave forms of IUGR pregnancy that shows—persistence of post-systolic or early diastolic notch, and little end diastolic filling, or absence of increased end diastolic flow velocity. The terminal diastolic wave stays very near the base line due to little end diastolic filling.

The Following Indices of Doppler Flow Velocimetry Waveform (FVW) are Useful in Studying One or More of Local Circulatory Changes—

Systolic/Diastolic Ratio (S/D Ratio)— it is defined as the ratio of the peak velocity of flow during systole (S) and the peak velocity of flow during diastole (D). Progressive increase in placental vascular resistance with decrease in diastolic flow until the flow ceases, followed by reversal of the flow are ominous signs that need prompt further evaluation of the fetus. S/D ratio is the easiest to calculate, and is also the most commonly used.—

The Pulsatility Index (PI) of the Flow— can be formulated as:

$$\text{Pulsatility Index (PI)}=S\text{–}D/\text{Mean velocity}$$

Uterine Artery (Ut. A) FVW Analysis— it gained importance in screening for pre-eclampsia and IUGR at 20-24 weeks gestation. End diastolic flow velocities are not consistently present until after 15 weeks.

Doppler Monitoring of Fetal Circulation—

From the fetal vessel Doppler Flow Velocimetry Waveforms (FVW) it is possible to obtain the index of resistance in fetal circulation, that in turn is the result of resistance to the circulation in the placental bed itself.

The Doppler Flow Velocimetry Waveforms are regularly used to assess resistance in fetal circulation, by monitoring more than one fetal blood vessel. It is based on the fact that there are sequential and definitive changes in doppler FVW resistance measurements in different vessels as the fetal IUGR is deteriorating, and that they are predictably typical in chronology.

1. Umbilical artery (UA)—60-70% of small placental arterial channels have to be compromised before the UA flow becomes abnormal. The S/D ratio is considered as abnormal if it is >$95^{th}$ percentile for gestational age, or if the diastolic flow is absent/reversed. Typically, the normal S/D ratio ranges as 1.5-2.5 in the third trimester. As the placental vascular resistance increases, the S/D ratio also increases. With the umbilical artery zero diastolic flow velocity, the perinatal mortality is 10%, and when the umbilical arterial flow is reversed, the perinatal mortality is 33% (Cunningham et al). Patients with oligohydromnios, but normal umbilical artery Doppler S/D ratio are less likely to have poor perinatal outcome. PI>2 SD (standard deviations) is considered as abnormal.

The development of terminal villi and their capillaries (the contribution of which is significant for the placental maternal-fetal exchange) increases exponentially during 31-36 weeks of gestation, and its failure could account for IUGR. It further contributes to the reduced umbilical artery end diastolic flow. Histometric support of this hypothesis is ascertained by observations of reduced terminal villi volumes as well as surface areas in IUGR pregnancies (Tesdale, 1984). Failure in the normal fall of maternal peripheral vascular resistance, usually by 16%, observed throughout normal pregnancy, can also be expected in this context.

The umbilical artery was the first fetal vessel to be studied in the normal and in the IUGR fetuses, and it was found out that the S/D ratio was elevated above $95^{th}$ percentile in 85% cases of IUGR. The umbilical artery changes can be interpreted as due to: (1) the increased impedance in the umbilical artery blood flow as the direct effects of the resistance in the placental blood flow, and further as the fetal effects on the 'forcefulness of flow' and the 'critical closing pressure', the latter seen in small caliber vessels ('law of Lawplace') (see the discussion in a later section); (2) the changes in the viscosity of fetal blood, causing sluggishness of the laminar flow, due to fetal polycythemia induced by fetal hypoxia; (3) the loss of the umbilical artery compliance, which in other words is the effect of critical closing pressure, as mentioned. It is worthwhile noting that the umbilical artery has helically arranged muscles wherein 50% contraction (by impaired luminal flow volume or impaired luminal forcefulness of flow) causes complete occlusion, whereas 50% contraction of the simple circular muscle of other small caliber arteries merely reduces their lumen caliber (Von Heyek, 1935), this further adversely affecting the 'critical closing pressure'.

2. Middle cerebral artery (MCA)—it was adequately stressed earlier that in the setting of uteroplacental insufficiency, the fetal anatomy naturally facilitates directing more blood flow to vital organs like the brain, heart and the adrenal glands apart from the physiological vascular autoregulation. The fetal brain normally has a high resistance flow pattern (probably due to 'dural penetration' by the cranial arteries apart from pressure effects of the surrounding cerebrospinal fluid) compared to other large vessels. However, the Doppler FVW form study of the IUGR fetus depicts in the middle cerebral arteries an increase in end-diastolic blood flow velocity that in turn is reflected as low Doppler index of flow resistance. The MCA being positioned perpendicular to the mid-line of the brain, the Doppler beam can be easily positioned along the mid-point of the vessel, with a minimal angle.

The reduction in the fetal abdominal circumference (AC) precedes the Doppler abnormalities of both fetal umbilical artery and of the MCA. The decrease in the vascular resistance of MCA, and the increased vascular resistance of umbilical artery were also found to begin more than 3 weeks earlier than the non-reassuring fetal heart rate recordings (Galan et al). The above are early signs of fetal response, and their loss or reversal is considered as a late or ominous sign in a decompensating fetus with heart failure, when fetal mortality approaches 50%. Doppler FVWs elsewhere, especially on the venous (precordial) side, will be found abnormal as well.

The ratio of MCA pulsality index (MCAPI) and the UA pulsality index (UAPI), that is, the ratio MCAPI:UAPI was found to be more valuable in recent studies, by Shahinaj et al from Tirana, Albanie. It incorporates data that indicates not only placental state (in UA), but also the consequent fetal response (in MCA), which is advantageous in predicting perinatal outcome.

As was noted earlier, in normal pregnancy the cerebral arteries show high resistance flow pattern at any time during gestation, with resistance higher than placental resistance, and a resulting MCAPI:UAPI ratio of 1.08. The results of taking the above ratio into consideration (with ratio of 1.08 as normal, and <1.08 as abnormal) added positively to predicting the outcome.

The following are the reference abnormal values pertaining to the vascular Doppler velocimetry—
S/D ratio>2.6 or >95th percentile in the umbilical artery (UA) (abnormal)
Resistance Index (RI)>0.58, in the uterine artery (Ut. A) circulation (abnormal)
Pulsality index (PI)>2 SD, in the umbilical artery (UA) (abnormal)
>5th percentile in the MCA (abnormal)
MCAPI:UAPI<1.08 (abnormal) (Shahinaj et al)

Venous and Cardiac Flows—
the Doppler velocimetry has been used to study the venous circulation of the IUGR fetuses, like the circulation—in the umbilical vein, the hepatic veins, the ductus venosus, and in the inferior vena cava (IVC). Interesting correlation was found between the abnormal changes in these vessels, and the fetal acid-base changes.

(a) Ductus venosus—A decrease in the velocity of a-wave is the characteristic abnormality in the ductus venosus. In the normal venous flow pattern, the a-wave form is characterized as below—The ascent of a-wave—it represents the dynamic phase of atrial systole, with rise of atrial pressure causing the regurgitation of blood into the ductus venosus resulting a sharp positive wave, then followed by a descent; The descent of a-wave—it represents the subsequent fall in the atrial pressure during the adynamic phase of atrial systole. Absent or reversed flow velocity of a-wave indicates continued fetal deterioration.

Baschat and colleagues (2007) in their study involving 604 neonates delivered less than 33 weeks gestational age, and whose ultrasound abdominal circumference (AC) was less than 5th percentile, concluded that changes in the ductus venosus Doppler velocimetry are primary in predicting neonatal outcome. The changes were due to fetal myocardial deterioration and acidemia. If the ductus venosus shows reversal of blood flow at 26-28 weeks, it is a late sign, as the fetus has already sustained irreversible multi-organ damage. It implies that one may not wait for these changes to decide for delivery.

(b) Umbilical vein—normally the umbilical vein blood flow is monotonous, and the presence of pulsations or nicking corresponding with FUR is secondary to ventricular failure. It is a late sign of a decompensating fetus. Changes caused by fetal breathing can mimic nicking or pulsations of umbilical vein, and can be differentiated by looking for their coincidence with fetal breathing motions. The rate of the umbilical vein pulsations seen in the umbilical vein Doppler waveform should be recorded when possible, when fetal breathing movements are of concern as in an unequivocal BPPS (biophysical profile scoring).

There are Three Identified Umbilical Vein Flow Patterns—
(1) a monotonous umbilical vein flow pattern is normal in a resting fetus (as normally the pulsations of great veins are not retrogradely transmitted into distal veins, unless the great veins are enormously engorged); (2) an undulating umbilical vein flow pattern corresponding to fetal inspirations (transmitted from closely approximated liver and diaphragm) that are lower in frequency, and further confirmed by coincidence with fetal diaphragmatic movements; (3) a wave flow pattern corresponding in rate with that of the fetal heart rate itself—the waves originate in the right atrium, and propagate in a retrograde manner into the venous tree, and in proper context represent late stage of fetal heart failure, with associated fetal hypoxia and acidosis.

The Tests to be Relied on, and the Sequence (Chronology) of Fetal Monitoring for Predicting the Fetal Well-being/Time of Delivery, in IUGR—

In monitoring an IUGR fetus, a study of Doppler changes cross-sectional in time is important. But a chronology of the longitudinal changes (the serial changes in time) and its reliable correlation with fetal deterioration in time are even more important, to assess the risk of prematurity vs. sudden fetal demise, to deliver the severely distressed fetuses just in time. In 2001 and 2002, three Doppler FVW studies clarified that a deteriorating fetus does show a particular sequence of Doppler changes prior to a significantly abnormal non-stress test (NST), and an abnormal biophysical profile (BPP) that would normally warrant immediate delivery. The well differentiated chronology of Doppler changes is categorized as early and late changes, and is incorporated as follows—

1. Early Doppler Changes—
   (a) Decreased abdominal circumference (AC)—seen in an asymmetrically grown fetus.
   (b) Umbilical artery—
      (1) increased PI (pulsatility index): manifests 3 weeks before the abnormal FHR tracing.
      (2) reduced end diastolic blood flow velocity.
   (c) Middle cerebral artery (MCA)—decreased PI which also manifests 3 weeks before the abnormal FHR tracing.
2. Late Doppler Changes—
   (a) Umbilical artery—Absent End Diastolic Flow Velocity (AEDV), and following that the Reversed End Diastolic Flow Velocity (REDV) are late signs that have showed effects up to 2 years of postnatal life of an IUGR baby.
   (b) MCAPI:UAPI (ratio)—recent studies proved that the ratio is reliable and sensitive.
   (c) Ductus Venosus Doppler changes—decrease in the a-wave velocity.
   (d) Umbilical vein Doppler abnormalities—show the presence of pulsations or nicking in the umbilical vein FVW.
3. BPP (Biophysical Profile) abnormality.
4. NST (Non-stress test) abnormality.
5. FHR (fetal heart rate) tracing abnormality.
6. Oligohydromnios—since AF volume is the function of fetal urine output and the renal perfusion, the presence of clinical and U/S confirmed oligohydromnios should be of concern.

The Biophysical Profile (BPP)—

The biophysical profile testing uses 5 components to be evaluated during a stretch of 30 minutes duration. Each component is scored either as 0 or as 2, with a total best composite score as 10, and the worst as 0. The scoring criteria are tabulated in Table-6 of FIG. 18, 30 Minute Biophysical Profile (BPP) Scoring.

The Standard BPP Score (BPPS) Interpretation, and the Normally Pursued Action Plan—

Score 8-10—normal; score 6—equivocal or suspicious, repeat test the next day; score 4—repeat test in 12 hours; a repeat score 6, plan immediate obstetric interference.

Among the 12, 620 women tested weekly with BPP, Manning and co-workers reported the following statistical significance of the test: false negative rate—0.06%;
   false positive rate—40% with BPPS of 6, and
      0% with BPPS of 0.

The fetal umbilical vein (containing oxygenated blood) blood pH shows the following correlation with the BPP score (Manning et al): BPPS 8-10—pH 7.37 (in the normal range); BPPS 6—pH 7.33; BPPS 4—pH 7.28; BPPS 2—pH 7.2; BPPS 0—pH 7.08.

The Non-Stress Test (NST)—
Basis for the Test—
   if the fetus is neither acidotic nor hypoxic, the fetal heart rate accelerates with the fetal movement.

In association with or following fetal movements, the fetal heart rate shows transient heart rate accelerations, and there should be at least 2 such transient fetal heart rate accelerations within 20 minute period, after the test is started. Each heart rate acceleration should normally last at least 15 seconds, with the peaking of the fetal heart rate by at least 15 beats per minute above the base line. Conventionally, it is done once a week, but doing twice a week reduced fetal demise by threefold. It implies with certainty, but not always, that the fetus will survive in-utero until the next test, that is, until one week. But in high risk pregnancy remote from term, the test can be repeated even daily, or twice daily. However, the NST observations must be interpreted as per the gestational age, because fetuses less than 34 weeks do not always respond by 'accelerations of 15 beats lasting 15 seconds' criterion. It is prudent to allow 40 minute or longer wait period for fetal sleep cycle, to conclude as an insufficient fetal reactivity. A time saving, and more reliable way of doing BPP/NST is the below described acoustic stimulation test (AST).

The Acoustic Stimulation Test (AST)— some times the fetal sleep cycles can be longer, and to eliminate the possibility of a false nonreactive test, loud external sounds have to be used to startle and wake up the sleeping fetus. A commercially available acoustic stimulator can be used to elicit acoustic stimulus on the maternal abdomen, repeated up to 3 times, for up to 3 seconds (ACOG 2007). With the use of the AST, the standard time duration mentioned in the above table can be observed for all the relevant tests, without a wait period of 40 minutes or more.

False negative tests are exceptionally low with NST. Large clinical trials inferred false negative results to be less than 0.7%. NST also more frequently identified a fetus in jeopardy than the Doppler FVW pattern had identified.

The Feto-Placental Pathogenesis as Depicted in the Doppler FVW Form and in BPP Score Abnormalities, and their Possible Remedial Measures—

Feto-Placental Pathogenesis as Depicted in the Doppler Ultrasound—

Undoubtedly, the fetal vascular Doppler abnormalities had originated from placental resistance, but there is also no doubt that subsequent fetal contribution significantly worsens the picture, making it a vicious cycle. The vascular resistance that manifests in the umbilical artery has two components—placental and fetal. The placental component needs no further explanation. The fetal component is multi factorial, but the root cause is hypoglycemia with no energy reserve or lack of ATP for efficient contraction/tone anywhere in the fetal musculature (poor tone, reflected in BPP) including the myocardium, that results in poor cardiac contractility, and suboptimal stroke volume/low cardiac out-put. To start with, the systolic output needs to be sufficient, so that there is enough reserve volume in the systemic arterial tree during diastole, after the blood runs off into the smaller vessels and veins. The flow through a vessel is dependent on two factors—(1) the pressure difference between the two ends of a blood vessel concerned, that is, the umbilical artery in this setting, and (2) the impedance to flow, that is, the vascular resistance within the vessel, expressed as:

$$F = P_1 - P_2/R$$

wherein, F represents the rate or forcefulness of flow through a vessel, $P_1$ the pressure at the origin of the vessel, and $P_2$ the pressure at the other end of the vessel, and R, the impedance to flow. It has to be noted that it is the difference in the pressure between the two ends of the vessel, and not the absolute pressure within the vessel that determines the rate or forcefulness of flow (Guyton A C). To exemplify the statement—if the blood pressure at both the ends of a vessel is 60 mm/Hg, the flow ceases, though there is optimal absolute pressure of 60 mm/Hg within the vessel. If the blood pressure is 80 mm/Hg proximally, and 60 mm/Hg distally, blood flow distally is possible.

It can be noted that an optimal pressure at the proximal aorta can be only achieved by effective stroke volume that lasts in the arterial tree through the cardiac diastole also (i.e. what has remained after the blood runs-off into the capillaries and the veins during systole). No doubt there is high pressure distally in the fetal umbilical artery due to placental resistance, but there is low pressure at the fetal proximal aorta level also, due to inefficient fetal cardiac contractility. This in turn can be proximally due to many factors that can build up as a vicious cycle. ATP needed for effective cardiac contraction can not be generated for various reasons like— (1) fetal hypoglycemia, (2) failure of pyruvic acid to enter or continue in citric acid cycle due to fetal vitamin/mineral deficiency, or else (3) fetal hypoxia.

To compensate hypoxia, the fetus responds by tachycardia to draw more of oxygen from the placental bed. But tachycardia can only happen at the expense of diastolic time (systolic time is constant whatever be the heart rate), drawn from each cardiac cycle, and in turn at the expense of coronary filling, because coronaries fill only during diastole. That means, the fetal heart is working more, but any more than optimal average rate of 140 per minute, other than transient, can lead to coronary ischemia in a hypoxic fetus, and what seems as compensatory tachycardia does not serve the purpose of increased myocardial oxygenation, but will certainly cause increase in long-term cardiac work load, leading first to compensated cardiac failure, and later, decompensated failure manifesting as bradycardia.

As the great veins and the venous tree comprise high compliance and high capacitance vessels, the venous side accommodates many times more blood than the arterial side, during the process of compensated or decompensated cardiac failure that further reduces the blood getting into the heart. This in turn leads to progressive diminishing of cardiac stroke volume during systole. Essentially, the fetus is in hypotensive state that is responsible for ineffective maintenance of diastolic blood pressure that is shown as decreased diastolic flow velocity of Doppler waveforms, or even as reversal of flow. Thus the fetal hypoglycemia and hypoxia with ineffective cardiac contraction, and low $P_1$-$P_2$ can be directly proportional to the diminished forcefulness of the flow, which is added to the inversely proportional high peripheral resistance R, contributed by the placental resistance. Fetal polycythemia and increased blood viscosity also contribute to decreased flow velocity, and the high fetal sympathetic tone due to continued intrauterine stress can additionally contribute to persistent fetal tachycardia. With fetal heart rate as 140 per minute, each cardiac cycle lasts 0.428 seconds. If fetal HR goes up to 160 per minute, the cardiac cycle lasts only 0.375 seconds. The decreased time of 0.053 seconds which is 12.38% decrease of the normally allowed time for each cardiac cycle (with the optimal 140 beats per minute) is happening by consistent cut off from the 'diastolic coronary filling time'. That is, for the fetus, it is 2 hours and 58 minutes per day loss in the coronary filling time. It is imposed on the top of the long-term strain of increased cardiac work load of 20 extra beats per minute. Restoration of fetal heart rate to optimal number early on, can prevent fetal myocardial work load.

It is worthy of note that the umbilical arteries being the branches of fetal internal iliac arteries, are not high caliber vessels to start with, and in turn they are subjected to the physical laws of 'critical closing pressure' seen in small caliber vessels, as is dictated by the law of Laplace. Though each umbilical artery receives 20.5% of the fetal total cardiac out-put (Rudolph and Heyman, 1968), the absolute flow through these vessels is very less, that is, only 100 ml per minute/kg at 22 weeks, and 300 ml per minute/kg at 37-38 weeks (Gill and co-workers, 1981). The above are even lower volumes, if calculated per fetal cardiac cycle, flowing into the placental circuit. One may consider that they are proportional to the fetal size, but the dynamics and the physical laws of blood flow are neither different nor forgiving, because they are directed to the fetal vessels. In an adult, at 20 mm/Hg blood pressure, blood flow in the smaller vessels entirely ceases, that being the 'critical closing pressure' (Guyton A C). The vasomotor tone of the smaller arteries is always attempting to constrict these vessels to smaller diameters, whereas the blood pressure inside is attempting to dilate them. When the pressure in a vessel falls, also decreasing the vascular diameter, the muscular forces tending to keep the vessel wall stretched, decrease extremely rapidly (Guyton A C).

The Law of Laplace States— the circumferential force (F) tending to stretch the muscle fibers of a vessel wall is proportional to the diameter (D) of the vessel times the pressure (P) with in the vessel. It can be shown as: $F \propto D \times P$.

The law explains that more the blood pressure falls, decreasing the effective diameter of a vessel, furthermore the vessel wall will close, which also is a vicious cycle. To make the situation worse, the umbilical artery has helically arranged muscles wherein 50% contraction causes complete occlusion, whereas 50% contraction of a simple circular muscle merely reduces its lumen caliber (Van Heyek, 1935). Hence, it is imperative that adequate fetal cardiac contractility, optimal stroke volume, and normal range diastolic blood pressure are maintained in fetal arterial tree, and in turn in the small caliber umbilical arteries.

BPP—

Impaired energy reserve/ATP is responsible for lowered over-all fetal movements, and the lowered muscle tone (just as the lowered fetal cardiac muscle contractility described above) that are reflected in the lowered score of BPP (BPPS). Essentially, the low BPPS represents a fetus of low energy, i.e overall fetal apathy.

The Possible Corrective Measures—

Maternal Rest in Fully Turned Left Lateral Attitude, in a Trendelenburg's Position—

It may be noted that in a cephalic presentation with the placenta located in the upper uterine segment, when the mother is in standing or sitting posture, the blood in the aorta and the hypogastric vessels (that form umbilical arteries) of the fetus have their blood flow towards placenta, flowing against gravity. Gravity may also make the loops of umbilical cord to settle in the lower uterine segment (unless interrupted by fetal body parts) from where the blood has to flow upwards towards the placenta, also against gravity. The force of gravity is an undeniable phenomenon that needs no further proof. Hence this writing advocates maternal bed rest in left lateral Trendelenburg's position (head end inclined lower than the foot end, best achieved by raising the foot end of the bed by solid blocks) that can have impact in overcoming the forces of gravity, and the placental resistance. Only 'fully turned' left lateral position can be relied on, and improving the 'critical closing pressure' is paramount on the easily compromised helically structured umbilical artery muscle fibers.

Though the fetal position is unstable earlier in pregnancy, yet in this position the placenta and the umbilical cord will be still situated at a lower level than the fetal heart. The uterine artery course that becomes descending instead of ascending can compensate maternal abdominal aortic flow that becomes ascending. This maternal positioning also takes into consideration of the facts that the maternal cardiac function is appropriately hyper-dynamic to pump efficiently into the ascending thoraco-abdominal aortic column, and the uterine circulation that is locally sub-optimal for whatever pathology, is deservingly benefited by the descending column of blood within the uterine artery.

With the loops of the umbilical cord also displaced nearer to the placental plane of the upper uterine segment, the blood flow is not against gravity which can improve the flow impedance in the umbilical artery. While the foot end of the bed is raised by blocks, the mother should have one or two pillows under her head and neck, to avoid pressure effects in the head in due course, like facial puffiness, nasal congestion etc., the symptoms that manifest even during normal pregnancy. Trendelenburg's position though theoretically appealing, can be impractical. Hence, at least bed rest in general can have tremendous benefit, if advocated with correction of other major deficits.

It is also helpful to inquire if the mother has gastroesophageal reflex disease (GERD) to be treated with medications for GERD, and to be advised to sleep as advocated above.

The term lower uterine segment though generally used in obstetrics during labor, in this writing, it is used throughout to denote the lower anatomical part of the uterus, and must be so understood.

Correction of unobvious maternal factors, though considered as insignificant, they can still help, in case they are few of the many culprits operating in unison. It is the tight fitting maternal clothing, especially the pre-pregnant bra that she had long ago outgrown during pregnancy. Full chest expansion, especially to allow for the needed pregnancy adaptation of respiration, is very important, and the front wire-rimmed bras have to be especially discouraged, as they restrict the full expansion of the anterior hemi-thorax with decremented tidal volume, defeating the fine timing of the nature's concert of pregnancy orchestration. The progesterone-driven pregnancy hyperventilation has a purpose. In pregnancy, the minute volume increases by 40% almost entirely by increase in tidal volume rather than respiratory rate, that causes decrease in expiratory reserve volume, with alveolar ventilation increasing by 65%, and the $PCO_2$ decreasing significantly for the needed gradient at the placental level (Hytten F. E). Low oxygen concentration in any area of the lung due to hypoventilation causes pulmonary vasoconstriction in that area, an adaptation to direct the blood flow to better aerated lung fields, a feature unique to pulmonary circulation. If the hypoventilation (with reduced $PO_2$ of alveolar air) is generalized due to mechanically restricted chest expansion, generalized pulmonary vasoconstriction can ensue, with resultant lowered $PO_2$ of maternal arterial blood, that will be added to the higher value of $PCO_2$, both values not adapted to pregnancy range. If there is shortness of breath due to ill-fitting clothing, the mother may attribute it as the natural consequence of pregnancy itself.

The mother should be further advised to wear increasing sizes of bras as the pregnancy advances. The best way to demonstrate that she is wearing a tight fitting bra is to let the nurse unhook the bra, and observe how much apart the bra ends will recede from each other during full inspiration, and to let the mother be surprised to feel that gap with her hand, and know the measure of chest circumference she is not allowing to expand. The nurse should be trained to observe/document the concerned observations. The chest expansion/measurement can be more while sitting than standing. The best option of the mother is to try the bra size while sitting, and buy one size larger.

Tight fitting jeans (or outgrown dress pants, or tight dress skirts) should also be curtailed, as they can press the gravid uterus against the great vessels. Such tight garments can have an effect worse than supine hypotensive syndrome, as the pressure on the uterus can be all through the wakeful hours also. The patient may be considering to replace her regular garments only when it becomes impossible to wear, without knowing the adverse effects on her pregnancy, and with compensated asthma, COPD, heart diseases, smoking etc. the effect on pregnancy can be significant. In fact, these subtle factors can be operating in IUGR with no known etiology.

The D-Glucose Supplements and the IUGR Diet Directly or Indirectly Accomplish the Following Beneficial Effects on Fetal Cardiac Function, Whether or not Reflected Through the Doppler Flow Velocimetry—

(1) By maternal hypertonic D-glucose supplements, an adequate supply of D-glucose to both the fetus and the placenta is ensured. The placenta consumes 50-60% of glucose getting into the placental interface, and 80% of it is converted into lactate that is supplied to the fetus during times of need. Fetal heart (and also the fetal brain and skeletal muscle) efficiently metabolizes lactate just as it metabolizes glucose (see also the section 'The improvement of fetal lactic acidosis/pyruvic acidosis). Maternal IV glucose supplements during midnight, or IUGR-diet snacks in between meals are valuable to ensure almost continuous fetal D-glucose supply, or else to improve placental lactate reserves, the latter stored with no $ATP/O_2$ expended by the placenta.

(2) Cessation of fatty acid and amino acid oxidation for energy/ATP yielding catabolic purposes saves 33%+ of oxygen, improving myocardial oxygenation, fetal compensatory tachycardia, coronary filling, cardiac work load, and cardiac function needed for optimal stroke volume restoring end diastolic flow velocity. Oxygen therapy that is part of this treatment protocol, further relieves fetal hypoxia, and as a result the tachycardia and the cardiac work load.

(3) D-glucose supplements by any route: by generating $CO_2$, can heighten the Bohr effect of fetal oxygen delivery to the extent of overcoming fetal hemoglobin-$O_2$ affinity; improve fetal hypoxia by many other means (as described in the section of 'The improvement of fetal hypoxia') with the consequent relief of fetal polycythemia that in turn relieving the sluggish laminar flow in all vessels.

(4) Fetal energy and volition for swallowing the sweetened AF improves, with the restored oxygen supply from AF that by Bohr effect maximally oxygenates—(a) the portal and the inferior vena caval blood before reaching the right atrium, (b) the pulmonary blood after entering the left atrium.

(5) The IUGR diet with rich supply of essential amino acids of which arginine is a part, will contribute to the synthesis of nitric oxide (the body's integral element needed for vasodilation throughout) in the terminal villus vasculature as well as in the umbilical vessels, improving the umbilical artery compliance, end diastolic flow velocity/volume, the critical closing pressures, platelet aggregation, and hypoxia, with consequently improved fetal cardiac function.

The hypertonic D-glucose and IUGR diet exert their invaluable effect, first of all, by breaking the vicious cycle of established adverse path ways, after which the fetal milieu can be better amenable to any positive physiochemical benefits of such therapeutic maneuvers. Hence their therapeutic trial is warranted (especially when a fetus is not viable for delivery) either the fetus is in compensated, or decompensated (cardiac) failure, and whatever be the nature of Doppler FVW form at the outset. Just as in an adult, the fetal cardiac failure may not be untreatable, especially when it is primarily directed to the inciting pathology, probably with no long term adversities, as also in the adult.

The Clinical Aspects of Hypertonic Glucose Supplements to the Mother—

The novel invention sets forth desirable attributes for successful treatment of a so far truly evasive disease entity in the specified art of obstetrics, encompassing a treatment that is: safe, simple, minimally invasive, risk free in terms of feto-maternal mortality/morbidity, non-anxiety provoking, and most important of all, one that was proved successful, as evidenced by a successful case study of a severe fetal IUGR, treated by the author inventor. Being simple, its method is easily reproducible over desirable long term with similar anticipation of success. More importantly, the treatment is based on sound and infallible scientific model conforming to the needed 'as a whole inquiry' approached and clarified with biochemical/physiological rationale befitting every new encounter as seen in the preceding sections.

In alleviating the placental insufficiency of fetal IUGR, an accelerated 'Facilitate diffusion' of glucose can be achieved in the afflicted placenta, by creating transient hyperglycemia in the mother by hypertonic D-glucose 25-50%, up to 50-100 cc twice or thrice a day, given as a bolus intravenous injection over a period of 3-5 minutes, such treatment initiated as soon as it is confirmed that the fetal IUGR is placental vascular in origin. When the therapeutic trials of maternal IV treatments are exhausted without substantial benefit, as later discussed in detail, the transamniotic isotonic D-glucose supplements are initiated, the amniotic cavity accessed through a subcutaneously implanted pregnancy-port (SIPP) catheter via an extraperitoneal suprapubic approach, with novel structural and operational modalities that are easy to implement.

Apart from the classic preeclampsia/eclampsia, the varied pathological states subject to fetal growth restriction of vascular origin, and can be similarly benefited are: chromosomal anomalies found to be associated with reduced number of small muscular arteries in the tertiary stem villi, chronic placental separation, extensive localized placental infarction, circumvallate placenta, velamentous insertion of the cord, one or both the twins affected due to reduced trophoblastic area available to each, to mention a few (this list is not construed to be exhaustive). They are unseemingly though clinically responsible for the diminutive placental exchange, and for the fetal IUGR. Clinical diagnosis of a vascular pathology is not feasible in all circumstances, and hence as a diagnosis of exclusion, any suspected fetal IUGR can be offered a therapeutic trial.

Accounting Legal Implications—

The treatment of fetal IUGR with maternal hypertonic glucose supplements is not without legal implications, if not done discretely. This is due to the unavoidable interference with the maternal carbohydrate metabolism. The natural course of diabetes in a patient ultimately destined for it, during pregnancy or after, becomes imperceptible from what is benignly interfered with pertaining to carbohydrate metabolism, through the treatment itself (refer 1 (b) of the section 'The author's theory to account for the manifest maternal hyperinsulinemia during normal pregnancy' to understand the natural history of gestational diabetes). For that reason, adequate patient education and a strong therapeutic alliance with the patient are paramount. This needs the patient's equal participation in all decisions for her treatment. Strong basic knowledge is important to clarify patient's questions/concerns, and for confident clinical management also required in invoking patient's confidence, as for either, there is no short cut.

The Essence, the Summary of What was Elaborately Discussed, and to be Conveyed to the Patient in a Plain Language is— pregnancy is a natural state of fat deposition and also a state of more fat release into the blood of the mother. Insulin is necessary to make use of, and to control the levels of blood sugar, but the elevated fats in pregnancy can block the action of insulin in the mother that can causes 'insulin resistance'. As the baby predominantly uses glucose for growth and energy, it is meant to spare the mother from using the blood sugar, for more of it to get to the baby, while she gets energy from more of fats now circulating in the blood. Mostly, such changes will not raise the mother's blood sugar. However, lack of the insulin action being responsible for diabetes, sometimes the described changes such as the blocked insulin action in the mother, can cause 'pregnancy induced diabetes'. Following delivery, the described pregnancy changes—(i) may resolve—if 'insulin resistance' is reversed, when the excess fats in the mother's blood slowly normalize, (ii) may not resolve—if 'insulin resistance' is not reversed, because certain changes it tends to cause, can become permanent. The consequence is the interplay between hereditary or the predisposing factors vs. others. Thus, pregnancy itself is a natural risk for diabetes. More of overweight people who naturally have high fat content in their body as well as in their blood, also tend to be diabetic.

Careful history taking with regard to family history of diabetes, and for clues of previous gestational diabetes is important. IUGR in a diabetic pregnancy is rare, but possible, when hyperglycemia is marginal, and such rare encounters that can put the obstetrician in a dilemma, need in depth discussion. Whereas the hyperglycemia can be just few numbers above cut off values, the induced hyperglycemia is more pronounced by its higher blood sugar range, and hence significant in overcoming the placental impedance. In this situation, making decision about maternal versus fetal well-being can be daunting, and needs significant understanding on the patient's part. It has to be honestly informed to the patient that postponing the treatment of her diabetes by few months will not significantly affect the natural course of the disease, as the disease consequences slowly evolve over very long term, and after delivery, every stringent measure followed through years will equally contribute to the best ultimate outcome. This is also assured by the specialist (who should be called throughout, as 'diabetes specialist' instead of an endocrinologist) for the needed patient trust, apart from relieving her anxiety and possible indecision. In these patients, correcting other factors as are described throughout this discussion, and ongoing IUGR-diet, can be invaluable and paramount, along with the therapeutic trial of induced maternal hyperglycemia.

Careful monitoring to prevent adverse events of diabetes is necessary, and information pertaining must be given to the patient as written instructions, apart from her signed alliance to cooperate with/follow needed frequent monitoring. Above all, decision for treatment should be entirely made by the patient, along with her signing a therapeutic alliance for 'no physician responsibility' for what ever be the course of diabetes (if worsened soon after pregnancy, or years later), or the outcome of the baby. Indeed, the course can be unpredictable for number of reasons, and one can be the patient's non-compliance itself later on, in the treatment of her mild diabetes. The patent's chart should be preserved even after the obstetric relationship is over, as any patient, if needed to be treated with insulin for uncontrolled diabetes later on in life can be aggrieved for such need and out-come, and can pursue legal course, forgetting all 'therapeutic-agreements' she made years ago. Demonstration of fetal growth soon after treatment will be a gratifying incentive both to the patient and to her obstetrician to follow the same, until the fetal viability is assured for an earliest possible delivery. These patients should be watched for hyperosmolar syndrome, ketoacidosis etc. just like any other diabetic patient, and treated similarly. Hyperglycemia is targeted only to the extent that the desired fetal growth is achieved, and no more. Fetal anomalies due to uncontrolled diabetes are as a result of uncontrolled ketonemia in the first trimester, and such danger is never a clinical consequence during the second trimester and later, when the patient is being treated.

A sincerely vigilant attitude, both clinically and personally towards the patient from early on is important to gain her trust, which also enables the patient to ungrudgingly and understandingly accept any adverse outcome, and to realize that her physician had done the best that can be possibly done, in her situation. A written summary of: the natural course of diabetes, the unique effect pregnancy itself has on blood sugar control, the contemplated modality of treatment, and the imperceptibility of the effects of treatment from the natural course of diabetes for those destined for it—should be given as a hand-out to all, on the first encounter. The obstetrician should take time to answer all the patient's concerns and questions, and then proceed with clinical decision making carefully but swiftly, as there is no time to waste, as each day passed has its toll on the fetus, and the ultimate pregnancy outcome, a matter that needs to be conveyed to the patient also.

Maternal Diabetes Screening—

In the majority, as the onset of fetal IUGR falls around the time that the mother is screened for diabetes at 28 weeks, the obstetrician is already aware of the patient's glucose tolerance, and if not, it can be immediately ascertained. The screening is done with 50 g oral glucose, without regard to prandial state, or time of the day. To test, a single venous sample is drawn at 1 hour. The normal blood glucose level cut-off at—130 mg/dL—has 90% sensitivity, and at—140 mg/dL—has 80% sensitivity (Metzger B E et al).

The American Diabetic Association (ADA) and the ACOG agree with either of the threshold values. For all positive tests, WHO and ADA recommend a 3 hour OGTT (oral glucose tolerance test) with 75 g of glucose and the diagnosis of diabetes mellitus is made when two or more venous plasma glucose values are at or above the following standardized values, approved by the ADA—

Fasting—95 mg/dL; 1 hour—180 mg/dL; 2 hours—155 mg/dL; 3 hours—140 mg/dL.

In a patient whose screening was normal, but is diagnosed with persistent impaired glucose tolerance post-partum—it is difficult to ascertain whether it was due to diabetes that the patient was destined to develop during pregnancy, or it was due to pancreatic beta cell stress induced by the treatment. Whatever be the cause, healthy patient with sufficient pancreatic reserve/no inherent predisposition should not develop overt diabetes before or after delivery. It is only a susceptible patient whose reserves are exhausted by the therapeutic challenge, will be developing diabetes, but earlier. Such possibility also should be explained to the patient before treatment, not overlooking to clarify that the unmasking of the disease happened only earlier, and would be otherwise inevitable a short time later. It is the risk the mother should decide to accept for the sake of delivering a viable and reasonably healthy infant. A mother with previous adverse pregnancy outcomes would not mind it at all, especially after delivering her well grown child. The post-partum diabetes management in these patients is no different, and an endocrinology consult and also a dietary consult can be better done as a group consultation, involving the obstetrician also initially, so that he or she is aware of the input and the counseling given to the patient. Similar group consultation is better for pre-natal patients also, at least once, and the obstetrician in turn should clarify to the specialists what is being expected, and if satisfied, it is time-saving to involve same specialists for all patients.

Patient Parameters to Account for Before/During Therapy—

1. Thiamine—all patients should be given 100 mg of IV/IM thiamine ($B_1$ vitamin) before IV hypertonic D-glucose treatment. This is done even with prior oral supplements in a compliant patient. The obstetrician should document such therapy in terms of point in time, that is, prior to IV glucose treatment. It is for the reason that after glucose load, thiamine deficiency can precipitate pyruvic acidosis in a previously malnourished patient. Malnutrition is not uncommon in this subset of patients—due to alcoholism, hyper-emesis, and pregnancy pica in the socioeconomically well-to-do cultures, but under-nutrition can be a contributing factor in the developing countries.

2. Multivitamins/minerals—all patients should have IV multivitamins/minerals supplements that include generous amounts of phosphorous (assuming patient's renal function as optimal).

3. Magnesium—magnesium supplement is considered separately due to its specific deficit in malnourished patients, and due to the vital role of magnesium in all biologic functions where ATP is involved, which is ubiquitous, as it is Mg-ATP that actually participates in such reactions.

4. Potassium levels are needed to be monitored initially during IV hypertonic glucose treatment to note occasional undue fluctuations.

The above IV supplements are repeated every 1-2 weeks to ensure maximal allowable concentrations in the maternal compartment, to attain on going $V_{max}$ that is instantaneous, at the placental interface.

IV Hypertonic D-Glucose Treatment, and the Blood Glucose Parameters—

The amount of IV hypertonic 25-50% glucose supplements given to the patient (mother) as 50-100 cc bolus twice or thrice daily should be individualized. As evidenced by the treatment done by the author, such maternal therapy is deemed very safe, and well tolerated in individuals with no inherent predisposition to impaired glucose tolerance. However, it is a good idea to start with a smaller dose such as 50 cc of 25% glucose, and to progressively but swiftly increase to 100 cc of 50% glucose. Such progressive therapeutic augmentation is done in the hospital, as the devised protocol, with also monitoring of blood glucose values, and of the potassium response initially.

With 25 G of glucose (equal to 25% glucose as 100 cc, or 50% glucose as 50 cc of therapeutic hypertonic glucose supplements), injected as IV bolus over a 3-5 minute period, the following blood glucose levels can be expected—a peak of 175 mg % at 15 minutes, 125 mg % at 30 minutes, and back to normal non-pregnant level of 75 mg % at 1 hour, and further declining to slightly lower levels of 70 mg % during the second hour. These levels were the average results of 120 pregnant women tested during pregnancy by Spellacy W N et al in 1964-65.

The above numbers also demonstrate that in a healthy pregnancy (with respect to glucose metabolism, and not IUGR) the normal glucose levels can be attained in the maternal circulation in a short time. In the same token, advocating the therapy in between meals and at mid-night, and additional frequent intake of IUGR-diet snacks will create more of such hyperglycemic peaks in the mother, without inducing adverse effects on the carbohydrate metabolism. In fact, the IV hypertonic glucose supplements mimic post-prandial glucose peak, and can be compared to a situation where a mother has a tremendous appetite and is eating three meals and also equal sized snacks in between. That type of food intake is not uncommon during pregnancy, and the body's response to short-term glucose fluctuations spanning limited duration such as during the later few months of pregnancy is very forgiving, though it may not be the case with the patient's predisposition to diabetes. Midnight infusions impose inconvenience to the mother, but they truly aim in preventing early morning hypoglycemic phase that can be otherwise prevalent even in healthy pregnant women. During such short but many of the hyperglycemic peaks in a day, the placenta can transmit D-glucose in an exceeding 'speed mode' of $V_{max}$ (refer the Michaelis-Menten model, discussed in the foregoing sections) when the surplus of the hexose sugar is stored both as fetal liver glycogen and the placental lactate that are utilized, as the circulating glucose levels tend to fall.

Management of IUGR Pregnancy Around the Time of Hospitalization

The management of an IUGR pregnancy clinches on the correct diagnosis of its existence. A correct diagnosis, and proper timing of delivery as planned, is made by the following—1. confirming the current gestational age as per the first trimester ultrasound, and the previously correlated uterine size, 2. the gestational age corrected as per the CLMP which was earlier discussed, 3. any reliable previously discussed U/S indicators of true fetal gestational age.

When fetal IUGR is confirmed, the patient shall be hospitalized with decreased physical activity and bed rest, and the fetal surveillance is started. This includes fetal movement charts, clinical and ultra-sonogram assessment of fetal growth and amniotic fluid (AF) volume, non-stress test (NST), biophysical profile (BPP), fetal heart rate (FHR) monitoring, Doppler Flow Velocimetry Waveforms (FVW), AF lactate/lactic acid (AF-LA) levels, and also clinical evaluation of the mother. A full profile of the tests is shown in FIG. 20, as Table-7, The fetal monitoring/treatment intervention table, that can be tailored to the physician's discretion, as clinically warranted.

In most cases of IUGR, as pregnancy can be quite remote from term, and fetal viability improbable (with prematurity added to growth restriction), irrespective of the base-line lab values i.e. unsatisfactory Doppler velocimetry, or non-assuring FHR/BPP, hypertonic glucose treatments are advised. As discussed, its multifaceted effects upon IUGR pregnancy are unparalleled. The aim is to reverse pathology of whatever severity, at any stage of pregnancy. The patient needs to be disclosed that the pregnancy outcome can be very unsatisfactory without it, though however, as with any treatment, 100% response and assured positive pregnancy outcome may not be guaranteed with it also, because the inclusion group is of varied pathology, some inherently unresponsive. The patient may also be informed that statistical data of the treatment is not available at the time, but it can be very promising. Patient also needs clarification that there is possibility of fetal demise with or without treatment, and hence treatment is strongly advised, as at least there will be satisfaction of trying what is feasible, and that the treatment will be continued until desired fetal maturity, for elective delivery.

Base Line Diagnostics— all baseline diagnostics are documented in the comprehensive 7 day 'The fetal monitoring/treatment intervention table (table-7 of FIG. 20), devised for the regular outpatient or for in-hospital charting, for any needed diagnostics, and for the indicated plans of intervention.

Starting the Patient on IUGR Diet—

Special emphasis should be made that along with the diet that usually contains complex carbohydrates, intake of rapidly absorbable simple hexose sugar as 25 grams of glucose powder in water before each meal and each snack—should be a mandate of the dietary protocol. The diet also includes at least 1 egg with each meal and breakfast, for the desired essential amino acid intake (the egg being a 'reference protein' in terms of its essential amino acid content, and being acceptable even for a habitual vegetarian) to ensure one of the benefits among many—the arginine supply needed for feto-placental nitric acid synthesis, for relieving placental and umbilical vascular impedance. Arginine is also an insulin-secretagogue, whose action can be preserved even when glucose stimulated insulin secretion is impaired (Powers A C). This works in favor of improving maternal glucose tolerance in those with a predisposition for gestational diabetes.

The Protocol of Maternal IV Hypertonic D-Glucose Therapy Preparations of D-Glucose—

The hypertonic D-glucose is supplied by the manufacturers in a prefilled disposable syringe with optional stick-guard safety needle (MIN-I-JET) in the standard strengths of 25% (2.5 g in 10 ml) and 50% (25 g in 50 ml) solutions, as below—

25 g of 25% strength (denoted in this treatment protocol as $DG_{25}$)—supplied as 10 vials of 10 ml, each 10 ml vial containing 2.5 g of glucose (a total of 25 g of D-glucose in a total of 100 ml).

25 g of 50% strength (denoted in this treatment protocol as $DG_{50}$)—supplied as 1 vial of 50 ml (a total of 25 g of D-glucose in 50 ml).

The Amniotic Fluid Lactic Acid/Lactate (AF-LA) Level, or Lactic Acid/Creatinine Ratio (L/C Ratio) as Therapeutic Aid in Clinical Decision Making—

AF-lactic acid levels or L/C ratio can be a tool of decision making, and can be specifically directed to finding the lactic acid level before and after D-glucose therapy, for adjusting the dose of the supplements, if there are also accompanying changes in BPP scores. With the therapeutic benefits of D-glucose on fetoplacental ATP generation, arginine transport, NO synthesis, and vasculogenesis leading to fall in placental impedance, the patients if started on $O_2$ therapy due to elevated lactic acid levels, can be swiftly or gradually weaned off from either the intermittent oxygen therapy (IOT), or the continuous oxygen therapy (COT) while D-glucose treatments are continued, as the aim is to send the patients home, stabilized on an optimal but tolerable dose of $DG_{25-50}$, without home oxygen therapy, the latter being not feasible in all cases. With elevated AF lactate levels (>10.1 mmol/L—Pardi et al, 1987) only COT is started initially, with IV glucose therapy supplemented after the lactate level normalizes. Any patient if resistant to IV $DG_{25}$ treatment even with continuous oxygen therapy (COT), it clearly indicates significant fetal hypoglycemia due to placental impedance that needs to be interfered with intraamniotic isotonic D-glucose treatment. Below normal AF lactic acid level in this setting clinches that the problem is fetal hypoglycemia, with or without fetal hypoxia.

The Maternal IV $DG_{25-50}$ Treatment

With normal/normalized AF lactate levels, the patients are divided into following groups based on the gestational ages and the baseline BPP scores.

26-31 weeks gestation—with BPP score≥8 (26-31, Group A),
with BPP score≤6 (26-31, Group B).
≥32 weeks gestation—with BPP score≥8 (32, Group A),
with BPP score≤6 (32, Group B).

Maternal IV Hypertonic D-Glucose Treatment Protocol for the Gestational Ages of 26-31 Weeks, and with the Baseline BPP Score≥8 (26-31, Group A)—

With normal BPP score accompanied by IUGR, it can be considered that the fetal growth restriction is mild to moderate. This fetus is obviously not acidotic, as there is a direct correlation between the BPP score and fetal acidemia. It can also be reasonably expected that the fetus tolerates hypertonic glucose treatments in moderate doses without requiring oxygen therapy in the manner it may be otherwise required with very low BPP scores accompanied by severe hypoxia. The following is the most feasible therapeutic interventional protocol for this group of mothers—

DAY-1: Start $DG_{25}$ as 50 ml (12.5 g of D-glucose) thrice daily (10 am, 4 pm, and 1 am).

DAY-2: 8-9 am—check BPP. If score remains as baseline, continue same treatment on day-2.

DAY-3: increase the dose to $DG_{50}$ as 50 ml (25 g of D-glucose) thrice daily.

DAY-4: 8-9 am—check BPP. If score remains same, continue the treatment on day-4.

DAY-5: if the patient is stable with no fetal heart rate (FHR) changes (as described below), and with BPP score≥8, the patient is discharged home with the last maximal dose tolerated, to be further increased to $DG_{50}$ as 75 ml thrice daily, and later $DG_{50}$ as 100 ml thrice daily, as pregnancy advances.

Intermittent HER (Fetal Heart Rate) Monitoring— it is done for 2 hours starting ½ hour before the therapy initially, and later, whenever the dose increments are made. That is, on day-1, it is first monitored about the 10 am dosing, and if found to be tolerated, the monitoring is again done on day-3 about the 10 am dosing, when the dose increment is made. Such monitoring starting ½ hour before the therapy facilitates pre-therapy and post-therapy FHR comparison for a definite attribution of the change to the therapy itself. Doing BPP on day-2 is an additional safeguard apart from its needed documentation. For any adverse FHR changes, IOT (the intermittent oxygen therapy) is started with 6 L $O_2$ by nasal cannula to be continued for 2 hours and then to be tapered every ½ hour as 6 L-5 L-4 L-2 L-stop. Weaning from IOT, or advancing to Continuous Oxygen Therapy (COT) with slow increments of $DG_{25-50}$ in the latter situation, is in a manner similar to that shown in the algorithmic flow sheet for GROUP-B show FIG. 19, Maternal IV hypertonic D-Glucose treatment protocol depicting—ALGORITHM FLOW SHEET FOR GROUP-B, 26-31 WEEKS (BPP SCORE≤6). The FIG. 19 Algorithm includes frequent BPP testing.

The Rationale of BPP Monitoring as a Proxy for AF-LA/pH Values—

Though the initial decision making was based on the AF-LA level, the subsequent follow up is not feasible to be solely based on AF-LA levels. Any deficit, either fetal hypoglycemia or hypoxia, by failing to generate ATP is reflected in the fall of BPP score, due to fetal hypotonia.

Oxygen therapy can be added at this point to the ongoing D-glucose therapy. The physician can check AF lactic acid levels, though infrequently, when the BPP score shows no improvement with sufficiently titrated oxygen therapy.

In cases with both the FHR change, and fall of BPPS by 2 or more, at any time during treatments of DAYS 1-5, as above: the FHR changes are treated with intermittent $O_2$ therapy (IOT), as mentioned above. The thrice daily D-glucose dose can also be changed to twice daily, at 1 am and 10 am, and the response observed with further monitoring. This patient may be increased to higher dose very gradually. Other needed testing as appropriate can be also incorporated. As the patient falls into group-B with BPP score falling by 2, similar plan as outlined in the algorithm flow sheet of FIG. 19, for GROUP-B is thereof applicable now.

Days 1, 2, 3 (or more) (for example) can be more days in the real time patient care, with unforeseen delays of response. This seeming time-line is indeed a therapeutic mode line. Numbers for the days were introduced because they are better tools of chronology, and of mutual communication in unambiguous terms. The time-line only indicates suggested minimal time, and similar plan can be continued with more time allowed for specified increments.

At the end of 1-2 weeks of hospitalization, or as needed—the fetal size is checked by ultrasound, as there will be discernable increment in fetal growth parameters by 2 weeks, at times the catch-up growth more than normally expected. Such observation of response is the best prognostic indicator compared to any other standard monitoring modalities, to continue the maternal IV hypertonic glucose treatment.

Maternal IV Hypertonic D-Glucose Treatment Protocol for the Gestational Age of 26-31 Weeks, and with the Baseline BPP Score≤6 (26-31 GROUP-B)—

FIG. 19 shows the ALGORITHM FLOW SHEET FOR GROUP-B, 26-31 weeks (BPP score≤6): for D-glucose 25% ($DG_{25}$) maternal intravenous (IV) therapy, starting twice daily (1 am & 10 am), with progressive increments.

Diagnostic and Treatment Indicators—

IOT—as a routine, intermittent $O_2$ therapy as 6 L/minute by nasal cannula is done 'as needed', for any adverse FHR change, and also soon after a noted fallen BPP score (to be tapered as described, after 2 hours). The 'as needed' treatment can be made a 'standing order' for the nursing staff to be immediately responsive. IOT is also electively incorporated into the protocol (as in the Algorithm of FIG. 19) for patients with moderate to severe feto-placental hypoxia who are shown to be intolerant of optimal D-glucose therapy without concomitant IOT also, and had failed weaning challenge off IOT, during each $DG_{25-50}$ maternal supplement. The IOT, as already described, is tapered after 2 hours.

Intermittent FHR monitoring—in addition to BPP testing, intermittent FHR monitoring can be started ½-1 hour before the treatment in a similar manner as specified for the preceding group. For any adverse FHR changes, IOT as 6 L $O_2$ is started as earlier discussed.

COT/IOT Weaning by 'Every Day Challenge' (EVDC) of CAT-3—

In the protocol algorithm as shown in FIG. 19, for the patient group of CAT-3, while trying to change COT to IOT when every day weaning attempts (EVDC) are commenced, patient's COT is tapered starting at 6 am, with ½ hour decrements as 6 L-5 L-4 L-2 L-stop. FHR tracing response can also be observed, and recorded with FHB monitoring starting at 5-5.30 am, to be intermittently observed throughout the day, as needed. COT is only switched to IOT if BPPS is maintained at least as 6. Similar FHR monitoring during oxygen weaning can be incorporated for CAT-4 management also, or at any time for any patient for additional and immediate observation of fetal response to weaning, and for charting the same. While BPP is time taking needing the presence of a physician or any specially trained professional, FHR observation is easier, and is a familiar monitoring technique to all the care-takers. Any non-assuring tracing can be an indication to immediately restart oxygen therapy, as a standing order. Whereas the FHR tracing helps to identify the requisite for an oxygen therapy or a need for its change, the BPP confirms such requisite and the needed precise change by virtue of the objective and the quantitative power of its score (as 0-10), to therapeutically proportionate the IV $DG_{25-50}$ treatment. The daily monitoring is continued until the patient is stabilized on a particular $DG_{25-50}$ dose before discharge, with or without elected oxygen therapy. Any patient in this group or any other group if not stabilized even with continuous oxygen therapy it indicates that there is significant impedance to placental D-glucose transfer.

As discussed, and as depicted in the Algorithm protocol of FIG. 19, with the most distressed group being CAT-3 having BPPS of 4 or less on COT, the patients of this group will need SIPP catheter placement for transamniotic isotonic D-glucose supplements, if there is no satisfactory improvement of BPPS after 1-2 days of treatment with COT with also an ongoing D-glucose supplement. Severe placental impedance to D-glucose is the probable suspect, and a confirmatory AF-LA testing should be done, and low AF-LA levels support, dominant fetal hypoglycemia. Normal or elevated AF-LA can be found with both hypoglycemia or normoglycemia, as predominant hypoxia can complicate either, but with COT the AF-LA should proportionally change, with also improvement in BPP score, unless there is also failed placental $O_2$ transfer. All the confounding variables that can also have bearing on the BPP score need to be addressed by IUGR-diet and IV supplements of vitamins and minerals, manipulating their placental transport to $V_{max}$, if not done already. Transamniotic glucose therapy is worthy of a therapeutic trial to coax the fetus to swallow on volition, more of the sweetened AF, with its continuous and substantive $O_2$ supply, by means as discussed earlier, a natural supply about the 'milieu interior'.

The Maternal IV Hypertonic 50% Glucose ($DG_{50}$) Treatments for Gestational Ages 32 Weeks or More—

For BPPS of 8 or More (32, GROUP-A)—the Protocol and the Management of Complications of this GROUP is Same as the Previous Group (that is, 26-31 GROUP-A).

However, this gestational age group can be started on $DG_{50}$ for all BPP scores. If the fetus responds to treatments without a need for Oxygen therapy, and with a BPPS of 8 or more, the treatment is continued up to 34-35 weeks, to plan delivery by checking the L/S (lecithin/sphingomylin) ratio, for the needed corticosteroid therapy. For planning delivery, along with twice weekly NST/BPP, twice weekly Doppler velocimetry is also helpful.

For BPPS of 6 or less (32, GROUP-B)— the mother is hospitalized, and immediately started on 6-8 L/minute of continuous oxygen therapy (COT). The AF is drawn for testing of L/S ratio, and of the lactate/lactic acid levels, and an immediate intravenous corticosteroid injection is done for the mother. Following, a maternal IV infusion of all B-complex factors and minerals along with trace elements in maximal allowed doses is given, this being common and an implied preliminary treatment for all mothers, as was discussed at the outset of this treatment protocol. The effects of vitamin deficits on the most distressed fetuses are discussed in the last section 'The neonatal care of an IUGR baby'. After the patient is stabilized on COT, the FIG. 19 algorithm protocol is followed (while the AF-LA levels also are found in or brought to an acceptable range), until the fetus acquires reasonable weight gain, with cesarean delivery planned at 34-35 weeks. The pregnancy not being remote from term, the management of this group is not difficult and protracted. Even 32 weeks neonates are more prone for morbidity/mortality compared to their AGA counterparts (especially for a decline in IQ scores, prematurity being added to IUGR), and hence allowing even few more weeks of intrauterine stay can be a saving measure.

To summarize, the fetal IUGR treatment with maternal IV hypertonic D-glucose supplements, with or without transamniotic isotonic D-glucose fetal supplements is evaluated, monitored, and treated, at base line and subsequently by the following—

(1) Amniotic fluid lactate/lactic acid (AF-LA) level: when AF-LA level is found higher at base line with lowered Biophysical Profile Score (BPPS), reflective of fetal hypoxia, prior to IV D-glucose therapy, the mother is treated with continuous oxygen therapy (COT), effectively normalizing AF-LA level.

(2) Fetal Bio-Physical Profile score (BPPS): wherein BPPS is chosen as proxy to the infrequently done AF-LA levels for the quantitative power of the BPPS (in the range of 0-10), to therapeutically proportionate the maternal IV $DG_{25-50}$ treatment, the fetal hypoxia and intolerance of D-glucose lowering BPP score, being reflective of fetal lactic acidosis.

(3) Low AF-LA and lowered BPPS encountered at baseline: the lowered AF-LA level being reflective of fetal hypoglycemia, the mother is treated only with IV hypertonic D-glucose therapy.

(4) A 2 hour stretch of fetal heart rate (FHR) tracings starting ½ hour before the initial therapy, and about each increment of maternal IV $DG_{25-50}$ treatment: wherein the adverse FHR changes being reflective of fetal intolerance of D-glucose treatment, due to fetal hypoxia and anaerobic glycolysis, the mother is treated with an intermittent oxygen therapy (IOT) about the time of daily IV $DG_{25-50}$ therapy.

(5) With the mother on IOT about the time of daily IV $DG_{25-50}$ therapy: if she fails the weaning challenge off the IOT, with accompanying adverse FHR changes or falling BPP scores, she is treated with continued IOT.

(6) With the mother on IOT: if she is showing $DG_{25-50}$ intolerance with adverse FHR changes, or fallen BPP scores, however, improving with continuous oxygen therapy (COT)—she is treated with an effective dose D-glucose along with COT.

(7) With the mother on COT: wherein she is manifestly unresponsive to IV $DG_{25-50}$ with no improvement in BPP scores or else deteriorating BPP scores, as also shown by low AF-LA levels reflective of unresolved fetal hypoglycemia, the fetus is treated with transamniotic D-glucose supplements through extraperitoneal suprapubic amniotomy, by a Subcutaneously Implantable Pregnancy Port (SIPP) catheter.

Vascular Access for Glucose Therapy—

Once definitive fetal growth is observed, the mother is a potential candidate for continued IV glucose treatments. In view of at least 6 more weeks to pass, with prospective elective abdominal delivery soon after, a peripherally applied central venous catheter access has to be strongly contemplated, and performed before discharge, as this is the best time for such procedure. This is applicable to all groups remote from term. Simpler and modified materials and methods for such peripheral venous access are described later. The possibility of not finding a vein after few days, and remote from the time of fetal viability can be anxiety provoking to the patient, and to her care-takers as well. For patients not very remote from term, and have good visible veins at both the wrists, elbows, and ankles, can be confidently maintained on regular IV line with hep-lock. If the available veins are exhausted just around the time of fetal viability and elective delivery, subclavian triple lumen central line placement can be an option for such patients.

Patient Education, and Maternal Care by Home Health Nurse—

All the patients need to be educated about the treatment, and the strict aseptic manner under which the intravenous access has to be conducted, for the patients to continue the treatment at home. A home health nurse needs to be assigned to monitor the patient, and to attend her at home, when ever needed.

The above hospitalization of the mother with bed rest/oxygen weaning, an average of 7 days or more, should be viewed as days less than those a premature/dysmature baby may otherwise have to spend in NICU (neonatal intensive care unit), but with unpredictable outcome, despite the trauma invariably inflicted, even in its most hospitable and an intensely caring new world.

The Transamniotic Isotonic Glucose Supplements, and the Means of Amniotic Cavity Access, Either Diagnostic or Therapeutic—

Any patient if not stabilized even with continuous oxygen therapy (COT) that is titrated to the maternal IV hypertonic glucose supplements and the fetal response—it indicates that there is significant impedance to placental transfer, and transamniotic D-glucose supplements are indicated as the last resort as maximum oxygen support is already in place. The patient needs to be informed about an uncertain therapeutic outcome, as it is only doing everything feasible. At this point, the existence of infection/genetic fetal compromise needs to be ruled out.

When the amniotic cavity access is one time, or more, the 'sterile patch technique' (devised by the author inventor) is strongly advised. It involves placing any conventionally used antiseptic patch like skin cleaning device, like an 'alcohol patch' over the well cleaned skin puncture site of the maternal abdomen, through which the needle is inserted, while care is observed for the center of the 'sterile-patch' to be untouched by the injector's hand. The amniotic cavity is accessed under ultrasound guidance to avoid the placental site, while the bladder is completely emptied, to avoid inadvertent bladder entry. Uterine cramping, vaginal spotting, or fever need to be watched for. AF leak occurs in 1-2% of cases, but stops in 2-3 days. Consequential miscarriage is not common, as the amniotic membrane seals, and AF accumulates (Marion S V et al). When there is question of whether or not AF was aspirated for the required testing, the crystalline arborization test can be used. Rh sensitization is possible and anti-D immunoglobulin (Rhogam) is indicated for Rh-negative susceptible mothers, even after single amniotomy. As a general rule, a pool of AF can be accessed in the mid suprapubic area (better by upward displacement of fetal head), in case the placenta is visualized to be located elsewhere, and in this site, the separation of the recti reduces the intervening maternal tissue (Whitfeld C R, 1978), the fetus being untouched by the needle. AF pocket can also be found by careful palpation, near the fetal limbs, or behind the fetal neck in case of breech.

Additional Comments on the Above Protocol—

1) When there is equivocal AF measurements lowering the BPP score—check the Umbilical artery S/D ratio. Patients with oligohydromnios but with normal umbilical artery Doppler S/D ratio are less likely to have poor perinatal outcome. With normal Umbilical artery S/D ratio, grade AF pocket measurements as score 2, hydrate the patient with 1 liter of fluids, and reevaluate.

2) If there is doubtful fetal breathing—when there is doubtful fetal breathing with unequivocal score or lowering of the BPP score, check umbilical venous Doppler for clarification. During fetal breathing, the umbilical vein waveforms are undulating, such wave forms corresponding to fetal inspirations, with a frequency much lower than fetal heart rate.

3) Correlation of BPP with fetal blood pH—BPP score of 8-10 corresponds well with fetal blood pH—a score of 8-10 corresponds to a pH of 7.37 which is in the normal range, a score of 6 corresponds to a pH of 7.33, and a score of 4 corresponds to a pH of 7.28 (Manning et al).

4) $O_2$ Therapy—The uterine placental vasculature during pregnancy is unique in that it is refractory to changes in blood gas tensions ($PO_2$ and $PCO_2$). Therefore, $O_2$ therapy either due to maternal or fetal causes will not cause placental vasoconstrictive response, and hence there is no adverse effect on fetoplacental blood flow. The fact that the $O_2$ demands are more for aerobic oxidation during peak blood glucose levels, and such demands can be less as the levels decline, and further, the progressive alleviation of fetal hypoxia by 33+%, 400%, and 10% via different metabolic consequences, as a multifaceted response due to maternal D-glucose therapy—make the oxygen deacclimatization tapering tolerable to the fetus.

5) $O_2$ therapy and $CO_2$ production—Renewed glucose metabolism in the fetus, and maternal hyperoxygenation can generate proportional amount of $CO_2$. However, maternal hyperoxygenation also facilitates Haldane effect at the placental level, that is, more of $O_2$ picked up by fetal hemoglobin facilitates more of $CO_2$ to be released. Therefore, by therapeutically improved fetal oxygenation, a resultant fetal hypercapnia may not be feared, due to cause and effect phenomenon of Haldane effect. This was discussed in more detail in the earlier section of 'The improvement of fetal hypercapnia'.

Continued Prenatal Monitoring of Fetal Well-being and of Fetal Growth Parameters, after the Patient is Discharged Home—

1) Uterine height: is monitored every two weeks, as a measurement in centimeters.

2) Fetal U/S: is monitored every two weeks, to affirm and document ongoing fetal growth.

3) Fetal heart tracing: is monitored weekly, or earlier if mother reports suboptimal fetal movements.

4) Maternal monitoring and documentation of fetal movements: it is done daily, for 1 hour at a stretch. 10 fetal movements count in 1 hour duration is assuring. If were found to be less, the mother should continue counting for one more hour. If they are fewer than 10 movements in the 2 hour period, she should contact the physician. An alternate way of fetal movement monitoring is, to count them for 30 minutes at a stretch, 2-3 times daily. Normally, there should be at least 4 strong movements during each 30 minute period. Encourage the patient to maintain peaceful atmosphere at home, and to use a ring buzzer over the abdomen to startle the fetus from sleep before the 1 hour monitoring, to make the results more reliable. The fetal monitoring should be formally documented, on a sheet provided to her, just as the self-administered glucose treatments.

5) BPP: it is monitored twice weekly—after the patient is stabilized on optimal $DG_{25-50}$ and sent home, and it is done earlier if mother reports suboptimal fetal movements. Either done as impatient or outpatient, the BPP score is interpreted as follows—Score 8-10—normal; score 6—equivocal or suspicious, and the test needs to be repeated the next day; score 4—the test needs to be repeated in 12 hours, and if repeat score is ≤6, immediate obstetric interference has to be planned, as per the protocol, which is transamniotic D-glucose supplements through extraperitoneal suprapubic amniotomy, by a Subcutaneously Implantable Pregnancy Port (SIPP) catheter. Score interpretation is similar even after the port placement, however, the obstetric interference in this situation is fetal delivery.

6) AF-LA levels: low levels with IOT or COT, along with no improvement in BPPS, indicate unresolvable fetal hypoglycemia, as the situation is treatment-refractory to maternal IV hypertonic D-glucose treatments, probably due to severe placental impedance, pointing a need for trans-amniotic fetal glucose supplements.

7) UA and MCA velocimetry: it is monitored weekly—starting at 30 weeks, to plan or to be warned of the impeding need for fetal delivery, for possible acute over chronic declining in the placental reserve, as exponential growth in the volume of placental terminal villi capillaries occurs starting 31-36 weeks failure of which is reflected in Doppler FVW forms. The S/D ratio and PI are reliable parameters. One may not wait for manifest 'Absent End Diastolic Flow Velocity' (AEDV), or the 'Reversed End Diastolic Flow Velocity' (REDV).

8) AF—L/S (lecithin/sphingomylin) ratio: it is done at 32 weeks.

9) Umbilical venous Doppler: it is done any time for equivocal fetal breathing off-setting the BPP score. It has to be noted that non-assuring venous doppler signs are late signs, as fetal heart failure and multi-organ damage are known to have already occurred, and hence not used as monitoring techniques of continued fetal well-being in this protocol.

10) contraction stress test without oxytocin: Periodically, to be assured of continued fetal well-being in utero.

Table-7, 'The fetal monitoring and treatment intervention table', shown in FIG. 20, and Table-8, '30 Minute biophysical profile score charting', shown in FIG. 21, are devised to tabulate the above discussed patient diagnostics and therapeutics, on an on-going basis, even for out-patient purposes.

The Planning of Elective Fetal Delivery by Cesarean—

An IUGR baby with precarious placental reserve, and/or maintained on intermittent or continuous oxygen therapy (IOT or COT), is rarely expected to survive the stress of labor. On the other hand, mothers who either needed no oxygen or were successfully weaned of oxygen, persistently maintained 8-10 BPP score, did not manifest olgohydromnios, had not demonstrated RDFV in umbilical Doppler velocimetry, and who demonstrated satisfactory periodic contraction stress test (CST) assuring continued fetal well-being and a reasonable placental reserve, if go into spontaneous labor around the time of planned elective delivery, a vaginal delivery can be tried with: continuous electronic fetal monitoring as the mother is maintained on 8 L/minute continuous oxygen therapy; continuous $DG_5$ IV fluids while she is kept in left lateral position to ensure adequate placental perfusion, with also periodic blood pressure monitoring, to be compared with the baseline; the IV $DG_{50}$ as per the regular timings; the operating room kept ready for emergency cesarean. For others, cesarean delivery around the elected time of delivery is prudent. With all the time and effort spent in prolonging the intrauterine fetal stay for the delivery of a well grown baby with its best potential preserved, when the time has arrived for its delivery, swaying in favor of a cesarean is no doubt better.

Useful Decision Tools for Immediate Delivery of a Viable Fetus—

In planning immediate delivery, along with twice a week CST and BPP, twice a week Doppler velocimetry is also helpful.

1. The Umbilical artery velocimetry (S/D ratio, PI, and MCAPI:UAPI) is done weekly, starting 30 weeks (after the base line study at the first encounter, for comparison)—to be warned of the possible acute over chronic declining in the placental reserve. S/D ratio and PI are the useful monitoring parameters and their abnormalities manifest 1-3 weeks earlier than nonreactive NST, or falling of BPP score, for the physician to be more watchful for the impeding delivery, as early as 34 weeks, and be prepared by finding the L/S ratio, if not done already. Though Doppler velocimetry was disregarded on admission, its improvement with treatment, followed by subsequent adverse changes are duly regarded for needed action plan.

2. Reversal of brain sparing effect in the MCA-PI—it signifies the failed fetal compensatory adaptation to a worsening uterine habitat. Once observed, prolonging pregnancy is not a wise choice. It is a strong indication for immediate delivery, after a steroid injection, with or without AF-L/S ratio results.

3. AF-L/S (lecithin/sphingomylin) ratio is done at 32 weeks, and if not found to be more than 2, corticosteroid injection is indicated. However, many IUGR babies are found to have L/S ratio more than 2, even before 32 weeks, presumably due to the chronic stress of inhospitable uterine habitat. The AF sphingomylin concentration remains static through the later months of gestation, but the terminal surge of the surfactant lecithin (the dipalmitoyl lecithin) in the fetal lung is reflected through the increased AF-L/S ratio. A ratio of ≤2 is associated with respiratory distress syndrome (RDS) which is of higher incidence in the neonates born before 32 weeks. The L/S ratio of >2, yet associated RDS is mostly seen with maternal DM (Whitfield C R et al, 1974).

4. Helpful tools indicating fetal maturity when dates are doubtful—(a) the Transcerebellar Diameter (TCD) is valuable (as the nomogram by Goldstein et al, 1987, showing TCD in millimeters as $10^{th}$, $50^{th}$, and $90^{th}$ percentiles) in an IUGR pregnancy, and it remains consistent with the standardized values corresponding with the gestational age throughout pregnancy, independent of fetal IUGR, (b) Bony ossifications—the ossification of distal femoral epiphysis occurs predictably around 32 weeks, and that of the proximal tibial epiphysis around 35 weeks, these two noted as prominent echoes distinct from the rest. Presence of distal femoral epiphysis of greater than 3 mm, and the presence of any proximal tibial epiphysis indicate a mature lung in almost all IUGR fetuses (Galan H L, 2003).

Table-7, THE FETAL MONITORING/TREATMENT INTERVENTION TABLE, shown in FIG. 20, and the 30 MINUTE BIOPHYSICAL PROFILE SCORE CHARTING, shown in Table-8 of FIG. 21, are devised to tabulate the above discussed patient diagnostics and therapeutics, on an on-going basis.

The Procedural Description of the Vascular Access for the Maternal Intravenous Hypertonic D-Glucose Supplements—

A patient who responded to the therapeutic IV hypertonic D-glucose treatments, or the D-glucose transamniotic treatments, as indicated by definitive ultrasonic parameters of fetal growth response, but at a gestational age remote from term, needs a secure vascular access that tends to last for an average period of 6-7 weeks. Broviac catheter that is a peripherally placed central venous catheter is an ideal tool in this situation, as it can be managed by the patient at home, without significant risk of sepsis.

The vascular access can be done via skin cut down in the anticubital fossa, and with a venipuncture preferably through the basilic vein. Different pediatric sizes of Broviac central venous catheters are available, and the appropriate size can be chosen for this purpose. The catheter was originally designed for total parental nutrition (TPN) for which the placement of the catheter tip should be in one of the larger central veins, and placement of the catheter tip as proximally as possible is advisable for the hypertonic strength of D-glucose being infused. Smaller pediatric size Broviac catheter allows placement of the catheter through the patient's forearm. Mentioning to the patient that a baby needle and a baby catheter are sufficient for the procedure instead of the adult size (after making sure that the patient may not misunderstand that it is for her baby in-utero) will reduce apprehension, and can improve patient-acceptance. However, the steps of the procedure should be specifically outlined to the patient, and it should also be clarified that it is not a simple procedure like the regular peripheral venous access that people are mostly familiar with, and may mistake for. Such informed decision making will avoid any unforeseen patient resentment later.

The Broviac catheter is made of soft radiopaque rubber, with a small Dacron felt cuff at a specified distance from the external end. The internal diameter is less than 1 mm for the pediatric sizes, and the catheter consists of a thin walled intravascular segment and a thick walled extra-vascular portion. The extravascular portion is tunneled through the subcutaneous tissue to a separate skin exit site, distant from the venotomy site. The Dacron cuff is so located about the catheter that it will be positioned within the subcutaneous tunnel, and the fibrous tissue ingrowth into the cuff acts as an effective barrier to the bacteria possibly migrating from the skin into the venous system along the outer surface of the catheter.

Technique of the Broviac Catheter Placement and the after Care—

Though typically the catheter is placed by venous cut down, it can also be placed in a manner similar to subclavian central venous access, using a guide-wire (the Seldinger technique). The patient's left forearm is chosen for a right handed person, so that the patient can self-inject. As the chosen catheter entry site is the anticubital fossa (where the scar can merge with the ante-cubital crease), the catheter exit site can be somewhere on the medial aspect of the forearm, where it is less obvious, yet can be easily cared for, by the patient.

To start with, an appropriate size pediatric triple lumen central venous access set should also be procured along with the pediatric Broviac catheter. A portable ultrasonic device allows visual confirmation of the location and the course of the target vein. A small cut (of 1 cm) is made in the skin, over the proposed venipuncture (venotomy) site. As the cubital veins are very superficially located, it is better to lift a skin fold, cut with scissors, and widen the skin incision to desired length (avoiding the scalpel contact with the superficial vessels). From there a subcutaneous tunnel is made to the chosen skin exit site on the medial aspect of the forearm. When the tunneling instrument approaches the skin exit site, a small incision, about 1 cm, is made at the skin exit site. The tunneling instrument at its exit picks up the catheter tip to be brought to the venotomy site, while retreating in its course. The basilic vein is entered through the needle supplied in the triple lumen set. Using a guide wire also supplied in the set, the Broviac catheter tip is threaded into the vein over the guide wire, in a similar manner that a central vein catheter is placed, as in the Seldinger technique. The catheter is passed to the proximal destination, up to a distance that allows the Dacron cuff to be positioned in the middle of the patient's forearm inside the subcutaneous tunnel. The venotomy site incision is closed, and the catheter is fixed to the skin exit site by mono-filament nylon that is removed after 1-2 weeks by which time fibrous ingrowth into the Dacron cuff has taken place. Sterile povidone iodine ointment and a sterile dressing are applied to the exit site, and the catheter is filled with heparin treated saline, and closed with hep-lock. The loop of the redundant catheter if any, is taped to the medial aspect of the forearm.

The patient has to be advised that even the hep-lock needs to be cleaned with a povidone iodine ointment, and after use, covered with sterile tape seal, so that the hep-lock is kept clean, whatever be the patient's activity. The hep-lock has to be injected with sterile gloved hand through any sterile skin patch, like an alcohol patch, placed over the hep-lock. The hep-lock is changed more frequently in view of the long catheter in-dwelling time, and hence needed stringent care. The extra-cutaneous redundant part of the catheter is also cleaned with the ointment, and taped to the hand by sterile adhesive dressing. The procedure being least traumatic and least invasive, it is easy to gain patient acceptance, as it is essentially like any simple peripheral venous catheter placement with least injury to the vessel wall, and in addition, with multiple measures against sepsis, for the needed indwelling time. Ideally, the catheter placement is done in the controlled environment of an operating room, under aseptic precautions.

If the physician has not found any suitable tunneling instrument in the armamentarium of the available surgical tools, to use in the small curvilinear confines of the fore arm, as aesthetics are also essential in an exposed anatomical site like the fore arm of an young female, the author inventor of this writing advocates to use a Hegar cervical dilator (or a Hank cervical dilator) for this purpose. Its smooth and delicate curvilinear structure suits the contour of the fore arm, and with the smallest size dilator having 21 cm length, and 3-4 mm diameter (half of the dilator has 3 mm diameter, whereas the other half has 4 mm diameter) (Gynex), any rough manipulations invariable with other instruments in this area, can be avoided. It can also make the needed incisions to a minimum size. However, the procedure needs some modification (as devised by the author inventor, and hence named as Sumathi Paturu's subcutaneous tunneling technique for venotomy' (to be differentiated from any other prevailing subcutaneous tunneling technique for venotomy), and the devised technique is used for catheter amniotomy also in this specification). It can be done in the following manner, using also a straight urinary catheter as a passage sheath for the dilator.

Sumathi Paturu's Subcutaneous Tunneling Technique for Venotomy—

To start with, a sterile Hegar dilator is passed into a suitable size sterile straight rubber urinary catheter, and so enclosed, the catheter tip can be negotiated through the venotomy incision site to the skin exit site located distally on the medial aspect of the fore arm. Following the exit of the tunneled instruments at the distal skin exit site, the instruments can be gently moved side to side (not rotated on their axis), so that a wider and suitable caliber subcutaneous tunnel is created, as it needs to accommodate the Dacron cuff. Following that, the Hegar dilator can be removed retreating through the venotomy site, leaving the urinary catheter in the subcutaneous tunnel. The urinary catheter tip can be cut to expose its whole caliber at the skin exit site. From this widened cut end, the tip of the Broviac's catheter can be passed to reach the venotomy site in the anticubital area. After the exit of the tip of the Broviac's catheter from the urinary catheter end, the urinary catheter can be removed over the Broviac's catheter, which it had enveloped. It is done from the venotomy site. It can be noted that only the tip and the proximal length of the Broviac's catheter have to pass through the urinary catheter.

If the creation of the tunnel in the tunnel-initiating site poses a problem, a curved hemostat or curved scissors can be used to separate the tissues, and to create the needed cleavage in the subcutaneous plane, but being mindful that only the tip of these instruments is curved for a confined length. In a very lean person, or if the exit site is chosen on the anterior aspect of the fore arm, the tunnel can be relatively linear, and most of the instruments are suitable in this situation, though a hinge in an instrument always makes its maneuvering caliber wider. The tunneling can be initiated in the medial forearm also, wherein the instrument negotiation is substantially easier.

The size of the urinary catheter is chosen in such a manner that its movement over the Hegar dilator is easy, but the fit not too loose. Leaving the tip as it is, the catheter can be cut at the other end to start with, to use only the needed length for this purpose, that is, 1-2 inches longer than the curvilinear length of the proposed subcutaneous tunnel. This procedure is suitable for any subcutaneous instrumental tunneling and venotomy, for any regular catheter or for any port-catheter placement, in any preferred venotomy site.

The tunneling instruments need to be very carefully maneuvered. A 'skin-lift' technique can be used—that is, lifting up a 'leading skin fold' over the planned subcutaneous passage line so that the tunneling instruments stay immediately underneath the skin fold as they proceed (abutting the skin), keeping away from the deeper plane where nerves and veins like the basilic vein traverse. If needed, few superficial skin sutures without ligatures can be placed with a very thin needle, along the passage line of the tunneling instruments, to be lifted by hemostats, and the said sutures removed immediately. Such precautions avoid unforeseen complications, as the anatomy of the superficial veins of the fore arm and the cubital fossa is very variable, however, familiar to a surgeon.

Further precautions that can be observed to prevent infection of the catheter is—antibiotic lock technique (Messing B), that is used successfully in the medical field, to treat and prevent central venous catheter infections. The technique involves injecting an antibiotic solution (preferably vancomycin 2 mg/ml) into the catheter lumen, and allowing the antibiotic to sit in the line for at least 12 hours, before surgically inserting it into the patient. The catheter is periodically re-injected and the antibiotic is made to sit in a similar manner, after clamping the catheter at the skin entry site. It has to be done after completely emptying the blood column from the redundant catheter by antibiotic injection, before clamping the catheter at the skin entry site, and allowing the antibiotic solution to stand in the redundant catheter lumen until the time of the next D-glucose injection. It prevents possible infection introduced into the interior of the catheter lumen during the daily use, which the Dacron cuff may not prevent. Vancomycin like penicillin, is pregnancy category-B.

The Transamniotic Isotonic D-Glucose Fetal Supplements

The biochemical benefits attributable to normoglycemic status of the fetus, possibly achieved by the additional modality of the transamniotic isotonic D-glucose ($DG_5$ isotonic, or $D_5$ water) treatment are similar to what were elaborately discussed under the section of 'Maternal intravenous hypertonic D-glucose supplements'. However, being an invasive procedure, though minor in nature, it is advised as the last modality of treatment when all else fails, including the concomitant continuous oxygen therapy (COT) with the maternal IV hypertonic D-glucose treatments. No improvement of BPP score during increments of maternal D-glucose therapy while on COT points to the probable diagnosis of ongoing fetal hypoglycemia due to severe placental impedance, when other contributing factors are ruled out. The vast area of the fetal interior exposed to the glucose enriched AF can effectively absorb the supplemented glucose before its decline in the AF in a span of 3 hours. The transamniotic D-glucose supplements being not therapeutically all-inclusive in relieving the fetal growth restriction, the placental supplies of D-glucose through maternal treatment should be ongoing, and paramount. It is for the reason that normally the placental glucose requirements are equal to, or more than that of the fetal, as the placenta extracts 50-60% of glucose entering maternal sinusoids for its multitude of functional requirements, the most important being supplying glucose to the fetus itself in the form of lactate, when transfer of D-glucose from the maternal compartment itself is low, as during maternal sleep cycles/maternal fasting.

Despite a last resort, nutritional supplements via amniotic fluid (AF) is scientifically an attractive proposition. The phenomenon of intrauterine fetal swallowing is taken advantage of in this modality of treatment. 5% isotonic D-glucose solution can be safely instilled into the amniotic cavity without adversely affecting osmotic forces. 5% D-glucose which is isotonic with maternal extracellular fluids should be isotonic with the AF, because the normal osmolality of the maternal plasma and the fetal plasma are in the range of 260-275 mosm, and so also is the osmolality of AF from 20-30 weeks. Instillation of 100 cc of 5% D-glucose twice daily is a supplementation of 10 G. of glucose that would amount to 41 kilocalories of energy supplement to the fetus, and it can be administered thrice daily (62 kilocalories) or four times daily, as the pregnancy advances. Even if AF is replaced every 3 hours, still substantial amounts can get into the fetal body.

Studies of transamniotic fetal feeding (TAFF) of pregnant rabbit models were conducted by Mulvihill et al in 1985 using 10% dextrose solution which had been associated with increase in fetal weight. However, studies of Flake et al with solutions of dextrose, amino acids, and of lipids, either alone or in combination did not reverse growth restriction in the natural runt rabbit fetus. The reasons for these controversial results can only be postulated. Too much of dextrose without required vitamins (especially of the B-complex factors like thiamine) needed as cofactors for the carbohydrate metabolism (presuming that the rabbit's biochemistry is similar to human) could be overwhelming to the fetus. Too much of lipid or of amino acid supplements with or without glucose can be a stress to the oxidative machinery of the fetus, the beta oxidation of fats, and the amino acid catabolism for energy-yielding purposes being oxygen/ATP consuming path-ways. It can make the existing hypoxia worse, and the co-administration of glucose not very beneficial. The concomitant maternal treatments that include prior IV supplements of vitamins/minerals, and also the IUGR diet with maximal daily supplements of vitamins, minerals, and of trace elements will compliment and make the transamniotic fetal treatments fulfilling, as the maternal route appropriately relies upon treating the fetoplacental unit as a whole. The maternal supplements added to the AF 5% D-glucose supplements further improve voluntary fetal swallowing because of the improved taste, as in the research studies a new born seemed very discriminative in preferring oral sugar solutions (Johnson P & Salisbury D M). The AF contains valuable constituents, as shown in the Table-9 (FIG. 22, The amniotic fluid composition during normal pregnancy). The D-glucose supplements can be increased to 200 cc, which also relieves the oligohydromnios. The AF normally has amino acid content similar to maternal extracellular fluids, and her IUGR diet with essential amino acids will also increase the AF levels. The glucose enhanced fetal AF swallowing improves fetal intake of all its constituents.

The AF, containing valuable constituents as shown in the Table-9, had been proved to be essential for optimal fetal growth. The transamniotic glucose supplement could be more beneficial than it seems, and can be given a therapeutic trial when COT is not feasible, to coax the fetus into more volitional swallowing of the sweetened AF, to be benefited by virtue of its substantive and naturally continuous oxygen supply from the 'milieu interior'.

As the daily puncturing of amniotic sac is replete with dangerous sepsis for the needed duration of the treatment involved in human pregnancy, the invention contemplates to achieve such daily transamniotic access through a Subcutaneously Implanted Pregnancy Port Catheter (SIPP catheter) placement, accomplished through a minimally invasive extraperitoneal (from outside of the peritoneum) suprapubic amniotomy. There is least danger of infection, and great ease of daily use, after its one time insertion.

The Novel Transamniotic Insertion of the Subcutaneously Implanted Pregnancy Port with Catheter (SIPP Catheter)—

The novel procedure of the extraperitoneal suprapubic transamniotic port-catheter placement is tailored for obstetric purposes, and is devised by the author inventor, while the subcutaneously implantable (intravenous) catheter with port was originally devised decades ago by past inventors for exclusive use through the intravenous route. The catheter part of the device of the instant specification is also modified by the author inventor to be suitable for transuterine approach of the amniotic cavity, and is further configured to relieve malfunctions unique to the milieu. The port, however mostly retaining its original structure as was devised, can be used safely through the long duration of pregnancy, encompassing a 'sterile-patch technique', also devised by the author inventor, to make its use sepsis-free, the introduction of infection into the amniotic cavity being a much feared complication inherent to countless number of port punctures involved.

The sterile patch technique for transamniotic infusion of isotonic D-glucose—as was described in an earlier section, it involves placing on the well cleaned (port) puncture site of the maternal abdomen, any antiseptic patch-like skin cleaning device, like an 'alcohol patch', without touching the center of the patch, through which the amniotic cavity can be accessed using a straight needle. The corners of the patch can also be carefully taped for a stable placement.

The Access Site of the Amniotic Cavity, for the Extraperitoneal Transamniotic SIP Port Catheter Placement—

As a general rule, a pool of AF can be accessed in the mid suprapubic area (by upward displacement of fetal head), in case the placenta is visualized to be located elsewhere. The separation of the recti reduces the intervening maternal tissue (Whitfield C R, 1978), and it virtually eliminates fetal injury, as the fetal body as a whole is out of reach. If the mother is kept in Trendelenburg's posture for few minutes, it also allows the cord to settle in the upper uterine pole, when the mother can be brought back to the supine position, with a slight leftward tilt for surgery.

The Structural and Functional Description of the Subcutaneously Implanted Pregnancy Port (SIPP) with Catheter—

The diagrams used to illustrate the design of the SIP port with catheter are not necessarily drawn to scale, and are shown in: (a) FIG. 10—A perspective view of a Subcutaneously Implanted Pregnancy Port (SIPP), and the distal end of its articulating port-catheter; (b) FIG. 11—A perspective view of the proximal end of a Subcutaneously Implanted Pregnancy Port (SIPP) catheter with an attachable winged cuff.

The SIP Port and the Catheter—

Figure 10:
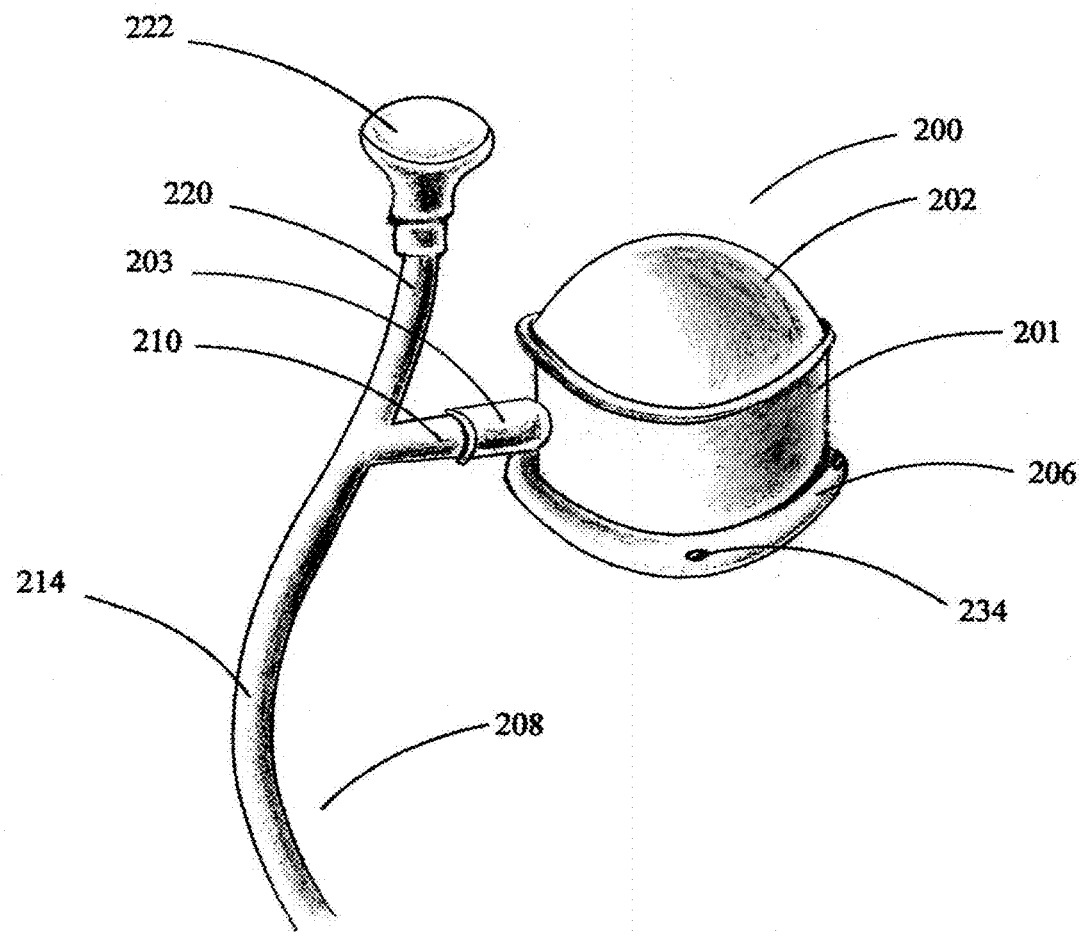
FIG. 10: A perspective view of a Subcutaneously Implanted Pregnancy Port (SIPP), and the distal end of its articulating port catheter—as an instrument modified for obstetric surgical purposes, during human pregnancy.

The SIP port is devised as a subcutaneously implantable port (200) with a housing reservoir body (201) containing a dome or diaphragm shaped septum (202) (FIG. 10). The septum or dome (202) is made of implantable medical grade rubber, a silicone elastomer. The dome (202) is capable of being punctured by a needle (a Huber needle is conventionally used, but regular needle is intended for transamniotic use) for fluid infusion, and is also capable of resealing upon removal of the needle. The reservoir body (201) is conventionally made of a wide variety of materials like titanium, steel, ceramic, or plastic. For obstetric purposes, to be used for a relatively shorter duration, a medical grade plastic can be chosen. It makes the housing reservoir (201) light weight to be well stabilized without down-sliding over the enlarging convexity of the maternal abdomen during pregnancy. The dome septum (202) can be as small as 2 centimeter diameter for this purpose, but bigger sizes are not precluded. When the dome septum (202) is 2 centimeter diameter, the largest dimension of the port (200) itself is about 2.5 cm. The bottom or under surface of the body frame of the housing reservoir (201) is contoured as concave shaped, to sit with well approximation over the convex contour of the maternal abdomen. The silicone dome (202) is configured as hemispherical in contour, whatever be the shape of the reservoir body (201). The reservoir body (201) of the port (200) is expanded in its perimeter as a flat plate (206) of 0.3 cm (206) of 0.3 cm width that has three apertures (234) placed equidistant in three of its four quadrants so as to secure the port (200) in its subcutaneous port-pocket by suture ligature, with any preferred non-absorbable material.

In the quadrant devoid of an aperture, the reservoir body (201) is connected to the catheter (208) through a port stem or segment (210), and a locking collar (203). The stem or segment (210) that couples the port (200) and the catheter (208) is made of a similar material as the catheter (208), whereas the locking collar (203), devised as an extension of the port (200), is made of a similar material as the port body (201) itself. The catheter (208) is made of polyurethane, with an internal diameter of 0.89, and a length ranging 50-70 cm, though other dimensions are not precluded. Its intrauterine portion is thin, and the rest, especially the extra-pelvic portion is thicker in the substance thickness of its walls. Maternal abdominal dimension vary widely. Hence, a wide range of lengths is devised to be available. The catheter length further accommodates for the changing size of the bladder, and for the enlarging size of the uterus through pregnancy. The SIPP catheter has a distinct distal end and a distinct proximal end that are further described as follows.

The Distal End of the Catheter—

The port unit (200) connected to the catheter (208) through port stem or segment (210) is actually a small off-shoot of the catheter (208) from its distal end (214), as shown in the FIG. 10.

The catheter (208) distal to the port segment (210) has a length of 2-3 cm that is configured as a distal segment (220) of the catheter with a detachable silicone rubber trumpet-like terminal (222), 1 cm in its largest diameter (with plastic underlay except under the terminal flat sheet), and structured like a hep-lock device capable to be punctured with a 18-19 gauge needle, as a means of passing a guide-wire through the catheter length. Said guide-wire is passed into the catheter lumen to relieve any block (by the amniotic fluid solid components), not relieved by infusions through the catheter, of the isotonic D-glucose with the force of a bolus. The guide-wire used for the purpose of inserting the catheter (208) initially is saved, autoclaved, and used for this purpose, if necessary. An additional trumpet (222) is supplied in the set, in case the trumpet leaks, due to punctures involving an 18 gauze needle. Such leaks can be identified by a local swelling. The distal trumpet segment (220) and the detachable trumpet (222), configured to be the direct continuation of the catheter lumen, enable the guide-wire's passage easy and uninterrupted. The trumpet (222) joint with the trumpet segment (220) is a tight threaded coupling that prevents dislodgement of the connection. As the extra-uterine catheter (208), especially the distal end (214) being much thicker with a substantially larger lumen also, blockage by amniotic fluid particulate matter is not an occurrence in the distal catheter (214), including the trumpet segment (220), and the port segment (210).

The Proximal End of the Catheter and the Catheter Cuff—

Figure 11:
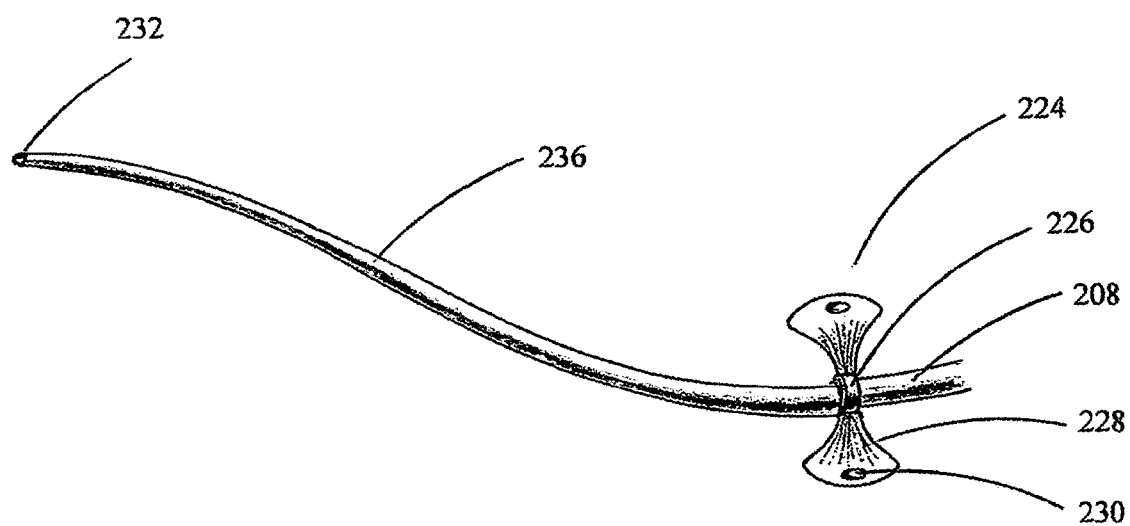
FIG. 11: A perspective view of the proximal end of a Subcutaneously Implanted Pregnancy Port (SIPP) Catheter, with an attachable winged cuff—the said cuff devised to anchor the proximal SIPP catheter to the exterior of the lower uterine segment, following an amniotomy intrauterine insertion of the proximal end of the SIPP catheter.

The proximal part (236) of the catheter (208) is shown in FIG. 11. Its terminal has a small hole (232) that communicates with a fluid cavity, which is the amniotic cavity fluid pocket (136). The proximal part (236) of the catheter (208) has a butterfly-like winged polyurethane attachable stabilizer (224) having a central cuff (226) with a slit through its axial length that can be opened to envelope the circumference of the proximal segment (236), and to be positioned immediately outside the uterine wall soon after the amniotomy catheter insertion. The cuff (226) is short in its axial length, only 2-3 mm. Its two wings (228) have centrally placed marginal apertures (230) to be sutured in place to the superficial layers of the myometrium, with a non-absorbable suture material, whereas the inside of the cuff (226) is glued to the exterior of the proximal catheter (236) with biocompatible glue, so that the intrauterine part of the catheter (236) remains fixed and stable through pregnancy.

The Accessory Parts—

The SIP port and catheter set has accessory parts integral to the function of its insertion, in a manner that are required of the conventional Seldinger's vascular access technique, except that it is done through the uterine puncture site instead of a venotomy site of the conventional procedure. The accessories include a puncture dilator (similar to a vein dilator) with 0.89 mm of internal diameter, and a guide-wire made of steel having 0.64 mm diameter, and a length ranging 55-75 cm. The guide-wire is made in the conventional manner, comprising of helical wire coils over a core of straight solid wire having good column strength, but can be easily bent in a manner needed for the purpose of catheter insertion. The set uses regular needle, size 18-19, but the needle is longer (8-10 cm length), similar to a spinal needle.

A modified simpler device, yet with added safe-guards required of obstetric purposes, will be described in the continuation-in-part (CIP) of this application.

The Surgical Technique of the Placement of the Subcutaneously Implanted Pregnancy Port (SIPP) Catheter with Emphasis on the Related Pelvic Anatomy—

The anatomical description of the pelvis is invariable to understand the surgical procedure for the suprapubic transamniotic placement of the extraperitoneally inserted SIP port. The pelvic anatomy in the ensuing description is what is normally encountered in the non-pregnant female, and is so preserved through pregnancy.

The structural description of the pelvis-abdomen and the subsequent narration of the surgical procedure are done in the anatomical position, the conventional manner. All the drawings are illustrated in erect right sagittal/median view to relate/orient unambiguously to the organ descriptions narrated in the conventional erect anatomical position. This refers to a surgical illustration also (FIG. 9), though a supine position is conventionally used for most of the abdominal/supra-pubic surgeries, including that described in the specification.

The Normal Anatomy of the Pelvic Organs—

Figure 7:
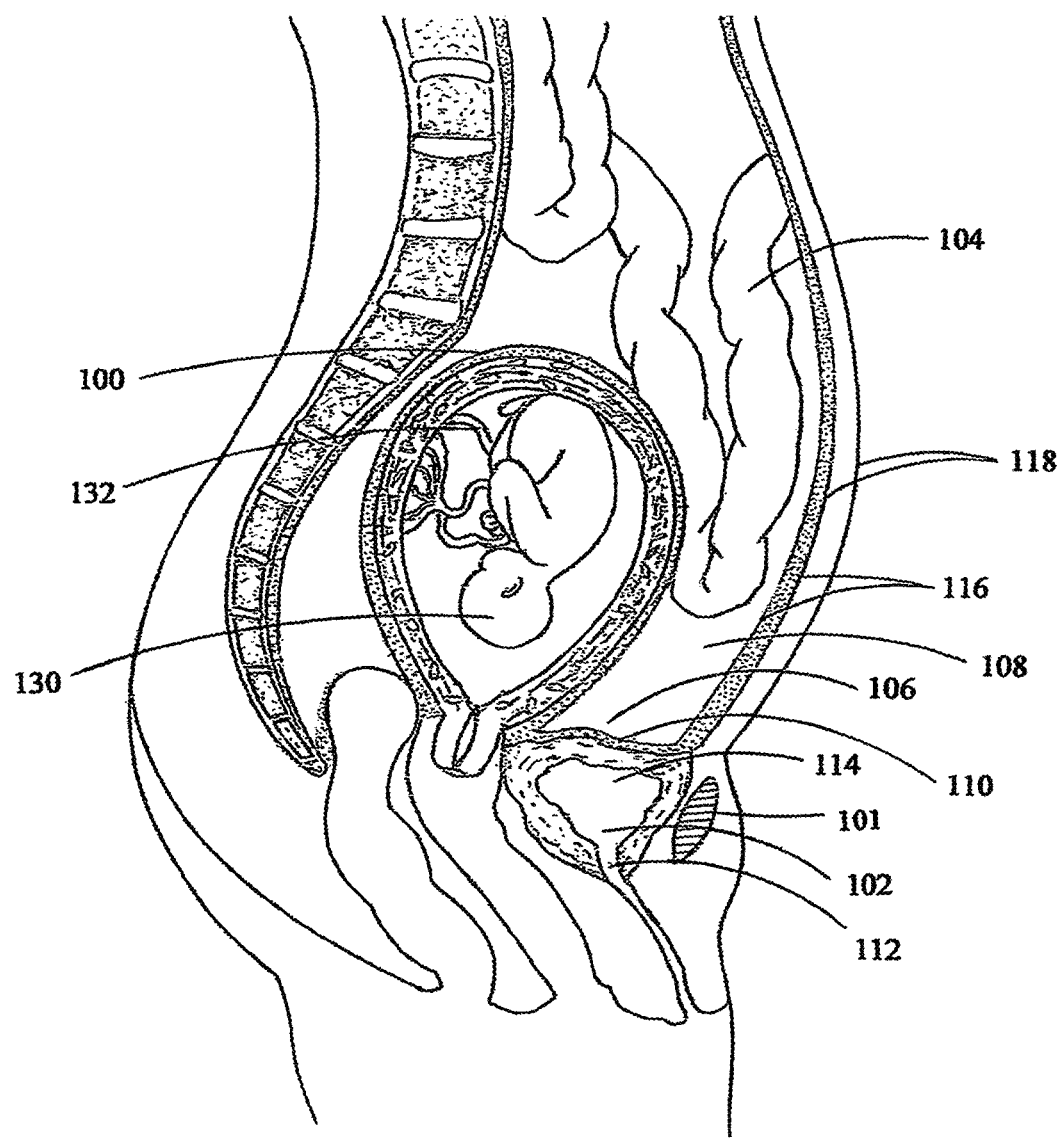
FIG. 7: A perspective right sagittal view (a median section) illustrating the normal anatomy of the human pelvis and the lower abdomen during pregnancy.

As seen in the FIG. 7, in the human pregnant female, for the SIP port catheter placement via the suprapubic approach, the major organ encountered is the urinary bladder (102) that is located anterior to the uterus (100) and posterior to the pubic symphysis (101). The urinary bladder (102) is a hollow organ that receives urine, and empties it intermittently on volition. The changeable anatomical milieu as the bladder fills can be taken advantage of, as it is the aim of this surgical procedure to place the SIPP catheter through an extraperitoneal suprapubic route, as its redundant pelvic course can otherwise make the loops of small intestines (104) get entangled/trapped during early pregnancy, when there is enough room in the pelvis (106) and abdomen (108) for such event to happen, causing bowel ischemia and gangrene. Anterior to the uterus (100), the urinary bladder (102) lies immediately below the pelvic peritoneum (110), and when empty, the bladder is positioned wholly within the pelvis (106). As it fills with urine, its neck (112) and lower part remain stationary, while the upper part (114) balloons up (FIG. 8) lifting up the peritoneum (116) off the anterior wall (118) of the lower abdomen (108) (reference—Brash JC. Cunningham's Manual of Practical Anatomy, volume-2, Thorax and Abdomen, 12$^{th}$ edition, page 452, 1962, Oxford university press) and in this situation, the uterus can be reached extraperitoneally in this surgical procedure, through a supra-pubic incision (122), for the placement of the SIP port catheter (208).

Sumathi Paturu's Technique of Extraperitoneal Suprapubic Pelvic/Uterine Approach and Amniotomy Through SIP Port Catheter, Also Involving Sumathi Paturu's Subcutaneous Tunneling Technique for a Remote Port Placement—

Sumathi Paturu's technique of extraperitoneal suprapubic pelvic/uterine approach is devised by the author inventor, and hence so named, to specifically and particularly identify the procedure and technique (as is conventionally done for any surgical procedure), and the technique is referred with that name in this disclosure.

The surgical procedure for the placement of the SIPP catheter is planned as elective surgery. The placental position is confirmed to be in the upper uterine segment prior to surgery. The patient will be started on IV D$_5$W at 84 ml/hour, and inserted with an indwelling Folley's catheter, the night before. The Folley's catheter end is clamped and taped to the patient's thigh, facilitating the catheter bulb to remain in position, occluding the internal urethral meatus, so that the bladder distends to about 4-5 cm above the pubic symphysis. The patient rests in left lateral position, and is mildly sedated, to blunt her discomfort.

For the surgery, the patient is made to lie in a supine position with a slight left lateral tilt, maintained throughout. In a right handed patient, the SIP port is placed over the right side of the abdominal wall, so that the patient will be able to self-inject. An area just medial to the right anterior superior iliac spine is a suitable site to create the port-pocket, as its distension during pregnancy is minimal so that the port will be stable in its position. As the largest dimension of the port is about 2.5 cm in diameter, a skin incision about that size is appropriate to insert the port into its subcutaneous port pocket (hence forth called as port site). To start with, a 1 cm incision is made at the port site. To create a subcutaneous tunnel, a suitable size Hank cervical dilator available in 19.2-26.9 cm length range (Gynex), and a wide variety of small diameter sizes, is used. It is sigmoid shaped with a smooth curvilinear configuration that can be easily negotiated over the convexity of the maternal abdomen. To start with, a preferred small diameter size Hank dilator is ensheathed in a suitable sized straight urinary catheter that allows free movement of the dilator within the rubber sheath. The ensheathed Hank dilator then is inserted through the 1 cm skin incision at the port site, and passed through the subcutaneous plane of the lower anterior abdominal wall, to course towards the pubic symphysis (hence forth the symphysis site). A sharp scissors can be used at the port site to create a plane of cleavage in the subcutaneous tissues.

A 2.5 cm (1 inch) transverse suprapubic incision (122, FIG. 9) is made in a manner similar to a Pfannenstiel incision, and the subcutaneous fat is cut and separated in all directions as much as possible from the superficial rectus sheath, and the sheathed Hank dilator is brought out through this incision of the symphysis site. The Hank dilator is removed from its envelope sheath of straight urinary catheter through the symphysis-site, by cutting the tip of the catheter to expose its whole lumen. Alternately, it can be removed from the port site also. The SIP catheter's tip (236) is then introduced through the end of the straight urinary catheter at the port-site, and is brought to the other end at the symphysis site. Then the straight urinary catheter is removed through the symphysis site, over the SIPP catheter it had ensheathed, so that the SIP catheter is left in the subcutaneous tunnel.

If the maneuver is difficult, the course of the tunneling Hank cervical dilator sheathed in the urinary catheter (and later the SIPP catheter also sheathed in the urinary catheter), can be interrupted in the midway (at the mid-inguinal area), and brought out through a small skin incision, to repeat similar procedure as started at the port-site, for the tunneling instruments to reach the symphysis destination. The tunneling instruments need to be very carefully maneuvered. As described earlier, a 'skin-lift' technique can be used—that is, lifting up a 'leading skin fold' over the planned subcutaneous passage line so that the tunneling instruments stay immediately underneath the skin fold as they proceed keeping away from the deeper plane where nerves and veins may traverse. If needed, few superficial unknotted skin sutures can be placed along the 'leading skin fold' to be lifted by a hemostats, and the said sutures removed immediately.

Figure 8:
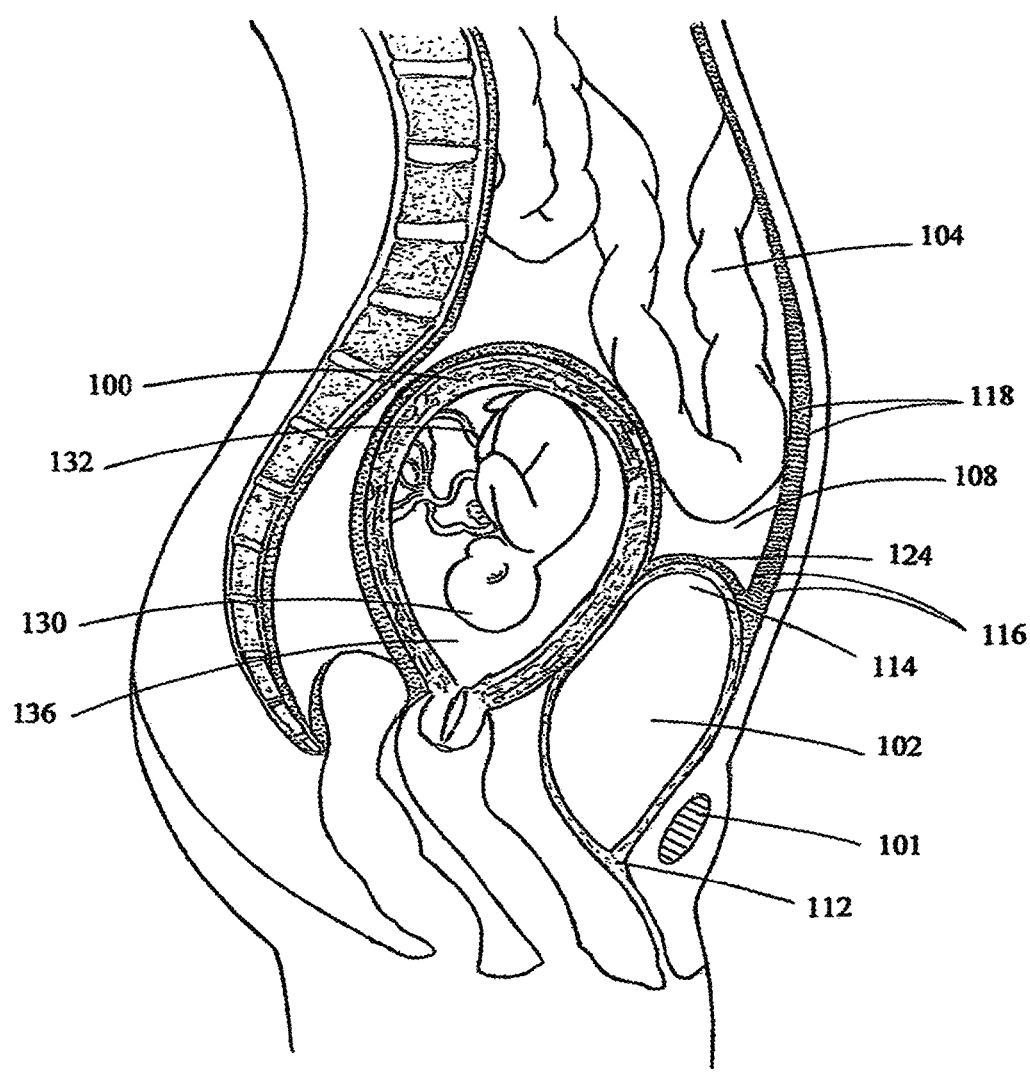
FIG. 8: A perspective right sagittal view illustrating the normal changes in the peritoneal anatomy of the pelvis/lower abdomen with a distended bladder, as also seen during human pregnancy.
Figure 9:
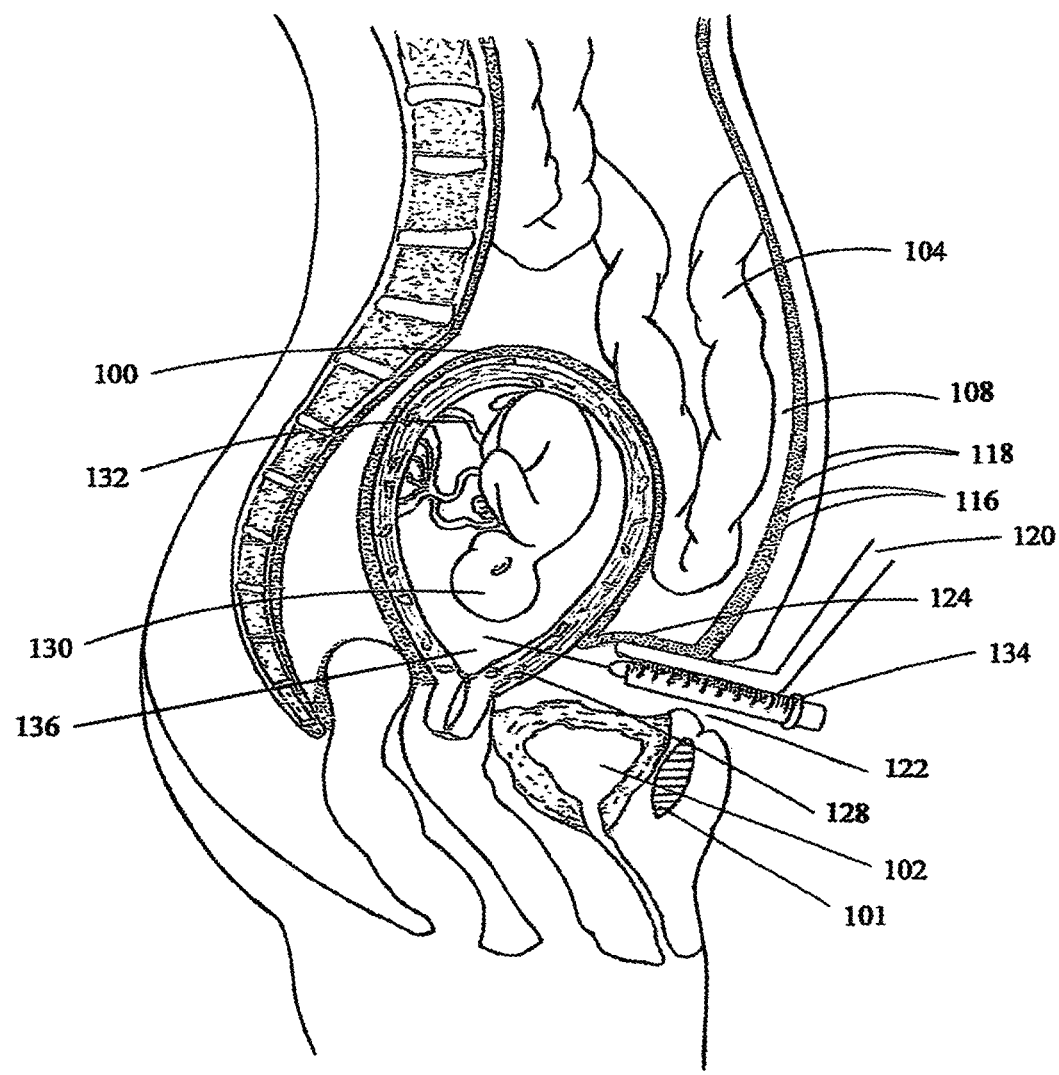
FIG. 9: A perspective illustration of a suprapubic extraperitoneal amniotomy through the anterior lower uterine segment—showing amniotomy needle insertion prior to the Subcutaneously Implanted Pregnancy Port (SIPP) catheter placement, depicted in an erect right lateral position, of a surgery generally performed in maternal supine position.

The 2.5 cm skin incision (122) at the symphysis site can be extended to 4-5 cm if necessary, in case of an obese abdomen. The exposed rectus sheath is incised vertically as much as possible, when it may be noted that the peritoneum of the lower abdominal wall is not encountered, and furthermore, the distended and bare upper part of the bladder (114), also devoid of the peritoneal covering (116) is immediately underlying the cut rectus sheath (FIG. 8). The peritoneum (116) of the anterior abdominal wall (118) is not visualized because it is lifted up along with the distended upper part of the bladder (114) being peeled away from the lower anterior abdominal wall (118). The said incision of the rectus sheath is made very carefully by always picking up a fold of the sheath, to cut it with scissors and then extend, so that the distended bladder underneath is not accidentally injured. After making a desired length incision, a moderate size L-shaped retractor (120) is inserted through the incision (122) in such a manner that the blade of the retractor (120) traverses vertically up anterior to the bladder (114), and behind the anterior abdominal wall (118) until it reaches the undersurface of the peritoneal shelf (124) that overlies the upper part of the bladder (114). Ultrasound guidance is helpful to delineate the anatomical distinctions of this area. At this time, the bladder is allowed to empty very gradually, as the retractor (120) blade is moved down much slower than the bladder (114) that is receding towards the pelvis (106). As the retractor blade (120) is moving down, its vertical position is gradually changed few degrees towards horizontal position each time, so that when the bladder (114) almost reaches pelvic position, the retractor blade (120) assumes a totally horizontal position that keeps the peritoneal shelf (124) above it (FIG. 9). As the superior surface of the receding bladder (114) is visualized at the incision (122) level, its emptying is put on hold, and the peritoneum is gently separated from its superior surface as far back as possible. At this point, the peritoneal shelf (124) below the retractor blade (120) is picked up by a hemostat for needed stretch and peritoneal clearing, to visualize the bare uterus in the next step. The bladder (102) is now allowed to empty further, while also completely separating the peritoneum if any, still adherent superiorly, over it. At this time the lower uterine segment (128) devoid of peritoneal covering comes into view.

The fetal head (130)/the presenting part is displaced upward, and held in that position by an assistant. The patient can also be kept in Trendelenburg's position, if loops of the umbilical cord (132) are visualized at the lower uterine pole (as seen through the ultrasound equipment), so that they will settle towards the opposite pole. The patient is then slowly put back to horizontal position, with the fetal head (130) still held up by an assistant. The 18-19 gauze amniotomy needle provided in the SIPP catheter kit, along with a syringe (134) is now inserted to traverse through the lower uterine segment (128) to reach the amniotic fluid pocket (136) below the fetal presenting part.

Clear white amniotic fluid fills the syringe (134). The 18-19 gauge needle can be moved gently in a wider circular motion to dilate the uterine puncture site (allowing more of myometrial, and less of amnion puncture to dilate), a maneuver better than introducing another instrument like a puncture dilator that can widen the amniotic membrane puncture with the chance of amniotic fluid leak at this site. The amnion being a delicate membrane, it can easily yield to the passage of the soft SIPP catheter over a guide-wire, and hence minimal instrumental maneuvers through it are better. At this time, the guide-wire provided in the SIPP kit, is introduced into the amniotic cavity through the needle, and after sufficient length of the guide-wire is in the amniotic cavity, the needle over it is removed. Following it, the distal end of the guide-wire is passed through the proximal part (236) of the SIPP catheter (208) that was already brought to the amniotomy site. As most of the catheter (208) in this situation is not free, and is located in the subcutaneous plane, it is the passage of the guide-wire into the catheter (208) (and not vice versa) that needs to be accomplished until the guide-wire is felt at the distal trumpet segment (220) that is opened now, by disarticulating the trumpet (222) to let out the guide-wire, when also the SIPP catheter (236) tip is passed into the amniotic cavity over the guide-wire, as the let out trumpet end of the guide-wire is secured by hand. Following it, with sufficient length of the catheter (236) within the lower uterine segment, the guide-wire is completely let out through the opening of the trumpet segment (220) in a swift motion (while the catheter entry into the uterus is also steadied), and the trumpet (222) is quickly articulated with its trumpet segment (220), not to allow too much of amniotic fluid leak. The trumpet segment (220) being configured as a direct continuation of the linear length of the catheter, the guide wire's exit is made easier and uninterrupted from this route. The amniotic cavity can be immediately injected with 50-100 cc or more of isotonic 5% dextrose, to replace the lost volume.

A 5-10 cm of intrauterine length of the proximal SIPP catheter (236) is required. A red mark on the proximal catheter (236) delineates this length. The cuff (226) of the catheter stabilizer (224) is encircled around the proximal SIPP catheter (236) outside this red mark, and is secured (glued) to the SIPP catheter exterior with a biocompatible adhesive (epoxyamine or the like). The apertures (230) of both the cuff wings (228) are sutured to the superficial muscular layers of the lower uterine segment (128) by non-absorbable material so that the catheter will not be dislodged, nor the intraamniotc catheter (236) length lowered. The retractor (120) and the hemostat keeping the peritoneum (124) away from the bladder (102) and the lower anterior abdominal wall are now removed to let the peritoneum (124) fall back to its normal anatomical position. About 10-15 cm of redundant length of the SIPP catheter (208) within the extraperitoneal pelvic space is sufficient to allow for the uterine rise and the bladder distention. The suprapubic incision (122) is closed in layers, while allowing the SIPP catheter (208) to stay in the subcutaneous and extraperitoneal planes, traversing from the port-site to the amniotomy site.

If the Lower Uterine Segment Devoid of Peritoneum is not Visualized—

If the lower uterine segment (128) devoid of peritoneum is not visualized, it indicates that the posterior utero-vesical fold of peritoneum is still attached low down to the lower uterine segment (128) when one may see two layers of the peritoneum covering the lower uterine segment (128), as the peritoneum is separated from the superior surface of the bladder (114) through the incision (122). The anterior fold represents the peritoneum separated from the superior surface of the bladder (114), whereas the posterior fold is the posterior part of the uterovesical fold of peritoneum, the peritoneum that normally covers the lower uterine segment (128). If such situation is encountered, a small transverse incision 1-2 cm size is made over both the peritoneal layers, a suitable size straight urinary catheter is passed between the myometrial wall of the lower uterine segment (128) and the posterior fold of the cut peritoneum, and the urinary catheter maneuvered down to reach the uterovesical junction. This can be accomplished by rolling and/or side to side movement of the urinary catheter with its tip sufficiently tough for this maneuver. The straight urinary catheter is picked up just anterior to the reflection of the uterovesical fold of peritoneum, this step aided by the finger guidance of the surgeon. If visualization is needed, a flexible fiber optic endoscope used for nasopharyngeal procedures (and available in any hospital operating rooms), is a suitable instrument in this narrow retropubic space. The tip of a gastroscope or of a Flex. Sigmoidoscope can also be used which are of wider caliber, but have directional control. The proximal end (236) of the SIPP catheter (208) (brought to the symphysis site earlier) can then be introduced through the urinary catheter tip that is cut and widened, so that the proximal SIPP catheter (236) can reach the lower uterine segment (128) retroperitoneally, passing through the urinary catheter that ensheathed it. It is brought out through the cut peritoneal opening emerging from the urinary catheter, when the urinary catheter itself is removed retreating its course over the SIPP catheter (236). Now the proximal SIPP catheter (236) is introduced into the amniotic cavity by amniotomy in a manner similar to the above described technique, using a 18-19 gauge needle, and a guide-wire.

After the cuff (226) of the attachable stabilizer (224) is glued to the proximal SIPP catheter (236) and the wings (228) sutured to the myometrium with non-absorbable sutures, both the layers of the cut peritoneum are sutured separately with an absorbable catgut, the posterior layer sutured first, and then the anterior layer. Following it, the retractor (120) holding the peritoneum (124) is removed. Now the SIPP catheter (208) is located completely extraperitoneally within the pelvis (106). Leaving sufficient redundant catheter (208) length of 10-15 cm within the extraperitoneal pelvis (106), the incision (122) is closed in layers.

If negotiating the urinary catheter retroperitoneally as above, is not successful—an amniotomy SIPP catheter insertion is done over a guide wire, through the already cut two peritoneal incisions, traversing the exposed bare lower uterine segment. However, in this case, the upper two edges of the cut peritoneum are sutured together with closely set chromic catgut sutures, so properly isolating the abdomen from the extraperitoneal pelvis. The lower cut edge of the posterior peritoneum is then sutured to the already sutured upper peritoneal edges, so covering the bare area of the uterus except at the catheter entry. The cut lower edge of the anterior peritoneum is folded on itself and sutured with catgut, to cover its raw area so that peritoneal adhesions may not form. The normal pelvic peritoneal anatomy is altered, but it will not interfere with normal bladder filling, or with the uterine rise. The anatomy can be restored back during the elective cesarean when also the catheter is removed. The procedure is a safe compromise obviating the finality of closing the surgical site without extraperitoneally inserting the catheter, as inserting intraperitoneally is not advocated in this writing.

Soon after the completion of the procedure at the amniotomy site, the port-site incision is extended to 2.5 cm size, and the distal SIPP catheter (214) structures, the trumpet (222), and the port (200) are inserted into port-pocket, and the port (200) sutured to the tissues with a non-absorbable material passed through the three apertures (234) of the port (200). Taking the tissue bites of the port pocket site at strategic places, with the needle-suture material before introducing the port into the port-pocket, followed by their suture ligatures, is easier and practical, to accomplish the SIP port placement in its destined subcutaneous plane.

An Alternative Technique—

Approaching the uterus obliquely at an angle 45 degrees from the midline sagittal plane is an alternate preferred method, the side of the fetal limbs elected for this lateral approach. When the bladder is distended, the uterus is peeled off its peritoneal covering over certain area on its anterolateral surface, due to some separation of the anterior fold of the broad ligament. Ultrasound guidance is absolutely essential for targeted entry of the needle. Giving the patient pyridium before surgery can make the urine color orange to differentiate it from the AF. If entry into the amniotic cavity is confirmed through a percutaneously inserted 18 gauze needle, a guide-wire is introduced, and the needle removed. Following the guide-wire track, the uterus is approached through a small incision in the anteriorolateral abdominal wall (similar to a Grid iron incision). If the bare area of the uterus is not delineated by ultrasound, there can be two layers of peritoneum anteriolaterally, just as it was encountered through suprapubic approach, but they are widely separated. The bladder can also be distended more to widen the bare area of the uterus. As the pelvic floor is roomy, it is easier to reach lower uterine segment using a straight urinary catheter, than it was done in the suprapubic approach however, a gastroscope with directional visibility being preferred in this site. Following it, the transamniotic SIPP catheter insertion is done over the guide wire, a longer needle in the surgical kit serving the purpose. This approach can be used, to preferably distend the extraperitoneal pelvic floor and the retroperitoneal abdominal space more, by slow balloon inflation in this space, as the bladder is emptied simultaneously, that will also serve multitude of purposes. It will be described in the continuation-in-pat (CIP) of this application.

The antepartum and the intrapartum management of the patient treated with D-glucose transamniotic supplements are similar to what was already described under the section of maternal IV hypertonic D-glucose treatments, as this is only an additional treatment to the on-going maternal IV D-glucose supplements. CAT-3 with BPPS≤4, on 6 L of continuous $O_2$ therapy (COT) is the most distressed group of the algorithmic protocol, and the score showing no improvement in 2-4 days is the end point at which placement of the SIPP catheter is contemplated. An elective Cesarean section is the preferred delivery mode of choice, as soon as sufficient fetal maturity is indicated, when the SIPP catheter is removed from its uterine attachment, and the port removed from its subcutaneous port pocket.

Neonatal Care of an IUGR Baby

The anaerobic metabolism of glucose secondary to chronic hypoxic insults if becomes significant in fetal IUGR, the lactic acidemia can progressively threaten the fetal existence in-utero. Huang et al (1999) and Rishi Kant O et al (2006) conducted studies of normal neonates, and those who sustained acute/chronic perinatal insults of hypoxia/asphyxia as fetus neonates, with resultant neonatal Hypoxic Ischaemic Encephalopathy (HIE). They studied the first few urine samples excreted within 6 hours after birth that presumably reflected the blood/urine chemistry after the hypoxic insult had resulted. Though creatinine excretion depends on glomerular filtration rate, and is reduced during fetal hypoxia/asphyxia, lactate continues to be excreted, with its level reflecting in the AF that is mostly composed of fetal urine (Rishi Kant et al).

The most recent and the only study of its kind was done in Netherlands by Torrance H et al that involved AF lactate measurements, as a reflection of fetal hypoxia. This study measured AF lactate creatinine ratio (L/C ratio) that enables normalization of the concerned AF lactate values when AF volume is variable as in oligohydromnios (IUGR), or polyhydromnios (diabetes). The study involved term, and preterm IUGR pregnancies. Arterial umbilical cord blood and the AF were collected simultaneously during cesarean delivery. The study inferred that the L:C ratio in general decreased with increasing gestational age, and that there was no correlation to the arterial cord blood lactate and the AF lactate, but there was statistically significant correlation between the arterial cord blood lactate, and the AF-L:C ratio for the reason that the latter value enabled normalization of AF lactate values despite the variable and unpredictable AF volumes.

What Causes Persistently Elevated Lactic Acid Levels and Severe Acidosis in the Neonate?

The inquiry is important in the optimal neonatal care of the IUGR fetus, as the care of such baby is a continuum that may not terminate abruptly at delivery. Soon after delivery, even the previously hypoxic fetus neonate starts to oxidize lactate to pyruvate aerobically, when $NAD^+$ is reduced to $NADH+H^+$ in many tissues of the body, and the pyruvate can be aerobically oxidized further in the citric acid cycle. If the neonate is deficient in thiamine (a co-factor needed to oxidize pyruvate to acetyl-CoA that continues into the citric acid cycle, as discussed before), as thiamine stores are usually limited even in normal adult, the lactic acidosis will simply change into pyruvic acidosis, that is no better, but it can still abruptly change/reduce the urine lactic acid/lactate level though the acidosis itself is yet to be resolved. Accordingly, an invariable fall of blood lactate can be reflected in the admixed urine.

It is imperative that as soon as delivered, the hypoxic baby, apart from being treated with oxygen, should be given thiamine (along with other B-complex factors) and magnesium IV, proportional to the body weight, to ensure rapid resolution of lactic and pyruvic acidosis. Magnesium is a necessary co-factor in glycolysis and citric acid cycle, as essentially in all reactions in which ATP is a substrate, the true substrate is $Mg^{2+}$-ATP, as $Mg^{2+}$ diminishes the dense anionic character of ATP, for it to be functional (Martin D). Entry of pyruvate into citric acid cycle as acetyl-coA, its formation aided by thiamine, and pyruvate's further more entry into the cycle also as oxaloacetate, aided by biotin (FIG. 12), are effectuated in most of fetal tissues following the first breath, due to universally predominant aerobic conversion of lactate to pyruvate. Such bimodal disposal of pyruvate when the essential co-factors (like thiamine) are also present rapidly lowers its concentration. Such lowering of its concentration greatly enhances the reversal of the reaction involving lactate dehydrogenase—as in a normal adult, it was shown that the rapid pyruvate disposal greatly enhances the reversal of the reaction involving lactate dehydrogenase oxidizing lactate to pyruvate (Guyton A C). Additionally, if fetal lactic acidosis was diagnosed before delivery, immediate neonatal glucose supplements must be deferred, as the pyruvate generated after the entry of supplemented glucose into the cells, can use up $NAD^+$ that can impair the ongoing conversion of existing lactate to pyruvate (see FIG. 2), thereby slowing the pathways helped by the vitamin supplements. The Cori cycle that is predominant in adults after intense muscular exercise, and disposes of the accumulated lactic acid by the hepatic pathways, may not be contextually very significant in the SGA neonates, as their renewed citric acid cycle pathway is energy generating, and furthermore, it is needed for the rapid resolution of the neonatal acidosis, to a greater extent by the generation $CO_2$ and then the bicarbonate through the citric acid cycle path way, the body's major source of $CO_2$.

Figure 12:
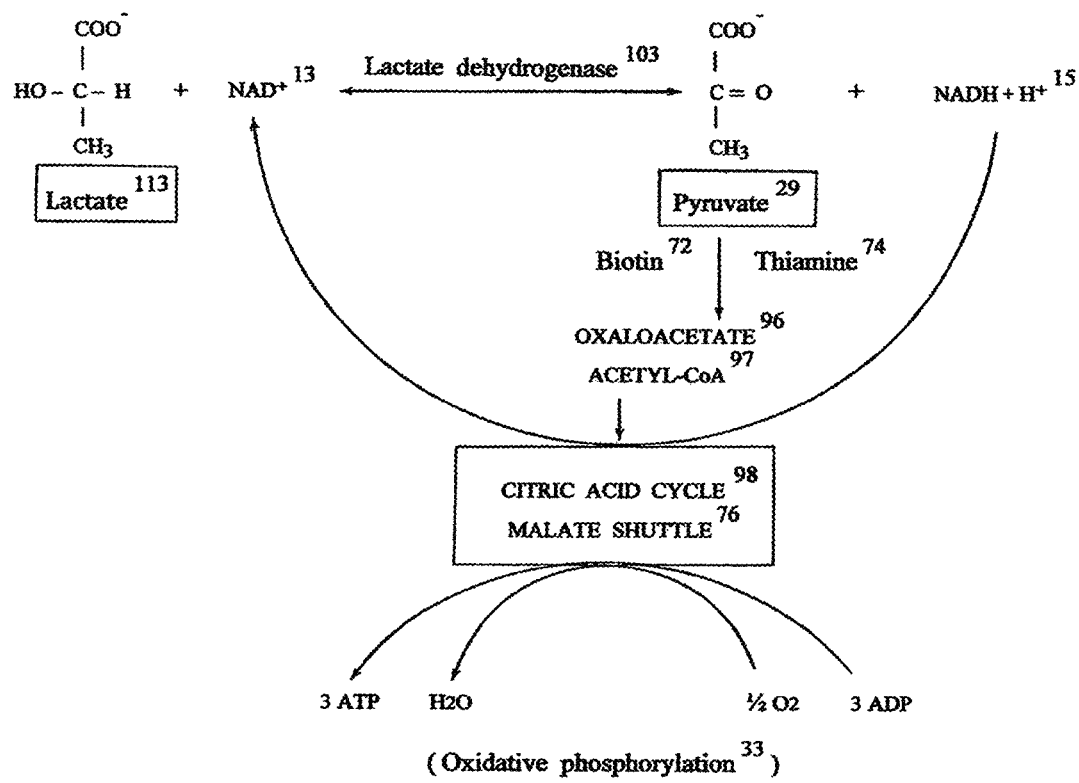
FIG. 12: A schematic illustration of the aerobic reversal of lactic acidosis in the neonate with the pathway opening to citric acid cycle, in conjunction with malate shuttle—also showing the means of disposing cytosolic $NADH+H^+$ to regenerate $NAD^+$ needed for such continued reversal.

It was mentioned in the section of 'Malate shuttle' (FIG. 3A) that this shuttle is what reaps the benefits of aerobiosis, by transferring the cytosolically generated 'reducing equivalents', the $NADH+H^+$ (15), to the mitochondrial oxidative phosphorylation (33). Hence, as shown in FIG. 12, it is obvious that this process is imperative during the reversal of anaerobic glycolysis and the aerobic recovery of lactate, and in turn for the on-going supply of $NAD^+$ (13) needed for such continued oxidation of lactate (113) to pyruvate (29) via the reaction catalyzed by lactate dehydrogenase (103). With adequate availability of biotin (72) and thiamine (74), the pathways to citric acid cycle (98) and malate shuttle (76) should be incessant and universally predominant in most tissues of the neonate. Lactate being the normal fetal fuel (derived by the dominant placental anaerobic synthesis, from D-glucose; refer the earlier section that discusses fetal lactic acidosis), and is aerobically metabolized to pyruvate in the fetal brain, heart, and skeletal muscle, by the action of lactate dehydrogenase, this pivotal enzyme is maintained in exponentially high levels in normal fetus/neonate (160-1500 U/L), and it could be more in an IUGR/SGA fetus neonate. The level in a healthy adult is only in the range of 100-250 U/L. It needs further emphasis that the term 'Reversal of the anaerobic process' does not imply to any extent, the exact reversal of the steps of anaerobic glycolysis that are intimately connected to the step-6 of the earlier described glycolytic process (FIG. 2), but rather wholly involves steps forward towards citric acid cycle and malate shuttle (the role of the 'cori cycle' being unclear in a neonate), as shown in FIG. 12 (a schematic illustration of the aerobic reversal of lactic acidosis in the neonate with the pathway opening to citric acid cycle, accomplished in conjunction with malate shuttle).

Supplements of phosphorous is equally needed for the pivotal role it plays in oxidative phosphorylation, the ultimate step in the aerobic oxidation of pyruvate within the mitochondria. The phosphate group that is added to ADP to form ATP is in fact derived from the inorganic phosphate ($H_2PO_4^-$) (the dihydrogen phosphate) (see the section oxidative phosphorylation). It has to be noted that oxidation and phosphorylation are tightly coupled (Mayes P A) within the mitochondrial respiratory chain, and without concomitant phosphorylation, there is no catabolic oxidation of pyruvate, or its subsequent intermediates of the citric acid cycle.

Optimal nicotinic acid levels are also essential to the neonate as the co-factor nicotinamide adenine dinucleotide, the $NAD^+$, ubiquitous in all cellular activities, is synthesized from this B-complex factor. A malnourished fetus-neonate deficient in needed vitamins and minerals can not be adequately resuscitated without correction of such deficits.

Though a significant correlation was found between urine lactate levels, and the occurrence/severity of HIE (with SGA babies as a subset of infants in this group) in the diagnostic and prognostic considerations of the foregoing studies, monitoring the blood lactic acid, pyruvic acid, and keto-acids is valuable in these neonates for therapeutic considerations, as failure to rapidly resolve blood lactic acidosis, pyruvic acidosis, and ketoacidosis in a SGA neonate that was chronically malnourished and hypoxic in-utero, can be reflective of vitamin and mineral deficiency. A multivitamin mineral supplement is indicated to this subset of infants (as biotin, riboflavin and pantothenic acid are also involved for the operation of citric acid cycle) to organize the whole metabolic chaos that is invariable after their prolonged existence in a depriving and hostile uterine habitat. Once citric acid cycle is set to be operative and is further sustained, the multifaceted pathology of, acidosis will resolve, without further clinical intervention in this regard.

The pyruvate (originating from lactate) entering citric acid cycle relieves acidosis by a 'triple effect', that is, by oxidation/elimination of excess lactate/pyruvate, resolution of ketoacidosis, as well as generation of bicarbonate, the citric acid cycle being the major generator of $CO_2$/bicarbonate, as the needed blood buffer base. Hence, the persistent acidosis in a well oxygenated SGA neonate is due to continued lactic acidosis, pyruvic acidosis, and keto-acidosis as well as lack of bicarbonate reserves, the etiology being common for all, that is, the vitamin and mineral deficiency, either singly or in any combination. Glucose has to be administered with caution, when high lactate level or a high lactate/creatinine ratio was identified in the AF, and excess blood lactic acid and or pyruvic acid levels are identified in the neonate. One may not wait for the blood vitamin and mineral reports to arrive, for supplementing them. They have to be given into the cord blood (while the blood is also drawn for lactic and pyruvic acid levels, and other needed blood chemistry) as soon as the cord is clamped, and while the baby is resuscitated, as finding a vein later can be time taking and distressing, apart from being an unduly delayed maneuver. The umbilical vein and the ductus venosus constrict immediately after birth, but typically close in 1-3 hours after birth, and the umbilical arteries obliterate in 3-4 days. Sodium bicarbonate is also very useful for the immediate relief of acidosis. Glucose supplements should be considered as soon as the pyruvate and lactate levels are found to be falling and approaching the normal range.

It is the aim of this invention to restore all IUGR/SGA afflicted fetuses/babies to their innate growth potential and optimal health, before and after they arrive into their terrestrial world.

Facts have had to mingle with conjecture and theory, and no excuse is made for the latter, for they must in part form the basis for future experiments, research and progress (Gemzell C. A, 1970).

DEDICATION—

To My Father—

Who, with his unquenchable thirst and indomitable passion for education at its finest, was, from elementary grade to MD, an incessant source of inspiration that had not passed away at his passing away.

To My Mother—

Who, with wisdom beyond her education, and with cheer that ever illuminated her countenance, gave up life's pleasures small and big, for her children unto her last.

To Dr. Peter A. Mayes (Biochemistry, UK)—

A Mentor to a world of students, by most unseen and unmet, yet familiar as if met.

This writing is dedicated to.

The invention claimed is:

1. A method of treating a maternal subject suffering from human fetal Intrauterine Growth Restriction (IUGR), due to vascular insufficiency of placental origin, comprising administering isotonic D-glucose by transamniotic catheter infusions, through a minimally invasive extraperitoneal suprapubic amniotomy encompassing a subcutaneously implanted pregnancy port (SIPP) catheter placement, such treatments done concurrently with bolus intravenous (IV) infusion of 25-50% hypertonic D-glucose, 50-100 cc, 2-3 times per day, the said supplements effectuating the following changes:
  1. induced maternal hyperglycemia,
  2. restored fetal normoglycemia,
  3. improvement of fetoplacental hypoxia,
  4. improvement of fetal hypercapnia, if any,
  5. improvement of fetal oliguria and oligohydromnios with improved fetal urea production,
  6. improvement of fetal acidosis including ketoacidosis,
  7. improvement of fetal lactic academia/lactic acidosis, consequent to improved fetal hypoxia, 8. improvement of fetal hypertriglyceridemia,
9. improved acquisition by the fetus of major nutrients, the amino acids and fats, and also of minerals, vitamins, and trace elements,
10. improved feto-maternal exchange by—(a) glucose derived ATP mediated placental L-arginine active transport, and synthesis of nitric oxide, the latter effectuating feto-placental vasorelaxation, (b) glucose derived ATP mediated placental D-lysine active transport, with consequent feto-placental neo-vasculogenesis,
11. improved rapid neuronal lipogenesis of fetal brain, with exponential glucose and oxygen salvage, primarily due to accomplished 2-citrate diversion towards the said neuronal lipogenesis, instead of 1-citrate diversion prevailing during glucose scarcity,
12. improved ATP production by restoring operating citric acid cycle.

2. The method of treating fetal IUGR of claim 1, wherein the induced maternal hyperglycemia with resultant placental substrate excess, and consequent insulin response, effectuate the following, as per the Michaelis-Menten model—(1) recruiting increasing number of surplus placental cell membrane carriers of D-glucose, by insulin effects; (2) said carriers operating with instantaneous maximal velocity ($V_{max}$), while the substrate excess exceeds the km value; (3) said $V_{max}$ further effectuating instantaneous feto-placental exchange even during shorter fetal systole, whereas the diastolic feto-placental flow itself may be reversed; (4) the heightened placental facilitated diffusion of D-glucose being the multiplied product of—attained instantaneous $V_{max}\times$ additionally recruited carriers all working at $V_{max}$.

3. The method of treatment of claim 1, wherein the maternal IV hypertonic D-glucose supplementation in conjunction with transamniotic D-glucose fetal supplementation facilitates the supply of the placental carbohydrate reserves to the fetus as lactate, the tolerance of the said treatments clinically monitored by amniotic fluid lactic acid testing, BPP (biophysical profile) scoring, and Fetal heart rate (FHR) monitoring.

4. The method of treatment of claim 1, wherein the optimally induced maternal hyperglycemia causes the following effects—
(1) the fetal hypoglycemia is corrected, and fetal hyperglycemia is not induced,
(2) the induced maternal hyperglycemia is transient,
(3) the maternal ketosis is not resulted and neither are the first trimester ketosis-induced fetal anomalies, said otherwise observed in uncontrolled maternal diabetes mellitus.

5. The method of claim 1, wherein the induced fetal normoglycemia results in substantive oxygen and ATP salvage, effectuated through optimized major fetal metabolic pathways within the fetus, by the following means:
(1) obviating the oxygen consuming beta oxidation of free fatty acids;
(2) averting ketoacidosis consequent to fatty acid oxidation, wherein the ketone bodies are otherwise oxidized in preference to glucose, thus saturating the oxidative machinery;
(3) averting further ketoacidosis, the insulin resulting from the fetal normoglycemic status being antilipolytic;
(4) obviating fetal body protein breakdown for energy requirements, which otherwise is a process of exceeding oxygen and ATP consumption far worse than that of fatty acid oxidation, many amino acid end products entering citric acid cycle with 'ATP debt', as the relatively non-toxic urea production from toxic ammonia of protein break-down demanding high ATP needs.

6. The method of treatment for fetal intrauterine growth restriction of placental origin of claim 1, wherein the maternal intravenous hypertonic D-glucose treatments with or without concomitant transamniotic D-glucose supplementation, inducing maternal hyperglycemia and restoring fetal normoglycemia, effectuate the following:
(1) improving fetal hypoxia by: (a) obviating beta oxidation and reducing the consequent $O_2$ needs by 33%, (b) obviating fetal body protein breakdown for energy needs, their catabolic ATP and oxygen demands more than that of beta oxidation, (c) causing placental iron 'active transport' increasing fetal mean corpuscular hemoglobin concentration (MCHC), said iron active-transport effectuated by predominantly D-glucose derived ATP, (d) said higher MCHC further improving fetal polycythemia, laminar flow of fetal and placental vessels, the diastolic flow velocity, and thereby the oxygen transport, (e) heightening placental/fetal L-arginine active-transport needed of nitric oxide synthesis, subject to improving feto-placental vasculogenesis, vasorelaxation, and the vascular 'critical closing pressure', (f) more $CO_2$ generated by preferential fetal glucose metabolism heightening 'Bohr Effect' of $O_2$ pick up in the fetal tissues, to the extent of overcoming the $O_2$ affinity to fetal hemoglobin, (g) improved fetal hypotonia causing improved fetal swallowing of amniotic fluid, with substantive amount of $O_2$, diffused from uterine myometrium, (h) advocated maternal bed rest in left lateral Trendelenburg's position overcoming the forces of gravity, and the resistance of the placenta located normally in the upper uterine segment, by improving the reversed diastolic umbilical vessel/placental flow;
(2) improving fetal hypercapnia, if any, by: (a) the restored fetal lipogenesis, sequestrating $CO_2$, (b) the restored fetal urea synthesis eliminating $CO_2$, (c) the relieved placental hypoxia as in section (1) above, and further along with maternal $O_2$ therapy enhancing $O_2$ uptake by the fetal hemoglobin at the placental sinusoids, in turn releasing more of $CO_2$, as per the Haldane effect, (d) the improved MCHC preserving/restoring the fetal hemoglobin-$O_2$ affinity, and thereby the naturally heightened fetal Haldane effect of $CO_2$ release;
(3) improving fetal oliguria and oligohydromnios by: (a) restored fetal urea production, responsible for urea-induced fetal osmotic diuresis, (b) higher circulating maternal glucose itself improving amniotic fluid volume by osmotic effects, (c) improved fetal urea synthesis by incorporation of $CO_2$ entering portal circulation, by improved fetal hypotonia and swallowing of amniotic fluid high in $CO_2$ diffused from uterine myometrium;
(4) improving fetal acidosis by: (a) the $CO_2$ produced in predominantly glucose-operative citric acid cycle generating body's bicarbonate base reserve, (b) obviating beta oxidation of fats by optimized insulin levels antagonizing lipolysis, otherwise deemed for ketoacidosis, (c) the D-glucose replenishing oxaloacetate to citric acid cycle further preventing ketoacidosis, d) the D-glucose induced lipogenesis utilizing hydrogen ions;
(5) improving fetal hypertriglyceridemia by the optimized levels of insulin antagonizing the lipolytic action of the enzyme lipoprotein lipase, such fetal lipolysis otherwise subject to esterification of liberated free fatty acids and glycerol into triglycerides in the fetal tissues;

(6) improving growth and maturation of fetal brain, by the optimal levels of D-glucose effectuating a process of rapid neuronal 'Lipogenesis via Glycolysis Abbreviated Citric acid Cycle' (LGACC), wherein—(a) 2 citrate molecules instead of one, from one molecule of D-glucose are preferentially diverted into fetal brain's fatty acid synthesis, (b) said 2-citrate diversion expending 200% less of glucose and 400% less of oxygen by bypassing many steps of citric acid cycle, yet generating optimal ATP by the exceeding amount of acetyl-CoA synthesis needed for the synthesis of brain's phospholipids and glycolipids, (c) the prevailing/cycling $CO_2$ during the fetal brain's rapid neuronal lipogenesis, locally heightening the Bohr effect of $O_2$ release;

(7) improving fetal D-glucose/citric acid cycle generation of ATP, ubiquitous and essential for: (a) all feto-placental cellular activities, (b) active transport needed for transplacental passage against a concentration gradient;

(8) improving fetal acquisition of nutrients/elements by restored placental transport, fetal synthesis, or by added means as the 'IUGR-diet', effectuating: (a) essential amino acid transport—by FACILITATED DIFFUSION controlled by glucose induced circulating insulin, the IUGR-diet providing maternal-fetal amino acid gradient of more than 1 OR by D-glucose derived ATP requiring ACTIVE TRANSPORT when the maternal-fetal amino acid ratio is less than 1, whereas the fetus itself synthesizes the non-essential amino acids from supplemented D-glucose, (b) essential free fatty acid transport—by SIMPLE DIFFUSION down the concentration gradient, such gradient helped by the IUGR diet, whereas the fetus itself synthesizes non-essential free fatty acids from supplemented D-glucose, (c) vitamins, minerals and trace elements transport—by D-glucose derived ATP driven ACTIVE TRANSPORT, (d) said fetal acquisition helped by IUGR-diet improvising substrate concentration, leading to instantaneous $V_{max}$ of the additionally recruited placental carriers;

(9) improving fetal lactic academia—(a) consequent to D-glucose therapy itself improving fetal hypoxia as in the foregoing, (b) by D-glucose generated ATP driven active transport of vitamin/mineral supplements, the supplemented thiamine aiding pyruvate entering citric acid cycle, thereby heightening the oxidation of lactate to pyruvate;

(10) improving placental, fetal and umbilical vessel nitric acid synthesis by D-glucose generated ATP driven placental active-transport of L-arginine, and further by its transport into the endothelial cells by glucose-insulin action, the nitric oxide synthesis from L-arginine also needing as coenzyme, the NADPH derived from D-glucose mediated feto-placental pentose phosphate pathway, the said nitric oxide effectuating: (a) vasodilatation of the placental sinusoidal spaces, (b) vasodilatation of fetal vessels including umbilical vessels, to over-ride their 'critical closing pressure' as governed by the 'law of Lawplace', and readily manifest in the helically arranged muscle fibers of the umbilical vessels, (c) preventing feto-placental and umbilical vessel platelet aggregation and vaso-occlusion.

7. The method of treatment for fetal intrauterine growth restriction (IUGR) of placental origin of claim 1 further comprising evaluating, monitoring, and/or treating the maternal subject at base line and subsequently by the following indicators:

(1) amniotic fluid lactate/lactic acid (AF-LA) level: wherein, when AF-LA level is found h at base line with lowered Biophysical Profile Score (BPPS), reflective of fetal hypoxia, prior to IV D-glucose therapy, the mother is treated with continuous oxygen therapy (COT) normalizing the AF-LA level;

(2) fetal Bio-Physical Profile score (BPPS) of 0-10: wherein BPPS is chosen as a proxy to the infrequently done AF-LA levels for the quantitative power of BPPS, to therapeutically proportionate the maternal IV $DG_{25-50}$ treatment, the fetal hypoxia/intolerance of D-glucose lowering BPPS, being reflective of fetal lactic acidosis;

(3) low AF-LA and lowered BPPS encountered at baseline: wherein the lowered AF-LA level being reflective of fetal hypoglycemia, the mother is treated only with IV hypertonic D-glucose therapy;

(4) 2 hour stretch of fetal heart rate (FHR) tracings starting ½ hour before each increment of maternal IV $DG_{25-50}$ treatment: wherein the adverse FHR changes being reflective of fetal intolerance of D-glucose treatment consequent to fetal hypoxia and anaerobic glycolysis, the mother is treated with an intermittent oxygen therapy (IOT) about the time of daily IV $DG_{25-50}$ therapy;

(5) with the mother on IOT about the time of daily IV $DG_{25-50}$ therapy: wherein she is failing the weaning challenge off the IOT, with accompanying adverse FHR changes or falling BPP scores, she is treated with continued IOT;

(6) with the mother on IOT: wherein she is showing $DG_{25-50}$ intolerance with adverse FHR changes, or fallen BPP scores, however, improving with continuous oxygen therapy (COT), she is treated with an effective dose D-glucose with COT;

(7) with the mother on COT: wherein she is showing IV $DG_{25-50}$ unresponsiveness by adverse FHR changes and lower BPP scores, yet with low AF-LA levels, the fetus is treated with transamniotic D-glucose supplementation through extraperitoneal suprapubic amniotomy by a Subcutaneously Implantable Pregnancy Port (SIPP) catheter.

8. The method of treatment for human fetal intrauterine growth restriction (IUGR) of placental origin of claim 1, wherein the fetal IUGR treated with maternal IV hypertonic D-glucose therapy intended for extended duration, a percutaneously inserted central venous catheter, exemplified by Broviac's catheter with a Dacron cuff delivering the said therapy, is inserted into the maternal basilic vein at the cubital fossa, by means of a needle and a guide wire, or by any suitable means, said Broviac's catheter subcutaneously placed by a novel technique, named as Sumathi Paturu's subcutaneous tunneling technique, the sequential steps of which are as follows—

(a) by mapping the surface anatomy of the basilic vein about the cubital fossa, its location and course visually confirmed by a portable ultrasonic machine, a small 1 cm cut is made over the proposed venipuncture (venotomy) site lifting a skin fold, and cutting with scissors;

(b) a smallest size Hegar cervical dilator, a smoothly curved sigmoid shaped instrument, and its ensheathing straight urinary catheter of a size sufficient to allow free movement of the dilator, are chosen as the tunneling instruments, and from the venotomy site, a subcutaneous tunnel is made to the chosen skin exit site on the medial aspect of the forearm, wherein through a 1 cm skin incision, the tunneling instruments are brought out, the tunneling instruments throughout traversing under a lifted skin fold, thereby avoiding injury to deeper structures;

(c) the Hegar dilator is removed from its urinary catheter sheath, by allowing the dilator to retreat its course through the venotomy site;

(d) the urinary catheter tip at the skin exit site is cut, for the proximal end of the Broviac catheter to be introduced and brought to the venotomy site, and it can be the surgeons option to initiate the tunneling on the medial side of the forearm also, with easier instrumental maneuvering;

(e) the urinary catheter is removed thereafter from the venotomy site over the Broviac catheter it had ensheathed, while the Broviac catheter tip brought to the venotomy site is inserted into the vein through a guide-wire, and the catheter tip is negotiated into a larger proximal vein to a distance that the Dacron cuff is situated in the middle fore arm.

* * * * *